US008470330B2

(12) United States Patent
Maddon et al.

(10) Patent No.: US 8,470,330 B2
(45) Date of Patent: Jun. 25, 2013

(54) PSMA ANTIBODIES AND USES THEREOF

(75) Inventors: Paul J. Maddon, Scarsdale, NY (US);
Gerald P. Donovan, Kittery, ME (US);
William C. Olson, Yorktown Heights,
NY (US); Norbert Schuelke, East
Walpole, MA (US); Jason Gardner,
Wayne, PA (US); Dangshe Ma,
Millwood, NY (US); Jaspal S. Kang,
Surrey (CA); Larry Green, San
Francisco, CA (US)

(73) Assignees: PSMA Development Company, LLC,
Tarrytown, NY (US); Amgen Fremont Inc., Thousand Oaks, CA (US)

( * ) Notice: Subject to any disclaimer, the term of this patent is extended or adjusted under 35 U.S.C. 154(b) by 0 days.

(21) Appl. No.: 12/845,686

(22) Filed: Jul. 28, 2010

(65) Prior Publication Data

US 2011/0165081 A1    Jul. 7, 2011

Related U.S. Application Data

(63) Continuation of application No. 10/976,352, filed on Oct. 27, 2004, now abandoned, which is a continuation-in-part of application No. 10/695,667, filed on Oct. 27, 2003, now abandoned, which is a continuation-in-part of application No. 10/395,894, filed on Mar. 21, 2003, now Pat. No. 7,850,971, which is a continuation-in-part of application No. PCT/US02/33944, filed on Oct. 23, 2002.

(60) Provisional application No. 60/335,215, filed on Oct. 23, 2001, provisional application No. 60/362,747, filed on Mar. 7, 2002, provisional application No. 60/412,618, filed on Sep. 20, 2002.

(51) Int. Cl.
*A61K 39/00* (2006.01)
*A61K 39/395* (2006.01)

(52) U.S. Cl.
USPC ............ 424/183.1; 424/130.1; 424/133.1; 424/138.1; 424/155.1; 424/174.1; 424/178.1; 424/181.1; 530/350; 530/387.1; 530/387.3; 530/387.7; 530/388.8; 530/391.3; 530/391.7

(58) Field of Classification Search .......... 424/130.1, 424/133.1, 138.1, 155.1, 174.1, 178.1, 181.1, 424/183.1; 530/350, 387.1, 387.3, 387.7, 530/388.8, 391.3, 391.7
See application file for complete search history.

(56) References Cited

U.S. PATENT DOCUMENTS

| | | |
|---|---|---|
| 4,554,101 A | 11/1985 | Hopp |
| 5,055,559 A | 10/1991 | Hellstrom et al. |
| 5,091,178 A | 2/1992 | Hellstrom et al. |
| 5,153,118 A | 10/1992 | Wright, Jr. et al. |
| 5,162,504 A | 11/1992 | Horoszewicz |
| 5,192,684 A | 3/1993 | Tanihara et al. |
| 5,281,699 A | 1/1994 | Chang |
| 5,489,525 A | 2/1996 | Pastan |
| 5,491,088 A | 2/1996 | Hellstrom et al. |
| 5,538,866 A | 7/1996 | Israeli et al. |
| 5,578,484 A | 11/1996 | Horoszewicz |
| 5,672,592 A | 9/1997 | Jackson et al. |
| 5,688,657 A | 11/1997 | Tsang et al. |
| 5,738,867 A | 4/1998 | Spitler |
| 5,770,429 A | 6/1998 | Lonberg et al. |
| 5,773,292 A | 6/1998 | Bander |
| 5,788,963 A | 8/1998 | Murphy et al. |
| 5,789,245 A | 8/1998 | Dubensky, Jr. et al. |
| 5,795,877 A | 8/1998 | Jackson et al. |
| 5,804,602 A | 9/1998 | Slusher et al. |
| 5,807,548 A | 9/1998 | Shitara et al. |
| 5,843,723 A | 12/1998 | Dubensky, Jr. et al. |
| 5,922,845 A | 7/1999 | Deo et al. |
| 5,925,362 A | 7/1999 | Spitler et al. |
| 5,935,818 A | 8/1999 | Israeli et al. |
| 5,968,915 A | 10/1999 | Jackson et al. |
| 5,981,209 A | 11/1999 | Slusher et al. |
| 6,011,021 A | 1/2000 | Slusher et al. |
| 6,015,694 A | 1/2000 | Dubensky, Jr. et al. |
| 6,017,903 A | 1/2000 | Slusher et al. |
| 6,046,180 A | 4/2000 | Jackson et al. |
| 6,107,090 A | 8/2000 | Bander |
| 6,136,311 A | 10/2000 | Bander |
| 6,150,508 A | 11/2000 | Murphy et al. |
| 6,158,508 A | 12/2000 | Lemetayer et al. |
| 6,200,765 B1 | 3/2001 | Murphy et al. |

(Continued)

FOREIGN PATENT DOCUMENTS

| | | |
|---|---|---|
| EP | 0 173 951 A2 | 3/1986 |
| EP | 0 354 129 A1 | 2/1990 |

(Continued)

OTHER PUBLICATIONS

McDevitt et al. (Cancer Res. Nov. 1, 2000; 60 (21): 6095-100).*
U.S. Appl. No. 08/621,399, filed Mar. 25, 1996, Murphy et al.
US 6,290,956, 09/2001, Bander (withdrawn).
[No Author Listed] "Bristol-Myers Squibb Completes Acquisition of Medarex, Inc." Bristol-Mtyers Squibb Press Release. Sep. 1, 2009.
[No Author Listed] "Exhibit 1." Evidence filed by Helmut during the opposition proceedings of European Patent Publication No. 956506. Filed Dec. 1, 2009.
[No Author Listed] "Medarex Announces Filing of Investigational New Drug Application for MDX-070; Fully Human Anti-PSMA Antibody Candidate for Prostrate Cancer." Press Release. PR Newswire. Monday, Jan. 6, 2003, 4:36 P.M. 2 pages.

(Continued)

*Primary Examiner* — Stephen Rawlings
(74) *Attorney, Agent, or Firm* — Wolf, Greenfield & Sacks, P.C.

(57) ABSTRACT

The invention includes stable multimeric, particularly dimeric, forms of PSMA protein, compositions and kits containing dimeric PSMA protein as well as methods of producing, purifying and using these compositions. Such methods include methods for eliciting or enhancing an immune response to cells expressing PSMA, including methods of producing antibodies to dimeric PSMA, as well as methods of treating cancer, such as prostate cancer.

31 Claims, 63 Drawing Sheets

U.S. PATENT DOCUMENTS

| | | |
|---|---|---|
| 6,214,345 B1 | 4/2001 | Firestone et al. |
| 6,224,870 B1 | 5/2001 | Segal et al. |
| 6,242,259 B1 | 6/2001 | Polo et al. |
| 6,313,159 B1 | 11/2001 | Jackson et al. |
| 6,328,969 B1 | 12/2001 | Houghton et al. |
| 6,329,201 B1 | 12/2001 | Polo et al. |
| 6,372,726 B1 | 4/2002 | Slusher et al. |
| 6,376,236 B1 | 4/2002 | Dubensky, Jr. et al. |
| 6,383,759 B1 | 5/2002 | Murphy et al. |
| 6,387,888 B1 | 5/2002 | Mincheff et al. |
| 6,395,718 B1 | 5/2002 | Slusher et al. |
| 6,413,948 B1 | 7/2002 | Slusher et al. |
| 6,426,196 B1 | 7/2002 | Dubensky, Jr. et al. |
| 6,444,657 B1 | 9/2002 | Slusher et al. |
| 6,458,775 B1 | 10/2002 | Jackson et al. |
| 6,475,389 B2 | 11/2002 | Kawinski et al. |
| 6,569,432 B1 | 5/2003 | Israeli et al. |
| 6,649,163 B1 | 11/2003 | Bander |
| 6,653,129 B1 | 11/2003 | Bander et al. |
| 6,770,450 B1 | 8/2004 | Bander |
| 6,897,062 B1 | 5/2005 | Heston et al. |
| 6,953,668 B1 | 10/2005 | Israeli et al. |
| 6,962,981 B1 | 11/2005 | Murphy |
| 7,037,647 B1 | 5/2006 | Israeli et al. |
| 7,045,605 B2 | 5/2006 | Bander et al. |
| 7,070,782 B1 | 7/2006 | Israeli et al. |
| 7,105,159 B1 | 9/2006 | Israeli et al. |
| 7,112,412 B1 | 9/2006 | Bander et al. |
| 7,163,680 B2 | 1/2007 | Bander et al. |
| 7,192,586 B2 | 3/2007 | Bander et al. |
| 7,201,900 B2 | 4/2007 | Murphy et al. |
| 7,381,407 B1 | 6/2008 | Murphy et al. |
| 7,399,461 B2 | 7/2008 | Heston et al. |
| 7,476,513 B2 | 1/2009 | Murphy et al. |
| 7,514,078 B2 | 4/2009 | Bander et al. |
| 7,659,241 B2 | 2/2010 | Senter et al. |
| 7,666,414 B2 | 2/2010 | Bander |
| 7,666,425 B1 | 2/2010 | Bander |
| 7,850,971 B2 | 12/2010 | Maddon et al. |
| 8,114,965 B2 | 2/2012 | Maddon et al. |
| 2001/0036928 A1 | 11/2001 | Chamberlain et al. |
| 2002/0013295 A1 | 1/2002 | Slusher et al. |
| 2002/0015704 A1 | 2/2002 | Bander |
| 2002/0049712 A1 | 4/2002 | Kawinski et al. |
| 2002/0151503 A1 | 10/2002 | Slusher et al. |
| 2002/0155093 A1 | 10/2002 | Houghton et al. |
| 2002/0164318 A1 | 11/2002 | Houghton et al. |
| 2003/0003101 A1 | 1/2003 | Bander |
| 2003/0013191 A1 | 1/2003 | Cussenot et al. |
| 2003/0017965 A1 | 1/2003 | Slusher et al. |
| 2003/0027246 A1 | 2/2003 | Pedyczak et al. |
| 2003/0031667 A1 | 2/2003 | Deo et al. |
| 2003/0031673 A1 | 2/2003 | Bander |
| 2003/0046714 A1 | 3/2003 | Simard et al. |
| 2003/0064912 A1 | 4/2003 | Slusher et al. |
| 2003/0083374 A1 | 5/2003 | Jackson et al. |
| 2003/0161832 A1 | 8/2003 | Bander |
| 2003/0220239 A1 | 11/2003 | Simard et al. |
| 2004/0001846 A1 | 1/2004 | Israeli et al. |
| 2004/0002478 A1 | 1/2004 | Kozikowski et al. |
| 2004/0018519 A1 | 1/2004 | Wright, Jr. |
| 2004/0024188 A1 | 2/2004 | Murphy et al. |
| 2004/0033229 A1 | 2/2004 | Maddon et al. |
| 2004/0037843 A1 | 2/2004 | Fikes et al. |
| 2004/0105865 A1 | 6/2004 | Bander |
| 2004/0120958 A1 | 6/2004 | Bander et al. |
| 2004/0132101 A1 | 7/2004 | Lazar et al. |
| 2004/0136998 A1 | 7/2004 | Bander et al. |
| 2004/0161776 A1 | 8/2004 | Maddon et al. |
| 2004/0180354 A1 | 9/2004 | Simard et al. |
| 2004/0198657 A1 | 10/2004 | Heston et al. |
| 2004/0213791 A1 | 10/2004 | Bander |
| 2004/0253246 A1 | 12/2004 | Israeli et al. |
| 2005/0064504 A1 | 3/2005 | Heston et al. |
| 2005/0142144 A1 | 6/2005 | Simard et al. |
| 2005/0202020 A1 | 9/2005 | Ross et al. |
| 2005/0215472 A1 | 9/2005 | Schulke et al. |
| 2005/0260234 A1 | 11/2005 | Simard et al. |
| 2006/0024316 A1 | 2/2006 | Spitler et al. |
| 2006/0062793 A1 | 3/2006 | Webb et al. |
| 2006/0074008 A1 | 4/2006 | Senter et al. |
| 2006/0088539 A1 | 4/2006 | Bander |
| 2006/0177450 A1 | 8/2006 | Israeli et al. |
| 2006/0234271 A1 | 10/2006 | Su et al. |
| 2006/0275212 A1 | 12/2006 | Bander et al. |
| 2007/0020278 A1 | 1/2007 | Ross et al. |
| 2007/0036719 A1 | 2/2007 | Cuello et al. |
| 2007/0128671 A1 | 6/2007 | Murphy et al. |
| 2007/0148662 A1 | 6/2007 | Israeli et al. |
| 2007/0160617 A1 | 7/2007 | Ma et al. |
| 2007/0237712 A1 | 10/2007 | Rajasekaran et al. |
| 2007/0254316 A1 | 11/2007 | Rodriguez et al. |
| 2008/0286284 A1 | 11/2008 | Maddon et al. |
| 2009/0010945 A1 | 1/2009 | Alley et al. |
| 2009/0060908 A1 | 3/2009 | Cardarelli et al. |
| 2009/0238755 A1 | 9/2009 | Bander |
| 2009/0285843 A1 | 11/2009 | Simard et al. |
| 2009/0311225 A1 | 12/2009 | Koduri |
| 2011/0250216 A1 | 10/2011 | Ma et al. |

FOREIGN PATENT DOCUMENTS

| | | |
|---|---|---|
| EP | 0 624 377 A2 | 11/1994 |
| EP | 0 627 940 B1 | 12/1994 |
| EP | 1 178 317 A1 | 2/2002 |
| EP | 1 482 031 A1 | 12/2004 |
| EP | 1 512 755 A2 | 3/2005 |
| EP | 1 553 414 A1 | 7/2005 |
| EP | 1 571 141 A2 | 9/2005 |
| EP | 02802198.8 | 7/2006 |
| EP | 02802198.8 | 9/2006 |
| EP | 1 917 970 A2 | 5/2008 |
| EP | 10184938.8 | 7/2011 |
| EP | 10184957.8 | 7/2011 |
| EP | 10184938.8 | 12/2011 |
| EP | 10184957.8 | 1/2012 |
| WO | WO 93/10763 A1 | 6/1993 |
| WO | WO 94/09820 A1 | 5/1994 |
| WO | WO 95/04548 A1 | 2/1995 |
| WO | WO 96/08570 A1 | 3/1996 |
| WO | WO 96/26272 A1 | 8/1996 |
| WO | WO 96/39185 A1 | 12/1996 |
| WO | WO 97/04802 A1 | 2/1997 |
| WO | WO 97/35616 A1 | 10/1997 |
| WO | WO 97/48409 A1 | 12/1997 |
| WO | WO 98/02463 A1 | 1/1998 |
| WO | WO 98/03873 A1 | 1/1998 |
| WO | WO 98/13046 A1 | 4/1998 |
| WO | WO 98/24884 A1 | 6/1998 |
| WO | WO 98/53812 A1 | 12/1998 |
| WO | WO 99/47554 A1 | 9/1999 |
| WO | WO 99/56779 A1 | 11/1999 |
| WO | WO 00/01668 A2 | 1/2000 |
| WO | WO 00/06723 A1 | 2/2000 |
| WO | WO 00/14257 A1 | 3/2000 |
| WO | WO 00/18933 A1 | 4/2000 |
| WO | WO 00/38785 A2 | 7/2000 |
| WO | WO 00/52156 A1 | 9/2000 |
| WO | WO 00/61605 A1 | 10/2000 |
| WO | WO 00/62063 A1 | 10/2000 |
| WO | WO 01/09192 A1 | 2/2001 |
| WO | WO 01/19956 A2 | 3/2001 |
| WO | WO 01/74845 A2 | 10/2001 |
| WO | WO 01/85798 A2 | 11/2001 |
| WO | WO 01/87325 A1 | 11/2001 |
| WO | WO 02/40059 A2 | 5/2002 |
| WO | WO 02/46448 A2 | 6/2002 |
| WO | WO 02/062368 A2 | 8/2002 |
| WO | WO 02/069907 A2 | 9/2002 |
| WO | WO 02/089747 A2 | 11/2002 |
| WO | WO 02/096460 A1 | 12/2002 |
| WO | WO 02/098897 A2 | 12/2002 |
| WO | PCT/US02/33944 | 1/2003 |
| WO | WO 03/023026 A1 | 3/2003 |
| WO | WO 03/024388 A2 | 3/2003 |
| WO | PCT/US02/33944 | 5/2003 |
| WO | WO 03/034903 A2 | 5/2003 |
| WO | WO 03/040165 A2 | 5/2003 |

| | | |
|---|---|---|
| WO | WO 03/040169 A2 | 5/2003 |
| WO | WO 03/057921 A1 | 7/2003 |
| WO | WO 03/060523 A1 | 7/2003 |
| WO | WO 03/064606 A2 | 8/2003 |
| WO | WO 03/073828 A2 | 9/2003 |
| WO | PCT/US02/33944 | 10/2003 |
| WO | WO 2004/010957 A2 | 2/2004 |
| WO | PCT/US02/33944 | 6/2004 |
| WO | WO 2004/067564 A2 | 8/2004 |
| WO | WO 2004/067570 A2 | 8/2004 |
| WO | WO 2004/098535 A2 | 11/2004 |
| WO | WO 2005/001038 A2 | 1/2005 |
| WO | WO 2005/027966 A2 | 3/2005 |
| WO | PCT/US2004/036120 | 5/2005 |
| WO | WO 2005/042029 A2 | 5/2005 |
| WO | PCT/US2004/036120 | 8/2005 |
| WO | WO 2005/070456 A2 | 8/2005 |
| WO | WO 2005/084390 A2 | 9/2005 |
| WO | WO 2005/094882 A1 | 10/2005 |
| WO | WO 2005/123129 A2 | 12/2005 |
| WO | WO 2006/013014 A2 | 2/2006 |
| WO | WO 2006/076525 A2 | 7/2006 |
| WO | WO 2006/089230 A2 | 8/2006 |
| WO | WO 2006/089231 A2 | 8/2006 |
| WO | WO 2006/093991 A1 | 9/2006 |
| WO | WO 2006/096754 A2 | 9/2006 |
| WO | WO 2006/110745 A2 | 10/2006 |
| WO | WO 2006/125481 A1 | 11/2006 |
| WO | WO 2007/000935 A1 | 1/2007 |
| WO | WO 2007/002222 A1 | 1/2007 |
| WO | WO 2007/038658 A2 | 4/2007 |
| WO | WO 2007/059190 A2 | 5/2007 |
| WO | PCT/US2006/024182 | 6/2007 |
| WO | WO 2007/103288 A2 | 9/2007 |
| WO | PCT/US2006/024182 | 1/2008 |

OTHER PUBLICATIONS

[No Author Listed] "Medarex: Pipeline." Available at http://www.medarex.com/Development/Pipeline.html. Last accessed Mar. 17, 2009.

[No Author Listed] "Promising Findings" from Novel Antibody-Chemotherapeutic MLN2704 Prostate Cancer Clinical Trial . . . PSA Rising. Feb. 22, 2005. Available at http://www.psa-rising.com/med/chemo/millennium05.html. Last accessed Jan. 19, 2010. 8 pages.

[No Author Listed] "Researchers Unveil Image of Prostate Cancer Drug Target." Howard Hughes Medical Institute. Apr. 14, 2005. Available at http://www.hhmi.org/news/bjorkman3.html. Last accessed Jan. 19, 2010. 2 pages.

[No Author Listed] Basic and Clinical Immunology. Appleton & Lange. Daniel P. Stites, et al., Ed 1991:229-51.

[No Author Listed] Fundamental Immunology. Raven Press. William E. Paul, Ed 1989:628-9, 647-51.

[No Author Listed] Immunochemical Techniques Part J: Phagocytosis and Cell-Mediated Cytotoxicity, Methods of Enzymology. Academic Press Inc. Sabato et al., Eds. 1986;132:554-68.

[No Author Listed] Latest Cancer Findings Presented At ASCO Meeting by Physician-scientists. Medical News Today. http://www.medicalnewstoday.com/articles/109424.php. Jun. 2, 2008. 3 pages. Last accessed online Oct. 29, 2008.

[No Author Listed] Monoclonal Antibodies: Production, engineering and clinical application.. Cambridge University Press. Mary A. Ritter, et al., Ed 1995, pp. 9-33, 21-2, 32-3, 60-83, 386-7, 441-3.

[No Author Listed] New York-Presbyterian/Weill Cornell Physician-Scientists Present Latest Cancer Findings at American Society of Clinical Oncology (ASCO) Meeting. http://www.nyp.org/news/hospital/nypwc-presents-asco.html. May 30, 2008. 3 pages. Last accessed Oct. 29, 2008.

[No Author Listed] NYP/ Weill Cornell physician-scientists present latest cancer findings at ASCO meeting. Bio-Medicine. http://biomedicine.org/medicine-news-1/NYP-Weill-Cornell-physician-scientists-p... May 31, 2008. 4 pages. Last accessed Oct. 29, 2008.

[No Author Listed] P5368 Phosphate buffered saline. Sigma-Aldrich product sheet. Last accessed online from http://www.sigmaaldrich.com/catalog/ProductDetail... on Mar. 2, 2010. 2 pages.

[No Author Listed] Physician-Scientists Present Latest Cancer Findings at ASCO Meeting. Newswise. http://www.newswise.com/articles/view/541288. Released: May 30, 2008. 08:00 ET. 3 pages. Last accessed Oct. 28, 2008.

[No Author Listed] Progenics and Cytogen Report Positive Preclinical Results for Experimental Prostate Cancer Drug—In laboratory studies, human monoclonal antibody killed prost. Progenics Pharmaceuticals, Inc. Press Release. Washington, D.C. Sep. 23, 2002. Available at http://www.lifesciencesworld.com/life-science-news/view/535?page=1495. Last accessed Jul. 26, 2011. 1 page.

[No Author Listed] Progenics Initiates Phase 1 Clinical Study of Targeted Therapy for Prostate Cancer. Progenics Pharmaceuticals Press Release. Sep. 8, 2008. 3 pages.

[No Author Listed] Radiolabeled J591 Antibody Delivers Lethal Hit to Advanced Prostate Cancers in Phase 1 Trial. Cancer Biol & Ther. 2004;3(8):699-700.

Abbas et al., II. Lymphocyte Spectifity and Activation. In: Cellular and Molecular Immunology. W.B. Saunders; Philadelphia. 1991:54.

Abdel-Nabi et al., Monoclonal antibodies and radioimmunoconjugates in the diagnosis and treatment of prostate cancer. Semin Urol. Feb. 1992;10(1):45-54.

Ablin "Immunotherapy for prostatic cancer. Previous and Prospective Considerations[1]", Oncology (1975) vol. 31, 177-202.

Aggarwal et al., Comparative study of PSMA expression in the prostate of mouse, dog, monkey, and human. Prostate. Jun. 15, 2006;66(9):903-10.

Allen, Ligand-targeted therapeutics in anticancer therapy. Nat Rev Cancer. Oct. 2002;2(10):750-63.

Alvarez et al., Intermolecular disulfide bonds are not required for the expression of the dimeric state and functional activity of the transferrin receptor. EMBO J. Aug. 1989;8(8):2231-40.

Analysis of binding of 3F5.4G6 antibody to PSMA provided by Dr. Bander. mAb comparison. 9 pages. Last printed Nov. 2008.

Anidjar et al., In vivo model mimicking natural history of dog prostate cancer using DPC-1, a new canine prostate carcinoma cell line. Prostate. Jan. 1, 2001;46(1):2-10.

Anilkumar et al., Association of prostate-specific membrane antigen with caveolin-1 and its caveolae-dependent internalization in microvascular endothelial cells: implications for targeting to tumor vasculature. Microvasc Res. Jul.-Sep. 2006;72(1-2):54-61. Epub May 19, 2006.

Anilkumar et al., Prostate-specific membrane antigen association with filamin A modulates its internalization and NAALADase activity. Cancer Res. May 15, 2003;63(10):2645-8.

Arceci et al., The potential for antitumor vaccination in acute myelogenous leukemia. J Mol Med. Feb. 1998;76(2):80-93. Review.

Arlen et al., Therapeutic vaccines for prostate cancer: a review of clinical data. Curr Opin Investig Drugs. Jun. 2005;6(6):592-6. Review.

Axelrod et al., "Preclinical results and human immunohistochemical studies with $^{90}$Y-CYT-356: A new prosate cancer therapeutic agent". AUA 87th Annual Meeting. 1992:Abstract No. 596.

Baccala et al., Expression of prostate-specific membrane antigen in tumor-associated neovasculature of renal neoplasms. Urology. Aug. 2007;70(2):385-90.

Bacich et al., Cloning, expression, genomic localization, and enzymatic activities of the mouse homolog of prostate-specific membrane antigen/NAALADase/folate hydrolase. Mamm Genome. Feb. 2001;12(2):117-23.

Ballangrud et al., 7th Conference on Radioimmunodetection and Radioimmunotherapy of Cancer, Princeton NJ, 1998. Growth and characterization of LNCaP prostate cancer cell spheroids. Clin Cancer Res. Oct. 1999;5(10 Suppl):3171s-3176s.

Ballou et al., Tissue localization of methotrexate-monoclonal-IgM immunoconjugates: anti-SSEA-1 and MOPC 104E in mouse teratocarcinomas and normal tissues. Cancer Immunol Immunother. 1992;35(4):251-6.

Bander et al., Phase I radioimmunotherapy (RIT) trial of humanized monoclonal (mAb) antibody J591 to the extracellular domain of prostate specific membrane antigen (PSMAext) radiolabeled with 177leutetium (177Lu) in advanced prostate cancer (Pca). 2003 ASCO Annual Meeting. Proc Am Soc Clin Oncol. 2003;22. Abstract 1612.

Bander et al., Phase I radioimmunotherapy (RIT) trials of humanized monoclonal antibody (mAb) J591 to the extracellular domain of prostate specific membrane antigen (PSMA ext) radiolabeled with 90Y or 177Lu in advanced prostate cancer (Pca). 2002 ASCO Annual Meeting. Biologic and Targeted Therapies; Antibodies. Abstract No. 18.

Bander et al., Phase II trial of 177Lutetium radiolabeled anti-prostate-specific membrane antigen (PSMA) monoclonal antibody J591 (177Lu-J591) in patients (pts) with metastatic androgen-independent prostate cancer (AIPC). J Clin Oncol. 2007 ASCO Annual Meeting Proceedings Part 1. 2007;25(18S). Abstract 15523.

Bander et al., Targeted systemic therapy of prostate cancer with a monoclonal antibody to prostate-specific membrane antigen. Semin Oncol. Oct. 2003;30(5):667-77.

Bander, Current status of monoclonal antibodies for imaging and therapy of prostate cancer. Semin Oncol. Oct. 1994;21(5):607-12.

Bander, Immunotherapy of Prostate Cancer. State of the Science. Genitourinary. Dec. 13-14, 2002. 9 pages.

Barinka et al., Identification of the N-glycosylation sites on glutamate carboxypeptidase II necessary for proteolytic activity. Protein Sci. Jun. 2004;13(6):1627-35.

Barinka et al., Substrate specificity, inhibition and enzymological analysis of recombinant human glutamate carboxypeptidase II. J Neurochem. 2002;80:477-87.

Barren et al., Monoclonal antibody 7E11.C5 staining of viable LNCaP cells. Prostate. Jan. 1, 1997;30(1):65-8.

Basler et al., Advances in prostate cancer immunotherapies. Drugs Aging. 2007;24(3):197-221. Review.

Beachy et al., Production of insulinomimetic antibodies against rat adipocyte membranes by hybridoma cells. J Supramol Struct. 1980;13(4):447-56.

Bentel et al., Chapter 9. Androgen Receptor Gene Mutations in Prostate Cancer. Prostate: Basic and Clinical Aspects (R.K. Naz, ed.) CRC Press, New York. 1997:219-43.

Bhaskar et al., E-selectin up-regulation allows for targeted drug delivery in prostate cancer. Cancer Res. Oct. 1, 2003;63(19):6387-94.

Bier et al., Anti-(epidermal growth factor) receptor monoclonal antibodies for the induction of antibody-dependent cell-mediated cytotoxicity against squamous cell carcinoma lines of the head and neck. Cancer Immunol Immunother. May 1998;46(3):167-73.

Bocchia et al., Antitumor vaccination: where we stand. Haematologica. Nov. 2000;85(11):1172-206. Review.

Bodey et al., Failure of cancer vaccines: the significant limitations of this approach to immunotherapy. Anticancer Res. Jul.-Aug. 2000;20(4):2665-76. Review.

Boon et al., Toward a genetic analysis of tumor rejection antigens. Adv Cancer Res. 1992;58:177-210. Review.

Brown et al., A novel monoclonal antibody 107-1A4 with high prostate specificity: generation, characterization of antigen expression, and targeting of human prostate cancer xenografts. Prostate Cancer Prostatic Dis. Jun. 1998;1(4):208-215.

Brüggemann et al., "Strategies for expressing human antibody repertoires in transgenic mice", Immunology Today, Aug. 1996, 17(8):391-7.

Bzdega et al., Molecular cloning of a peptidase against N-acetylaspartylglutamate from a rate hippocampal cDNA library. J Neurochem. Dec. 1997;69(6):2270-7.

Caldas et al., Humanization of the anti-CD18 antibody 6.7: an unexpected effect of a framework residue in binding to antigen. Mol Immunol. May 2003;39(15):941-52.

Caron et al., Biological and immunological features of humanized M195 (anti-CD33) monoclonal antibodies. Cancer Res. Dec. 15, 1992;52(24):6761-7.

Carter et al., Prostate-specific memrane antigen is a hydrolase with substrate and pharmacologic characteristics of a neuropeptidase. Proc Natl Acad Sci USA. Jan. 23, 1996;93(2):749-53.

Carter, Improving the efficacy of antibody-based cancer therapies. Nat Rev Cancer. Nov. 2001;1(2):118-29.

Chandler et al., Functional specificity of jejunal brush-border pteroylpolyglutamate hydrolase in pig. Am J Physiol. Jun. 1991;260(6 Pt 1):G865-72.

Chandler et al., Pteroylpolyglutamate hydrolase from human jejunal brush-borders. J Biol Chem. Jan. 15, 1986;261(2):928-33.

Chang et al., Five different anti-prostate-specific membrane antigen (PSMA) antibodies confirm PSMA expression in tumor-associated neovasculature. Cancer Res. Jul. 1, 1999;59(13):3192-8.

Chang et al., Metastatic renal cell carcinoma neovasculature expresses prostate-specific membrane antigen. Urology. Apr. 2001;57(4):801-5.

Chang et al., Monoclonal antibodies: will they become an integral part of the evaluation and treatment of prostate cancer—focus on prostate-specific membrane antigen? Review Article. Curr Opin Urology. 1999;9(5):391-95.

Chang et al., Prostate-specific membrane antigen is produced in tumor-associated neovasculature. Clin Cancer Res. Oct. 1999;5(10):2674-81.

Chang et al., Prostate-Specific Membrane Antigen: Much More Than a Prostate Cancer Marker. Mol Urol. 1999;3(3):313-320.

Chen et al., Antibody-cytotoxic agent conjugates for cancer therapy. Expert Opin Drug Deliv. Sep. 2005;2(5):873-90.

Chen et al., Cytotoxity of an internalizing 7E11-C5 MAB-SE immunoconjugate against DU145 prostate tumor cells. FASEB J. 1997;11(3):A403. Abstract #2334.

Chien et al., Significant structural and functional change of an antigen-binding site by a distant amino acid substitution: proposal of a structural mechanism. Proc Natl Acad Sci U S A. Jul. 1989;86(14):5532-6.

Chu et al., Aptamer mediated siRNA delivery. Nucleic Acids Res. Jun. 1, 2006;34(10):e73. 6 pages.

Colombatti et al., The prostate specific membrane antigen regulates the expression of IL-6 and CCL5 in prostate tumour cells by activating the MAPK pathways. PLoS One. 2009;4(2):e4608. Epub Feb. 26, 2009.

Cox et al., Identification of a peptide recognized by five melanoma-specific human cytotoxic T cell lines. Science. Apr. 29, 1994;264(5159):716-9.

Culver et al., In vivo gene transfer with retroviral vector-producer cells for treatment of experimental brain tumors. Science. Jun. 12, 1992;256(5063):1550-2.

Curnow, Clinical experience with CD64-directed immunotherapy. An overview. Cancer Immunol Immunother. Nov.-Dec. 1997;45(3-4):210-5.

Dai et al., Generation and characterization of monoclonal anti-idiotypic antibodies for dunning rat prostate tumor. FASEB J. 1988;2:A692. Abstract 2301.

Darshan et al., Taxanes inhibit AR nuclear accumulation and signaling in cells and metastatic prostate cancer patients. Novel Drug Targets, Agents, and Mechanisms: Poster Presentations—Proffered Abstracts. 99th AACR Annual Meeting. Apr. 12-16, 2008. Abstract 2808.

Dauphinais, Solving and Preventing Problems in Ligand Assay. Manual of Clinical Laboratory Immunology. American Society for Microbiology. 1986:88-109.

Davis et al., Crystal structure of prostate-specific membrane antigen, a tumor marker and peptidase. Proc Natl Acad Sci USA. Apr. 26, 2005;102(17):5981-6. Epub Apr. 18, 2005.

De Santes et al., Radiolabeled antibody targeting of the HER-2/neu oncoprotein. Cancer Res. Apr. 1, 1992;52(7):1916-23.

Decensi et al., Phase II study of the pure non-steroidal antiandrogen nilutamide in prostatic cancer. Italian Prostatic Cancer Project (PONCAP). Eur J Cancer. 1991;27(9):1100-4.

Devlin et al., Glutamate carboxypeptidase II: a polymorphism associated with lower levels of serum folate and hyperhomocysteinemia. Hum Mol Genet. Nov. 22, 2000;9(19):2837-44.

Dillman et al., Monoclonal antibodies for treating cancer. Ann Intern Med. Oct. 1, 1989;111(7):592-603. Review.

Donovan et al., Antibody and vaccine therapies targeting prostate specific membrane antigen (PSMA). Proceedings of the Annual Meeting of the AACR. New York, NY. Mar. 24, 2001;42:818. Abstract 4389.

Donovan et al., Clinical development of immunotherapies targeting prostate specific membrane antigen. 38th Annual Meeting American Society of Clinical Oncology. Alexandria, VA. May 18-21, 2002. Presentation. PSMA Development Company, LLC. Tarrytown, NY (joint venture between Progenics Pharmaceuticals, Inc. and Cytogen Corporation) and the Cleveland Clinic, Cleveland, OH. Proceedings of ASCO. 2002;21:25b. Abstract No. 1909.

Doronina et al., Development of potent monoclonal antibody auristatin conjugates for cancer therapy. Nat Biotechnol. Jul. 2003;21(7):778-84. Epub Jun. 1, 2003. Erratum.

Doronina et al., Immunoconjugates comprised of drugs with impaired cellular permeability: A new approach to targeted therapy. Abstracts of papers. ACS National Meeting. Aug. 2004;228:U908.

Durso et al., A novel alphavirus vaccine encoding prostate-specific membrane antigen elicits potent cellular and humoral immune responses. Clin Cancer Res. Jul. 1, 2007;13(13):3999-4008.

Dyring et al., Increased production of recombinant hIGFBP-1 in PEG induced autofusion of Chinese hamster ovary (CHO) cells. Cytotechnology. Jul. 1, 1997;24(3):183-191.

Elsässer-Beile et al., A new generation of monoclonal and recombinant antibodies against cell-adherent prostate specific membrane antigen for diagnostic and therapeutic targeting of prostate cancer. Prostate. Sep. 15, 2006;66(13):1359-70. Abstract and full text provided.

Ezzell et al., Cancer "Vaccines": An Idea Whose Time Has Come? J of NIH Res. 1995;7:46-49.

Faber et al., Characterization of the human androgen receptor transcription unit. J Biol Chem. Jun. 15, 1991;266(17):10743-9.

Faguet et al., A simple technique for the rapid enrichment of class and subclass hybridoma switch variants. A 1000-fold enrichment in half the time, for half the cost. J Immunol Methods. Oct. 15, 1993;165(2):217-24.

Fair et al., Prostate-specific membrane antigen. Prostate. Jul. 1, 1997;32(2):140-8.

Feng et al., Purification and Biochemical Characterization of the 7E11-C5 Prostate Carcinoma-Associated Antigen. Proceedings of the 82$^{nd}$ Meeting of the American Association for Cancer. 1991;32:239. Abstract No. 1418.

Fey et al., The polymerase chain reaction: a new tool for the detection of minimal residual disease in haematological malignancies. Eur J Cancer. 1991;27(1):89-94.

Finstad et al., Specificity analysis of mouse monoclonal antibodies defining cell surface antigens of human renal cancer. Proc Natl Acad Sci U S A. May 1985;82(9):2955-9. Abstract only.

Fishwild et al., "High-avidity human IgGκ monoclonal antibodies from a novel strain of minilocus transgenic mice" *Nature Biotechnology*, Jul. 1996, 14:845-51.

Francisco et al., cAC10-voMMAE, an anti-CD30-monomethyl auristatin E conjugate with potent and selective antitumor activity. Blood. Aug. 15, 2003;102(4):1458-65. Epub Apr. 24, 2003.

Frieden, Glutamic dehydrogenase. III. The order of substrate addition in the enzymatic reaction. J Biol Chem. Nov. 1959;234:2891-6.

Galsky et al., Phase I trial of the prostate-specific membrane antigen-directed immunoconjugate MLN2704 in patients with progressive metastatic castration-resistant prostate cancer. J Clin Oncol. May 1, 2008;26(13):2147-54. Epub Mar. 24, 2008.

Gao et al., Tumor vaccination that enhances antitumor T-cell responses does not inhibit the growth of established tumors even in combination with interleukin-12 treatment: the importance of inducing intratumoral T-cell migration. J Immunother. Nov.-Dec. 2000;23(6):643-53.

Garcia et al., Selenoprotein A component of the glycine reductase complex from Clostridium purinolyticum: nucleotide sequence of the gene shows that selenocysteine is encoded by UGA. J Bacteriol. Mar. 1991;173(6):2093-8.

Gardner et al., A novel alphavirus replicon vaccine encoding PSMA for immunotherapy of prostate cancer. AACR Meeting. San Francisco, CA. Apr. 6-10, 2002. PSMA Development Company, LLC. Tarrytown, NY (joint venture between Progenics Pharmaceuticals, Inc. and Cytogen Corporation) and The Cleveland Clinic, Cleveland, OH. Proceedings of AACR. 2002;43:609. Abstract No. 3017.

Gardner et al., Novel prime-boost combinations of PSMA-based vaccines for prostate cancer. PSMA Development Company, LLC (A joint venture between Progenics Pharmaceuticals Inc. and Cytogen Corp.), Tarrytown, NY. AlphaVax, Inc., Research Triangle Park, NC. Presentation. Proceedings of ASCO. 2005:183s. Abstract No. 2572.

Gardner et al., Recombinant soluble prostate-specific membrane antigen (rsPSMA) vaccine: preliminary findings of a Phase I safety/immunogenicity trial. J Clin Oncol. ASCO Annual Meeting Proceedings. 2004;22:14S. Abstract No. 2584. Abstract Only.

Gately et al., Regulation of human cytolytic lymphocyte responses by interleukin-12. Cell Immunol. Aug. 1992;143(1):127-42.

Genbank Submission; NIH/NCBI, Accession No. AAA60209.1, Israeli et al., Jan. 8, 1995.

Genbank Submission; NIH/NCBI, Accession No. X57349.1, Trowbridge et al., Jan. 23, 1991.

George et al., Differential effects of anti-beta2-glycoprotein I antibodies on endothelial cells and on the manifestations of experimental antiphospholipid syndrome. Circulation. Mar. 10, 1998;97(9):900-6.

Ghose et al., The design of cytotoxic-agent-antibody conjugates. CRC Critical Reviews in Therapeutic Drug Carrier Systems. 2000;3:263-359.

Ghosh et al., Effect of carbohydrate moieties on the folate hydrolysis activity of the prostate specific membrane antigen. The Prostate. 2003;57:140-151.

Giusti et al., Somatic diversification of S107 from an antiphosphocholine to an anti-DNA autoantibody is due to a single base change in its heavy chain variable region. Proc Natl Acad Sci U S A. May 1987;84(9):2926-30.

Goding, Monoclonal antibodies: principles and practice. Production and Application of Monoclonal Antibodies in Cell Biology Biochemistry and Immunology. Third Edition. Academic Press. Feb. 1996:1-5, 142-47.

Gong et al., Prostate-specific membrane antigen (PSMA)-specific monoclonal antibodies in the treatment of prostate and other cancers. Cancer Metastasis Rev. 1999;18(4):483-90. Review.

Goodman et al., Interaction of prostate specific membrane antigen with clathrin and the adaptor protein complex-2. Int J Oncol. Nov. 2007;31(5):1199-203.

Grauer et al., Identification, purification, and subcellular localization of prostate-specific membrane antigen PSM' protein in the LNCaP prostatic carcinoma cell line. Cancer Res. Nov. 1, 1998;58(21):4787-9.

Graves et al., Molecular modeling and preclinical evaluation of the humanized NR-LU-13 antibody. Clin Cancer Res. Apr. 1999;5(4):899-908.

Greenspan et al., Defining epitopes: It's not as easy as it seems. Nat Biotechnol. Oct. 1999;17(10):936-7.

Gregor et al., CTLA-4 blockade in combination with xenogeneic DNA vaccines enhances T-cell responses, tumor immunity and autoimmunity to self antigens in animal and cellular model systems. Vaccine. Apr. 16, 2004;22(13-14):1700-8.

Gregor et al., Induction of autoantibodies to syngeneic prostate-specific membrane antigen by xenogeneic vaccination. Int J Cancer. Sep. 1, 2005;116(3):415-21.

Gregorakis et al., Prostate-specific membrane antigen: Current and future utility. Semin Urol Oncol. Feb. 1998;16(1):2-12.

Grimaldi et al., Monoclonal Antibodies by Somatic Cell Fusion. ILAR Journal Online. 1995;37(3):1-12.

Grossbard et al., Monoclonal antibody-based therapies of leukemia and lymphoma. Blood. Aug. 15, 1992;80(4):863-78.

Gu et al., Precise engineering of targeted nanoparticles by using self-assembled biointegrated block copolymers. Proc Natl Acad Sci U S A. Feb. 19, 2008;105(7):2586-91. Epub Feb. 13, 2008.

Guinan et al., Immunotherapy of prostate cancer: a review. Prostate. 1984;5(2):221-30.

Gura et al., Systems for identifying new drugs are often faulty. Science. Nov. 7, 1997;278(5340):1041-2.

Güssow et al., Humanization of monoclonal antibodies. Methods Enzymol. 1991;203:99-121.

Haffner et al., Prostate specific membrane antigen (PSMA) as a prognostic and therapeutic marker in squamous cell carcinoma of the oral cavity. Prognostic Biomarkers 2. Poster Presentations—Proffered Abstracts. 99$^{th}$ AACR Annual Meeting. Apr. 12-16, 2008. Abstract 5545.

Halsted et al., Folylpoly-gamma-glutamate carboxypeptidase from pig jejunum. Molecular characterization and relation to glutamate carboxypeptidase II. J Biol Chem. Aug. 7, 1998;273(32):20417-24.

Harada et al., Target molecules in specific immunotherapy against prostate cancer. Int J Clin Oncol. Aug. 2003;8(4):193-9.

Harlow et al., Antibodies: A Laboratory Manual. Cold Spring Harbor Laboratory Press. 1988:47, 55-61, 72-77, 88, 92-97, 100-03, 114-16, 124, 128-35, 148, 156-57, 207.

Heston, Chapter 11. Biologic implications for prostatic function following identification of prostate-specific membrane antigen as a novel folate hydrolase/neurocarboxypeptidase. Prostate: Basic and Clinical Aspects (R.K. Naz, ed.) CRC Press, New York. 1997:267-98.

Heston, Characterization and glutamyl preferring carboxypeptidase function of prostate specific membrane antigen: a novel folate hydrolase. Urology. Mar. 1997;49(3A Suppl):104-12.

Holmes et al., Analysis of glycosylation of prostate-specific membrane antigen derived from LNCaP cells, prostatic carcinoma tumors, and serum from prostate cancer patients. Prostate Suppl. 1996;7:25-9.

Holmes, PSMA specific antibodies and their diagnostic and therapeutic use. Expert Opin Investig Drugs. Mar. 2001;10(3):511-9.

Hong et al., The production of polyclonal and monoclonal antibodies in mice using novel immunization methods. J Immunol Methods. Jun. 21, 1989;120(2):151-7.

Hopp et al., A computer program for predicting protein antigenic determinants. Mol Immunol. Apr. 1983;20(4):483-9.

Hopp et al., Prediction of protein antigenic determinants from amino acid sequences. Proc Natl Acad Sci U S A. Jun. 1981;78(6):3824-8.

Horoszewicz et al., LNCaP model of human prostatic carcinoma. Cancer Res. Apr. 1983;43(4):1809-18.

Horoszewicz et al., Monoclonal antibodies to a new antigenic marker in epithelial prostatic cells and serum of prostatic cancer patients. Anticancer Res. Sep.-Oct. 1987;7(5B):927-35.

Huang et al., Anti-tumor effects and lack of side effects in mice of an immunotoxin directed against human and mouse prostate-specific membrane antigen. Prostate. Sep. 15, 2004;61(1):1-11.

Huang et al., hZimp7, a novel PIAS-like protein, enhances androgen receptor-mediated transcription and interacts with SWI/SNF-like BAF complexes. Mol Endocrinol. Dec. 2005;19(12):2915-29. Epub Jul. 28, 2005.

Huber et al., Retroviral-mediated gene therapy for the treatment of hepatocellular carcinoma: an innovative approach for cancer therapy. Proc Natl Acad Sci U S A. Sep. 15, 1991;88(18):8039-43.

Humphrey et al., Anti-synthetic peptide antibody reacting at the fusion junction of deletion-mutant epidermal growth factor receptors in human glioblastoma. Proc Natl Acad Sci U S A. Jun. 1990;87(11):4207-11.

Hutchins et al., Improved biodistribution, tumor targeting, and reduced immunogenicity in mice with a gamma 4 variant of Campath-1H. Proc Natl Acad Sci U S A. Dec. 19, 1995;92(26):11980-4.

Hynecek et al., $^{177}$LU-J591 monoclonal antibody (Lu-J591) therapy in metastatic castrate-resistant prostate cancer (metCRPC): Correlation of antibody-tumor targeting and treatment response. Oncology-Basic Science: Therapy, Metrics & Intervention Imaging for Assessment of Response or Therapy Planning. J Nucl Med. 2008;49(Supplement 1):144P. 2 pages.

Israeli et al., Expression of the prostate-specific membrane antigen. Cancer Res. Apr. 1, 1994;54(7):1807-11.

Israeli et al., Molecular cloning of a complementary DNA encoding a prostate-specific membrane antigen. Cancer Res. Jan. 15, 1993;53(2):227-30.

Israeli et al., Prostate-specific membrane antigen and other prostatic tumor markers on the horizon. Urol Clin North Am. May 1997;24(2):439-50. Review.

Israeli et al., Purification and Molecular Cloning of a New Prostate-Specific Antigen. Am Assoc Cancer Res. 1992;33:356. Abstract #2127.

Jacobs et al., Clinical use of tumor markers in oncology. Curr Probl Cancer. Nov.-Dec. 1991;15(6):299-350.

Jain et al., Optimization of radioimmunotherapy of solid tumors: biological impediments and their modulation. Clin Cancer Res. Mar. 1, 2007;13(5):1374-82. Epub Feb. 19, 2007.

Janeway et al., Immunology. Third Edition. Current Biology Ltd./ Garland Publishing, Inc., 1997, p. 3:23-24,8:1-2,8:18-19;8:26-29; 13:17-19.

Jaracz et al., Recent advances in tumor-targeting anticancer drug conjugates. Bioorg Med Chem. Sep. 1, 2005;13(17):5043-54.

Jayaprakash et al., Design and synthesis of a PSMA inhibitor-doxorubicin conjugate for targeted prostate cancer therapy. ChemMedChem. Mar. 2006;1(3):299-302.

Jeske et al., Phase II trial of the anti-prostate specific membrane antigen (PSMA) monoclonal antibody (mAb) J591 plus low-dose interleukin-2 (IL-2) in patients (pts) with recurrent prostate cancer (PC).2007 ASCO Annual Meeting. J Clin Oncol. 2007 ASCO Annual Meeting Proceedings Part 1. 2007;25(18S). Abstract 15558.

Jhanwar et al., Current status of therapy of solid tumors. J Nucl Med. Jan. 2005;46 Suppl 1:141S-50S.

Jiang et al., A novel peptide isolated from a phage display peptide library with trastuzumab can mimic antigen epitope of HER-2. J Biol Chem. Feb. 11, 2005;280(6):4656-62. Epub Nov. 9, 2004.

Jongeneel et al., Common acute lymphoblastic leukemia antigen expressed on leukemia and melanoma cell lines has neutral endopeptidase activity. J Clin Invest. Feb. 1989;83(2):713-7.

Kaneta et al., Selective cytotoxicity of adriamycin immunoconjugate of monoclonal antibody MSN-1 to endometrial adenocarcinoma in vitro and in vivo. Oncol Rep. Sep.-Oct. 2000;7(5):1099-106.

Kato et al., Further investigation of the epitope recognized by the new monoclonal antibody 2C9. Int J Urol. Aug. 2003;10(8):439-44.

Keer et al., Elevated transferrin receptor content in human prostate cancer cell lines assessed in vitro and in vivo. J Urol. Feb. 1990;143(2):381-5.

King, Applications and Engineering of Monoclonal Antibodies. CRC Press. 1998:6-9,54-58.

Kinoshita et al., Targeting epitopes in prostate-specific membrane antigen for antibody therapy of prostate cancer. Prostate Cancer Prostatic Dis. 2005;8(4):359-63.

Koren, Use of Anti-body Dependent Cell-Mediated Cytotoxicity (ADCC) Assay in Basic and Clinical Immunology. Immunochemical Techniques Part F: Conventional Antibodies, Fc Receptors, and Cytotoxicity. Methods of Enzymology. Langone et al., eds. Academic Press Inc. 1983;93:244-53.

Kronberger et al., PSMA expression in the neovasculature of colorectal cancers. New Molecular Targets/Mechanisms of Drug Action: Poster Presentations—Proffered Abstracts. Sixth AACR International Conference on Frontiers in Cancer Prevention Research. Philadelphia, PA. Dec. 5-8, 2007. Abstract A146.

Kronberger et al., PSMA expression in the neo-vasculature of solid tumors. Molecular Correlates 1: Poster Presentations—Proffered Abstracts. 99$^{th}$ AACR Annual Meeting. Apr. 12-16, 2008. Abstract 2181.

Kummer et al., Concepts of antibody-mediated cancer therapy. Cancer Invest. 1993;11(2):174-84.

Kuratsukuri et al., Induction of antibodies against prostate-specific membrane antigen (PSMA) by vaccination with a PSMA DNA vector. Eur Urol. Jul. 2002;42(1):67-73.

Kuratsukuri et al., Inhibition of prostate-specific membrane antigen (PSMA)-positive tumor growth by vaccination with either full-length or the C-terminal end of PSMA. Int J Cancer. Nov. 20, 2002;102(3):244-9.

Langone et al., Immunochemical Techniques Part F: Conventional Antibodies, Fc Receptors, and Cytotoxicity. Methods of Enzymology. Academic Press Inc. 1983;93:244-53.

Lapidus et al., Prostate-specific membrane antigen (PSMA) enzyme activity is elevated in prostate cancer cells. Prostate. Dec. 1, 2000;45(4):350-4.

Lawrence et al., Crystal structure of the ectodomain of human transferrin receptor. Science. Oct. 22, 1999;286(5440):779-82.

Lee et al., Anti-idiotypic antibody for dunning rat prostate tumor. Proc AACR. 1988;29:253. Abstract 1005.

Lee et al., Increased vaccine-specific T cell frequency after peptide-based vaccination correlates with increased susceptibility to in vitro stimulation but does not lead to tumor regression. J Immunol. Dec. 1, 1999;163(11):6292-300.

Leek et al., Prostate-specific membrane antigen: evidence for the existence of a second related human gene. Br J Cancer. Sep. 1995;72(3):583-8.

Lewis et al., Differential responses of human tumor cell lines to anti-p185HER2 monoclonal antibodies. Cancer Immunol Immunother. Sep. 1993;37(4):255-63.

Li et al., The generation of antibody diversity through somatic hypermutation and class switch recombination. Genes & Dev. 2004;18:1-11.

Lifely et al., Glycosylation and biological activity of CAMPATH-1H expressed in different cell lines and grown under different culture conditions. Glycobiology. Dec. 1995;5(8):813-22.

Lin et al., A functional role of prostate-specific membrane antigen in prostate cancer metastasis. Tumor Biology 30: Proteases: Protease Inhibitors and Cancer. Proc Amer Assoc Cancer Res. 2006;47. Abstract 4373.

Liu et al., "Constitutive and antibody-induced internalization of prostate-specific membrane antigen1", Cancer Research (Sep. 15, 1998) vol. 58, 4055-4060.

Liu et al., Cell-Surface labeling and internalization by a fluorescent inhibitor of prostate-specific membrane antigen. Prostate. Jun. 15, 2008;68(9):955-64.

Liu et al., Monoclonal antibodies to the extracellular domain of prostate-specific membrane antigen also react with tumor vascular endothelium. Cancer Res. Sep. 1, 1997;57(17):3629-34.

Loening et al., Cryosurgery and immunotherapy for prostatic cancer. Urol Clin North Am. May 1984;11(2):327-36.

Lollini et al., Cancer immunoprevention: tracking down persistent tumor antigens. Trends. Immunol. Feb. 2003;24(2):62-6. Review.

Lollini et al., New target antigens for cancer immunoprevention. Curr Cancer Drug Targets. May 2005;5(3):221-8. Review.

Lonberg et al., "Antigen-specific human antibodies from mice comprising four distinct genetic modifications" Nature, Apr. 28, 1994, 368:856-9.

Longee et al., Disialoganglioside GD2 in human neuroectodermal tumor cell lines and gliomas. Acta Neuropathol. 1991;82(1):45-54.

Lopes et al., Immunohistochemical and Pharmacokinetic Characterization of the Site-specific Immunoconjugate CYT-356 Derived from Antiprostate Monoclonal Antibody 7E11-05. Cancer Res. 1991;50:6423-29.

Luthi-Carter et al., Hydrolysis of the neuropeptide N-acetylaspartylglutamate (NAAG) by cloned human glutamate carboxypeptidase II. Brain Res. Jun. 8, 1998;795(1-2):341-8.

Luthi-Carter et al., Molecular characterization of human brain N-acetylated alpha-linked acidic dipeptidase (NAALADase). J Pharmacol Exp Ther. Aug. 1998;286(2):1020-5.

Ma et al., Fully human anti-PSMA antibodies for prostate cancer therapy. Proc AACR. Jul. 2003;44(2):1295. Abstract No. 6471.

Ma et al., Fully human monoclonal antibodies to PSMA selectively target cytotoxins, radiotoxins and host immunity to prostate cancer. J Clin Oncol. ASCO Annual Meeting Proceedings. 2004;22:14S. Abstract No. 2546. Abstract Only.

Ma et al., Potent antitumor activity of an auristatin-conjugated, fully human monoclonal antibody to prostate-specific membrane antigen. Clin Cancer Res. Apr. 15, 2006;12(8):2591-6.

Ma et al., PSMA targeted toxin and radio-labelled antibody therapies for prostate cancer. J Urology. 2003;169:211. Poster 817.

Malmborg et al., BIAcore as a tool in antibody engineering. J Immunol Methods. Jun. 14, 1995;183(1):7-13.

Maresca et al., Molecular targeting of prostate cancer with small molecule inhibitors of prostate specific membrane antigen. J Nucl Med. 2007;48(2):25P.

Mariana et al., Monoclonal Antibody Internalization by Tumor Cells: an Experimental Model for Potential Radioimmunotherapy Applications. Nucl Med Biol. 1989;16(2):147-50.

Mariuzza et al., The structural basis of antigen-antibody recognition. Annu Rev Biophys Biophys Chem. 1987;16:139-59.

Martin, Streptokinase stability pattern during storage in various solvents and at different tempertures. Thromb Diath Haemorrh. Jun. 30, 1975;33(3):586-96.

Mays et al., MDX-070, a human anti-plasma antibody, administered as either a single dose or as multiple doses to patients with hormone-refractory prostate cancer. ASCO Annual Meeting, 2006. Abstract #14549.

McIntosh et al., Human dUTP pyrophosphatase: cDNA sequence and potential biological importance of the enzyme. Proc Natl Acad Sci U S A. Sep. 1, 1992;89(17):8020-4.

Meighan et al., Recombinant glutamate carboxypeptidase II (prostate specific membrane antigen—PSMA)—cellular localization and bioactivity analyses. J Protein Chem. May 2003;22(4):317-26.

Mhaka et al., Use of methotrexate-based peptide substrates to characterize the substrate specificity of prostate-specific membrane antigen (PSMA). Cancer Biol Ther. Jun. 2004;3(6):551-8. Epub Jun. 10, 2004.

Milowsky et al., Anti-PSMA mAb huJ591 specifically targets tumor vascular endothelial cells in patients with advanced solid tumor malignancies. 2002 ASCO Annual Meeting. Proc Am Soc Clin Oncol. 2002;21. Abstract 29.

Milowsky et al., Phase I trial of yttrium-90-labeled anti-prostate-specific membrane antigen monoclonal antibody J591 for androgen-independent prostate cancer. J Clin Oncol. Jul. 1, 2004;22(13):2522-31. Epub Jun. 1, 2004.

Milowsky et al., Phase I trial results of yttrium-90 ($^{90}$Y)-labeled anti-prostate specific membrane antigen (PSMA) monoclonal antibody (mAb) J591 in the treatment of patients with advanced prostate cancer (PC). 2003 ASCO Annual Meeting. Proc Am Soc Clin Oncol. 2003;22. Abstract 1583.

Milowsky et al., Vascular targeted therapy with anti-prostate-specific membrane antigen monoclonal antibody J591 in advanced solid tumors. J Clin Oncol. Feb. 10, 2007;25(5):540-7.

Mincheff et al., Human dendritic cells genetically engineered to express cytosolically retained fragment of prostate-specific membrane antigen prime cytotoxic T-cell responses to multiple epitopes. Cancer Gene Ther. Dec. 2003;10(12):907-17.

Mincheff et al., Naked DNA and adenoviral immunizations for immunotherapy of prostate cancer: a phase I/II clinical trial. Eur Urol. Aug. 2000;38(2):208-17.

Mlcochová et al., Prostate-specific membrane antigen and its truncated form PSM'. Prostate. Apr. 1, 2009;69(5):471-9.

Moffett et al., Preparation and characterization of new anti-PSMA monoclonal antibodies with potential clinical use. Hybridoma (Larchmt). Dec. 2007;26(6):363-72.

Monson, Recent progress in the use of monoclonal antibodies for imaging and therapy. Curr Opin Gen Surg. 1993:334-9.

Morris et al., Phase I evaluation of J591 as a vascular targeting agent in progressive solid tumors. Clin Cancer Res. May 1, 2007;13(9):2707-13.

Morris et al., Pilot trial of unlabeled and indium-111-labeled anti-prostate-specific membrane antigen antibody J591 for castrate metastatic prostate cancer. Clin Cancer Res. Oct. 15, 2005;11(20):7454-61.

Mukhopadhyay et al., Specific inhibition of K-ras expression and tumorigenicity of lung cancer cells by antisense RNA. Cancer Res. Mar. 15, 1991;51(6):1744-8.

Muprhy et al., Comparison of prostate specific membrane antigen, and prostate specific antigen levels in prostatic cancer patients. Anticancer Res. Jul.-Aug. 1995;15(4):1473-9.

Murphy et al., Comparison of prostate specific antigen, prostate specific membrane antigen, and LNCaP-based enzyme-linked immunosorbent assays in prostatic cancer patients and patients with benign prostatic enlargement. Prostate. Mar. 1995;26(3):164-8.

Murphy et al., Current evaluation of the tissue localization and diagnostic utility of prostate specific membrane antigen. Cancer. Dec. 1, 1998;83(11):2259-69.

Murphy et al., Higher-dose and less frequent dendritic cell infusions with PSMA peptides in hormone-refractory metastatic prostate cancer patients. Prostate. Apr. 1, 2000;43(1):59-62. Abstract only.

Murphy et al., Infusion of dendritic cells pulsed with HLA-A2-specific prostate-specific membrane antigen peptidase: a phase II prostate cancer vaccine trial involving patients with hormone-refractory metastatic disease. Prostate. Jan. 1, 1999;38(1):73-8.

Murphy et al., Isolation and Characterization of Monoclonal Antibodies Specific for the Extracellular Domain of Prostate Specific Membrane Antigen. J Urology. 1998;160:2396-401.

Murphy et al., Measurement of prostate-specific membrane antigen in the serum with a new antibody. Prostate. Apr. 1996;28(4):266-71.

Murphy et al., Measurement of serum prostate-specific membrane antigen, a new prognostic marker for prostate cancer. Urology. May 1998;51(5A Suppl):89-97.

Murphy et al., Phase I clinical trial: T-cell therapy for prostate cancer using autologous dendritic cells pulsed with HLA-A0201-specific peptidase from prostate-specific membrane. Prostate. Dec. 1996;29(6):371-80. Abstract only.

Murphy et al., Use of artifical neural networks in evaluating prognostic factors determining the response to dendritic cells pulsed with PSMA peptides in prostate cancer patients. Prostate. Jan. 2000;42(1):67-72. Abstract only.

Nanus et al., Clinical use of monoclonal antibody HuJ591 therapy: targeting prostate specific membrane antigen. J Urol. Dec. 2003;170(6 Pt 2):S84-8; discussion S88-9. Abstract only.

Nanus et al., Phase II trial of monoclonal antibody huJ591 in combination with low dose subcutaneous interleukin-2 in patients with recurrent prostate cancer (PC). 2002 ASCO Annual Meeting. Proc Am Soc Clin Oncol. 2002;21. Abstract 1838.

O'Keefe et al., Chapter 18. Prostate Specific Membrane Antigen. In: Prostate Cancer: Biology, Genetics, and the New Therapeutics. Chung et al., eds. Humana Press. Totowa, NJ. 2000:307-26.

O'Keefe et al., Prostate-specific suicide gene therapy using the prostate-specific membrane antigen promoter and enhancer. Prostate. Oct. 1, 2000;45(2):149-57.

Olson et al., Clinical trials of cancer therapies targeting prostate-specific membrane antigen. Rev Recent Clin Trials. Sep. 2007;2(3):182-90.

Ozaki et al., Humanized anti-HM1.24 antibody mediates myeloma cell cytotoxicity that is enhanced by cytokine stimulation of effector cells. Blood. Jun. 1, 1999;93(11):3922-30.

Palme et al., Molecular cloning and structural analysis of genes from *Zea mays* (L.) coding for members of the ras-related ypt gene family. Proc Natl Acad Sci U S A. Jan. 15, 1992;89(2):787-91.

Pantuck et al., Urologic Oncology: Extraordinary Opportunities for Discovery: Highlights from the 2nd Annual Winter Meeting of the Society of Urologic Oncology Dec. 1-2, 2001. Bethesda, MD. Rev Urol. 2003 Winter;5(1):26-8.

Persiani et al., In vivo antitumor effect of methotrexate conjugated to a monoclonal IgM antibody specific for stage-specific embryonic antigen-1, on MH-15 mouse teratocarcinoma. Cancer Immunol Immunother. 1989;29(3):167-70.

Pinto et al., Prostate-specific membrane antigen: a novel folate hydrolase in human prostatic carcinoma cells. Clin Cancer Res. Sep. 1996;2(9):1445-51.

Rajasekeran et al., A novel cytoplasmic tail MXXXL motif mediates the internalization of prostate-specific membrane antigen. Mol Biol Cell. Dec. 2003;14(12):4835-45. Epub Oct. 3, 2003.

Reinherz et al., Discrete stages of human intrathymic differentiation: analysis of normal thymocytes and leukemic lymphoblasts of T-cell lineage. Proc Natl Acad Sci U S A. Mar. 1980;77(3):1588-92.

Riechmann et al., Reshaping human antibodies for therapy. Nature. Mar. 4, 1988;332(6162):323-7.

Robinson et al., Hydrolysis of the brain dipeptide N-acetyl-L-aspartyl-L-glutamate. Identification and characterization of a novel N-acetylated alpha-linked acidic dipeptidase activity from rat brain. J Biol Chem. Oct. 25, 1987;262(30):14498-506.

Rochon et al., Western blot assay for prostate-specific membrane antigen in serum of prostate cancer patients. Prostate. Oct. 1994;25(4):219-23.

Rojas et al., Kinetics and inhibition of glutamate carboxypeptidase II using a microplate assay. Anal Biochem. Nov. 1, 2002;310(1):50-4.

Rokhlin et al., 5E10: a prostate-specific surface-reactive monoclonal antibody. Cancer Lett. Sep. 25, 1998;131(2):129-36.

Ronai et al., Complex regulation of somatic hypermutation by cis-acting sequences in the endogenous IgH gene in hybridoma cells. Proc Natl Acad Sci U S A. Aug. 16, 2005;102(33):11829-34. Epub Aug. 8, 2005.

Rossi et al., Selective stimulation of prostatic carcinoma cell proliferation by 2lransferring. Proc Natl Acad Sci U S A. Jul. 1, 1992;89(13):6197-201.

Rovenskáet al., Tissue expression and enzymologic characterization of human prostate specific membrane antigen and its rat and pig orthologs. Prostate. Feb. 1, 2008;68(2):171-82.

Sacha et al., Expression of glutamate carboxypeptidase II in human brain. Neuroscience. Feb. 23, 2007;144(4):1361-72. Epub Dec. 5, 2006.

Saijo, What are the reasons for negative phase III trials of molecular-target-based drugs? Cancer Sci. Oct. 2004;95(10):772-6. Review.

Salgaller et al., Report of immune monitoring of prostate cancer patients undergoing T-cell therapy using dendritic cells pulsed with HLA-A2-specific peptides from prostate-specific membrane antigen (PSMA). Prostate. May 1998;35(2):144-51. Abstract only.

Sambrook et al., Molecular Cloning, A Laboratory Manual. Cold Spring Harbour Laboratory Press, 1989:16.2-16.81.

Schägger et al., Blue native electrophoresis for isolation of membrane protein complexes in enzymatically active form. Anal Biochem. Dec. 1991;199(2):223-31.

Scheinberg et al. Monoclonal Antibody M195: A Diagnostic Marker for Acute Myelogenous Leukemia. Leukemia. 1989;3:440-5.

Scheinberg et al., A phase I trial of monoclonal antibody M195 in acute myelogenous leukemia: specific bone marrow targeting and internalization of radionuclide. J Clin Oncol. Mar. 1991;9(3):478-90.

Schmittgen et al., Expression of prostate specific membrane antigen and three alternatively spliced variants of PSMA in prostate cancer patients. Int J Cancer. Nov. 1, 2003;107(2):323-9.

Schneider et al., Primary structure of human transferrin receptor deduced from the mRNA sequence. Nature. Oct. 18-24, 1984;311(5987):675-8.

Schuelke et al., Human prostate specific membrane antigen (PSMA) is expressed as a non-covalent 21ransf and provides an attractive target for cancer immunotherapy. Eur J Cancer. 2002;38:S153. Poster 510.

Schülke et al., The homodimer of prostate-specific membrane antigen is a functional target for cancer therapy. Proc Natl Acad Sci USA. Oct. 28, 2003;100(22):12590-95.

Schülke et al., The native form of PSMA is a non-covalent homodimer: Implications for targeted immunotherapy of prostate and other cancers. Clin Can Res. 2003;9(Suppl):6228s. Abstract #C104.

Senter, Potent antibody drug conjugates for cancer therapy. Curr Opin Chem Biol. Jun. 2009;13(3):235-44. Epub May 4, 2009.

Sharkey et al., Targeted therapy of cancer: new prospects for antibodies and immunoconjugates. CA Cancer J Clin. Jul.-Aug. 2006;56(4):226-43.

Shawler et al., Induction of in vitro and in vivo antigenic modulation by the anti-human T-cell monoclonal antibody T101. Cancer Res. Dec. 1984;44(12 Pt 1):5921-7.

Shen et al., Targeting, internalization, and cytotoxicity of methotrexate-monoclonal anti-stage-specific embryonic antigen-1 antibody conjugates in cultured F-9 teratocarcinoma cells. Cancer Res. Aug. 1986;46(8):3912-6.

Silver et al., Prostate-specific Membrane Antigen Expression in Normal and Malignant Human Tissues. Clin Cancer Res. Jan. 1997;3(1):81-5.

Slovin et al., Fully synthetic carbohydrate-based vaccines in biochemically relapsed prostate cancer: clinical trial results with alpha-N-acetylgalactosamine-O-serine/threonine conjugate vaccine. J Clin Oncol. Dec. 1, 2003;21(23):4292-8.

Slovin et al., Phase I vaccine trial of recombinant soluble prostate specific-membrane antigen (rsPSMA) plus Alhydrogel(r) in patients with biochemically relapsed prostate cancer. ASCO Prostate Cancer Symposium. 2005. Abstract Only.

Slusher et al., Rat brain N-acetylated alpha-linked acidic dipeptidase activity. Purification and immunologic characterization. J Biol Chem. Dec. 5, 1990;265(34):21297-301.

Slusher et al., Suramin potently inhibits the enzymatic activity of PSM. Prostate. Jun. 15, 2000;44(1):55-60.

Small, Monoclonal antibody therapy for prostate cancer: finally a reality? J Clin Oncol. Jul. 1, 2004;22(13):2515-6. Epub Jun. 1, 2004.

Smith-Jones et al., In vitro characterization of radiolabeled monoclonal antibodies specific for the extracellular domain of prostate-specific membrane antigen. Cancer Res. Sep. 15, 2000;60(18):5237-43.

Sokoloff et al., A Dual-Monoclonal Sandwich Assay for Prostate-specific Membrane Antigen: Levels in Tissues, Seminal Fluid and Urine. Prostate. May 1, 2000;43(2):150-7.

Solin et al., Gene expression and prostate specificity of human prostatic acid phosphatase (PAP): evaluation by RNA blot analyses. Biochim Biophys Acta. Jan. 30, 1990;1048(1):72-7.

Song, Lokalisation und Gen—Expressionsregulation der neutralen Endopeptidase in der humanen Prostata. Ph.D. Thesis. Marburg 2003.

Soule, Ninth Annual CaP CURE Scientific Retreat. Oct. 23, 2002. 4 pages.

Speno et al., Site-directed mutagenesis of predicted active site residues in glutamate carboxypeptidase II. Mol Pharmacol. Jan. 1999;55(1):179-85.

Spira et al., Clonal variants of hybridoma cells that switch isotype at a high frequency. Proc Natl Acad Sci U S A. Apr. 12, 1994;91(8):3423-7.

Spitler et al., Cancer vaccines: the interferon analogy. Cancer Biother. 1995 Spring;10(1):1-3.

Stancoviski et al., Mechanistic aspects of the opposing effects of monoclonal antibodies to the ERBB2 receptor on tumor growth. Proc Natl Acad Sci U S A. Oct. 1, 1991;88(19):8691-5.

Strassburg et al., Baculovirus recombinant expressing a secreted form of a transmembrane carcinoma-associated antigen. Cancer Res. Feb. 15, 1992;52(4):815-21.

Su et al., Alternatively spliced variants of prostate-specific membrane antigen RNA: ratio of expression as a potential measurement of progression. Cancer Res. Apr. 1, 1995;55(7):1441-3.

Sulitzeanu et al., Antigen and Immunogen—A Question of Terminology. Cancer Immunol Immunother. 1981;11:291-92.

Sunada et al., Monoclonal antibody against epidermal growth factor receptor is internalized without stimulating receptor phosphorylation. Proc Natl Acad Sci U S A. Jun. 1986;83(11):3825-9.

Sundarapandiyan et al., Bispecific antibody-mediated destruction of phosphate cancer cells. Proceedings of the American Association of Cancer Research, Mar. 2000, 41:289 Abstract 1837.

Sutherland et al., Ubiquitous cell-surface glycoprotein on tumor cells is proliferation-associated receptor for transferrin. Proc Natl Acad Sci U S A. Jul. 1981;78(7):4515-9.

Sweat et al., Prostate-specific membrane antigen expression is greatest in prostate adenocarcinoma and lymph node metastatses. Urology. Oct. 1998;52(4):637-40.

Tagawa et al., Phase II trial of 177Lutetium radio-labeled anti-prostate-specific membrane antigen (PSMA) monoclonal antibody J591 (177Lu-J591) in patients (pts) with metastatic castrate-resistant prostate cancer (metCRPC). 2008 ASCO Annual Meeting. J Clin Oncol. 2008;26(May 20 Suppl.). Abstract 5140.

Taki, Production of a monoclonal antibody specifically reacted to prostate tissues. J. Aichi Med Univ Assoc. Nov. 1995;23(6):609-19.

Tate et al., Met-Independent Hepatocyte Growth Factor-mediated regulation of cell adhesion in human prostate cancer cells. BMC Cancer. Jul. 25, 2006;6:197. 15 pages.

Taylor et al., "A transgenic mouse that expresses a diversity of human sequence heavy and light chain immunoglobulins" *Nucleic Acids Research* (1992), 20(23):6287-6295.

Tazzari et al., An immunotoxin containing a rat IgM monoclonal antibody (Campath 1) and saporin 6: effect on T lymphocytes and hemopoietic cells. Cancer Immunol Immunother. 1988;26(3):231-6.

Thorpe et al., The First International Conference on Vascular Targeting: Meeting Overview. Cancer Res. Mar. 1, 2003;63(5):1144-7.

Tiffany et al., Characterization of the enzymatic activity of PSM: comparison with brain NAALADase. Prostate. Apr. 1, 1999;39(1):28-35.

Tino et al., Isolation and characterization of monoclonal antibodies specific for protein conformational epitopes present in prostate-specific membrane antigen (PSMA). Hybridoma. Jun. 2000;19(3):249-57.

Tortora et al., Microbiology, an Introduction. Benjamin/Cummings Publishing Co., Inc., 1991;423-426, 471.

Trail et al., Monoclonal antibody drug immunoconjugates for targeted treatment of cancer. Cancer Immunol Immunother. May 2003;52(5):328-37. Epub Jan. 16, 2003.

Tralongo et al., Vinorelbine and prednisone in older cancer patients with hormone-refractory metastatic prostate cancer. A phase II study. Tumori. Jan.-Feb. 2003;89(1):26-30. Abstract only.

Troyer et al., Biochemical characterization and mapping of the 7EII-C5.3 epitope of the prostate-specific membrane antigen. Urol Oncol. 1995;1:29-37.

Troyer et al., Detection and characterization of the prostate-specific membrane antigen (PSMA) in tissue extracts and body fluids. Int J Cancer. Sep. 4, 1995;62(5):552-8.

Troyer et al., Location of prostate-specific membrane antigen in the LNCaP prostate carcinoma cell line. Prostate. Mar. 1, 1997;30(4):232-42.

Troyer et al., Molecular characterization of the 7E11-C5 prostate tumor-associated antigen. J Urology. 1993;149:333A. Abstract #482.

Troyer et al., Subcellular Localization of the 7E11-C5 Prostate Specific Antigen. Proc Am Assoc Cancer Res. 1994;35:283. Abstract #1688.

Usui et al., Evaluation of ricin A chain-containing immunotoxins directed against glycolipid and glycoprotein on mouse lymphoma cells. Acta Med Okayama. Dec. 1994;48(6):305-9.

Vaughan et al., Human antibodies by design. Nat Biotechnol. Jun. 1998;16(6):535-9.

Velders et al., The impact of antigen density and antibody affinity on antibody-dependent cellular cytotoxicity: relevance for immunotherapy of carcinomas. Br J Cancer. Aug. 1998;78(4):478-83.

Vile et al., In vitro and in vivo targeting of gene expression to melanoma cells. Cancer Res. Mar. 1, 1993;53(5):962-7.

Vitetta et al., Immunotoxins. Arum Rev Immunol. 1985;3:197-212.

Vodinelich et al., Structure and function of the 24ransferring receptor—a possible role in the recognition of natural killer cells. Haematol Blood Transfus. 1983;28:472-4.

Vollmers et al., Adjuvant therapy for gastric adenocarcinoma with the apoptosis-inducing human monoclonal antibody SC-1: first clinical and histopathological results. Oncol Rep. May-Jun. 1998;5(3):549-52.

Vriesendorp et al., Radiolabeled immunoglobulin therapy: old barriers and new opportunities. Expert Rev Anticancer Ther. Oct. 2001;1(3):461-78.

Waltering et al., Increased expression of androgen receptor sensitizes prostate cancer cells to low levels of androgens. Cancer Res. Oct. 15, 2009;69(20):8141-9. Epub Oct. 6, 2009.

Wang et al., Intracellular pteroylpolyglutamate hydrolase from human jejunal mucosa. Isolation and characterization. J Biol Chem. Oct. 15, 1986;261(29):13551-5.

Wang et al., T-cell-directed cancer vaccines: the melanoma model. Expert Opin Biol Ther. Mar. 2001;1(2):277-90.

Webb et al., Characterization of prostate-tissue-directed monoclonal antibody, alpha-Pro 13. Cancer Immunol Immunother. 1984;17(1):7-17. Abstract only.

Webb et al., Rationale for immunotoxin therapy of metastatic prostate carcinoma formatted as a multi-stage delivery system. J Urol. Aug. 1989;142(2 Pt 1):425-32.

Weiner et al., New approaches to antibody therapy. Oncogene. Dec. 11, 2000;19(53):6144-51.

Wiedlocha et al., Specific killing of mouse leukemic cells with ricin A-chain immunotoxin. Arch Immunol Ther Exp (Warsz). 1989;37(1-2):101-13.

Wiels et al., Properties of immunotoxins against a glycolipid antigen associated with Burkitt's lymphoma. Cancer Res. Jan. 1984;44(1):129-33.

Williams et al., Analysis of prostate-specific membrane antigen splice variants in LNCap cells. Oligonucleotides. 2006 Summer;16(2):186-95.

Wolf, Herstellung and Charakterisierung rekombinanter Immunotoxine aus anti-PSMA single-chain-Antikörperfragmenten zur Therapie des Prostatakarzinoms. Ph.D. Thesis. Dec. 2005. 33 pages. 2 page German abstract. 31 page English translation.

Wright et al., Characterization of a new prostate carcinoma-associate marker. Antibody Immunoconjugates. Abstract #193.

Wright et al., Expression of prostate-specific membrane antigen in normal, benign and malignant prostate tissues. Urol Oncol. 1995;1:18-28.

Wright et al., Upregulation of prostate-specific membrane antigen after androgen-deprivation therapy. Urology. Aug. 1996;48(2):326-34.

Wu et al., Arming antibodies: prospects and challenges for immunoconjugates. Nat Biotechnol. Sep. 2005;23(9):1137-46.

Xiao et al., Generation of a baculovirus recombinant prostate-specific membrane antigen and its use in the development of a novel protein biochip quantitative immunoassay. Protein Expr Purif. Jun. 2000;19(1):12-21.

Xu et al., Antibody-induced growth inhibition is mediated through immunochemically and functionally distinct epitopes on the extracellular domain of the c-erbB-2 (HER-2/neu) gene product p185. Int J Cancer. Feb. 1, 1993;53(3):401-8.

Young et al., Efficient isolation of genes by using antibody probes. Proc Natl Acad Sci U S A. Mar. 1983;80(5):1194-8.

Zaks et al., Immunization with a peptide epitope (p369-377) from HER-2/neu leads to peptide-specific cytotoxic T lymphocytes that fail to recognize HER-2/neu+ tumors. Cancer Res. Nov. 1, 1998;58(21):4902-8.

Notice of Opposition for EP Publication No. 0668777 mailed Jul. 11, 2007.

Notice of Opposition for EP Publication No. 0668777 mailed Jul. 13, 2007.

Notice of Opposition Added Subject Matter for EP Publication No. 0668777 mailed Nov. 25, 2009.

Summons to Attend Oral Proceedings for EP Publication No. 0668777 mailed Jun. 26, 2009.

Declaration of Dr. Brigitte Huber filed in EP Opposition of Publication No. 0668777 dated Jan. 13, 2010.

Declaration of Dr. William Olson filed in EP Opposition of Publication No. 0668777 dated Jan. 12, 2010.

Declaration of Dr. Alton Boynton filed in EP Opposition of Publication No. 0668777 dated Nov. 25, 2009.

Declaration of Ron Israeli filed in EP Opposition of Publication No. 0668777 dated Apr. 4, 2008.

Declaration of John Rodwell, Ph.D. filed in EP Opposition of Publication No. 0668777 dated Apr. 22, 2008.

Declaration of Dr. Warren D. W. Heston filed in EP Opposition of Publication No. 0668777 dated Apr. 5, 2008.

Declaration of John Horoszewicz filed in EP Opposition of Publication No. 0668777 dated Jun. 14, 1999.

Declaration of Paul Kaladas filed in EP Opposition of Publication No. 0668777 dated Jun. 11, 1999.

Declaration of John Rodwell, Ph.D. filed in EP Opposition of Publication No. 0668777 dated Jun. 10, 1999.

Declaration of Bruce L. Jacobson, Ph.D. filed in EP Opposition of Publication No. 0668777 dated Nov. 25, 2009.

Experimental analysis of a selection of anti-PSMA antibodies provided by Dr. Bander. mAb Comparision.

Letter regarding the opposition procedure for Publication No. 0668777 dated Apr. 28, 2008.

Letter regarding the opposition procedure for Publication No. 0668777 dated Nov. 6, 2008.

Written submission in preparation to/during oral proceedings for Publication No. 0668777 dated Nov. 25, 2009.

Letter regarding the opposition procedure for Publication No. 0668777 from Gareth Williams dated Nov. 27, 2009.

Letter regarding the opposition procedure for Publication No. 0668777 from Dr. Hans Rainer-Jaenichen dated Nov. 27, 2009.

Third Party Observations for EP Publication No. 0668777 mailed Nov. 27, 2009.

Letter regarding the opposition procedure for Publication No. 0668777 dated Dec. 8, 2009.

Letter dealing with oral proceedings for Publication No. 0668777 dated Jan. 13, 2010.

Letter regarding the opposition procedure for Publication No. 0668777 dated Jan. 18, 2010.

Letter regarding the opposition procedure for Publication No. 0668777 dated Jan. 20, 2010.

Minutes of Oral Proceedings for Publication No. 0668777 dated Jan. 27, 2010.

Interlocutory Decision in opposition proceedings of Publication No. 0668777 dated May 5, 2010.

Notice of Appeal for Publication No. 0668777 dated Jun. 29, 2010.

Third Party Observations submitted for EP Publication No. 0668777 mailed Aug. 13, 2004.

Reply to Office Communication submitted for EP Publication No. 0668777 mailed Nov. 30, 2004 (discusses 3$^{rd}$ Party Observations).

Third Party Observations submitted for EP Publication No. 0668777 mailed Mar. 7, 2005.

Reply to Office Communication submitted EP Publication No. 0668777 mailed Aug. 18, 2005 (discusses 3$^{rd}$ Party Observations).

Withdrawal of Appeal for EP Publication No. 0668777 mailed Sep. 2, 2010.

Confirmation of Withdrawal of Appeal for EP Publication No. 0668777 mailed Sep. 13, 2010.

Maintenance of the patent with the documents specified in the final decisions for EP Publication No. 0668777 dated Sep. 14, 2010.

Communication pursuant to Rule 82(2) EPC for EP Publication No. 0668777 mailed Sep. 17, 2010.

Termination of Opposition Proceedings for EP Publication No. 0668777 mailed Jan. 7, 2011.

Decision to Maintain European Patent for EP Publication No. 0668777 mailed Jan. 13, 2011.

Declaration of Dr. Mohan Srinivasan filed in EP Opposition of Publication No. 1210374 dated Apr. 24, 2008.

Declaration of Professor Eric Holmes filed in EP Opposition of Publication No. 1210374 dated Apr. 24, 2008.

Declaration of Dr. William Olson filed in EP Opposition of Publication No. 1210374 dated Feb. 20, 2009.

Notice of Opposition for Publication No. 1210374 dated Jul. 11, 2007.

Letter regarding the opposition procedure for Publication No. 1210374 dated Apr. 25, 2008.

Letter regarding the opposition procedure for Publication No. 1210374 dated Oct. 24, 2008.

Summons to Attend Oral Proceedings for Publication No. 1210374 dated Nov. 14, 2008.

Third Party Observations for Publication No. 1210374 dated Feb. 11, 2009.

Letter regarding the opposition procedure for Publication No. 1210374 from G. C. Woods dated Feb. 20, 2009.

Letter regarding the opposition procedure for Publication No. 1210374 from Timothy Jump dated Feb. 20, 2009.

CV for Nils Lonberg dated Feb. 20, 2009 for EP Publication No. 1210374.

Letter regarding the opposition procedure for Publication No. 1210374 dated Apr. 7, 2009.

Letter regarding the opposition procedure for Publication No. 1210374 dated Mar. 27, 2009.

Letter of Opposition for Publication No. 1210374 dated Apr. 23, 2009.

Letter regarding opposition procedure for Publication No. 1210374 dated Apr. 24, 2009.

Communication inviting the parties to file observations for Publication No. 1210374 dated May 4, 2009.

Decision Revoking the European patent Publication No. 1210374 dated Oct. 15, 2009.

Termination of Opposition Proceedings for Publication No. 1210374 dated Jan. 28, 2010.

Communication to Parties Concerning the Termination of Opposition Proceedings for Publication No. 1210374 mailed Feb. 2, 2010.

Notice of Opposition for EP Publication No. 0956506 dated Dec. 1, 2006.

Letter regarding the opposition procedure for EP Publication No. 0956506 dated Jul. 11, 2007.

Summons to Attend Oral Proceedings for EP Publication No. 0956506 dated May 27, 2008.

Letter regarding the opposition procedure for EP Publication No. 0956506 dated Sep. 26, 2008.

Fax dealing with oral proceedings during the opposition procedure for EP Publication No. 0956506 dated Nov. 20, 2008. Sent 12:13.

Fax dealing with oral proceedings during the opposition procedure for EP Publication No. 0956506 dated Nov. 20, 2008. Sent 12:18.

Fax dealing with the oral proceedings during the opposition procedure for EP Publication No. 0956506 dated Nov. 24, 2008.

Letter regarding Oral Proceedings for Opposition Procedure for EP Publication No. 0956506 mailed Nov. 20, 2008.

Minutes of the Oral Proceedings for EP Publication No. 0956506 dated Jan. 30, 2009.

Decision Rejecting EP Publication No. 0956506 dated Feb. 2, 2009.

Statement on grounds of appeal for EP Publication No. 0956506 dated Jun. 12, 2009.
Fax relating to Appeal Procedure for EP Publication No. 0956506 dated Nov. 2, 2009.
Communication of Board of Appeals for EP Publication No. 0956506 mailed Nov. 2, 2009.
Withdrawal of Appeal for EP Publication No. 0956506 mailed Apr. 28, 2011.
Termination of Opposition Proceedings for EP Publication No. 0956506 dated May 10, 2011.
Confirmation of Withdrawal of Appeal for EP Publication No. 0956506 mailed May 10, 2011.
Notice of Opposition for EP Publication No. 0914155 mailed Nov. 22, 2006.
Summons to Attend Oral Proceedings for EP Publication No. 0914155 mailed Jun. 30, 2008.
Letter regarding the opposition procedure for EP Publication No. 0914155 mailed Dec. 19, 2008.
Submissions by Patentee for EP Publication No. 0914155 mailed Dec. 22, 2008.
Third Party Observations for EP Publication No. 0914155 mailed Dec. 22, 2008.
Letter regarding the opposition procedure for EP Publication No. 0914155 mailed Jan. 12, 2009.
Letter regarding opposition procedure for EP Publication No. 0914155 mailed Jan. 14, 2009.
Letter regarding opposition procedure for EP Publication No. 0914155 mailed Jan. 16, 2009.
Minutes of the Oral Proceedings for EP Publication No. 0914155 mailed Feb. 6, 2009.
Decision revoking EP Publication No. 0914155 mailed Feb. 6, 2009.
Termination of Opposition Proceedings for EP Publication No. 0914155 dated May 26, 2009.
Communication to Parties Concerning Termination of Opposition Proceedings for EP Publication No. 0914155 mailed May 29, 2009.
Castelletti et al., Biochem. J. 2008, 409:149-57.
Jascur et al., Biochemistry 1991, 30:1908-15.
Pangalos et al., J. Biol. Chem. 1999, 274(13): 8470-83.

* cited by examiner

Human IgG1 cloning — Into pcDNA

Construction of pcDNA-huCκ and pcDNA-huIgG1

|  |  | PCR product | Vector |
|---|---|---|---|
| Cκ | Sense | 5' XbaI HindIII BamHI NheI 3' | 5' NheI NotI 3' |
|  | Anti-sense | EcoRI NotI | (pcDNA.neo) |
| Cγ1 | Sense | 5' XbaI KpnI HindIII BamHI NheI 3' | 5' NheI/PmeI 3' |
|  | Anti-sense | EcoRI XhoI PmeI | (pcDNA Hygro) |

Construction of pcDNA-Ab (V-C cassette)

|  |  | PCR product | Vector |
|---|---|---|---|
| Vκ | Sense | BglII or BamHI (if necessary)* | 5' BamHI NheI 3' |
|  | Anti-sense | NheI | (pcDNA-huCκ) |
| Vγ1 | Sense | BglII or BamHI (if necessary)* | 5' BamHI NheI 3' |
|  | Anti-sense | XbaI | (pcDNA-huIgG1) |

*BamHI primer is used if the V region has an internal BglII site

Human IgG cloning — V-C cassette from pcDNA into "production" vector
Insert from pcDNA Igκ     5' HindIII or BamHI (if alternate sense primer used)
        3' EcoRI, NotI, XhoI, XbaI or PmeI
IgG1    5' KpnI, HindIII or BamHI (if alternate sense primer used)
        3' EcoRI*, XhoI or PmeI

*2$^{nd}$ EcoRI site present in hygromycin resistance gene

Primers used for V region amplification
Vκ-sense:
5' GA<u>AGATCT</u>CACC ATG + 20-23 bp leader sequence 3'
     BglII    Kozak
Vκ anti-sense (reverse/complementary):
5' AACTA <u>GCT AGC</u> AGT TCC AGA TTT CAA CTG CTC ATC AGA T 3'
          S   A    T   G   S   K   L   Q   E   D   S  (aa.23-13 Cκ)
         NheI
Cloning site of NheI codes for A S —therefore no amino acid change due to cloning.

Vγ-sense:
5' GA<u>AGATCT</u>CACC ATG + 17-29bp leader sequence 3'
     BglII    Kozak
Vγ anti-sense (reverse/complementary):
5' GC <u>TCT AGA</u> GGG TGC CAG GGG GAA GAC CGA T 3'
      (R)  S   P   A   L   P   F   V   S  (aa.14-7 Cγ1)
      XbaI
Cloning into
5' CG <u>GCT AGC</u>
       S   (A)

Cloning site junction of XbaI/NheI (TCT AGC) codes for S S —therefore no amino acid change due to cloning.

FIG. 13

| mAb | Cell Based Immunoreactivity (%) | |
|---|---|---|
| | PSMA | 3T3 |
| 006 | 85.8 | 1.0 |
| 026 | 83.4 | 1.4 |
| mJ591 | 46.2 | 1.7 |
| IgG | 5.9 | 0.7 |

FIG. 42B

PSMA ANTIBODIES AND USES THEREOF

RELATED APPLICATIONS

This application is a continuation application of U.S. Application Ser. No. 10/976,352 filed Oct. 27, 2004, (abandoned), which is a continuation-in-part of U.S. Application Ser. No. 10/695,667 filed Oct. 27, 2003, (abandoned), which is a continuation-in-part of U.S. Application Ser. No. 10/395,894 filed Mar. 21, 2003, now U.S. Pat. No. 7,850,971, which is a continuation-in-part of International Application No. PCT/US02/33944 designating the United States, filed Oct. 23, 2002, which claims the benefit under 35 U.S.C. §119 of U.S. Application No. 60/335,215 filed Oct. 23, 2001, expired, U.S. Application No. 60/362,747 filed Mar. 7, 2002, expired, and U.S. Application No. 60/412,618 filed Sep. 20, 2002, expired, the entire contents of each of which are incorporated herein by reference.

FIELD OF THE INVENTION

This invention relates generally to the field of cancer associated polypeptides and formulations of and kits including these polypeptides. In particular, the invention relates, in part, to formulations of multimeric forms of PSMA proteins, particularly dimeric PSMA, and methods of their processing, purification, production and use.

BACKGROUND OF THE INVENTION

Prostate cancer is the most prevalent type of cancer and the second leading cause of death from cancer in American men, with an estimated 179,000 cases and 37,000 deaths in 1999, (Landis, S. H. et al. *CA Cancer J. Clin.* 48:6-29 (1998)). The number of men diagnosed with prostate cancer is steadily increasing as a result of the increasing population of older men as well as a greater awareness of the disease leading to its earlier diagnosis (Parker et al., 1997, *CA Cancer J. Clin.* 47:5-280). The life time risk for men developing prostate cancer is about 1 in 5 for Caucasians, 1 in 6 for African Americans. High risk groups are represented by those with a positive family history of prostate cancer or African Americans.

Over a lifetime, more than ⅔ of the men diagnosed with prostate cancer die of the disease (Wingo et al., 1996, *CA Cancer J. Clin.* 46:113-25). Moreover, many patients who do not succumb to prostate cancer require continuous treatment to ameliorate symptoms such as pain, bleeding and urinary obstruction. Thus, prostate cancer also represents a major cause of suffering and increased health care expenditures.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. Patients with bulky, high-grade tumors are less likely to be successfully treated by radical prostatectomy.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, confocal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When gonadotropin-releasing hormone agonists are administered testosterone concentrations are ultimately reduced. Flutamide and other nonsteroidal, anti-androgen agents block binding of testosterone to its intracellular receptors. As a result, it blocks the effect of testosterone, increasing serum testosterone concentrations and allows patients to remain potent—a significant problem after radical prostatectomy and radiation treatments.

Cytotoxic chemotherapy is largely ineffective in treating prostate cancer. Its toxicity makes such therapy unsuitable for elderly patients. In addition, prostate cancer is relatively resistant to cytotoxic agents.

Relapsed or more advanced disease is also treated with anti-androgen therapy. Unfortunately, almost all tumors become hormone-resistant and progress rapidly in the absence of any effective therapy.

Accordingly, there is a need for effective therapeutics for prostate cancer which are not overwhelmingly toxic to normal tissues of a patient, and which are effective in selectively eliminating prostate cancer cells.

SUMMARY OF THE INVENTION

The present invention relates, in part, to multimeric, particularly dimeric, forms of PSMA protein, compositions and kits containing dimeric PSMA protein as well as methods of producing, purifying, processing and using these compositions.

In one aspect compositions comprising multimeric forms of PSMA protein are provided. In some embodiments, these compositions contain isolated PSMA protein, at least 5% of which is in the form of PSMA protein multimer. In other embodiments at least 10%, 15%, 20%, 25%, 30%, 35%, 40%, 45%, 50%, 55%, 60%, 65%, 70%, 75%, 80%, 85%, 90%, 95% or more of the isolated PSMA protein is in the form of a PSMA protein multimer. In other embodiments the PSMA protein multimer is a PSMA protein dimer, wherein the PSMA protein dimer is formed by the covalent or non-covalent association of two PSMA proteins. In some embodiments the PSMA protein dimer is engineered to form a stable PSMA dimer through covalent bonds. In some embodiments the covalent bonds are disulfide bonds. Preferably, the PSMA protein dimer is associated in the same way as that of native PSMA dimer or is associated in such a way as to form at least one antigenic epitope that can be used to generate antibodies that recognize the native PSMA dimer. These antibodies, preferably, recognize the native PSMA dimer and not PSMA monomer or recognize the native PSMA dimer with greater specificity. In some embodiments of the invention the percent dimer can be calculated in terms of the number of PSMA protein molecules in the dimeric form versus the total number of PSMA protein (monomer, dimer or other multimer). In other embodiments the percent dimer can be calculated in terms of the number of PSMA dimers relative to the number of PSMA monomers, PSMA dimers and PSMA multimers.

In some embodiments the PSMA protein multimers comprise the full-length PSMA protein (SEQ ID NO: 1) or a fragment thereof. In other embodiments the PSMA protein multimer comprises the extracellular portion of PSMA (amino acids 44-750 of SEQ ID NO: 1) or a fragment thereof. In still other embodiments the PSMA protein multimer comprises the amino acids 58-750 of SEQ ID NO: 1 or a fragment thereof. In yet other embodiments the PSMA protein multimer comprises the amino acids 610-750 of SEQ ID NO: 1 or a fragment thereof. The fragments are capable of forming a PSMA multimer that can be used to generate antibodies that recognize PSMA, preferably native PSMA dimer. Typically, the PSMA multimers are homomultimers, meaning that the two or more PSMA molecules are the same. In other embodiments, the PSMA multimers are heteromultimers, whereby at least two of the PSMA proteins are not the same. In still other embodiments the PSMA proteins can be functionally equivalent proteins, whereby the PSMA protein is conservatively substituted.

In another aspect of the invention compositions comprising isolated multimeric PSMA protein, wherein the composition comprises less than 35% of a monomeric PSMA protein are provided. In still other embodiments the composition comprises less than 20% of the monomeric PSMA protein. In yet other embodiments the composition comprises less than 15% of the monomeric PSMA protein. In still other embodiments the composition comprises less than 5% of the monomeric PSMA protein. In some preferred embodiments the isolated multimeric PSMA protein is an isolated dimeric PSMA protein.

In some aspects of the invention, agents and compositions thereof that preserve or promote multimeric association of PSMA, particularly dimeric association, are provided. In some embodiments these agents include metal ions, salts, or pH adjusting agents. These agents that preserve or promote multimeric PSMA associations can do so individually or do so in combination. Therefore, in another aspect of the invention, a composition comprising PSMA protein multimers in conjunction with metal ion are provided. In some embodiments these compositions comprise at least 0.25 molar equivalents of metal ion to PSMA protein (total PSMA protein regardless of its form). In other embodiments at least 0.3, 0.4, 0.5, 0.6, 0.7, 0.8, 0.9, 1, 1.3, 1.5, 1.7, 2, 3, 4, 5, or more molar equivalents of metal ion to PSMA protein are present in the composition. In other embodiments the metal ion is in molar excess to PSMA protein. In some preferred embodiments the compositions provided are free of chelating agents.

In yet another aspect of the invention compositions comprising PSMA protein in a solution that promotes or preserves multimeric association of PSMA protein are provided. In some embodiments the solution that promotes or preserves multimeric association of PSMA protein is a solution that promotes or preserves dimeric association of PSMA protein. In other embodiments the solution that promotes or preserves dimeric association of PSMA protein has a pH that ranges from 4 to 8. In still other embodiments the solution that promotes or preserves dimeric association of PSMA protein has a pH that ranges from 5 to 7. Other embodiments include compositions wherein the solution that promotes or preserves dimeric association of PSMA protein has a pH that ranges from 5.5 to 7. In still other embodiments the solution that promotes or preserves dimeric association of PSMA protein has a pH of 6.

In still another aspect of the invention compositions comprising PSMA protein in a solution that promotes or preserves multimeric association of PSMA protein, wherein the solution comprises a salt, are provided. In some embodiments, the cationic component of the salt is sodium, potassium, ammonium, magnesium, calcium, zinc or a combination thereof, and the anionic component of the salt is chloride, sulfate, acetate or a combination thereof. In preferred embodiments the salt is sodium chloride, sodium sulfate, sodium acetate or ammonium sulfate. In some embodiments the salt is present at a concentration in the range of 50 mM to 2M. In other embodiments the salt is present at a concentration in the range of 100 mM to 300 mM. In still other embodiments the salt is present at a concentration of 150 mM.

In yet another aspect of the invention a composition comprising PSMA protein in a solution that promotes or preserves dimeric association of PSMA protein, wherein the solution comprises metal ions, are provided. In some embodiments the metal ions are zinc ions, calcium ions, magnesium ions, cobalt ions, manganese ions or a combination thereof. In still other embodiments the metal ions are zinc ions and calcium ions. In yet other embodiments the zinc ions and calcium ions are present at a concentration in the range of 0.1 mM to 5 mM. In still other embodiments the zinc ions are present at a concentration that is lower than the concentration of the calcium ions. In some embodiments the zinc ions are present at a concentration of 0.1 mM and the calcium ions are present at a concentration of 1 mM. In other embodiments the metal ions are magnesium ions. In some of these embodiments the magnesium ions are present at a concentration in the range of 0.1 mM to 5 mM. In other embodiments the magnesium ions are present at a concentration of 0.5 mM. In another embodiment the metal ions are magnesium and calcium ions. In a preferred embodiment the compositions are free of chelating agents.

In still a further aspect of the invention a composition comprising isolated PSMA protein in a solution that promotes or preserves dimeric association of PSMA protein wherein the solution comprises (a) 5 to 20 mM of sodium phosphate, sodium acetate or a combination thereof, (b) 100 to 300 mM sodium chloride or sodium sulfate, and (c) 0.1 to 2 mM of at least one metal ion is provided. In one embodiment the solution has a pH in the range of 4 to 8. In another embodiment the solution has a pH in a range of 5 to 7. In still another embodiment the solution has a pH in a range of 6 to 6.5. The metal ion in some embodiments is a zinc ion, calcium ion, magnesium ion, cobalt ion, manganese ion or a combination thereof.

In still another aspect of the invention a composition comprising isolated PSMA protein in a solution that promotes or preserves dimeric association of PSMA protein wherein the solution comprises (a) 1.47 mM potassium phosphate, monobasic, (b) 8.1 mM sodium phosphate, dibasic, (c) 2.68 mM potassium chloride, (d) 0.14 M sodium chloride, (e) 0.9 mM calcium chloride, and (f) 0.49 mM magnesium chloride; and wherein the solution has a pH of 7.0 is provided. In one embodiment the isolated PSMA protein is at a concentration of between 0.2 mg/mL and 10 mg/mL. In still a further embodiment the isolated PSMA protein is at a concentration of between 2 mg/mL and 5 mg/mL. In other embodiments the isolated PSMA protein is at a concentration of about 0.1, 0.2, 0.3, 0.4, 0.5, 0.6, 0.7, 0.8, 0.9, 1, 1.2, 1.4, 1.6, 1.8, 2, 2.2, 2.5, 3, 3.5, 4, 4.5, 5, 5.5, 6, 6.5, 7, 7.5, 8, 8.5, 9, 9.5, 10, 11, 12, 13, 14, 15, 17, 20, 22, 25, 30, 35, 40, 45, 50 mg/mL or more. In another embodiment the isolated PSMA protein is at a concentration of 0.2 mg/mL. In still a further embodiment the isolated PSMA protein is at a concentration of 2 mg/mL. In some embodiments the compositions provided further comprise an adjuvant. In one embodiment the adjuvant is a saponin-based adjuvant. In another embodiment the saponin-based adjuvant is QS-21. The adjuvant in some embodiments is in an amount of about 10, 15, 20, 25, 30, 35, 40, 45, 50, 55, 60, 65, 70, 75, 80, 85, 90, 100, 110, 120, 130, 140, 150, 175, 200, 225, 250, 300 µg or more. In one embodiment the QS-21 is in an amount of between 50 µg and 150 µg. In another embodiment the QS-21 is in an amount of 50 µg. In another embodiment the QS-21 is in an amount of 100 µg. When such compositions are administered to a subject, in some embodiments, the amount of the adjuvant is the amount of the adjuvant per dose to the subject.

In another aspect of the invention a composition comprising PSMA protein which also comprises an agent that promotes or preserves multimeric association, particularly dimeric association of PSMA protein, is provided, wherein the composition is stable when stored at −80° C. In other aspects of the invention the composition is stable when stored at −20° C. In still other aspects the composition is stable when stored at 4° C. In yet another aspect of the invention the composition is stable when stored at room temperature.

Another aspect of the invention provides a method of promoting or preserving dimeric association of PSMA protein in a solution by obtaining a solution of PSMA protein, and adjusting the pH to be in the range of 4 to 8. In some embodiments the pH is adjusted to be in the range of 5 to 7. In other embodiments the pH is adjusted to be in the range of 5.5 to 7. In yet other embodiments the pH is adjusted to be 6.

In another aspect of the invention a method of processing a PSMA protein by contacting the PSMA protein in a solution with a first agent that promotes or preserves dimeric association of PSMA protein in an amount effective to promote or preserve PSMA protein dimer formation is provided. In some embodiments the amount effective to promote or preserve PSMA protein dimer formation is enough to promote or maintain at least 5% of the PSMA protein in the solution in dimer form. In other embodiments at least 10%, 15%, 20%, 25%, 30%, 35%, 40%, 45%, 50%, 55%, 60%, 65%, 70%, 75%, 80%, 85%, 90%, 95% or more of the PSMA protein in the solution is in dimer form. The percentage of the dimer form of PSMA is calculated in terms of the total amount of the various forms of PSMA protein. In other words the percentage is calculated according to the number of PSMA dimers relative to the number of PSMA monomers, dimers and other multimers. In some embodiments the first agent that promotes or preserves dimeric association of PSMA protein is a salt, metal ion or a pH adjusting agent. The cationic components of the salt can include sodium, potassium, ammonium, magnesium, calcium, zinc or a combination thereof, while the anionic component of the salt can include chloride, sulfate, acetate or a combination thereof. In some embodiments the salt is sodium chloride, sodium sulfate, sodium acetate or ammonium sulfate. In other embodiments the salt is present at a concentration in the range of 50 mM to 2M. In still other embodiments the salt is present at a concentration in the range of 100 mM to 300 mM. In yet other embodiments the salt is present at a concentration of 150 mM. In some embodiments of the invention the method further includes combining the PSMA protein solution with an adjuvant or diluent. The adjuvant or diluent can be combined with the PSMA protein in an amount to dilute the salt concentration to 100 mM to 300 mM. In some embodiment the salt concentration is diluted to 150 mM. In certain embodiments this is done prior to administering the solution to a subject. In other embodiments the first agent is a metal ion and the metal ion is a zinc ion, calcium ion, magnesium ion, cobalt ion, manganese ion or a combination thereof. In some embodiments the metal ion is a combination of zinc ion and calcium ion. In still other embodiments the zinc ion and calcium ion are present at a concentration in the range of 0.1 mM to 5 mM. In yet other embodiments the zinc ion is present at a concentration that is lower than the concentration of the calcium ion. In still further embodiments the zinc ion is present at a concentration of 0.1 mM, and the calcium ion is present at a concentration of 1 mM. In other embodiments the metal ion is a magnesium ion. In some of these embodiments the magnesium ion is present at a concentration in the range of 0.1 mM to 5 mM. In still other of these embodiments the magnesium ion is present at a concentration of 0.5 mM. In the embodiments where the first agent is a solution of a certain pH, the pH of the solution can be adjusted to be in the range of 4 to 8. In some embodiments the pH of the solution is adjusted to be in the range of 5 to 7. In still other embodiments the pH of the solution is adjusted to be in the range of 5.5 to 7. In yet other embodiments the pH of the solution is adjusted to be 6.

In some embodiments the method further comprises contacting the PSMA protein with a second agent that promotes or preserves dimeric association of PSMA protein, wherein the second agent is different than the first agent. A second agent that is different than the first agent includes agents that are of a different type or different class. The second agent, therefore, can be a metal ion, salt or pH adjusting agent. In some embodiments where the first agent is a metal ion the second agent can be a salt, pH adjusting agent or a solution with a certain pH. In other embodiments the first agent is a salt, and the second agent is a metal ion, pH adjusting agent or a solution with a certain pH. In still another embodiment the first agent is a pH adjusting agent or a solution with a certain pH and the second agent is a metal ion or a salt. In yet other embodiments the first agent can be a salt, metal ion, pH adjusting agent or a solution with a certain pH and the second agent can be of the same class but a different type within the same class of agents. For instance if the first agent is a salt such as sodium chloride, the second agent can also be a salt but a different type, e.g., ammonium sulfate.

In another aspect of the invention a method of purifying a sample containing PSMA protein by subjecting the sample containing PSMA to chromatography in the presence of an agent that preserves or promotes the dimeric association of PSMA is provided. In some embodiments the agent that promotes or preserves the dimeric association of PSMA is a metal ion, a salt or a solution with a pH in the range of 4 to 8 or a combination thereof. In a preferred embodiment the metal ion is a combination of calcium ion and magnesium ion. In one such embodiment the calcium ion and magnesium ion are each present at a concentration in the range of 0.1 mM to 5 mM. In a further embodiment the calcium ion and magnesium ion are present at a concentration of 1 mM and 0.5 mM, respectively. In other embodiments wherein the agent that promotes or preserves the dimeric association of PSMA is a salt, the salt is present at a concentration in the range of 50 mM to 2M. In some of these embodiments the salt is present at a concentration of 2M. In still other embodiments where the agent that promotes or preserves the dimeric association of PSMA is a solution with a pH in the range of 4 to 8, the pH of the solution is in the range of 5 to 7. In still other embodiments the pH of the solution is in the range of 6 to 7.5.

In other aspects of the invention a method of purifying a sample containing PSMA protein by applying the sample to a first column, washing the first column with a first wash solution containing salt and metal ions, and collecting the PSMA protein that elutes from the first column is provided. In some embodiments the salt is ammonium sulfate at a saturation of no more than 35% in the wash solution.

In embodiments of the invention the method further comprises dialyzing or diafiltering the eluted PSMA protein with a first salt solution at a pH in the range of 6 to 7.5 to yield a dialyzed or diafiltrated solution containing PSMA protein. In some of these embodiments the first salt solution has a salt concentration of at least 5 mM. In still other of these embodiments the first salt solution is a 10 mM sodium phosphate solution with a pH of 7.

In still other embodiments of the invention the method further comprises loading the eluted PSMA protein, dialyzed or diafiltrated solution containing PSMA protein onto a second column, washing the second column with a second salt solution, and collecting the PSMA eluted by the second salt solution. In some embodiments the second salt solution has a salt concentration of 100 mM to 2M. In certain of these embodiments the second salt solution is 2M sodium chloride in 10 mM sodium phosphate. In still other embodiments the second salt solution has a pH in the range of 6 to 7.5.

In yet another embodiment of the invention the method further comprises dialyzing or diafiltrating the PSMA eluted by the second salt solution with a metal ion solution, applying the dialyzed or diafiltrated PSMA eluted by the second salt solution onto a third column, washing the third column with a second wash solution containing salt and metal ions and collecting the PSMA eluted. In some of these embodiments the pH is maintained in the range of 6 to 7.5 through all of the purification steps.

In other embodiments the method further comprises separating the different forms of PSMA protein, wherein the different forms of PSMA protein are monomeric, dimeric or other multimeric forms of PSMA. In some of these embodiments the different forms of PSMA protein are separated by size exclusion chromatography.

In yet another aspect of the invention a method of identifying an agent which promotes or preserves dimeric association of PSMA protein by determining the amount of a form of PSMA protein in a sample prior to exposure to a candidate agent, exposing the sample to the candidate agent, determining the amount of the form of PSMA protein in the sample after the exposure, and comparing the amount of the form of PSMA protein in the sample prior to and after the exposure is provided. In some embodiments the form of PSMA protein is monomer or dimer. In other embodiments the form of PSMA can be another multimer form with three or more associated PSMA proteins.

In another aspect of the invention a method of treating a subject to elicit or enhance an immune response to cells in the subject expressing PSMA, comprising administering to the subject an effective amount of any of the compositions given herein is provided. In some embodiments the expressed PSMA is expressed on the cell surface. In other embodiments the method further comprises administering one or more booster doses of a composition comprising PSMA protein. In some of these embodiments the composition comprising PSMA protein is a composition of PSMA protein dimer. In still other embodiments the booster dose composition further comprises an adjuvant. In yet other embodiments the booster dose composition can be any of the compositions provided herein. In still other embodiments the composition is administered by intravenous, intramuscular, subcutaneous, parenteral, spinal, intradermal or epidermal administration. In this aspect of the invention the subject has cancer or is at risk of having cancer. In some embodiments the subject has also been treated for cancer. In some embodiments the cancer is a primary tumor or is metastatic cancer. In a preferred embodiment the subject has prostate cancer. In some embodiments the subject is a non-castrate patient who, preferably, has received primary therapy, such as prostatectomy or radiation therapy. In one embodiment the non-castrate patient has a serum testosterone level that is greater than or equal to 180 ng/mL. In other embodiments the subject is a castrate patient who, preferably, has completed a course of hormonal therapy.

In one embodiment the castrate patient has a serum testosterone level of less than 50 ng/mL. In still other embodiments the subject is a patient who has received a conventional cancer therapy for prostate cancer.

In another aspect of the invention methods of treating a subject with cancer, such as prostate cancer, are provided. Such methods comprise administering to a subject at least one of the compositions provided herein. In one embodiment the method comprises administering to the subject a therapeutically effective amount of a composition comprising isolated PSMA protein in a solution that promotes or preserves dimeric association of the PSMA protein, wherein the composition is effective in treating prostate cancer. In another embodiment the method further includes the administration of an adjuvant, which preferably, is contained in the composition comprising the isolated PSMA protein. In some embodiments the adjuvant is a saponin-based adjuvant. In other embodiments the methods further include administering to the subject a conventional cancer therapy. Conventional cancer therapy includes, but is not limited to, surgery, radiation, cryosurgery, thermotherapy, hormone therapy or chemotherapy.

In still another aspect of the invention a method of inhibiting metastasis in a subject with cancer is also provided. One example of such a method includes administering to the subject a therapeutically effective amount of a composition comprising isolated PSMA protein in a solution that promotes or preserves dimeric association of the PSMA protein, wherein the composition is effective in inhibiting metastasis. In one embodiment the method also includes the administration of an adjuvant, which preferably, is a component of the composition of the isolated PSMA protein. In another embodiment the method further comprises administering to the subject a conventional prostate cancer therapy.

In another aspect of the invention a method of eliciting an immune response by administering to a subject an effective amount of any of the compositions provided is given. In some embodiments the method further comprises administering one or more booster doses of a composition comprising PSMA protein. In certain of these embodiments the composition comprising PSMA protein is a composition comprising PSMA protein dimer. In still other embodiments the booster dose composition is any of the compositions given herein. In yet another embodiment the booster dose compositions can also include an adjuvant.

In other aspects of the invention kits which contain any of the compositions provided and instructions for use are provided. In some aspects the kit contains a multimeric composition provided herein, an adjuvant and instructions for mixing. In other aspects the kit includes one of the compositions provided herein, a diluent and instructions for mixing. In some embodiments the composition is provided in a vial or ampoule with a septum or a syringe. In other embodiments the composition is in lyophilized form.

The compositions provided herein can further comprise a therapeutic agent (e.g., a cytokine, an anti-cancer agent, an adjuvant, etc.). In some embodiments the adjuvant is alum; monophosphoryl lipid A; a saponin; a saponin fraction; a saponin-based adjuvant, such as SAPONIMMUNE; a chemically modified saponin; QS-7; QS-17; QS-18; QS-21; a polysaccharide-based adjuvant, such as POLYSACCIMMUNE; a synthetic adjuvant, such as SYNTHIMMUNE; an immunostimulatory oligonucleotide; incomplete Freund's adjuvant; complete Freund's adjuvant; vitamin E; a water-in-oil emulsion prepared from a biodegradable oil; MONTANIDE, such as MONTANIDE ISA51 and MONTANIDE ISA720; Quil A; micellular mixtures of Quil A and cholesterol known as immunostimulating complexes (ISCOMS); a MPL and mycobacterial cell wall skeleton combination; ENHANZYN; RC-529; RC-552; CRL-1005; L-121; alpha-galactosylceramide; a composition of biodegradable particles composed of poly-lactide-co-glycolide (PLG) or other similar polymers; a composition of aluminum or iron oxide beads or a combination thereof. Other specific examples of adjuvants include QS-21 fractions, such as crude QA-21, a QA-21H form, QA-21-V1; QA-21-V2; a combination of QA-21-V1 and QA-21-V2, and chemically modified forms or combinations thereof. In some embodiments the preferred adjuvant is QS-21.

As used herein a "saponin-based adjuvant" is any adjuvant that is based on or includes a saponin or portion thereof. Therefore, saponin-based adjuvants include saponins, saponin fractions and modified saponins (e.g., chemically modified saponins).

In another embodiment the compositions provided herein can also include a cancer therapeutic agent. Cancer therapeutic agents include any agent used to treat cancer in a subject. In some embodiments the cancer therapeutic agent is a chemotherapeutic agent, such as, for example, docetaxel. Cancer therapeutic agents also include anti-inflammatory agents and immunomodulatory agents. The anti-inflammatory agent in one embodiment is prednisone. In another embodiment the immunomodulatory agent is a cytokine.

In other embodiments the compositions provided can also include at least one buffer. Buffers include PBS (phosphate buffered saline), citric acid, sodium citrate, sodium acetate, acetic acid, sodium phosphate, phosphoric acid, sodium ascorbate, tartartic acid, maleic acid, glycine, sodium lactate, lactic acid, ascorbic acid, imidazole, sodium bicarbonate, carbonic acid, sodium succinate, succinic acid, histidine, sodium benzoate, benzoic acid and combinations thereof.

In some embodiments the compositions provided further include a free amino acid. These free amino acids can be naturally or non-naturally occurring. In some embodiments the free amino acids are non-acidic free amino acids. Examples of non-acidic free amino acids include glycine, proline, isoleucine, leucine, alanine, arginine and combinations thereof.

Compositions of PSMA protein multimers including a surfactant are also provided. Such surfactants include TWEEN20, TWEEN80, Triton X-100, dodecylmaltoside, cholic acid, CHAPS and combinations thereof.

Also provided are compositions of PSMA protein multimers that comprise a cryoprotectant, an antioxidant, a preservative or a combination thereof. Examples of cryoprotectants include a sugar, a polyol, an amino acid, a polymer, an inorganic salt, an organic salt, trimethylamine N-oxide, sarcosine, betaine, gamma-aminobutyric acid, octapine, alanopine, strombine, dimethylsulfoxide and ethanol. When the cryoprotectant is a sugar the sugar can be sucrose, lactose, glucose, trehalose or maltose. In other embodiments when the cryoprotectant is a polyol the polyol can be inositol, ethylene glycol, glycerol, sorbitol, xylitol, mannitol or 2-methyl-2,4-pentane-diol. When the cryoprotectant is an amino acid the amino acid can be Na glutamate, proline, alpha-alanine, beta-alanine, glycine, lysine-HCl or 4-hydroxyproline. When the cryoprotectant is a polymer the polymer can be polyethylene glycol, dextran or polyvinylpyrrolidone. When the cryoprotectant is an inorganic salt the cryoprotectant can be sodium sulfate, ammonium sulfate, potassium phosphate, magnesium sulfate or sodium fluoride. Finally, when the cryoprotectant is an organic salt the organic salt can be sodium acetate, sodium polyethylene, sodium caprylate, proprionate, lactate or succinate. Examples of antioxidants that are part of these composition in some embodiments include ascorbic acid, an ascorbic acid derivative, butylated hydroxy anisole, butylated hydroxy toluene, alkylgallate, dithiothreitol (DTT), sodium meta-bisulfite, sodium bisulfite, sodium dithionite, sodium thioglycollic acid, sodium formaldehyde sulfoxylate, tocopherol, a tocopherol derivative, monothioglycerol and sodium sulfite. Ascorbic acid derivatives, in some embodiments, include ascorbylpalmitate, ascorbylstearate, sodium ascorbate and calcium ascorbate, while tocopherol derivatives include d-alpha tocopherol, d-alpha tocopherol acetate, dl-alpha tocopherol acetate, d-alpha tocopherol succinate, beta tocopherol, delta tocopherol, gamma tocopherol and d-alpha tocopherol polyoxyethylene glycol 1000 succinate. Examples of preservatives present in the compositions in some embodiments include benzalkonium chloride, chlorobutanol, parabens, thimerosal, benzyl alcohol and phenol.

The composition in some embodiments are physiologically acceptable compositions.

The compositions provided are, in some embodiments, in liquid or lyophilized form.

In some other embodiments the compositions provided are sterile.

In other aspects of the invention pharmaceutical compositions are provided which contain any of the compositions provided herein and a pharmaceutically acceptable carrier.

The present invention also relates, in part, to antibodies or antigen-binding fragments thereof which specifically bind the extracellular domain of prostate specific membrane antigen (PSMA), compositions containing one or a combination of such antibodies or antigen-binding fragments thereof, hybridoma cell lines that produce the antibodies, and methods of using the antibodies or antigen-binding fragments thereof for cancer diagnosis and treatment.

According to one aspect of the invention, isolated antibodies or an antigen-binding fragments thereof are provided. The antibodies or fragments thereof specifically bind to an extracellular domain of prostate specific membrane antigen (PSMA), and competitively inhibit the specific binding of a second antibody to its target epitope on PSMA. In a second aspect of the invention, isolated antibodies or antigen-binding fragments thereof are provided which specifically bind to an epitope on prostate specific membrane antigen (PSMA) defined by a second antibody. In each of the forgoing aspects of the invention, the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1, and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13.

In certain embodiments, the antibody or antigen-binding fragment thereof is selected from the group consisting of PSMA 3.7, PSMA 3.8, PSMA 3.9, PSMA 3.11 PSMA 5.4, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, and Abgenix 4.152.1. In other embodiments, the antibody or antigen-binding fragment thereof is selected from the group consisting of antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13, and antigen-binding fragments thereof.

In further embodiments, the antibody or antigen-binding fragments thereof is encoded by a nucleic acid molecule comprising a nucleotide sequence that is at least about 90% identical to the nucleotide sequence encoding the foregoing antibodies, preferably at least about 95% identical, more preferably at least about 97% identical, still more preferably at least about 98% identical, and most preferably is at least about 99% identical.

In some embodiments of the foregoing aspects, antigen-binding fragments of the isolated antibodies are provided. The antigen-binding fragments include (a) a heavy chain variable region encoded by a nucleic acid molecule comprising the coding regions or regions of a nucleotide sequence selected from the group consisting of nucleotide sequences set forth as: SEQ ID NOs: 14, 18, 22, 26 and 30, and (b) a light chain variable region encoded by a nucleic acid molecule comprising the coding region or region of a nucleotide sequence selected from the group consisting of nucleotide sequences set forth as: SEQ ID NOs: 16, 20, 24, 28 and 32. In other embodiments, the antigen-binding fragment includes (a) a heavy chain variable region comprising an amino acid sequence selected from the group consisting of amino acid sequences set forth as: SEQ ID NOs: 15, 19, 23, 27 and 31, and (b) a light chain variable region comprising an amino acid sequence selected from the group consisting of nucleotide sequences set forth as: SEQ ID NOs: 17, 21, 25, 29 and 33.

In a further embodiments of the invention, isolated antigen-binding fragments of antibodies, which include a CDR of the foregoing antigen-binding fragments are provided. Preferably the CDR is CDR3.

According to another aspect of the invention, expression vectors including an isolated nucleic acid molecule encoding the foregoing isolated antibodies or antigen-binding fragments are provided. Host cells transformed or transfected by these expression vectors also are provided.

In certain embodiments, the antibody or antigen-binding fragment thereof is selected for its ability to bind live cells, such as a tumor cell or a prostate cell, preferably LNCaP cells. In other embodiments, the antibody or antigen-binding fragment thereof mediates cytolysis of cells expressing PSMA. Preferably cytolysis of cells expressing PSMA is mediated by effector cells or is complement mediated in the presence of effector cells.

In other embodiments, the antibody or antigen-binding fragment thereof inhibits the growth of cells expressing PSMA. Preferably the antibody or antigen-binding fragment thereof does not require cell lysis to bind to the extracellular domain of PSMA.

In further embodiments, the antibody or antigen-binding fragment thereof is selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgAsec, IgD or IgE. In other embodiments, the antibody is a bispecific or multispecific antibody.

In still other embodiments, the antibody is a recombinant antibody, a polyclonal antibody, a monoclonal antibody, a humanized antibody or a chimeric antibody, or a mixture of these. In particularly preferred embodiments, the antibody is a human antibody, e.g., a monoclonal antibody, polyclonal antibody or a mixture of monoclonal and polyclonal antibodies. In still other embodiments, the antibody is a bispecific or multispecific antibody.

Preferred antigen-binding fragments include a Fab fragment, a F(ab')$_2$ fragment, and a Fv fragment CDR3.

In further embodiments, the isolated antibody or antigen-binding fragment is a monoclonal antibody produced by a hybridoma cell line selected from the group consisting of PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3247), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653).

In certain other embodiments, the antibody or antigen-binding fragment thereof binds to a conformational epitope and/or is internalized into a cell along with the prostate specific membrane antigen. In other embodiments, the isolated antibody or antigen-binding fragment thereof is bound to a label, preferably one selected from the group consisting of a fluorescent label, an enzyme label, a radioactive label, a nuclear magnetic resonance active label, a luminescent label, and a chromophore label.

In still other embodiments, the isolated antibody or antigen-binding fragment thereof is bound to at least one therapeutic moiety, such as a drug, preferably a cytotoxic drug, a replication-selective virus, a toxin or a fragment thereof, or an enzyme or a fragment thereof. Preferred cytotoxic drug include: calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. In other embodiments, the therapeutic moiety is an immunostimulatory or immunomodulating agent, preferably one selected from the group consisting of: a cytokine, chemokine and adjuvant.

In some embodiments, the antibodies or antigen-binding fragments of the invention specifically bind cell-surface PSMA and/or rsPSMA with a binding affinity of about $1 \times 10^{-9}$ M or less. Preferably, the binding affinity is about $1 \times 10^{-10}$ M or less, more preferably the binding affinity is about $1 \times 10^{-11}$ M or less. In other embodiments the binding affinity is less than about $5 \times 10^{-10}$ M.

In additional embodiments, the antibodies or antigen-binding fragments of the invention mediate specific cell killing of PSMA-expressing cells with an IC$_{50}$ of less than about $1 \times 10^{-10}$ M. Preferably the IC$_{50}$ is less than about $1 \times 10^{-11}$ M.

More preferably the $IC_{50}$ is less than about $1 \times 10^{-12}$M. In other embodiments the $IC_{50}$ is less than about $1.5 \times 10^{-11}$M.

In yet other embodiments, the isolated antibody or antigen-binding fragment thereof is bound to a radioisotope. The radioisotope can emit α radiations, β radiations, or γ radiations. Preferably the radioisotope is selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{212}$Pb, $^{224}$Ra and $^{223}$Ra.

According to another aspect of the invention, hybridoma cell lines are provided that produce an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1 and Abgenix 4.152.1. In some embodiments, the hybridoma cell line is selected from the group consisting of PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3247), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653).

According to a further aspect of the invention, compositions are provided that include the foregoing antibodies or antigen-binding fragments thereof and a pharmaceutically acceptable carrier, excipient, or stabilizer. Other compositions include a combination of two or more of the foregoing antibodies or antigen-binding fragments thereof and a pharmaceutically acceptable carrier, excipient, or stabilizer. In some embodiments, the compositions also include an antitumor agent, an immunostimulatory agent, an immunomodulator, or a combination thereof. Preferred antitumor agents include a cytotoxic agent, an agent that acts on tumor neovasculature, or a combination thereof. Preferred immunomodulators include α-interferon, γ-interferon, tumor necrosis factor-α or a combination thereof. Preferred immunostimulatory agents include interleukin-2, immunostimulatory oligonucleotides, or a combination thereof.

According to another aspect of the invention antibodies or antigen-binding fragments thereof that mediate antibody-dependent cellular cytotoxicity (ADCC) are provided. In some embodiments these antibodies or antigen-binding fragments thereof mediate ADCC of human prostate cancer cells. In other embodiments the antibodies are human antibodies. In still other embodiments the antibodies are capable of causing at least 5%, 10%, 15%, 20%, 25%, 30%, 35%, 40%, 50%, 75% or more cell lysis in vitro with an effector to target ratio of 5:1, 10:1, 15:1, 20:1, 25:1, 30:1, 40:1, 50:1 or more. In other embodiments these antibodies mediate more ADCC than control antibodies.

According to another aspect of the invention, kits for detecting prostate cancer for diagnosis, prognosis or monitoring are provided. The kits include the foregoing isolated labeled antibody or antigen-binding fragment thereof, and one or more compounds for detecting the label. Preferably the label is selected from the group consisting of a fluorescent label, an enzyme label, a radioactive label, a nuclear magnetic resonance active label, a luminescent label, and a chromophore label.

The invention in another aspect provides one or more of the foregoing isolated antibodies or antigen-binding fragments thereof packaged in lyophilized form, or packaged in an aqueous medium.

In another aspect of the invention, methods for detecting the presence of PSMA, or a cell expressing PSMA, in a sample are provided. The methods include contacting the sample with any of the foregoing antibodies or antigen-binding fragments thereof which specifically bind to an extracellular domain of PSMA, for a time sufficient to allow the formation of a complex between the antibody or antigen-binding fragment thereof and PSMA, and detecting the PSMA-antibody complex or PSMA-antigen-binding fragment complex. The presence of a complex in the sample is indicative of the presence in the sample of PSMA or a cell expressing PSMA.

In another aspect, the invention provides other methods for diagnosing a PSMA-mediated disease in a subject. The methods include administering to a subject suspected of having or previously diagnosed with PSMA-mediated disease an amount of any of the foregoing antibodies or antigen-binding fragments thereof which specifically bind to an extracellular domain of prostate specific membrane antigen. The method also includes allowing the formation of a complex between the antibody or antigen-binding fragment thereof and PSMA, and detecting the formation of the PSMA-antibody complex or PSMA-antigen-binding fragment antibody complex to the target epitope. The presence of a complex in the subject suspected of having or previously diagnosed with prostate cancer is indicative of the presence of a PSMA-mediated disease.

In certain embodiments of the methods, the PSMA-mediated disease is prostate cancer. In other embodiments, the PSMA-mediated disease is a non-prostate cancer, such as those selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma.

In preferred embodiments of the foregoing methods, the antibody or antigen-binding fragment thereof is labeled. In other embodiments of the foregoing methods, a second antibody is administered to detect the first antibody or antigen-binding fragment thereof.

In a further aspect of the invention, methods for assessing the prognosis of a subject with a PSMA-mediated disease are provided. The methods include administering to a subject suspected of having or previously diagnosed with PSMA-mediated disease an effective amount of an antibody or antigen-binding fragment thereof, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the prognosis.

In another aspect of the invention, methods for assessing the effectiveness of a treatment of a subject with a PSMA-mediated disease are provided. The methods include administering to a subject suspected treated for a PSMA-mediated disease an effective amount of the foregoing antibodies or antigen-binding fragments thereof, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the effectiveness of the treatment.

In certain embodiments of these two aspects of the invention, the PSMA-mediated disease is prostate cancer. In other embodiments, the PSMA-mediated disease is a non-prostate cancer. In those embodiments, the non-prostate cancer preferably is selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma. In still other embodiments, the antibody or antigen-binding fragment thereof is labeled. In further embodiments, a second antibody is administered to detect the first antibody or antigen-binding fragment thereof.

According to yet another aspect of the invention, methods for inhibiting the growth of a cell expressing PSMA are provided. The methods include contacting a cell expressing PSMA with an amount of at least one of the foregoing antibodies or antigen-binding fragments thereof which specifically binds to an extracellular domain of PSMA effective to inhibit the growth of the cell expressing PSMA.

According to another aspect of the invention, methods for inducing cytolysis of a cell expressing PSMA are provided. The methods include contacting a cell expressing PSMA with an amount of at least one of the foregoing antibodies or antigen-binding fragments thereof which specifically binds to an extracellular domain of PSMA effective to induce cytolysis of the cell expressing PSMA. In certain embodiments, the cytolysis occurs in the presence of an effector cell. In other embodiments, the cytolysis is complement mediated.

According to still another aspect of the invention, methods for treating or preventing a PSMA-mediated disease are provided. The methods include administering to a subject having a PSMA-mediated disease an effective amount of at least one of the forgoing antibodies or antigen-binding fragments thereof to treat or prevent the PSMA-mediated disease. In some embodiments, the PSMA-mediated disease is a cancer, such as prostate cancer or a non-prostate cancer (including the nonprostate cancers described elsewhere herein).

In yet a further aspect of the invention, methods for treating or preventing a PSMA-mediated disease are provided. The methods include administering to a subject having a PSMA-mediated disease or at risk of having a PSMA-mediated disease an amount of at least one of the foregoing antibodies or antigen-binding fragments thereof effective to treat or prevent the PSMA-mediated disease.

In some embodiments, the PSMA-mediated disease is a cancer, such as prostate cancer or a non-prostate cancer (including the nonprostate cancers described elsewhere herein).

In other embodiments, the method also includes administering another therapeutic agent to treat or prevent the PSMA-mediated disease at any time before, during or after the administration of the antibody or antigen-binding fragment thereof. In some of these embodiments, the therapeutic agent is a vaccine, and preferably the vaccine immunizes the subject against PSMA.

In still other embodiments, the antibody or antigen-binding fragment thereof is bound to at least one therapeutic moiety, preferably a cytotoxic drug, a drug which acts on the tumor neovasculature and combinations thereof. Preferred cytotoxic drugs are selected from the group consisting of: calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE.

In other embodiments, the antibody or antigen-binding fragment thereof is bound to a radioisotope and the radiations emitted by the radioisotope is selected from the group consisting of $\alpha$, $\beta$ and $\gamma$ radiations. Preferably, the radioisotope is selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Ho, $^{64}$Cu, $^{212}$Pb, $^{224}$Ra and $^{223}$Ra.

The present invention provides methods for modulating at least one enzymatic activity of PSMA. As used in preferred embodiments of the methods, "modulating" an enzymatic activity of PSMA means enhancing or inhibiting the enzymatic activity. Thus in certain aspects of the invention, methods for inhibiting an enzymatic activity of PSMA are provided, and in other aspects of the invention, methods for enhancing an enzymatic activity of PSMA are provided. The terms "enhancing" and "inhibiting" in this context indicate that the enzymatic activity of PSMA is enhanced or inhibited in the presence of an antibody that specifically binds PSMA, or antigen-binding fragment thereof, relative to the level of activity in the absence of such an antibody or antigen-binding fragment thereof. Enzymatic activities of PSMA include folate hydrolase activity, N-acetylated $\alpha$-linked acidic dipeptidase (NAALADase) activity, dipeptidyl dipeptidase IV activity and $\gamma$-glutamyl hydrolase activity.

Thus the invention in another aspect provides methods for modulating folate hydrolase activity. In certain embodiments of these methods, the activity is inhibited and in other embodiments, the activity is enhanced. The methods include contacting a folate hydrolase polypeptide with an amount of the foregoing isolated antibody or antigen-binding fragment thereof, under conditions wherein the isolated antibody or antigen-binding fragment thereof modulates the folate hydrolase activity. The folate hydrolase polypeptide can be isolated, contained in a sample such as a cell, a cell homogenate, a tissue, or a tissue homogenate, or contained in an organism. The organism preferably is an animal, particularly preferably a mammal.

In another aspect of the invention, methods for modulating N-acetylated $\alpha$-linked acidic dipeptidase (NAALADase) activity are provided. In certain embodiments of these methods, the activity is inhibited and in other embodiments, the activity is enhanced. The methods include contacting a NAALADase polypeptide with an amount of the foregoing isolated antibody or antigen-binding fragment thereof under conditions wherein the isolated antibody or antigen-binding fragment thereof modulates NAALADase activity. The NAALADase polypeptide can be isolated, contained in a sample such as a cell, a cell homogenate, a tissue, or a tissue homogenate, or contained in an organism. The organism preferably is an animal, particularly preferably a mammal.

In yet another aspect of the invention, methods for modulating dipeptidyl dipeptidase IV activity are provided. In certain embodiments of these methods, the activity is inhibited and in other embodiments, the activity is enhanced. The methods include contacting a dipeptidyl dipeptidase IV polypeptide with an amount of the foregoing isolated antibody or antigen-binding fragment thereof under conditions wherein the isolated antibody or antigen-binding fragment thereof modulates dipeptidyl dipeptidase IV activity. The dipeptidyl dipeptidase IV polypeptide can be isolated, contained in a sample such as a cell, a cell homogenate, a tissue, or a tissue homogenate, or contained in an organism. The organism preferably is an animal, particularly preferably a mammal.

In yet another aspect of the invention, methods for modulating γ-glutamyl hydrolase activity are provided. In certain embodiments of these methods, the activity is inhibited and in other embodiments, the activity is enhanced. The methods include contacting a γ-glutamyl hydrolase polypeptide with an amount of the foregoing isolated antibody or antigen-binding fragment thereof under conditions wherein the isolated antibody or antigen-binding fragment thereof modulates γ-glutamyl hydrolase activity. The γ-glutamyl hydrolase polypeptide can be isolated, contained in a sample such as a cell, a cell homogenate, a tissue, or a tissue homogenate, or contained in an organism. The organism preferably is an animal, particularly preferably a mammal.

Methods of specific delivery of at least one therapeutic agent to PSMA-expressing cells are provided according to another aspect of the invention. The methods include administering an effective amount of at least one of the foregoing antibodies or antigen-binding fragments thereof conjugated to the at least one therapeutic agent. In some embodiments, the therapeutic agent is a nucleic acid molecule, an antitumor drug, a toxin or a fragment thereof, an enzyme or a fragment thereof, a replication-selective virus, or an immunostimulatory or immunomodulating agent. Preferred antitumor drugs include cytotoxic drugs, drugs which act on the tumor neovasculature and combinations thereof. Preferred cytotoxic drugs include calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E and auristatin PHE. Preferred immunostimulatory or immunomodulating agent included cytokines, chemokines and adjuvants.

In still another aspect of the invention, isolated antibodies that selectively bind a PSMA protein multimer are provided. In preferred embodiments, the PSMA protein multimer is a dimer, and preferably at least one of the PSMA proteins forming the multimer is a recombinant, soluble PSMA (rsPSMA) polypeptide. Preferably the rsPSMA polypeptide consists essentially of amino acids 44-750 of SEQ ID NO:1.

In a further aspect of the invention, isolated antibodies are provided that selectively bind a PSMA protein multimer and modulate one or more enzymatic activities of the PSMA protein multimer. As used in preferred embodiments of this aspect of the invention, "modulating" an enzymatic activity of a PSMA multimer means enhancing or inhibiting the enzymatic activity. Thus in certain aspects of the invention, antibodies that inhibit an enzymatic activity of PSMA multimers are provided, and in other aspects of the invention, antibodies that inhibit an enzymatic activity of PSMA multimers are provided. The terms "enhancing" and "inhibiting" in this context indicate that the enzymatic activity of a PSMA multimer is enhanced or inhibited in the presence of an antibody that specifically binds the PSMA multimers, or antigen-binding fragment thereof, relative to the level of activity in the absence of such an antibody or antigen-binding fragment thereof. In some embodiments, the enzymatic activity is selected from the group consisting of folate hydrolase activity, NAALADase activity, dipeptidyl dipeptidase IV activity and γ-glutamyl hydrolase activity. In other embodiments, the enzymatic activity is in the extracellular domain of the PSMA molecule. In still other embodiments, the antibody or antigen-binding fragment thereof specifically binds to an extracellular domain of PSMA.

In a further aspect, an isolated antibody or antigen-binding fragment thereof is provided that selectively binds a PSMA protein multimer. In this aspect, the isolated antibody is raised by immunizing an animal with a preparation comprising a PSMA protein multimer. Preferred preparations used in raising the antibody include those having at least about 10%, 20%, 30%, 40%, 50%, 75%, 90%, or 95% PSMA protein multimer. Preferably the PSMA protein multimer is a dimer.

In yet another aspect of the invention, compositions are provided that include one or more of the foregoing isolated antibodies, and an immunostimulatory molecule, such as an adjuvant and/or and a cytokine. Preferably the immunostimulatory molecule is IL-2 or an immunostimulatory oligonucleotide. In certain embodiments, the foregoing compositions also include a pharmaceutically-acceptable carrier.

The invention also includes methods for inducing an immune response, including administering to a subject in need of such treatment an effective amount of the foregoing isolated antibodies or compositions.

The invention provides, in another aspect, isolated antibodies or antigen-binding fragments thereof that selectively bind a PSMA protein multimer and modulate at least one enzymatic activity of PSMA. As used in preferred embodiments of this aspect of the invention, "modulating" an enzymatic activity of a PSMA means enhancing or inhibiting the enzymatic activity. Thus in certain aspects of the invention, antibodies that inhibit an enzymatic activity of PSMA are provided, and in other aspects of the invention, antibodies that inhibit an enzymatic activity of PSMA are provided. The terms "enhancing" and "inhibiting" in this context indicate that the enzymatic activity of PSMA is enhanced or inhibited in the presence of an antibody that specifically binds PSMA, or antigen-binding fragment thereof, relative to the level of activity in the absence of such an antibody or antigen-binding fragment thereof. The enzyme, in certain embodiments, is selected from the group consisting of hydrolases and peptidases. Preferred hydrolases include folate hydrolase and γ-glutamyl hydrolase. In a particularly preferred embodiment of PSMA inhibition, the hydrolase is folate hydrolase and the antibody is mAb 5.4 or mAb 3.9. Preferred peptidases include NAALADase and dipeptidyl dipeptidase IV. In some embodiments, the enzyme is active in cancer cells and has lesser activity in normal cells than in cancer cells or, preferably, no activity in normal cells. In preferred embodiments, the cancer cells in which the enzyme is active are prostate cancer cells. Compositions including the foregoing isolated antibodies or antigen-binding fragments thereof, and a pharmaceutically acceptable carrier, also are provided by the invention.

In another aspect of the invention, compositions are provided that include an isolated PSMA protein multimer. Preferably the PSMA protein multimer is a dimer. In certain embodiments, the compositions include at least about 10%, 20%, 30%, 40%, 50%, 75%, 90%, or 95% PSMA protein multimer. In other embodiments, the PSMA protein multimer comprises noncovalently associated PSMA proteins. The PSMA proteins preferably are noncovalently associated under nondenaturing conditions.

In certain embodiments of the foregoing compositions, at least one of the PSMA proteins forming the multimer is a recombinant, soluble PSMA (rsPSMA) polypeptide. In other embodiments, the PSMA protein multimer is reactive with a conformation-specific antibody that specifically recognizes PSMA. Preferably, the PSMA protein multimer comprises PSMA proteins in a native conformation and/or the PSMA multimer is enzymatically active. In preferred embodiments, the enzymatic activity is folate hydrolase activity, NAALADase activity, dipeptidyl dipeptidase IV activity and/or γ-glutamyl hydrolase activity.

In still other embodiments, the foregoing compositions also include an adjuvant and/or a cytokine or other immunostimulatory molecule. Preferred cytokines include IL-2, IL-12, IL-18 and GM-CSF. In further embodiments, the foregoing compositions also include a pharmaceutically acceptable carrier.

According to yet another aspect of the invention, methods for inducing an immune response are provided. The methods include administering to a subject in need of such treatment an effective amount of one or more of the foregoing compositions.

In a further aspect, the invention includes isolated recombinant soluble PSMA (rsPSMA) protein multimers and isolated rsPSMA protein dimers. In some embodiments, the dimer includes noncovalently associated rsPSMA proteins, and preferably the rsPSMA proteins are noncovalently associated under nondenaturing conditions. In other embodiments, the isolated rsPSMA dimer is reactive with a conformation-specific antibody that specifically recognizes PSMA.

In a certain preferred embodiment, the isolated rsPSMA dimer is enzymatically active, with the enzymatic activity selected from the group consisting of folate hydrolase activity, NAALADase activity, dipeptidyl dipeptidase IV activity and γ-glutamyl hydrolase activity.

In still another aspect of the invention, methods of screening for a candidate agent that modulates at least one enzymatic activity of a PSMA enzyme are provided. As used in preferred embodiments of the methods, "modulating" an enzymatic activity of PSMA means enhancing or inhibiting the enzymatic activity. Thus in certain aspects of the invention, methods for screening for a candidate agent that inhibits an enzymatic activity of PSMA are provided, and in other aspects of the invention, methods for screening for a candidate agent that enhances an enzymatic activity of PSMA are provided. The terms "enhancing" and "inhibiting" in this context indicate that the enzymatic activity of PSMA is enhanced or inhibited in the presence of a candidate agent relative to the level of activity in the absence of such an agent. The methods include mixing the candidate agent with an isolated PSMA protein multimer to form a reaction mixture, followed by adding a substrate for the PSMA enzyme to the reaction mixture, and determining the amount of a product formed from the substrate by the PSMA enzyme. A change in the amount of product formed in comparison to a control is indicative of an agent capable of modulating at least one enzymatic activity of the PSMA enzyme. A decrease in the amount of product formed in comparison to a control is indicative of an agent capable of inhibiting at least one enzymatic activity of the PSMA enzyme. An increase in the amount of product formed in comparison to a control is indicative of an agent capable of enhancing at least one enzymatic activity of the PSMA enzyme. In some embodiments the PSMA enzyme is selected from the group consisting of NAALADase, folate hydrolase, dipeptidyl dipeptidase IV and γ-glutamyl hydrolase. In other embodiments the PSMA multimer comprises recombinant, soluble PSMA. In yet other embodiments the candidate agent is selected from the group consisting of an antibody, a small organic compound, or a peptide.

In another aspect of the invention, candidate agents that modulate at least one enzymatic activity of PSMA are provided. The candidate agents are identified according to the foregoing methods. Thus in certain aspects of the invention, candidate agents that inhibit an enzymatic activity of PSMA are provided, and in other aspects of the invention, candidate agents that enhance an enzymatic activity of PSMA are provided. In certain embodiments, the agent is selected from a combinatorial antibody library, a combinatorial protein library, or a small organic molecule library.

The invention also provides methods for identifying compounds that promote dissociation of PSMA dimers. The methods include contacting a PSMA dimer with a compound under conditions that do not promote dissociation of the PSMA dimer in the absence of the compound, measuring the amount of PSMA monomer and/or dimer; and comparing the amount of PSMA monomer and/or dimer measured in the presence of the compound with that observed in the absence of the compound. An increase in the amount of PSMA monomer measured in the presence of the compound indicates that the compound is capable of promoting dissociation of the PSMA dimer. A decrease in the amount of PSMA dimer measured in the presence of the compound indicates that the compound is capable of promoting dissociation of the PSMA dimer. When the amounts of PSMA monomer and PSMA dimer are measured, the methods can include calculating a ratio of PSMA monomer to PSMA dimer and comparing the ratio obtained in the presence of the compound with that obtained in the absence of the compound. In such methods, an increase in the ratio measured in the presence of the compound indicates that the compound is capable of promoting dissociation of the PSMA dimer.

The use of the foregoing compositions, molecules and agents in the preparation of medicaments also is provided. In preferred embodiments, the medicaments are useful in the treatment of conditions related to hyperproliferative diseases including cancer, and diseases of inappropriate NAALADase activity, folate hydrolase activity, dipeptidyl dipeptidase IV activity and/or γ-glutamyl hydrolase activity.

Each of the limitations of the invention can encompass various embodiments of the invention. It is, therefore, anticipated that each of the limitations of the invention involving any one element or combinations of elements can be included in each aspect of the invention.

These and other aspects of the invention will be described in further detail in connection with the detailed description of the invention.

BRIEF DESCRIPTION OF THE DRAWINGS

FIG. 6 provides the results for the determination of the dimeric structure of PSMA.

FIG. 13 depicts the cloning protocol for IgG1 antibody cloning into pcDNA. The first four primers shown are set forth as SEQ ID NOs: 34-37, respectively, and the first two amino acid sequences shown are set forth as SEQ ID NOs: 38 and 39, respectively.

FIG. 28 illustrates the binding of the anti-PSMA Abs.

DETAILED DESCRIPTION OF THE INVENTION

Figure 1:
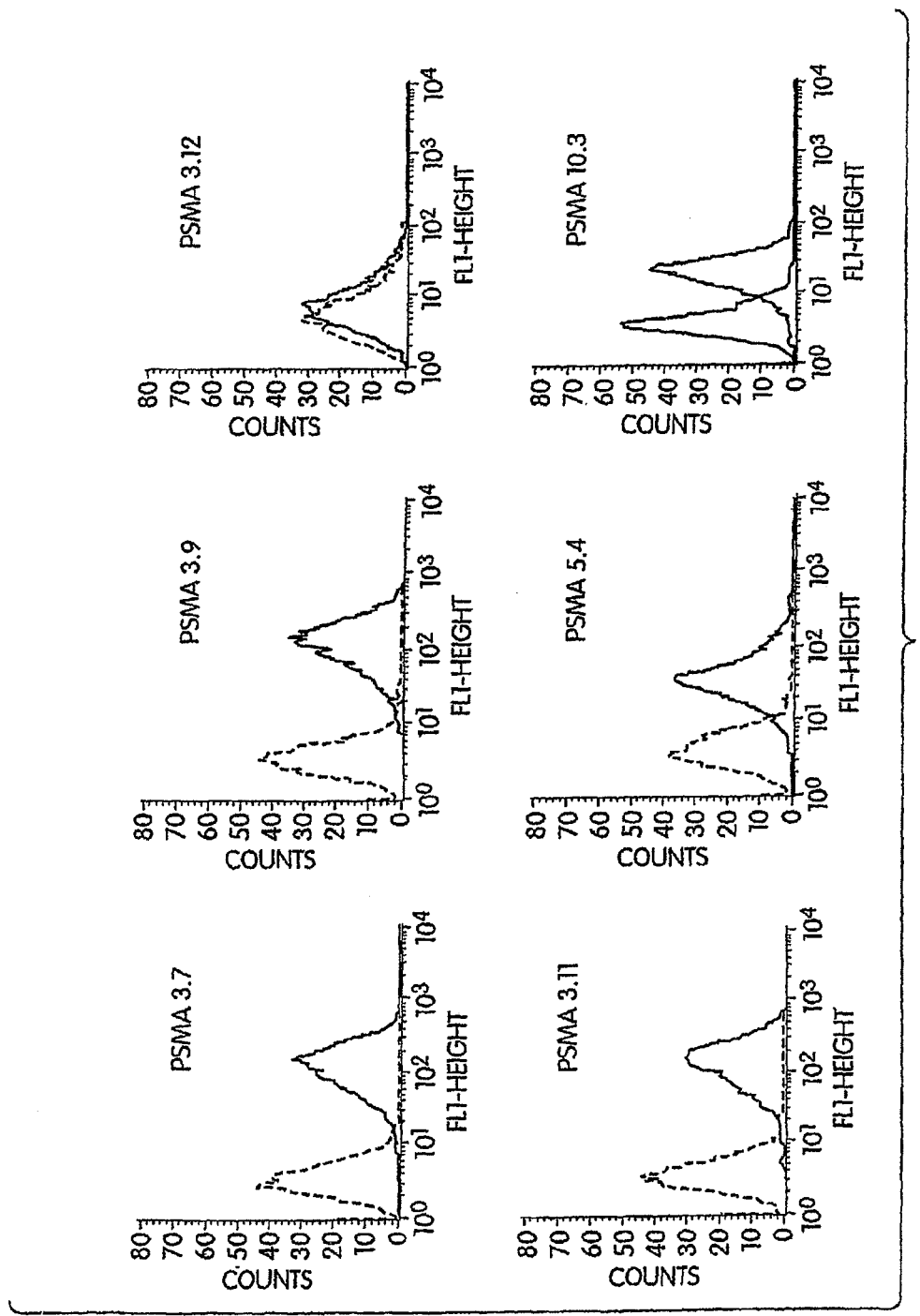
FIG. 1 depicts PSMA reactivity of mAbs as determined by flow cytometry. Anti-PSMA mAbs (3.7, 3.9, 3.11, 3.12, 5.4, and 10.3) incubated with either parental 3T3 cells (denoted by black lines) or 3T3 cells engineered to express cell-surface PSMA (3T3-PSMA; gray lines).

The present invention provides, in part, multimeric, particularly dimeric, forms of PSMA protein, compositions and kits containing dimeric PSMA protein as well as methods of producing, purifying, processing and using these compositions. Such methods include methods for eliciting or enhancing an immune response to PSMA and/or cells expressing PSMA. Such methods include methods of producing antibodies to dimeric PSMA as well as methods of treating cancer, such as prostate cancer.

Prostate specific membrane antigen (PSMA) is a 100 kD Type II membrane glycoprotein expressed in prostate tissues and was originally identified by reactivity with a monoclonal antibody designated 7E11-05 (Horoszewicz et al., 1987, *Anticancer Res.* 7:927-935; U.S. Pat. No. 5,162,504). PSMA was obtained in purified form (Wright et al., 1990, Antibody Immunoconjugates and Radio Pharmaceuticals 3:Abstract 193) and characterized as a type II transmembrane protein having sequence identity with the transferrin receptor (Israeli et al., 1994, *Cancer Res.* 54:1807-1811) and with NAALA-Dase activity (Carter et al., 1996, *Proc. Natl. Acad. Sci. U.S.A.* 93:749-753). More importantly, PSMA is expressed in increased amounts in prostate cancer, and elevated levels of PSMA are also detectable in the sera of these patients (Horoszewicz et al., 1987; Rochon et al., 1994, *Prostate* 25:219-223; Murphy et al., 1995, *Prostate* 26:164-168; and Murphy et al., 1995, *Anticancer Res.* 15:1473-1479). PSMA expression increases with disease progression, becoming highest in metastatic, hormone-refractory disease for which there is no present therapy. Provocative recent data indicates that PSMA is also abundantly expressed on the neovasculature of a variety of other important tumors, including bladder, pancreas, sarcoma, melanoma, lung, and kidney tumor cells, but not on normal vasculature.

It has been discovered that PSMA in its native form is a homodimer. When ordinary isolation techniques are followed, however, the native form of PSMA is not typically maintained. Compositions of isolated PSMA protein that include isolated multimeric PSMA, particularly dimeric PSMA, therefore, are provided. These compositions include isolated PSMA protein, wherein at least about 5% of the isolated PSMA protein is in multimeric form. Other compositions are provided where at least about 10%, 15%, 20%, 25%, 30%, 35%, 40%, 45%, 50%, 55%, 60%, 65%, 70%, 75%, 80%, 85%, 90%, 95% or more of the isolated PSMA protein is in multimeric form. In a preferred embodiment, the PSMA protein multimer composition contains substantially pure PSMA protein multimer, with substantially no PSMA protein monomer. It is understood that the list of specific percentages includes by inference all of the unnamed percentages between the recited percentages. It has further been discovered that certain agents preserve or promote the multimeric, particularly the dimeric, association of isolated PSMA. Compositions of isolated PSMA protein that include these agents as well as methods of purifying and processing isolated PSMA protein compositions are, therefore, also provided.

As used herein "PSMA protein" includes the full-length PSMA protein (provided as SEQ ID NO: 1) or a portion thereof. These proteins are capable of forming multimers or aggregates of PSMA protein. As used herein, a "multimer or aggregate of PSMA protein" refers to the association of two or more PSMA proteins. Preferably, the PSMA proteins described herein are those that are capable of forming a dimer like that of native PSMA by non-covalent interactions or engineered to form a stable native-like dimer through covalent bonds, such as disulfide bonds. "A dimer like that of native PSMA" includes two PSMA proteins that are associated in the same way as the protein as found in nature or in such a way as to allow for the generation of antibodies that recognize at least one antigenic epitope of the native dimer (i.e., associate in a way such as to form an antigenic region as found in the native PSMA dimer or one capable of generating cross-reacting antibodies). The antibodies generated to the dimers provided herein are, therefore, capable of recognizing the native dimer. Preferably, the antibodies generated recognize native PSMA dimer but not PSMA monomer or have greater specificity for the native PSMA dimer than the monomer. In some embodiments, the PSMA proteins provided herein are larger aggregates of PSMA (i.e., three or more PSMA protein that are associated). These aggregates are likewise capable of generating antibodies that recognize PSMA. In some embodiments, these antibodies do not recognize PSMA monomer but do recognize native PSMA dimer. In other embodiments, these antibodies have greater specificity for the native PSMA dimer rather than PSMA monomer.

PSMA multimers are typically homomultimers (i.e., the associated PSMA proteins are the same). However, in some embodiments the PSMA multimers can be heteromultimers, particularly heterodimers. As used herein a "PSMA heteromultimer" is a multimer of PSMA proteins that is composed of at least two different PSMA proteins. Examples include two PSMA fragments, where one is slightly longer than the other or when one has a conservative amino acid substitution and the other does not. The heteromultimers provided herein, like homomultimers, are capable of generating antibodies that recognize native PSMA dimer. In preferred embodiments the antibodies raised against the PSMA heteromultimers recognize native PSMA dimer but not PSMA monomer. In still other preferred embodiments these antibodies have greater specificity for native PSMA dimer rather than PSMA monomer.

PSMA protein capable of forming multimers, particularly dimers, include the full-length protein (SEQ ID NO: 1). In some embodiments the PSMA protein capable of forming a multimer is the extracellular portion of PSMA (amino acids 44-750 of SEQ ID NO: 1). In other embodiments the PSMA protein capable of forming a multimer is PSM' (amino acids 58-750 of SEQ ID NO: 1), an alternatively spliced form of PSMA. In yet other embodiments fragments of the full-length protein, the extracellular portion or PSM' are capable of forming multimers. For example, these fragments include truncated PSMA proteins that begin at amino acid 44, 45, 46, 47, 48, 49, 50, 51, 52, 53, 54, 55, 56, 57, 58, 59, 60, 61, 62, 63, 64, 65, etc. of SEQ ID NO: 1 and end at amino acid 750 of SEQ ID NO: 1. Other such truncated proteins begin at amino acid 44 of SEQ ID NO: 1 and end at amino acid 749, 748, 747, 746, 745, 744, 743, 742, 741, 740, etc. of SEQ ID NO: 1. Still other truncated proteins include those that begin at amino acid 44, 45, 46, 47, 48, 49, 50, 51, 52, 53, 54, 55, 56, 57, 58, 59, 60, 61, 62, 63, 64, 65, etc. of SEQ ID NO: 1 and end at amino acid 749, 748, 747, 746, 745, 744, 743, 742, 741, 740, etc. of SEQ ID NO: 1. In some embodiments the truncated PSMA protein includes the amino acids 601-750 of SEQ ID NO: 1 or a functional portion thereof capable of forming dimers. As provided herein, the PSMA proteins are intended to encompass any fragment of the PSMA protein that is capable of forming a multimer as provided herein. Therefore, any portion of SEQ ID NO: 1 is included in this definition as well as its functional variant. Functional variants are described further herein below.

In some embodiments the isolated PSMA protein is not full-length PSM' (amino acids 58-750 of SEQ ID NO: 1) or the full-length extracellular portion of PSMA (amino acids 44-750 of SEQ ID NO: 1). In other instances, the isolated PSMA protein is not full-length PSMA (SEQ ID NO: 1). The fragment can have a size of at least about 25, 50, 100, 125, 150, 175, 200, 250, 300, 350, 400, 450, 500, 550, 600, 650, 700, or 749 amino acids and every integer length therebetween. In some embodiments, these fragments include amino acids 63-68, 132-137 or 482-487 of SEQ ID NO:1. In some other preferred instances, the PSMA protein is not membrane-bound.

Compositions of PSMA protein with agents and/or solutions that preserve or promote the multimeric association, particularly the dimeric association, of PSMA also are provided. In some instances the agents are in a solution along with the PSMA protein but are not necessarily so. An agent or solution that "preserves or promotes the dimeric association of PSMA" is one that either maintains the dimeric association (dimerization) of PSMA over time or facilitates the dimeric association of monomeric forms of the PSMA protein. For example, any solution that increases the amount of PSMA dimers, maintains the amount of PSMA dimers or retards the disassociation of PSMA dimers is encompassed by the above definition. Although the dimeric state is specifically recited, these terms are also intended to encompass other multimeric states of PSMA, and therefore, compositions, kits and methods of production and use of other multimers of PSMA.

Preferably, the "preservation or promotion of dimeric PSMA" refers to the maintenance of the dimeric state of PSMA protein for at least about 5%, 10%, 20%, 30%, 40%, 50%, 60%, 70%, 80%, 90%, 95% or more of the PSMA dimers initially present in a composition. Preferred compositions comprising the dimeric form of PSMA have less than about 35% of the monomeric form of PSMA, preferably less than about 20%, more preferably less than about 15% of the monomeric form. In one embodiment the composition has less than about 5% of the monomeric PSMA protein. The preservation or promotion of dimeric PSMA also refers to the conversion of about 5%, 10%, 20%, 30%, 40%, 50%, 60%, 70%, 80%, 90%, 95% or more of the initially monomeric PSMA to dimeric form.

The promotion of dimerization or maintenance of the dimeric state can occur at any of a number of experimental or storage temperatures. In some instances the promotion or preservation of dimeric PSMA occurs at a temperature of about 45° C. or lower. In other instances the promotion or preservation of dimeric PSMA is at a temperature of about 37° C. The promotion or preservation can also be at a temperature range of about 20° C. to about 30° C. or about or below room temperature. In other instances the promotion or preservation is at a range of about 4° C. to about 20° C. In still other instances the promotion or preservation is at about −20° C. to about 4° C. or about −80° C. to about −20° C. The promotion or preservation of the dimeric state of PSMA can also occur in a composition of PSMA protein that is in solution or in a freeze-dried form, e.g., lyophilized form. The dimeric state can also be promoted or preserved over any period of time. In some instances the period of time is at least about 1, 2, 3, 4, 5, 6, 10, 15, 20, 24, 48, 72 or more hours. In other instances the period of time is at least about 1, 2, 3, 4, 5, 10, 15, 20, 25, 30 or more days. In still other instances the period of time is at least about 1, 2, 3, 4, 5, 6, 7, 8, 9, 10, 12, 15, 20, 25, 30 or more weeks. In yet other instances, the period of time is at least about 1, 2, 3, 6, 9, 12 or more months or as long as 2 years or more. The formulations provided herein are stable during long-term storage, i.e., the formulations preserve or promote the dimeric PSMA state.

It was surprisingly discovered that pH alone can influence the dimeric state of PSMA. As described below in the Examples section, the pH at which a PSMA solution is incubated can influence the multimeric form of PSMA as well as its recovery. Incubation at various pHs for 4 days at a temperature of about 45° C. influenced the dimerization or aggregation of PSMA protein as well as the recovery of PSMA protein by analytical TSK gel filtration chromatography. The benefits of pH on the preservation of dimeric rsPSMA (2 mg/ml in PBS+) are retained when the protein solution is diluted 10-fold in a variety of buffer solutions, each containing 2 mM glycine, 2 mM citric acid, 2 mM Hepes, 2 mM MES and 2 mM Tris Base.

The dimeric structure of PSMA according to the invention is preserved at a pH in the range of about 4 to about 8. Therefore, a solution that preserves or promotes the dimerization of PSMA is one with a pH of about 4, 4.5, 5, 5.5, 6, 6.5, 7, 7.5, or 8. Recovery of dimeric PSMA from a column was better at a pH in the range of about 5 to about 7, and these pH values are preferred. In some instances, a pH of about 6 is preferred. Thus, the invention provides formulations of PSMA in solution, wherein the pH is in the range from about 4 to about 8, preferably in the range from about 5 to about 7, more preferably in the range from about 5.5 to about 7, and most preferably in the range from about 6 to about 7.

An "agent that preserves or promotes the dimeric association of PSMA" is meant to encompass an agent that promotes or maintains the dimerization of PSMA. Such agents have been found to include pH adjusting agents (as discussed above), metal ions and salts. It has been discovered that these agents, individually or in combination, are able to preserve or promote dimeric association of PSMA. In some embodiments it is the combination of the metal ion, salt or pH adjusting agent that can promote or preserve dimeric association of PSMA, while the individual metal ion, salt or pH adjusting agent cannot. As provided in the Examples, the use of chelating agents, such as EDTA, converted dimeric PSMA into the monomer. This result indicated that the presence of metal ions can positively affect the stability of the dimer. Additionally, PSMA shares modest sequence and structural homology with human transferrin receptor (TfR), which contains additional metal-binding sites within its helical domains (Lawrence, C. M., et al. (1999) Science 286, 779-782). Therefore, metal ions are considered to be agents which promote or preserve the dimeric state of PSMA protein. Such metals ions include, but are not limited to, zinc ions (e.g., $Zn^{2+}$), calcium ions (e.g., $Ca^{2+}$), magnesium ions (e.g., $Mg^{2+}$), cobalt ions (e.g., $Co^{2+}$), manganese ions (e.g., $Mn^{2+}$) or combinations thereof.

In some instances these metal ions can be added to a composition of PSMA protein in the form of a salt. Such salts include zinc chloride, calcium chloride, magnesium chloride, cobalt chloride or manganese chloride. It has been further determined that compositions of PSMA protein, wherein the dimeric state is promoted or preserved, include at least about 0.1, 0.2, 0.3, 0.4, 0.5, 0.6, 0.7, 0.8, 0.9, 1, 2, 3, 4, 5 or more molar equivalents of metal ion to PSMA protein (total PSMA protein, i.e., total amount of PSMA protein molecules). In some instances, the molar equivalent of metal ions should be in molar excess to PSMA protein. In some specific solutions of PSMA protein (2 mg/ml in PBS+; diluted 10-fold), as provided in the Examples, it has further been found, that the metal ions are preferably present at a concentration in the range of about 0.1 mM to about 5 mM. The metal ions in some instances are present at a concentration in the range of about 0.1 mM to about 1 mM. In other embodiments the metal ions are present at a concentration in the range of about 0.1 mM to about 0.5 mM. In solutions where there is a combination of one or more types of metal ions, the one or more metal ions can be at the same concentration or at a different concentration. For example, one such solution can contain a concentration of calcium ions of about 0.5 mM and a concentration of zinc ions of a concentration that is greater than 0.1 mM but less than 0.5 mM. Because of the importance of metal ions in the dimerization of PSMA in some compositions, in some instances, it is preferred that the compositions do not contain a chelating agent.

It has also been found that salts preserve or promote PSMA dimerization. As shown below in the Examples, a dimer preparation that contained approximately 5% monomer initially was converted to 100% dimer upon incubation for 72 hours at ambient temperature in PBS+(phosphate-buffered saline containing 1 mM $Ca^{2+}$ and 0.5 mM $Mg^{2+}$, pH 7.2) supplemented with 2M sodium chloride. For a preparation that initially comprised >95% monomer, high salt similarly drove the equilibrium to mostly (81%) dimer within 72 hours.

Salts that preserve or promote PSMA dimerization can include those with a cationic component selected from the group consisting of sodium, potassium, ammonium, magnesium, calcium, zinc and combinations thereof, and those with an anionic component selected from the group consisting of chloride, sulfate, acetate and combinations thereof. In preferred embodiments the salt is sodium chloride, sodium sulfate, sodium acetate or ammonium sulfate. The salt can be present in a PSMA-containing composition at any concentration that preserves or promotes the dimerization of PSMA. In some instances the salt is present at a concentration in the range of about 50 mM to about 2M. The salt preferably is present at a concentration of about 100 mM to 300 mM. The salt more preferably is present at a concentration of about 150 mM.

In some cases where a high salt concentration is used to promote or preserve PSMA dimerization, the salt concentration can be diluted to within a physiologically acceptable range suitable for parenteral use prior to administration. As an example, the salt concentration can be diluted with an adjuvant or a diluent. Diluents and adjuvants are both well known in the art. An adjuvant is a substance which potentiates the immune response. Specific examples of adjuvants include monophosphoryl lipid A (MPL, SmithKline Beecham); saponins, including QS-7, QS-17, QS-18, QS-21 (Antigenics, New York, N.Y.; U.S. Pat. Nos. 6,524,584 and 6,645,495); saponin-based adjuvants, such as SAPONIMMUNE (GPI-0100) Series (Galenica Pharmaceuticals, Birmingham, Ala.; U.S. Pat. Nos. 5,977,081 and 6,080,725) and chemically modified saponins (Galenica Pharmaceuticals, U.S. Pat. No. 6,262,029); polysaccharide-based adjuvants, such as POLYSACCIMMUNE (GPI-0200) Series (Galenica Pharmaceuticals); synthetic adjuvants, such as SYNTHIMMUNE (GPI-0300) Series (Galenica Pharmaceuticals); biodegradable particles composed of poly-lactide-co-glycolide (PLG) or other similar polymers; immunostimulatory oligonucleotides (e.g., CpG oligonucleotides described by Kreig et al., Nature 374:546-9, 1995); incomplete Freund's adjuvant; complete Freund's adjuvant; vitamin E and various water-in-oil emulsions prepared from biodegradable oils such as squalene and/or tocopherol; MONTANIDE, such as MONTANIDE ISA51 and MONTANIDE ISA720, which are water-in-oil emulsions provided by Seppic (Paris, France); Quil A; micellular mixtures of Quil A and cholesterol known as immunostimulating complexes (ISCOMS); MPL and cell wall skeleton from mycobacterium combinations such as ENHANZYN (Corixa, Seattle, Wash.); RC-529 (Corixa); RC-552 (Corixa); CRL-1005; L-121; alpha-galactosylceramide (Fujii et al., *J. Exp. Med.,* 2003, Jul. 21; 198(2): 267-79); aluminum or iron oxide beads and combinations thereof. Other specific examples of adjuvants include QS-21 fractions, such as crude QA-21; a QA-21H form; QA-21-V1; QA-21-V2; a combination of QA-21-V1 and QA-21-V2; and chemically modified forms or combinations thereof. Preferred adjuvants include alum and QS-21. Other diluents include water suitable for injection, saline, PBS, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Therefore, in some aspects of the invention a preferred composition comprising isolated PSMA protein is a solution that promotes or preserves multimeric, particularly dimeric, association of PSMA protein comprising 5 to 20 mM sodium phosphate, sodium acetate or a combination thereof; 100 to 300 mM sodium chloride or sodium sulfate; and 0.1 to 2 mM of at least one metal ion. The metal ions can be chosen from zinc ions, calcium ions, magnesium ions, cobalt ions, manganese ions or a combination thereof. The pH of such a solution can also be adjusted to be in a range of about 4 to 8, preferable 5 to 7 and most preferable 6 to 6.5. Such a solution can also, optionally, include an adjuvant such as alum or a saponin-based adjuvant, such as QS-21.

Agents that preserve or promote PSMA dimerization can be used in compositions of PSMA protein or methods of processing such compositions. Furthermore, a method for identifying such agents is provided herein. Such a method includes the following steps: determining the amount of a form of PSMA in a sample prior to exposure to a candidate agent; exposing the sample to the candidate agent; determining the amount of the form of PSMA in the sample after the exposure; and comparing the amount of the form of PSMA in the sample prior to and after the exposure to the candidate agent. The form of PSMA can be a monomer or multimer, preferably the dimer. An agent which preserves and/or promotes dimer formation of PSMA protein is suitable for use in the compositions comprising PSMA protein dimers.

As described below the effect of buffering agent on the ability of PSMA to dimerize or maintain its dimerization was also tested. It was found that many can be used in a solution of PSMA without negatively impacting the dimeric state of PSMA. The sole exception for solutions of PSMA protein with 150 mM NaCl at a pH of 6 was citrate buffer. Interestingly, citrate buffer is known to function as a chelating agent. Therefore the formulations of PSMA described herein can include any buffer so long as the buffer is not one with a chelating effect that outweighs the preservation or promoting effect of the other properties of the formulation. Preferably optimal buffers include those with buffering capacity at a pH in the range of about 4 to about 8. More preferably, buffers are those with buffering capacity at a pH in the range of about 5 to about 7. Most preferably the buffers are those that have buffering capacity at a pH in the range of about 5.5 to about 7. Buffers in general are well known to those of ordinary skill in the art. Buffer systems include citrate buffers, acetate buffers, borate buffers, and phosphate buffers. Specific examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid. Buffers also include PBS and Hepes.

The effect of free amino acids on the dimeric state of rsPSMA (2 mg/ml in PBS+) dialyzed into 20 mM sodium acetate and 150 mM NaCl at a pH of about 6 was also tested. In general it was found that free amino acids did not have a strong negative effect on dimer association of PSMA and/or column recovery, with the exception of histidine, glutamic acid and aspartic acid used individually at the specific experimental conditions. Therefore, the formulations provided herein can also include a free amino acid or combination of free amino acids, provided that the free amino acid does not have a negative effect that outweighs the dimeric association promoting or preserving nature of the specific formulation. Such free amino acids can be naturally occurring, modified or non-naturally occurring free amino acids (i.e., compounds that do not occur in nature but that can be incorporated into a polypeptide chain; for example, non-natural amino acids that have been successfully incorporated into functional ion channels). Modified or non-naturally occurring free amino acids also include but are not limited to 2-aminoadipic acid; 3-aminoadipic acid; beta-alanine, beta-aminopropionic acid; 2-aminobutyric acid; 4-aminobutyric acid, piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine, sarcosine; N-methylisoleucine; 6-N-methyllysine; N-methylvaline; norvaline; norleucine and ornithine. In particular, free amino acids that do not have a negative effect on dimeric association of PSMA and/or column recovery include those that are non-acidic. Examples of these non-acidic free amino acids include glycine, proline, isoleucine, leucine, alanine and arginine.

In addition to free amino acids, surfactants and other excipients were also found not to have a negative impact on the dimeric state of PSMA. Therefore, surfactants as well as other excipients can be included in the compositions provided herein. Examples of surfactants include those known in the art and described herein. For example, surfactants include Triton X-100, dodecylmaltoside, cholic acid and CHAPS.

Examples of excipients include binders, coatings, compression/encapsulation aids, disintegrants, creams and lotions, lubricants, materials for chewable tablets, parenterals, plasticizers, powder lubricants, soft gelatin capsules, spheres for coating, spheronization agents, suspending/gelling agents, sweeteners and wet granulation agents. Specific examples of such excipients include acetyltriethyl citrate (ATEC); acetyltri-n-butyl citrate (ATBC); aspartame; aspartame and lactose; alginates; calcium carbonate; carbopol; carrageenan; cellulose acetate phthalate-based coatings; cellulose-based coatings; cellulose and lactose combinations; colorants for film coating systems; croscarmellose sodium; crospovidone; dextrose; dibutyl sebacate; ethylcellulose-based coatings; fructose; gellan gum; glyceryl behenate; honey; lactose; anhydrous; lactose; monohydrate; lactose and aspartame; lactose and cellulose; lactose and microcrystalline cellulose; L-HPC (Low-substituted HydroxyPropyl Cellulose); magnesium stearate; maltodextrin; maltose DC; mannitol DC; methylcellulose-based coatings; microcrystalline cellulose; methacrylate-based coatings; microcrystalline cellulose and carrageenan; microcrystalline cellulose and guar gum; microcrystalline cellulose and lactose; microcrystalline cellulose and sodium carboxymethylcellulose; molasses DC; polyvinyl acetate phathalate (PVAP); povidone; shellac; sodium starch glycolate; sorbitol, crystalline; sorbitol, special solution; starch DC; sucrose DC; sugar spheres; triacetin; triethylcitrate and xanthan gum. Other excipients include antioxidants and cryoprotectants.

Antioxidants are substances capable of inhibiting oxidation by removing free radicals from solution. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, butylated hydroxy toluene, alkylgallate, dithiothreitol (DTT), sodium meta-bisulfite, sodium bisulfite, sodium dithionite, sodium thioglycollic acid, sodium formaldehyde sulfoxylate, tocopherol and derivatives thereof (e.g., d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from about 0.01 to about 2%.

For a lyophilized product or a product stored in the cold, one or more cryoprotectants can be added. Typical cryoprotectants for proteins include but are not limited to: sugars such as sucrose, lactose, glucose, trehalose, maltose, and the like; polyols such as inositol, ethylene glycol, glycerol, sorbitol, xylitol, mannitol, 2-methyl-2,4-pentane-diol and the like; amino acids such as Na glutamate, proline, alpha-alanine, beta-alanine, glycine, lysine-HCl, 4-hydroxyproline; polymers such as polyethylene glycol, dextran, polyvinylpyrrolidone and the like; inorganics salts such as sodium sulfate, ammonium sulfate, potassium phosphate, magnesium sulfate, and sodium fluoride and the like; organics salts such as sodium acetate, sodium polyethylene, sodium caprylate, proprionate, lactate, succinate and the like; as well as agents such as trimethylamine N-oxide, sarcosine, betaine, gamma-aminobutyric acid, octapine, alanopine, strombine, dimethylsulfoxide, and ethanol.

The invention also involves methods for preparing or processing compositions of PSMA protein. Aqueous solutions of PSMA protein are included in these methods. Some of these methods include the step of adjusting the pH so that it is in the range of about 4 to about 8. In some methods the pH is adjusted to be in the range of about 5 to 7, and more preferably the pH is adjusted to be in the range of about 5.5 to 7. Most preferably the pH is adjusted to be about 6. The compositions can also contain any one or combination of an isotonicity agent, a buffering agent, a surfactant, an antioxidant, a cryoprotectant or other excipients. Preferably the compositions do not include a chelating agent.

According to another aspect of the invention, a composition of PSMA protein is processed by contacting the composition of PSMA protein with an agent that promotes or preserves the dimeric association of PSMA such as pH adjusting agents, metal ions and/or salts as provided above. Compositions that include these agents can also include agents selected from an isotonicity agent, a buffering agent, a surfactant, an antioxidant, a cryoprotectant and other excipients, but preferably, not a chelating agent. Such methods can also include further steps of contacting the composition of PSMA protein with other dimer promoting or preserving agents and/or pH adjusting steps when the PSMA protein is in a solution.

Additionally, in another aspect of the invention, a method of purifying PSMA protein is also provided. The methods of purifying PSMA include the use of any of the agents and/or solutions described herein that preserve or promote the multimeric, particularly dimeric, association of PSMA in conjunction with any of the separation techniques that are known to those in the art. Such separation techniques include chromatography (e.g., TSK gel filtration chromatography) and are described in more detail in the Examples below. For instance, a separation technique encompassed within this aspect of the invention can include the steps of loading a sample onto a column, eluting or washing the sample from the column and collecting the eluted fractions. Such steps can be repeated any of a number of times to produce the desired PSMA protein composition. These steps can, optionally, also include steps whereby the sample containing PSMA protein is dialyzed. Preferably, the sample containing PSMA protein is dialyzed into a solution that preserves or promotes the multimeric association of PSMA. In one embodiment, the solutions used in these methods contain a metal ion or a salt. In other embodiments, the solution is at a pH that preserves or promotes PSMA multimerization. The metal ion and salts, including concentration ranges, as well as pH ranges that can be used in these purification methods have been provided above. In some preferred embodiments, the pH of the solution can be at about 7 or 7.5. In other preferred embodiments, the metals are calcium ions, magnesium ions or combinations thereof. The calcium and magnesium ions are present, for instance, at a concentration of about 1 mM and of about 0.5 mM, respectively. In other preferred embodiments the salt is present at a concentration of about 2M.

The amount of dimeric PSMA in the compositions provided herein is effective to elicit or enhance an immune response to cells expressing PSMA. The compositions can, therefore, be used to immunize an animal for the purpose of raising antibodies to dimeric PSMA. The compositions provided herein can also be used to treat a subject suffering from a cancer, wherein the cancer cells or proximate neovasculature express PSMA. Such cancers can include prostate, bladder, pancreas, lung, colon, kidney, melanomas and sarcomas. In a preferred embodiment the cancer cell is a prostate cancer cell. The cancer cells can be cells of a primary tumor or can be those of a metastatic tumor.

The subject can be a non-castrate patient who has, in some embodiments, received primary therapy, such as prostatectomy and/or radiation therapy. As used herein, "non-castrate patient" refers to a patient in some embodiments with a serum testosterone level that is greater than or equal to about 180 ng/mL. The subject can also be a castrate patient who has, in some embodiments, completed a course of hormonal therapy. As used herein, the term "castrate patient" refers to a patient in some embodiments with a serum testosterone level of less than about 50 ng/mL. The compositions provided herein can also be administered to a patient who has received conventional cancer therapy.

Another aspect of the invention provides an isolated antibody or an antigen-binding fragment thereof which specifically binds to an extracellular domain of PSMA wherein the antibody or the antigen-binding fragment thereof competitively inhibits the specific binding of a second antibody to its target epitope on PSMA, and wherein the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, 4.248.2, 4.360.3, 4.7.1, 4.4.1, 4.177.3, 4.16.1, 4.22.3, 4.28.3, 4.40.2, 4.48.3, 4.49.1, 4.209.3, 4.219.3, 4.288.1, 4.333.1, 4.54.1, 4.153.1, 4.232.3, 4.292.3, 4.304.1, 4.78.1, and 4.152.1.

Another aspect of the invention provides an isolated antibody or an antigen-binding fragment thereof that specifically binds to an epitope on PSMA defined by an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, 4.248.2, 4.360.3, 4.7.1, 4.4.1, 4.177.3, 4.16.1, 4.22.3, 4.28.3, 4.40.2, 4.48.3, 4.49.1, 4.209.3, 4.219.3, 4.288.1, 4.333.1, 4.54.1, 4.153.1, 4.232.3, 4.292.3, 4.304.1, 4.78.1, and 4.152.1.

In particular embodiments, these antibodies are produced by hybridomas referred to herein as PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, and Abgenix 4.152.1, respectively. These hybridomas were deposited with American Type Culture Collection (ATCC), located at 10801 University Boulevard, Manassas, Virginia, 20110-2209, as an International Depository Authority and given the following Patent Deposit Designations (Table 1):

TABLE 1

| Antibody | Hybridoma/ Plasmid | Patent Deposit Designation | Date of Deposit |
| --- | --- | --- | --- |
| PSMA 3.7 | PSMA 3.7 | PTA-3257 | Apr. 5, 2001 |
| PSMA 3.9 | PSMA 3.9 | PTA-3258 | Apr. 5, 2001 |
| PSMA 3.11 | PSMA 3.11 | PTA-3269 | Apr. 10, 2001 |
| PSMA 5.4 | PSMA 5.4 | PTA-3268 | Apr. 10, 2001 |
| PSMA 7.1 | PSMA 7.1 | PTA-3292 | Apr. 18, 2001 |
| PSMA 7.3 | PSMA 7.3 | PTA-3293 | Apr. 18, 2001 |
| PSMA 10.3 | PSMA 10.3 | PTA-3347 | May 1, 2001 |
| | PSMA 10.3 HC in pcDNA (SEQ ID NO: 7) | PTA-4413 | May 29, 2002 |
| | PSMA 10.3 Kappa in pcDNA (SEQ ID NO: 13) | PTA-4414 | May 29, 2002 |
| PSMA 1.8.3 | PSMA 1.8.3 | PTA-3906 | Dec. 5, 2001 |
| PSMA A3.1.3 | PSMA A3.1.3 | PTA-3904 | Dec. 5, 2001 |
| PSMA A3.3.1 | PSMA A3.3.1 | PTA-3905 | Dec. 5, 2001 |
| Abgenix 4.248.2 | Abgenix 4.248.2 | PTA-4427 | Jun. 4, 2002 |
| Abgenix 4.360.3 | Abgenix 4.360.3 | PTA-4428 | Jun. 4, 2002 |
| Abgenix 4.7.1 | Abgenix 4.7.1 | PTA-4429 | Jun. 4, 2002 |
| Abgenix 4.4.1 | Abgenix 4.4.1 | PTA-4556 | Jul. 18, 2002 |
| Abgenix 4.177.3 | Abgenix 4.177.3 | PTA-4557 | Jul. 18, 2002 |
| Abgenix 4.16.1 | Abgenix 4.16.1 | PTA-4357 | May 16, 2002 |
| Abgenix 4.22.3 | Abgenix 4.22.3 | PTA-4358 | May 16, 2002 |
| Abgenix 4.28.3 | Abgenix 4.28.3 | PTA-4359 | May 16, 2002 |
| Abgenix 4.40.2 | Abgenix 4.40.2 | PTA-4360 | May 16, 2002 |
| Abgenix 4.48.3 | Abgenix 4.48.3 | PTA-4361 | May 16, 2002 |
| Abgenix 4.49.1 | Abgenix 4.49.1 | PTA-4362 | May 16, 2002 |
| Abgenix 4.209.3 | Abgenix 4.209.3 | PTA-4365 | May 16, 2002 |
| Abgenix 4.219.3 | Abgenix 4.219.3 | PTA-4366 | May 16, 2002 |
| Abgenix 4.288.1 | Abgenix 4.288.1 | PTA-4367 | May 16, 2002 |
| Abgenix 4.333.1 | Abgenix 4.333.1 | PTA-4368 | May 16, 2002 |
| Abgenix 4.54.1 | Abgenix 4.54.1 | PTA-4363 | May 16, 2002 |
| Abgenix 4.153.1 | Abgenix 4.153.1 | PTA-4388 | May 23, 2002 |
| Abgenix 4.232.3 | Abgenix 4.232.3 | PTA-4389 | May 23, 2002 |
| Abgenix 4.292.3 | Abgenix 4.292.3 | PTA-4390 | May 23, 2002 |
| Abgenix 4.304.1 | Abgenix 4.304.1 | PTA-4391 | May 23, 2002 |
| AB-PG1-XG1-006 | AB-PG1-XG1-006 Heavy Chain (SEQ ID NO: 2) | PTA-4403 | May 29, 2002 |
| | AB-PG1-XG1-006 Light Chain (SEQ ID NO: 8) | PTA-4404 | |
| AB-PG1-XG1-026 | AB-PG1-XG1-026 Heavy Chain (SEQ ID NO: 3) | PTA-4405 | May 29, 2002 |
| | AB-PG1-XG1-026 | PTA-4406 | |
| AB-PG1-XG1-051 | AB-PG1-XG1-051 Light Chain (SEQ ID NO: 9) | PTA-4407 | May 29, 2002 |
| | AB-PG1-XG1-051 Heavy Chain (SEQ ID NO: 4) | | |
| | AB-PG1-XG1-051 Light Chain (SEQ ID NO: 10) | PTA-4408 | |
| AB-PG1-XG1-069 | AB-PG1-XG1-069 Heavy Chain (SEQ ID NO: 5) | PTA-4409 | May 29, 2002 |
| | AB-PG1-XG1-069 Light Chain (SEQ ID NO: 11) | PTA-4410 | |
| AB-PG1-XG1-077 | AB-PG1-XG1-077 Heavy Chain (SEQ ID NO: 6) | PTA-4411 | May 29, 2002 |
| | AB-PG1-XG1-077 Light Chain (SEQ ID NO: 12) | PTA-4412 | |

In another aspect of the invention, antibodies having particular sequences are provided. Specifically, the antibodies are selected from the group consisting of antibodies comprising: a heavy chain encoded by a nucleic acid molecule comprising the heavy chain coding region or regions of a nucleotide sequence selected from the group consisting of nucleotide sequences set forth as SEQ ID NOs: 2-7, and a light chain encoded by a nucleic acid molecule comprising the light chain coding region or regions of a nucleotide sequence selected from the group consisting of nucleotide sequences set forth as SEQ ID NOs: 8-13. Also provided are antigen-binding fragments of the foregoing antibodies.

The plasmids encoding the heavy and light chains of antibodies PSMA 10.3, AB-PG1-XG1-006, AB-PG1-XG1-026, AB-PG1-XG1-051, AB-PG1-XG1-069, AB-PG1-XG1-077 were also deposited with ATCC and are shown in Table 1 above. As used herein, the names of the deposited hybridomas or plasmids may be used interchangeably with the names of the antibodies. It would be clear to one of skill in the art when the name is intended to refer to the antibody or when it refers to the plasmids or hybridomas that encode or produce the antibodies, respectively. Additionally, the antibody names may be an abbreviated form of the name shown in Table 1. For instance antibody AB-PG1-XG1-006 may be referred to as AB-PG1-XG1-006, PG1-XG1-006, XG1-006, 006, etc. In another example, the antibody name PSMA 4.232.3 may be referred to as PSMA 4.232.1, 4.232.3, 4.232.1, 4.232, etc. It is intended that all of the variations in the name of the antibody refer to the same antibody and not a different one.

Antibodies are also provided that are encoded by particular sets of heavy and light chain sequences. In one embodiment an antibody (AB-PG1-XG1-006) encoded by a nucleic acid molecule which comprises the coding region or regions of the nucleic acid sequences set forth as: SEQ ID NOs: 2 and 8 is provided. In another embodiment the antibody (AB-PG1-XG1-026) is encoded by the nucleic acid molecules comprising the coding region or regions of nucleotide sequences set forth as: SEQ ID NOs: 3 and 9. In still another embodiment the antibody (AB-PG1-XG1-051) is encoded by the nucleic acid molecules comprising the coding region or regions of nucleotide sequences set forth as: SEQ ID NOs: 4 and 10. In yet another embodiment the antibody (AB-PG1-XG1-069) is encoded by the nucleic acid molecules comprising the coding region or regions of nucleotide sequences set forth as: SEQ ID NOs: 5 and 11. In another embodiment the antibody (AB- PG1-XG1-077) is encoded by the nucleic acid molecules comprising the coding region or regions of nucleotide sequences set forth as: SEQ ID NOs: 6 and 12. In yet another embodiment the antibody (PSMA 10.3) is encoded by the nucleic acid molecules comprising the coding region or regions of nucleotide sequences set forth as: SEQ ID NOs: 7 and 13.

In particularly preferred embodiments, the antibodies include a heavy chain variable region encoded by a nucleic acid molecule comprising the coding regions or regions of a nucleotide sequence selected from the group consisting of nucleotide sequences set forth as: SEQ ID NOs: 14, 18, 22, 26 and 30, and a light chain variable region encoded by a nucleic acid molecule comprising the coding region or region of a nucleotide sequence selected from the group consisting of nucleotide sequences set forth as: SEQ ID NOs: 16, 20, 24, 28 and 32. As used herein, a "coding region" refers to a region of a nucleotide sequence that encodes a polypeptide sequence; the coding region can include a region coding for a portion of a protein that is later cleaved off, such as a signal peptide.

Those of skill in the art will appreciate that the invention includes nucleic acids and polypeptides that include nucleotide and amino acid sequences presented herein. In some instances, the nucleotide and amino acid sequences may include sequences that encode or that are signal peptides. The invention embraces each of these sequences with, or without, the portion of the sequence that encodes or is a signal peptide.

Antibodies also are provided that include particular sets of heavy and light chain variable sequences. In one embodiment an antibody (AB-PG1-XG1-006) includes an immunoglobulin variable sequence encoded by nucleic acid molecules which included the coding region or regions of the nucleic acid sequences set forth as: SEQ ID NOs: 14 and 16 is provided. Likewise the antibody may include an immunoglobulin variable sequence which comprises the amino acid sequences set forth as SEQ ID NOs: 15 and 17. In another embodiment the antibody (AB-PG1-XG1-026) includes an immunoglobulin variable sequence encoded by nucleic acid molecules comprising the coding region or regions of nucleotide sequences set forth as: SEQ ID NOs: 18 and 20 or includes an immunoglobulin variable sequence which comprises the amino acid sequences set forth as SEQ ID NOs: 19 and 21. In still another embodiment the antibody (AB-PG1-XG1-051) includes an immunoglobulin variable sequence encoded by the nucleic acid molecules comprising the coding region or regions of nucleotide sequences set forth as: SEQ ID NOs: 22 and 24 or includes an immunoglobulin variable sequence which comprises the amino acid sequences set forth as SEQ ID NOs: 23 and 25. In yet another embodiment the antibody (AB-PG1-XG1-069) includes an immunoglobulin variable sequence encoded by the nucleic acid molecules comprising the coding region or regions of nucleotide sequences set forth as: SEQ ID NOs: 26 and 28 or includes an immunoglobulin variable sequence which comprises the amino acid sequences set forth as SEQ ID NOs: 27 and 29. In another embodiment the antibody (AB-PG1-XG1-077) includes an immunoglobulin variable sequence encoded by the nucleic acid molecules comprising the coding region or regions of nucleotide sequences set forth as: SEQ ID NOs: 30 and 32 or includes an immunoglobulin variable sequence which comprises the amino acid sequences set forth as SEQ ID NOs: 31 and 33.

In certain embodiments, the antibody is encoded by a nucleic acid molecule that is highly homologous to the foregoing nucleic acid molecules. Preferably the homologous nucleic acid molecule comprises a nucleotide sequence that is at least about 90% identical to the nucleotide sequence provided herein. More preferably, the nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes antibodies having the PSMA-binding properties and other functional properties described herein, which are encoded by nucleic acid molecules that hybridize under high stringency conditions to the foregoing nucleic acid molecules. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% FICOLL, 0.02% polyvinyl pyrrolidone, 0.02% Bovine Serum Albumin, 2.5 mM NaH$_2$PO$_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

In other preferred embodiments, the antibodies include a heavy chain variable region comprising an amino acid sequence selected from the group consisting of amino acid sequences set forth as: SEQ ID NOs: 15, 19, 23, 27 and 31, and a light chain variable region comprising an amino acid sequence selected from the group consisting of nucleotide sequences set forth as: SEQ ID NOs: 17, 21, 25, 29 and 33. Antigen-binding fragments of the foregoing also are provided, as described elsewhere herein.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., PSMA). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

An "isolated antibody", as used herein, is intended to refer to an antibody which is substantially free of other antibodies having different antigenic specificities (e.g., an isolated antibody that specifically binds to PSMA is substantially free of antibodies that specifically bind antigens other than PSMA). An isolated antibody that specifically binds to an epitope, isoform or variant of PSMA may, however, have cross-reactivity to other related antigens, e.g., from other species (e.g., PSMA species homologs). Moreover, an isolated antibody may be substantially free of other cellular material and/or chemicals. As used herein, "specific binding" refers to antibody binding to a predetermined antigen. Typically, the antibody binds with an affinity that is at least two-fold greater than its affinity for binding to a non-specific antigen (e.g., BSA, casein) other than the predetermined antigen or a closely-related antigen.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. Procedures for raising polyclonal antibodies are well known. For example anti-PSMA polyclonal antibodies are raised by administering PSMA protein subcutaneously to New Zealand white rabbits which have first been bled to obtain pre-immune serum. The PSMA can be injected at a total volume of 100 µl per site at six different sites, typically with one or more adjustments. The rabbits are then bled two weeks after the first injection and periodically boosted with the same antigen three times every six weeks. A sample of serum is collected 10 days after each boost. Polyclonal antibodies are recovered from the serum, preferably by affinity chromatography using PSMA to capture the antibody. This and other procedures for raising polyclonal antibodies are disclosed in E. Harlow, et. al., editors, Antibodies: A Laboratory Manual (1988), which is hereby incorporated by reference.

Monoclonal antibody production may be effected by techniques which are also well known in the art. The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with PSMA in the present invention. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986). In particular, mouse strains that have human immunoglobulin genes inserted in the genome (and which cannot produce mouse immunoglobulins) are preferred. Examples include the HUMAB-MOUSE strains produced by Medarex/GenPharm International, and the XENOMOUSE strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Alternatively, human somatic cells capable of producing antibody, specifically B lymphocytes, are suitable for fusion with myeloma cell lines. While B lymphocytes from biopsied spleens, tonsils or lymph nodes of an individual may be used, the more easily accessible peripheral blood B lymphocytes are preferred. The lymphocytes may be derived from patients with diagnosed prostate carcinomas or another PSMA-expressing cancer. In addition, human B cells may be directly immortalized by the Epstein-Barr virus (Cole et al., 1995, Monoclonal Antibodies and Cancer Therapy, Alan R. Liss, Inc., pp. 77-96). Although somatic cell hybridization procedures are preferred, in principle, other techniques for producing monoclonal antibodies can be employed such as viral or oncogenic transformation of B lymphocytes.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elseview, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies can be chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that retains only the antigen-binding CDRs from the parent antibody in association with human framework regions (see, Waldmann, 1991, *Science* 252:1657). Such chimeric or humanized antibodies retaining binding specificity of the murine antibody are expected to have reduced immunogenicity when administered in vivo for diagnostic, prophylactic or therapeutic applications according to the invention.

According to an alternative embodiment, the monoclonal antibodies of the present invention can be modified to be in the form of a bispecific antibody, or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multispecific antibody" is intended to include any agent, e.g., a protein, peptide, or protein or peptide complex, which has more than two different binding specificities which bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific antibodies which are directed to cell surface antigens, such as PSMA, and to Fc receptors on effector cells. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

A bispecific antibody can be formed of an antigen-binding region specific for the extracellular domain of PSMA and an antigen-binding region specific for an effector cell which has tumoricidal or tumor inhibitory activity. The two antigen-binding regions of the bispecific antibody are either chemically linked or can be expressed by a cell genetically engineered to produce the bispecific antibody. (See generally, Fanger et al., 1995 *Drug News & Perspec.* 8(3):133-137). Suitable effector cells having tumoricidal activity include but are not limited to cytotoxic T-cells (primarily $CD8^+$ cells), natural killer cells, etc. An effective amount of a bispecific antibody according to the invention is administered to a prostrate cancer patient and the bispecific antibody kills and/or inhibits proliferation of the malignant cells after localization at sites of primary or metastatic tumors bearing PSMA.

In certain embodiments, the antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse have been grafted onto human framework sequences (referred to herein as "humanized antibodies"). Human antibodies directed against PSMA are generated using transgenic mice carrying parts of the human immune system rather than the mouse system.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XENOMOUSE (Abgenix), HUMAB-MOUSE mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans.

Preferably, the mice are 6-16 weeks of age upon the first immunization. For example, a purified or enriched preparation of PSMA antigen (e.g., recombinant PSMA, PSMA-expressing cells, dimeric PSMA) is used to immunize the mice intraperitoneally (IP), although other routes of immunization known to one of ordinary skill in the art are also possible. PSMA antigen is injected in combination with an adjuvant, such as complete Freund's adjuvant, and preferably the initial injection is followed by booster immunizations with antigen in an adjuvant, such as incomplete Freund's adjuvant. The immune response is monitored over the course of the immunization protocol with plasma samples obtained by, for example, retroorbital bleeds. The plasma is screened by ELISA (as described below), and mice with sufficient titers of anti-PSMA human immunoglobulin are used for fusions. Mice are boosted intravenously with antigen 3 days before sacrifice and removal of the spleen.

In particular embodiments, the antibodies are produced by hybridomas referred to herein as PSMA 3.7 (PTA-3257), PSMA 3.8, PSMA 3.9 (PTA-3258), PSMA 3.11 (PTA-3269), PSMA 5.4 (PTA-3268), PSMA 7.1 (PTA-3292), PSMA 7.3 (PTA-3293), PSMA 10.3 (PTA-3247), PSMA 1.8.3 (PTA-3906), PSMA A3.1.3 (PTA-3904), PSMA A3.3.1 (PTA-3905), Abgenix 4.248.2 (PTA-4427), Abgenix 4.360.3 (PTA-4428), Abgenix 4.7.1 (PTA-4429), Abgenix 4.4.1 (PTA-4556), Abgenix 4.177.3 (PTA-4557), Abgenix 4.16.1 (PTA-4357), Abgenix 4.22.3 (PTA-4358), Abgenix 4.28.3 (PTA-4359), Abgenix 4.40.2 (PTA-4360), Abgenix 4.48.3 (PTA-4361), Abgenix 4.49.1 (PTA-4362), Abgenix 4.209.3 (PTA-4365), Abgenix 4.219.3 (PTA-4366), Abgenix 4.288.1 (PTA-4367), Abgenix 4.333.1 (PTA-4368), Abgenix 4.54.1 (PTA-4363), Abgenix 4.153.1 (PTA-4388), Abgenix 4.232.3 (PTA-4389), Abgenix 4.292.3 (PTA-4390), Abgenix 4.304.1 (PTA-4391), Abgenix 4.78.1 (PTA-4652), and Abgenix 4.152.1 (PTA-4653). These hybridomas were deposited pursuant to, and in satisfaction of, the requirements of the Budapest Treaty on the International Recognition of the Deposit of Microorganisms for the Purposes of Patent Procedure with the American Type Culture Collection ("ATCC") as an International Depository Authority and given the Patent Deposit Designations shown above and in Table 1.

The present invention further provides nucleic acid molecules encoding anti-PSMA antibodies and vectors comprising the nucleic acid molecules as described herein. The vectors provided can be used to transform or transfect host cells for producing anti-PSMA antibodies with the specificity of antibodies described herein. In a preferred embodiment the antibodies produced will have the specificity of the antibodies AB-PG1-XG1-006, AB-PG1-XG1-026, AB-PG1-XG1-051, AB-PG1, XG1-069, AB-PG1-XG1-077 and PSMA 10.3. In one embodiment the vectors can comprise an isolated nucleic acid molecule encoding the heavy chain of the antibodies listed above encoded by a nucleic acid molecules comprising the coding region or regions of the nucleic acid sequences set forth as SEQ ID NO: 2-7. In another embodiment, the vectors can comprise the nucleic acid sequences encoding the light chain of the antibodies set forth as SEQ ID NOs: 8-13. In a further embodiment the vectors of the invention may comprise a heavy chain and a light chain sequence. In a further embodiment, plasmids are given which produce the antibodies or antigen binding fragments described herein. Plasmids of the invention include plasmids selected from the group consisting of: AB-PG1-XG1-006 Heavy Chain (SEQ ID NO: 2), AB-PG1-XG1-006 Light Chain (SEQ ID NO: 8), AB-PG1-XG1-026 Heavy Chain (SEQ ID NO: 3), AB-PG1-XG1-026 Light Chain (SEQ ID NO: 9), AB-PG1-XG1-051 Heavy Chain (SEQ ID NO: 4), AB-PG1-XG1-051 Light Chain (SEQ ID NO: 10), AB-PG1-XG1-069 Heavy Chain (SEQ ID NO: 5), AB-PG1-XG1-069 Light Chain (SEQ ID NO: 11), AB-PG1-XG1-077 Heavy Chain (SEQ ID NO: 6), AB-PG1-XG1-077 Light Chain (SEQ ID NO: 12), PSMA 10.3 Heavy Chain (SEQ ID NO: 7), and PSMA 10.3 Kappa (SEQ ID NO: 13).

The isolated antibody or antigen-binding fragment thereof preferably is selected for its ability to bind live cells expressing PSMA. In order to demonstrate binding of monoclonal antibodies to live cells expressing the PSMA, flow cytometry can be used. For example, cell lines expressing PSMA (grown under standard growth conditions) or prostate cancer cells that express PSMA are mixed with various concentrations of monoclonal antibodies in PBS containing 0.1% TWEEN 80 and 20% mouse serum, and incubated at 37° C. for 1 hour. After washing, the cells are reacted with fluorescein-labeled anti-human IgG secondary antibody (if human anti-PSMA antibodies were used) under the same conditions as the primary antibody staining. The samples can be analyzed by a fluorescence activated cell sorter (FACS) instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Binding of the antibody or antigen-binding fragment thereof to live cells expressing PSMA can inhibit the growth of the cells or mediate cytolysis of the cells. Cytolysis can be complement mediated or can be mediated by effector cells. In a preferred embodiment, the cytolysis is carried out in a living organism, preferably a mammal, and the live cell is a tumor cell. Examples of tumors which can be targeted by the antibodies of the invention include, any tumor that expresses PSMA, such as, prostate, bladder, pancreas, lung, colon, kidney, melanomas and sarcomas. In a preferred embodiment the tumor cell is a prostate cancer cell.

The testing of antibody cytolytic activity in vitro by chromium release assay can provide an initial screening prior to testing in vivo models. This testing can be carried out using standard chromium release assays. Briefly, polymorphonuclear cells (PMN), or other effector cells, from healthy donors can be purified by FICOLL Hypaque density centrifugation, followed by lysis of contaminating erythrocytes. Washed PMNs can be suspended in RPMI supplemented with 10% heat-inactivated fetal calf serum and mixed with $^{51}$Cr labeled cells expressing PSMA, at various ratios of effector cells to tumor cells (effector cells:tumor cells). Purified anti-PSMA IgGs can then be added at various concentrations. Irrelevant IgG can be used as negative control. Assays can be carried out for 0-120 minutes at 37° C. Samples can be assayed for cytolysis by measuring $^{51}$Cr release into the culture supernatant. Anti-PSMA monoclonal antibodies can also be tested in combinations with each other to determine whether cytolysis is enhanced with multiple monoclonal antibodies.

Antibodies which bind to PSMA also can be tested in an in vivo model (e.g., in mice) to determine their efficacy in mediating cytolysis and killing of cells expressing PSMA, e.g., tumor cells. These antibodies can be selected, for example, based on the following criteria, which are not intended to be exclusive:

1) binding to live cells expressing PSMA;
2) high affinity of binding to PSMA;

3) binding to a unique epitope on PSMA (to eliminate the possibility that antibodies with complimentary activities when used in combination would compete for binding to the same epitope);
4) opsonization of cells expressing PSMA;
5) mediation of growth inhibition, phagocytosis and/or killing of cells expressing PSMA in the presence of effector cells;
6) modulation (inhibition or enhancement) of NAALA-Dase, folate hydrolase, dipeptidyl peptidase IV and/or γ-glutamyl hydrolase activities;
7) growth inhibition, cell cycle arrest and/or cytotoxicity in the absence of effector cells;
8) internalization of PSMA;
9) binding to a conformational epitope on PSMA;
10) minimal cross-reactivity with cells or tissues that do not express PSMA; and
11) preferential binding to dimeric forms of PSMA rather than monomeric forms of PSMA.

Preferred antibodies of the invention meet one or more, and preferably all, of these criteria. In a particular embodiment, the antibodies are used in combination, e.g., as a pharmaceutical composition comprising two or more different anti-PSMA antibodies or binding fragments thereof. For example, anti-PSMA antibodies having different, but complementary activities can be combined in a single therapy to achieve a desired therapeutic or diagnostic effect. An illustration of this would be a composition containing an anti-PSMA antibody that mediates highly effective killing of target cells in the presence of effector cells, combined with another anti-PSMA antibody that inhibits the growth of cells expressing PSMA.

In a preferred aspect of the invention, the antibody or antigen-binding fragment thereof binds to a conformational epitope within the extracellular domain of the PSMA molecule. To determine if the selected human anti-PSMA antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. Antibodies that bind to native protein but not denatured protein are those antibodies that bind conformational epitopes, and are preferred antibodies.

In another preferred aspect of the invention, the antibody or antigen-binding fragment thereof binds to a dimer-specific epitope on PSMA. Generally, antibodies or antigen-binding fragments thereof which bind to a dimer-specific epitope preferentially bind the PSMA dimer rather than the PSMA monomer. To determine if the selected human anti-PSMA antibodies bind preferentially (i.e., selectively and/or specifically) to a PSMA dimer, each antibody can be tested in assays (e.g., immunoprecipitation followed by Western blotting) using native dimeric PSMA protein and dissociated monomeric PSMA protein. A comparison of the results will indicate whether the antibodies bind preferentially to the dimer or to the monomer. Antibodies that bind to the PSMA dimer but not to the monomeric PSMA protein are preferred antibodies.

Preferred antibodies include antibodies that competitively inhibit the specific binding of a second antibody to its target epitope on PSMA. To determine competitive inhibition, a variety of assays known to one of ordinary skill in the art can be employed. For example, the cross-competition assays set forth in Examples 4 and 21 can be used to determine if an antibody competitively inhibits binding to PSMA by another antibody.

These examples provide cell-based methods employing flow cytometry or solid phase binding analysis. Other assays that evaluate the ability of antibodies to cross-compete for PSMA molecules that are not expressed on the surface of cells, in solid phase or in solution phase, also can be used. These assays preferably use the PSMA multimers described herein.

Certain preferred antibodies competitively inhibit the specific binding of a second antibody to its target epitope on PSMA by at least about 10%, 20%, 30%, 40%, 50%, 60%, 70%, 80%, 90%, 95%, or 99% Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other preferred antibodies include antibodies that specifically (i.e., selectively) bind to an epitope on PSMA defined by a second antibody. To determine the epitope, one can use standard epitope mapping methods known in the art. For example, fragments (peptides) of PSMA antigen (preferably synthetic peptides) that bind the second antibody can be used to determine whether a candidate antibody binds the same epitope. For linear epitopes, overlapping peptides of a defined length (e.g., 8 or more amino acids) are synthesized. The peptides preferably are offset by 1 amino acid, such that a series of peptides covering every 8 amino acid fragment of the PSMA protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies can be determined using standard methodologies including surface plasmon resonance (BIACORE; see Example 22) and ELISA assays. For examination of conformational epitopes, larger PSMA fragments can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

In one embodiment of the invention the antibody or antigen-binding fragment thereof binds to and is internalized with PSMA expressed on cells. The mechanism by which the antibody or antigen-binding fragment thereof is internalized with the prostate specific membrane antigen is not critical to the practice of the present invention. For example, the antibody or antigen-binding fragment thereof can induce internalization of PSMA. Alternatively, internalization of the antibody or antigen-binding fragment thereof can be the result of routine internalization of PSMA. The antibody or antigen-binding fragment thereof can be used in an unmodified form, alone or in combination with other compositions. Alternatively, the antibody or antigen-binding fragment thereof can be bound to a substance effective to kill the cells upon binding of the antibody or antigen-binding fragment thereof to prostate specific membrane antigen and upon internalization of the biological agent with the prostate specific membrane antigen.

The human PSMA antibodies of the present invention specifically bind cell-surface PSMA and/or rsPSMA with sub-nanomolar affinity. The human PSMA antibodies of the present invention have binding affinities of about $1\times10^{-9}$M or less, preferably about $1\times10^{-10}$M or less, more preferably $1\times10^{-11}$M or less. In a particular embodiment the binding affinity is less than about $5\times10^{-10}$M.

An antibody can be linked to a detectable marker, an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents that may be conjugated to the anti-PSMA antibodies of the present invention include dolastatins (U.S. Pat. Nos. 6,034,065 and 6,239,104) and derivatives thereof. Of particular interest is dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins that are less preferred in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Other chemotherapeutic agents are known to those skilled in the art.

Toxin-conjugated forms of the PSMA antibodies of the present invention mediate specific cell killing of PSMA-expressing cells at picomolar concentrations. The toxin-conjugated PSMA antibodies of the present invention exhibit $IC_{50}$s at concentrations of less than about $1\times10^{-10}$M, preferably less than about $1\times10^{-11}$M, more preferably less than about $1\times10^{-12}$M. In a particular embodiment an $IC_{50}$ is achieved at a concentration of less than about $1.5\times10^{-11}$M.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein) and interferon inducible protein 10 (U.S. Pat. No. 5,994,292). A number of antiangiogenic agents currently in clinical trials are also contemplated. Agents currently in clinical trials include: 2ME2, Angiostatin, Angiozyme, Anti-VEGF RhuMAb, Apra (CT-2584), AVICINE, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, IRESSA (ZD1839), Marimastat, METASTAT (Col-3), NEOVASTAT, Octreotide, Paclitaxel, Penicillamine, PHOTOFRIN, PHOTOPOINT, PI-88, Prinomastat (AG-3340), PTK787 (ZK22584), R0317453, Solimastat, Squalamine, SU 101, SU 5416, SU-6668, Suradista (FCE 26644), Suramin (Metaret), Tetrathiomolybdate, Thalidomide, TNP-470 and VITAXIN. Additional antiangiogenic agents are described by Kerbel, J. Clin. Oncol. 19(18s):45s-51s, 2001, which is incorporated by reference herein Immunomodulators suitable for conjugation to anti-PSMA antibodies include α-interferon, γ-interferon, and tumor necrosis factor alpha (TNFα).

The coupling of one or more toxin molecules to the anti-PSMA antibody is envisioned to include many chemical mechanisms, for instance covalent binding, affinity binding, intercalation, coordinate binding, and complexation. The toxic compounds used to prepare the anti-PSMA immunotoxins are attached to the antibodies or PSMA-binding fragments thereof by standard protocols known in the art.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In preferred embodiments, it is contemplated that one may wish to first derivatize the antibody, and then attach the toxin component to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene.

In addition, protein toxins can be fused to the anti-PSMA antibody or PSMA binding fragment by genetic methods to form a hybrid immunotoxin fusion protein. To make a fusion immunotoxin protein in accordance with the invention, a nucleic acid molecule is generated that encodes an anti-PSMA antibody, a fragment of an anti-PSMA antibody, a single chain anti-PSMA antibody, or a subunit of an anti-PSMA antibody linked to a protein toxin. Such fusion proteins contain at least a targeting agent (e.g., anti-PSMA antibody subunit) and a toxin of the invention, operatively attached. The fusion proteins may also include additional peptide sequences, such as peptide spacers which operatively attach the targeting agent and toxin compound, as long as such additional sequences do not appreciably affect the targeting or toxin activities of the fusion protein. The two proteins can be attached by a peptide linker or spacer, such as a glycine-serine spacer peptide, or a peptide hinge, as is well known in the art. Thus, for example, the C-erminus of an anti-PSMA antibody or fragment thereof can be fused to the N-terminus of the protein toxin molecule to form an immunotoxin that retains the binding properties of the anti-PSMA antibody. Other fusion arrangements will be known to one of ordinary skill in the art.

To express the fusion immunotoxin, the nucleic acid encoding the fusion protein is inserted into an expression vector in accordance with standard methods, for stable expression of the fusion protein, preferably in mammalian cells, such as CHO cells. The fusion protein can be isolated and purified from the cells or culture supernatant using standard methodology, such as a PSMA affinity column.

Radionuclides typically are coupled to an antibody by chelation. For example, in the case of metallic radionuclides, a bifunctional chelator is commonly used to link the isotope to the antibody or other protein of interest. Typically, the chelator is first attached to the antibody, and the chelator-antibody conjugate is contacted with the metallic radioisotope. A number of bifunctional chelators have been developed for this purpose, including the diethylenetriamine pentaacetic acid (DTPA) series of amino acids described in U.S. Pat. Nos. 5,124,471, 5,286,850 and 5,434,287, which are incorporated herein by reference. As another example, hydroxamic acid-based bifunctional chelating agents are described in U.S. Pat. No. 5,756,825, the contents of which are incorporated herein. Another example is the chelating agent termed p-SCN-Bz-HEHA (1,4,7,10,13,16-hexaazacyclo-octadecane-N,N',N'', N''',N'''',N'''''-hexaacetic acid) (Deal et al., *J. Med. Chem.* 42:2988, 1999), which is an effective chelator of radiometals such as $^{225}$Ac. Yet another example is DOTA (1,4,7,10-tetraazacyclododecane N,N',N'',N'''-tetraacetic acid), which is a bifunctional chelating agent (see McDevitt et al., Science 294:1537-1540, 2001) that can be used in a two-step method for labeling followed by conjugation.

In another aspect, the invention provides compositions comprising a multimeric (e.g., dimeric) PSMA protein, an isolated antibody, an antibody derivatized or linked to other functional moieties, or an antigen-binding fragment thereof or a combination of one or more of the aforementioned multimeric PSMA proteins, antibodies or antigen-binding fragments thereof. The compositions include a physiologically or pharmaceutically acceptable carrier, excipient, or stabilizer mixed with the isolated multimeric PSMA protein, antibody or antigen-binding fragment thereof. In a preferred embodiment, the compositions include a combination of multiple (e.g., two or more) isolated multimeric PSMA proteins, antibodies or antigen-binding portions thereof of the invention. Preferably, each of the antibodies or antigen-binding portions thereof of the composition binds to a distinct conformational epitope of PSMA. In one embodiment, anti-PSMA antibodies having complementary activities are used in combination, e.g., as a pharmaceutical composition, comprising two or more anti-PSMA antibodies. For example, an antibody that mediates highly effective cytolysis of target cells in the presence of effector cells can be combined with another antibody that inhibits the growth of cells expressing PSMA. As used herein, "target cell" shall mean any undesirable cell in a subject (e.g., a human or animal) that can be targeted by a composition of the invention. In preferred embodiments, the target cell is a cell expressing or overexpressing PSMA. Cells expressing PSMA typically include tumor cells, such as prostate, bladder, pancreas, lung, kidney, colon tumor cells, melanomas, and sarcomas.

Pharmaceutical compositions of the invention also can be administered in combination therapy, i.e., combined with other agents. For example, the combination therapy can include a composition of the present invention with at least one anti-tumor agent, immunomodulator, immunostimulatory agent, or other conventional therapy. For instance, the agent may be bound or conjugated to or formed as a recombinant fusion molecule with the PSMA antibodies of the present invention for directed targeting of the agent to PSMA-expressing cells.

In some embodiments the various agents can be administered concomitantly. In other embodiments the agents are administered separately (prior to or subsequent to each other). The compositions provided herein can be given to any patient in need thereof. As one example, the compositions provided herein can be given to a conventional cancer treatment-experienced patient. For instance a composition of dimeric PSMA can be administered to such a patient at some time subsequent to a conventional cancer therapy. Conventional cancer therapy, such as for prostate cancer, includes one or more of the following: surgery, radiation, cryosurgery, thermotherapy, hormone treatment, chemotherapy, etc. In one embodiment the therapy received prior to administration of a composition of dimeric PSMA is at least prostatectomy and/or radiation. In another embodiment the therapy received prior to administration of a composition of dimeric PSMA is at least castration and hormonal therapy. In yet another embodiment the therapy received prior to administration of a composition of dimeric PSMA is at least chemotherapy. In one embodiment for prostate cancer the chemotherapy is preferably the administration of the chemotherapeutic agent, docetaxel, alone or in combination with an anti-inflammatory compound. The anti-inflammatory compound in one embodiment is prednisone. Therefore, in some embodiments compositions and methods are provided for treating patients with a composition containing dimeric PSMA that is administered concomitantly with, subsequent to, or prior to conventional cancer therapy. In one such embodiment the methods provided include the administration of docetaxel (75 mg/m$^2$ q3 weeks) plus the anti-inflammatory agent, prednisone (5 mg po bid), concomitantly with, subsequent to, or prior to the administration of dimeric PSMA compositions as provided herein.

In one embodiment patients amenable to treatment using dimeric PSMA include those who have not received conventional cancer treatment. In another embodiment patients amenable to treatment using dimeric PSMA include those who have evidence of cancer despite having received one or more conventional cancer therapies. Patients therefore can include patients with biochemically progressive prostate cancer such as non-astrate patients (serum testosterone greater than or equal to 180 ng/mL). In some embodiments these patients have received definitive primary therapy such as prostatectomy or radiation. Patients can also include castrate patients (serum testosterone less than 50 ng/mL), who in some embodiments have completed a course of hormonal therapy. Patients can also include patients having radiographic evidence of disease progression. In one embodiment such a treatment regimen is indicated in hormone-refractory prostate cancer patients.

The PSMA antibodies of the present invention may be used as a targeting moiety for delivery of replication-selective virus to PSMA-expressing cells for tumor therapy. Replication-competent virus such as the p53 pathway targeting adenovirus mutant d11520, ONYX-015, kill tumor cells selectively (Biederer, C. et al., J. Mol. Med. 80(3):163-175, 2002).

The compositions of the present invention may include or be diluted into a pharmaceutically-acceptable carrier. As used herein, "pharmaceutically acceptable carrier" or "physiologically acceptable carrier" means one or more compatible solid or liquid fillers, diluents or encapsulating substances which are suitable for administration to a human or other mammal such as a primate, dog, cat, horse, cow, sheep, or goat. Such carriers include any and all salts, solvents, dispersion media, coatings, antibacterial and antifungal agents, isotonic and absorption delaying agents, and the like that are physiologically compatible. The term "carrier" denotes an organic or inorganic ingredient, natural or synthetic, with which the active ingredient is combined to facilitate the application. The carriers are capable of being comingled with the preparations of the present invention, and with each other, in a manner such that there is no interaction which would substantially impair the desired pharmaceutical efficacy or stability. Preferably, the carrier is suitable for oral, intranasal, intravenous, intramuscular, subcutaneous, parenteral, spinal, intradermal or epidermal administration (e.g., by injection or infusion). Suitable carriers can be found in Remington's Pharmaceutical Sciences, Mack Publishing Company, Easton, Pa. Depending on the route of administration, the active compound, i.e., antibody or PSMA multimer may be coated in a material to protect the compound from the action of acids and other natural conditions that may inactivate the compound.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. The components of the pharmaceutical compositions also are capable of being co-mingled with the molecules of the present invention, and with each other, in a manner such that there is no interaction which would substantially impair the desired pharmaceutical efficacy. Such preparations may routinely contain salts, buffering agents, preservatives, compatible carriers, and optionally other therapeutic agents, such as supplementary immune potentiating agents including adjuvants, chemokines and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical preparations of the invention also may include isotonicity agents. This term is used in the art interchangeably with iso-osmotic agent, and is known as a compound which is added to the pharmaceutical preparation to increase the osmotic pressure to that of 0.9% sodium chloride solution, which is iso-osmotic with human extracellular fluids, such as plasma. Preferred isotonicity agents are sodium chloride, mannitol, sorbitol, lactose, dextrose and glycerol.

Optionally, the pharmaceutical preparations of the invention may further comprise a preservative, such as benzalkonium chloride. Suitable preservatives also include but are not limited to: chlorobutanol (0.3-0.9% W/V), parabens (0.01-5.0%), thimerosal (0.004-0.2%), benzyl alcohol (0.5-5%), phenol (0.1-1.0%), and the like.

The formulations provided herein also include those that are sterile. Sterilization processes or techniques as used herein include aseptic techniques such as one or more filtration (0.45 or 0.22 micron filters) steps.

An anti-PSMA antibody composition may be combined, if desired, with a pharmaceutically-acceptable carrier.

The pharmaceutical compositions may contain suitable buffering agents, including: acetic acid in a salt; citric acid in a salt; boric acid in a salt; and phosphoric acid in a salt.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of PSMA multimers and/or anti-PSMA antibodies, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The therapeutics of the invention can be administered by any conventional route, including injection or by gradual infusion over time. The administration may, for example, be oral, subcutaneous, intravenous, intraperitoneal, intramuscular, intracavity, intratumor, or transdermal. In some embodiments subcutaneous or intramuscular administration is preferred. When antibodies are used therapeutically, preferred routes of administration include intravenous and by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp. 1694-1712; incorporated by reference). Those of skill in the art can readily determine the various parameters and conditions for producing antibody aerosols without resorting to undue experimentation.

The pharmaceutical preparations of the invention, when used in alone or in cocktails, are administered in therapeutically effective amounts. Effective amounts are well known to those of ordinary skill in the art and are described in the literature. A therapeutically effective amount will be determined by the parameters discussed below; but, in any event, is that amount which establishes a level of the drug(s) effective for treating a subject, such as a human subject, having one of the conditions described herein. An effective amount means that amount alone or with multiple doses, necessary to delay the onset of, inhibit completely or lessen the progression of or halt altogether the onset or progression of the condition being treated. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

An "effective amount" is that amount of an anti-PSMA antibody or PSMA multimer that alone, or together with further doses, produces the desired response, e.g. treats a malignancy in a subject. The term is also meant to encompass the amount of an anti-PSMA antibody and/or PSMA multimer that in combination with a chemotherapeutic agent produces the desired response. This may involve only slowing the progression of the disease temporarily, although more preferably, it involves halting the progression of the disease permanently. This can be monitored by routine methods. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of anti-PSMA antibodies or PSMA multimers for producing the desired response in a unit of weight or volume suitable for administration to a patient. The response can, for example, be measured by determining the physiological effects of the anti-PSMA antibody or PSMA multimer, such as regression of a tumor or decrease of disease symptoms. Other assays will be known to one of ordinary skill in the art and can be employed for measuring the level of the response.

The doses of anti-PSMA antibodies or PSMA multimers administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion.

In general, doses can range from about 10 µg/kg to about 100,000 µg/kg. In one embodiment, the dose is about 50 mg. In another embodiment, the dose is about 250 mg. In still another embodiment, the dose is about 500 mg, 1000 mg or greater. Based upon the composition, the dose can be delivered once, continuously, such as by continuous pump, or at periodic intervals. The periodic interval may be weekly, bi-weekly, or monthly. The dosing can occur over the period of one month, two months, three months or more to elicit an appropriate humoral and/or cellular immune response. Desired time intervals of multiple doses of a particular composition can be determined without undue experimentation by one skilled in the art. Other protocols for the administration of anti-PSMA antibody or PSMA multimers will be known to one of ordinary skill in the art, in which the dose amount, schedule of administration, sites of administration, mode of administration and the like vary from the foregoing.

Dosage may be adjusted appropriately to achieve desired drug levels, locally or systemically. Generally, daily oral doses of active compounds will be from about 0.1 mg/kg per day to 30 mg/kg per day. It is expected that IV doses in the range of 0.01-1.00 mg/kg will be effective. In the event that the response in a subject is insufficient at such doses, even higher doses (or effective higher doses by a different, more localized delivery route) may be employed to the extent that patient tolerance permits. Continuous IV dosing over, for example, 24 hours or multiple doses per day also are contemplated to achieve appropriate systemic levels of compounds.

In general, doses of radionuclide delivered by the anti-PSMA antibodies of the invention can range from about 0.01 mCi/Kg to about 10 mCi/kg. Preferably the dose of radionuclide ranges from about 0.1 mCi/Kg to about 1.0 mCi/kg. The optimal dose of a given isotope can be determined empirically by simple routine titration experiments well known to one of ordinary skill in the art.

Administration of anti-PSMA antibody or PSMA multimer compositions to mammals other than humans, e.g. for testing purposes or veterinary therapeutic purposes, is carried out under substantially the same conditions as described above.

The compositions (antibodies to PSMA and derivatives/conjugates thereof and PSMA multimers) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is intended to include humans and non-human animals. Preferred subjects include a human patient having a disorder characterized by expression, typically aberrant expression (e.g., overexpression) of PSMA. Other preferred subjects include subjects that are treatable with the compositions of the invention. This includes those who have or are at risk of having a cancer or who would otherwise would benefit from an enhanced or elicited immune response to cells expressing PSMA. In preferred embodiments these cells express PSMA on their surface.

One aspect of the present invention relates to a method of detecting cancerous cells or portions thereof in a biological sample (e.g., histological or cytological specimens, biopsies and the like), and, in particular, to distinguish malignant tumors from normal tissues and non-malignant tumors. This method involves providing an antibody or an antigen-binding binding fragment thereof, probe, or ligand, which binds to an extracellular domain of PSMA of such cells, e.g., an anti- PSMA antibody. The anti-PSMA antibody is bound to a label that permits the detection of the cells or portions thereof (e.g., PSMA or fragments thereof liberated from such cancerous cells) upon binding of the anti-PSMA antibody to the cells or portions thereof. The biological sample is contacted with the labeled anti-PSMA antibody under conditions effective to permit binding of the anti-PSMA antibody to the extracellular domain of PSMA of any of the cells or portions thereof in the biological sample. The presence of any cells or portions thereof in the biological sample is detected by detection of the label. In one preferred form, the contact between the anti-PSMA antibody and the biological sample is carried out in a living mammal and involves administering the anti-PSMA antibody to the mammal under conditions that permit binding of the anti-PSMA antibody to PSMA of any of the cells or portions thereof in the biological sample. Again, such administration can be carried out by any suitable method known to one of ordinary skill in the art.

In addition, the anti-PSMA antibodies of the present invention can be used in immunofluorescence techniques to examine human tissue, cell and bodily fluid specimens. In a typical protocol, slides containing cryostat sections of frozen, unfixed tissue biopsy samples or cytological smears are air dried, formalin or acetone fixed, and incubated with the monoclonal antibody preparation in a humidified chamber at room temperature. The slides are then washed and further incubated with a preparation of a secondary antibody directed against the monoclonal antibody, usually some type of anti-mouse immunoglobulin if the monoclonal antibodies used are derived from the fusion of a mouse spleen lymphocyte and a mouse myeloma cell line. This secondary antibody is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or exfoliated cells, i.e., single cell preparations from aspiration biopsies of tumors using the anti-PSMA antibodies of this invention. The anti-PSMA antibodies of the invention are particularly useful in quantitation of live tumor cells, i.e., single cell preparations from aspiration biopsies of prostate tumors by computer enhanced fluorescence image analyzer or with a flow cytometer. The antibodies of the invention are particularly useful in such assays to differentiate benign from malignant prostate tumors since the PSMA protein to which the anti-PSMA antibodies bind is expressed in increased amounts by malignant tumors as compared to benign prostate tumors. The percent PSMA positive cell population, alone or in conjunction with determination of other attributes of the cells (e.g., DNA ploidy of these cells), may, additionally, provide very useful prognostic information by providing an early indicator of disease progression.

In yet another alternative embodiment, the antibodies of the present invention can be used in combination with other known antibodies to provide additional information regarding the malignant phenotype of a cancer.

The method of the present invention can be used to screen patients for diseases associated with the presence of cancerous cells or portions thereof. Alternatively, it can be used to identify the recurrence of such diseases, particularly when the disease is localized in a particular biological material of the patient. For example, recurrence of prostatic disease in the prostatic fossa may be encountered following radical prostatectomy. Using the method of the present invention, this recurrence can be detected by administering a short range radiolabeled antibody to the mammal and then detecting the label rectally, such as with a transrectal detector probe.

Alternatively, the contacting step can be carried out in a sample of serum or urine or other body fluids, including but not limited to seminal fluid, prostatic fluid, ejaculate, and the like, such as to detect the presence of PSMA in the body fluid. When the contacting is carried out in a serum or urine sample, it is preferred that the biological agent recognize substantially no antigens circulating in the blood other than PSMA. Since intact cells do not excrete or secrete PSMA into the extracellular environment, detecting PSMA in serum, urine, or other body fluids generally indicates that cells are being lysed or shed. Thus, the biological agents and methods of the present invention can be used to determine the effectiveness of a cancer treatment protocol by monitoring the level of PSMA in serum, urine or other body fluids.

In a particularly preferred embodiment of the method of detecting cancerous cells in accordance with the present invention, the anti-PSMA antibodies or an antigen-binding fragment thereof, binds to and is internalized with the prostate specific membrane antigen of such cells. Again, the biological agent is bound to a label effective to permit detection of the cells or portions thereof upon binding of the biological agent to and internalization of the biological agent with the prostate specific membrane antigen.

Biological agents suitable for detecting cancerous cells include anti-PSMA antibodies, such as monoclonal or polyclonal antibodies. In addition, antibody fragments, half-antibodies, hybrid derivatives, probes, and other molecular constructs may be utilized. These biological agents, such as antibodies, antigen-binding fragments thereof, probes, or ligands, bind to extracellular domains of prostate specific membrane antigens or portions thereof in cancerous cells. As a result, the biological agents bind not only to cells which are fixed or cells whose intracellular antigenic domains are otherwise exposed to the extracellular environment. Consequently, binding of the biological agents is concentrated in areas where there are prostate cells, irrespective of whether these cells are fixed or unfixed, viable or necrotic. Additionally or alternatively, these biological agents bind to and are internalized with prostate specific membrane antigens or portions thereof in normal, benign hyperplastic, and to a greater degree in cancerous cells.

The PSMA multimers and antibodies or antigen-binding fragments thereof can also be utilized in in vivo therapy of cancer. The PSMA multimers and antibodies or antigen-binding fragments thereof can be used with a compound which kills and/or inhibits proliferation of malignant cells or tissues. For instance, the antibodies can be covalently attached, either directly or via linker, to such a compound following administration and localization of the conjugates. When the antibody is used by itself, it may mediate tumor destruction by complement fixation or antibody-dependent cellular cytotoxicity. Alternatively, the PSMA multimer or antibody may be administered in combination with a chemotherapeutic drug to result in synergistic therapeutic effects (Baslya and Mendelsohn, 1994 *Breast Cancer Res. and Treatment* 29:127-138). A variety of different types of substances can be directly conjugated for therapeutic uses, including radioactive metal and non-metal isotopes, chemotherapeutic drugs, toxins, etc. as described above and known in the art (see, e.g., Vitetta and Uhr, 1985, *Annu. Rev. Immunol.* 3:197).

The antibodies or antigen-binding fragments thereof of the invention can also be administered together with complement. Accordingly, within the scope of the invention are compositions comprising antibodies or antigen-binding fragments thereof and serum or complement. These compositions are advantageous in that the complement is located in close proximity to the human antibodies or antigen-binding fragments thereof. Alternatively, the antibodies or antigen-binding fragments thereof of the invention and the complement or serum can be administered separately.

The PSMA multimers or antibodies can be administered with one or more immunostimulatory agents to induce or enhance an immune response, such as IL-2 and immunostimulatory oligonucleotides (e.g., those containing CpG motifs). Preferred immunostimulatory agents stimulate specific arms of the immune system, such as natural killer (NK) cells that mediate antibody-dependent cell cytotoxicity (ADCC).

As provided elsewhere herein, the compositions provided can be administered with one or more adjuvants to induce or enhance an immune response. An adjuvant is a substance which potentiates the immune response. Adjuvants of many kinds are well known in the art. Specific examples of adjuvants include monophosphoryl lipid A (MPL, SmithKline Beecham); saponins including QS-21 (Antigenics); immunostimulatory oligonucleotides (e.g., CpG oligonucleotides described by Kreig et al., Nature 374:546-9, 1995); incomplete Freund's adjuvant; complete Freund's adjuvant; MONTANIDE; vitamin E and various water-in-oil emulsions prepared from biodegradable oils such as squalene and/or tocopherol, Quil A, Ribi Detox, CRL-1005, L-121, and combinations thereof.

Other agents which stimulate the immune response of the subject to PSMA multimer antigens can also be administered to the subject. For example, cytokines are also useful in vaccination protocols as a result of their lymphocyte regulatory properties. Many cytokines useful for such purposes will be known to one of ordinary skill in the art, including interleukin-2 (IL-2); IL-4; IL-5; IL-12, which has been shown to enhance the protective effects of vaccines (see, e.g., Science 268: 1432-1434, 1995); GM-CSF; IL-15; IL-18; combinations thereof, and the like. Thus cytokines can be administered in conjunction with antibodies, antigens, chemokines and/or adjuvants to increase an immune response.

Chemokines useful in increasing immune responses include but are not limited to SLC, ELC, MIP3α, MIP3β, IP-10, MIG, and combinations thereof.

The PSMA multimers or antibodies or antigen-binding fragments thereof of the present invention can be used in conjunction with other therapeutic treatment modalities. Current standard or conventional treatments for cancer, such as prostate cancer, include surgery, radiation, cryosurgery, thermotherapy, hormone treatment and chemotherapy. Subjects receiving one or more of the standard treatments may be referred to as treatment-experienced subjects. Hormone therapy includes treatment with one or more of the following modalities: a leutinizing hormone-releasing hormone agonist such as leuprolide, goserelin or buserelin; an antiandrogen, such as flutaminde or bicalutamide; a drug that prevents adrenal glands from making androgens, such as ketoconazole or aminoglutethimide; estrogens; and orchiectomy (castration). Chemotherapy may use any chemotherapeutic/antineoplastic agent known in the art. In some preferred embodiments the chemotherapeutic agent is a taxane, such as paclitaxel (TAXOL) or docetaxel (TAXOTERE). Chemotherapy may be used in combination with an anti-inflammatory compound such as a corticosteroid. Corticosteroids include cortisone, hydrocortisone, prednisone, prednisolone, triamcinolone, methylprednisolone, dexamethasone, betamethasone and the like. A preferred anti-inflammatory compound is prednisone.

Other therapeutic modalities that may be used in combination with PSMA multimers include the use of other vaccines and immunotherapies.

Also encompassed by the present invention is a method which involves using the PSMA multimers or antibodies or antigen-binding fragments thereof for prophylaxis. For example, these materials can be used to prevent or delay development or progression of cancer.

Use of the cancer therapy of the present invention has a number of benefits. Since the anti-PSMA antibodies or antigen-binding fragments thereof according to the present invention preferentially target prostate cancer cells, other tissue is spared. As a result, treatment with such biological agents is safer, particularly for elderly patients. Treatment according to the present invention is expected to be particularly effective, because it directs high levels of anti-PSMA antibodies or antigen-binding fragments thereof to the bone marrow and lymph nodes where prostate cancer metastases predominate. Moreover, tumor sites for prostate cancer tend to be small in size and, therefore, easily destroyed by cytotoxic agents. Treatment in accordance with the present invention can be effectively monitored with clinical parameters such as serum prostate specific antigen and/or pathological features of a patient's cancer, including stage, Gleason score, extracapsular, seminal, vesicle or perineural invasion, positive margins, involved lymph nodes, etc. Alternatively, these parameters can be used to indicate when such treatment should be employed.

Because the antibodies or antigen-binding fragments thereof of the present invention bind to living cells, therapeutic methods using these biological agents are much more effective than those which target lysed cells. For the same reasons, diagnostic and imaging methods which determine the location of living normal, benign hyperplastic, or cancerous cells are much improved by employing the antibodies or antigen-binding fragments thereof of the present invention. In addition, the ability to differentiate between living and dead cells can be advantageous, especially to monitor the effectiveness of a particular treatment regimen.

Also within the scope of the invention are kits comprising the compositions of the invention and instructions for use. The kits can further contain at least one additional reagent, such as complement, or one or more additional antibodies of the invention (e.g., an antibody having a complementary activity which binds to an epitope in PSMA antigen distinct from the first antibody). Other kits can include the PSMA multimers described herein below.

The kits provided herein include any of the compositions described and instructions for the use of these compositions. The instructions can include instructions for mixing a particular amount of an agent or solution that preserves or promotes the multimerization of PSMA with a particular amount of a PSMA composition. The instructions can also include instructions for mixing a particular amount of a diluent with a particular amount of a PSMA dimeric composition, whereby a final formulation for injection or infusion is prepared. Therefore, kits are also provided, which include the compositions of the invention and, optionally, an adjuvant (e.g., alum) or diluent and instructions for mixing. Kits are also provided wherein the compositions of the inventions are provided in a vial or ampoule with a septum or a syringe. Other kits where the composition is in lyophilized form are also provided. The instructions, therefore, would take a variety of forms depending on the presence or absence of diluent or other agents (e.g., therapeutic agents). The instructions can include instructions for treating a patient with an effective amount of dimeric PSMA. It also will be understood that the containers containing the pharmaceutical preparation, whether the container is a bottle, a vial with a septum, an ampoule with a septum, an infusion bag, and the like, can contain indicia such as conventional markings which change color when the pharmaceutical preparation has been autoclaved or otherwise sterilized.

Kits containing the antibodies or antigen-binding fragments thereof of the invention can be prepared for in vitro diagnosis, prognosis and/or monitoring cancer by the immunohistological, immunocytological and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain one or more anti-PSMA antibodies or antigen-binding fragments thereof or PSMA. A second container means or series of container means may contain a label or linker-label intermediate capable of binding to the primary anti-PSMA antibodies (or fragment thereof).

It should be understood that the pharmaceutical preparations of the invention will typically be held in bottles, vials, ampoules, infusion bags, and the like, any one of which may be sparged to eliminate oxygen or purged with nitrogen. In some embodiments, the bottles vials and ampoules are opaque, such as when amber in color. Such sparging and purging protocols are well known to those of ordinary skill in the art and should contribute to maintaining the stability of the pharmaceutical preparations. The pharmaceutical preparations also, in certain embodiments, are expected to be contained within syringes.

Kits for use in in vivo tumor localization and therapy method containing the anti-PSMA antibodies or antigen-binding fragments thereof conjugated to other compounds or substances can be prepared. The components of the kits can be packaged either in aqueous medium or in lyophilized form. When the antibodies or antigen-binding fragments thereof are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

In one aspect of the invention, a method for modulating at least one enzymatic activity of PSMA, the activity selected from the group consisting of N-acetylated α-linked acidic dipeptidase (NAALADase), folate hydrolase, dipeptidyl dipeptidase IV and γ-glutamyl hydrolase activity or combination thereof in vitro or in vivo. The modulation may be enhancement or inhibition of at least one enzymatic activity of PSMA.

In a preferred embodiment, the invention provides methods for inhibiting at least one enzymatic activity of PSMA, the activity selected from the group consisting of N-acetylated α-linked acidic dipeptidase (NAALADase), folate hydrolase, dipeptidyl dipeptidase IV and γ-glutamyl hydrolase activity or combination thereof in vitro or in vivo. The method comprises contacting a NAALADase, a folate hydrolase, a dipeptidyl dipeptidase IV and/or a γ-glutamyl hydrolase with an amount of an isolated antibody or antigen-binding fragment thereof of the invention under conditions wherein the isolated monoclonal antibody or antigen-binding fragment thereof inhibits NAALADase, folate hydrolase, dipeptidyl dipeptidase IV or γ-glutamyl hydrolase activity.

Tissue levels of NAALADase can be determined by detergent solubilizing homogenizing tissues, pelleting the insoluble material by centrifugation and measuring the NAALADase activity in the remaining supernatant. Likewise, the NAALADase activity in bodily fluids can also be measured by first pelleting the cellular material by centrifugation and performing a typical enzyme assay for NAALADase activity on the supernatant. NAALADase enzyme assays have been described by Frieden, 1959, *J. Biol, Chem.*, 234:2891. In this assay, the reaction product of the NAALADase enzyme is glutamic acid. This is derived from the enzyme catalyzed cleavage of N-acetylaspartylglutamate to yield N-acetylaspartic acid and glutamic acid. Glutamic acid, in a $NAD(P)^+$ requiring step, yields 2-oxoglutarate plus NAD(P)H in a reaction catalyzed by glutamate dehydrogenase. Progress of the reaction can easily and conveniently be measured by the change in absorbance at 340 nm due to the conversion of $NAD(P)^+$ to $NAD(P)H$.

Folate hydrolase activity of PSMA can be measured by performing enzyme assays as described by Heston and others (e.g., *Clin. Cancer Res.* 2(9):1445-51, 1996; *Urology* 49(3A Suppl):104-12,1997). Folate hydrolases such as PSMA remove the gamma-linked glutamates from polyglutamated folates. Folate hydrolase activity can be measured using substrates such as methotrexate tri-gamma glutamate (MTX-Glu3), methotrexate di-gamma glutamate (MTXGlu2) and pteroylpentaglutamate (PteGluS), for example using capillary electrophoresis (see *Clin. Cancer Res.* 2(9):1445-51, 1996). Timed incubations of PSMA with polyglutamated substrates is followed by separation and detection of hydrolysis products.

The invention also includes isolated antibodies and binding fragments thereof that selectively bind PSMA multimers. As used herein, particularly with respect to the binding of PSMA multimers by the anti-PSMA antibodies and binding fragments, "selectively binds" means that an antibody preferentially binds to a PSMA protein multimer (e.g., with greater avidity, greater binding affinity) rather than to a PSMA protein monomer. In preferred embodiments, the antibodies of the invention bind to a PSMA protein multimer with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 7-fold, 10-fold, 20-fold, 30-fold, 40-fold, 50-fold, 70-fold, 100-fold, 200-fold, 300-fold, 500-fold, 1000-fold or more than that exhibited by the antibody for a PSMA protein monomer. Preferably, the antibody selectively binds a PSMA protein multimer, and not a PSMA protein monomer, i.e., substantially exclusively binds to a PSMA protein multimer. Most preferably, the antibody selectively binds a PSMA protein dimer.

The isolated antibody or binding fragment that selectively binds a PSMA protein multimer can, in some embodiments, modulate enzymatic activity of the PSMA protein multimer. In one such embodiment, the antibody inhibits at least one enzymatic activity such as NAALADase activity, folate hydrolase activity, dipeptidyl dipeptidase IV activity, γ-glutamyl hydrolase activity, or combinations thereof. In another embodiment, the antibody enhances at least one enzymatic activity such as NAALADase activity, folate hydrolase activity, dipeptidyl dipeptidase IV activity, γ-glutamyl hydrolase activity, or combinations thereof.

As described elsewhere herein, a PSMA protein multime is a protein complex of at least two PSMA proteins or fragments thereof. The PSMA protein multimers can be composed of various combinations of full-length PSMA proteins (e.g., SEQ ID NO:1), recombinant soluble PSMA (rsPSMA, e.g., amino acids 44-750 of SEQ ID NO:1) and fragments of the foregoing that form multimers (i.e., that retain the protein domain required for forming dimers and/or higher order multimers of PSMA). In preferred embodiments, at least one of the PSMA proteins forming the multimer is a recombinant, soluble PSMA (rsPSMA) polypeptide. Preferred PSMA protein multimers are dimers, particularly those formed from recombinant soluble PSMA protein. A particularly preferred embodiment is a rsPSMA homodimer.

The PSMA protein multimers referred to herein are believed to assume a native conformation and preferably have such a conformation. The PSMA proteins in certain embodiments are noncovalently bound together to form the PSMA protein multimer. For example, it has been discovered that PSMA protein noncovalently associates to form dimers under non-denaturing conditions, as described in the Examples below.

The PSMA protein multimers can, and preferably do, retain the activities of PSMA. The PSMA activity may be an enzymatic activity, such as folate hydrolase activity, NAALADase activity, dipeptidyl peptidase IV activity and γ-glutamyl hydrolase activity. Methods for testing the PSMA activity of multimers are well known in the art (reviewed by O'Keefe et al. in: *Prostate Cancer: Biology, Genetics, and the New Therapeutics*, L. W. K. Chung, W. B. Isaacs and J. W. Simons (eds.) Humana Press, Totowa, N.J., 2000, pp. 307-326), some of which are described in the Examples herein below.

As used herein with respect to polypeptides, proteins or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

Fragments of a PSMA protein preferably are those fragments which retain a distinct functional capability of the PSMA protein. Functional capabilities which can be retained in a fragment include binding of other PSMA molecules to form dimers and higher order multimers, interaction with antibodies, interaction with other polypeptides or fragments thereof, and enzymatic activity. Other PSMA protein fragments, e.g., other recombinant soluble fragments of SEQ ID NO:1, can be selected according to their functional properties. For example, one of ordinary skill in the art can prepare PSMA fragments recombinantly and test those fragments according to the methods exemplified below.

Modifications to a PSMA polypeptide are typically made to the nucleic acid which encodes the PSMA polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the PSMA amino acid sequence.

In general, modified PSMA polypeptides include polypeptides which are modified specifically to alter a feature of the polypeptide unrelated to its physiological activity. For example, cysteine residues can be added or substituted or deleted to promote or prevent unwanted disulfide linkages, respectively. Similarly, certain amino acids can be changed to enhance expression of a PSMA polypeptide by eliminating proteolysis by proteases in an expression system (e.g., dibasic amino acid residues in yeast expression systems in which KEX2 protease activity is present).

Modifications conveniently are prepared by altering a nucleic acid molecule that encodes the PSMA polypeptide. Mutations of a nucleic acid which encode a PSMA polypeptide preferably preserve the amino acid reading frame of the coding sequence, and preferably do not create regions in the nucleic acid which are likely to hybridize to form secondary structures, such a hairpins or loops, which can be deleterious to expression of the modified polypeptide.

Modifications can be made by selecting an amino acid substitution, or by random mutagenesis of a selected site in a nucleic acid which encodes the PSMA polypeptide. Modified PSMA polypeptides then can be expressed and tested for one or more activities (e.g., antibody binding, enzymatic activity, multimeric stability) to determine which mutation provides a modified polypeptide with the desired properties. Further mutations can be made to modified PSMA polypeptides (or to non-modified PSMA polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a PSMA coding sequence or cDNA clone to enhance expression of the polypeptide. The activity of modified PSMA polypeptides can be tested by cloning the gene encoding the modified PSMA polypeptide into a bacterial or mammalian expression vector, introducing the vector into an appropriate host cell, expressing the modified PSMA polypeptide, and testing for a functional capability of the PSMA polypeptides as disclosed herein. The foregoing procedures are well known to one of ordinary skill in the art.

The skilled artisan will also realize that conservative amino acid substitutions may be made in PSMA polypeptides to provide functionally equivalent PSMA polypeptides, i.e., modified PSMA polypeptides that retain the functional capabilities of PSMA polypeptides. These functionally equivalent PSMA polypeptides include those PSMA polypeptides or proteins that are capable of associating to form multimers, particularly dimers. As used herein, a "conservative amino acid substitution" refers to an amino acid substitution which does not alter the relative charge or size characteristics of the protein in which the amino acid substitution is made. Modified PSMA polypeptides can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

Exemplary functionally equivalent PSMA polypeptides include conservative amino acid substitutions of SEQ ID NO:1, or fragments thereof, such as the recombinant soluble PSMA polypeptide (amino acids 44-750 of SEQ ID NO:1). Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in PSMA polypeptides typically are made by alteration of a nucleic acid encoding a PSMA polypeptide. Conservatively substituted PSMA polypeptides include those with 1, 2, 3, 4, 5, 6, 7, 8, 9, 10, 15, 20, or more substitutions. Such substitutions can be made by a variety of methods known to one of ordinary skill in the art. For example, amino acid substitutions may be made by PCR-directed mutation, site-directed mutagenesis, or by chemical synthesis of a gene encoding a PSMA polypeptide. Where amino acid substitutions are made to a small fragment of a PSMA polypeptide, the substitutions can be made by directly synthesizing the peptide. The activity of functionally equivalent fragments of PSMA polypeptides can be tested by cloning the gene encoding the altered PSMA polypeptide into a bacterial or mammalian expression vector, introducing the vector into an appropriate host cell, expressing the altered PSMA polypeptide, and testing for a functional capability of the PSMA polypeptides as disclosed herein.

The PSMA protein multimers as described herein have a number of uses, some of which are described elsewhere herein. The multimers are useful for testing of compounds that modulate PSMA enzymatic activity or PSMA multimerization. The multimers can be used to isolate antibodies that selectively bind PSMA, including those selective for conformational epitopes, those selective for binding PSMA multimers and not PSMA monomers, and those that selectively modulate an enzymatic activity of PSMA. The multimers, particularly dimeric PSMA, also can be used to induce or increase immune responses to PSMA, as vaccine compositions.

Agents that selectively modulate an enzymatic activity of PSMA include agents that inhibit or enhance at least one enzymatic activity of PSMA, such as NAALADase activity, folate hydrolase activity, dipeptidyl dipeptidase IV activity, γ-glutamyl hydrolase activity, or combinations thereof.

Thus methods of screening for candidate agents that modulate at least one enzymatic activity of a PSMA enzyme are provided in accordance with the invention. The methods can include mixing the candidate agent with an isolated PSMA protein multimer to form a reaction mixture, thereby contacting the PSMA enzyme with the candidate agent. The methods also include adding a substrate for the PSMA enzyme to the reaction mixture, and determining the amount of a product formed from the substrate by the PSMA enzyme. Such methods are adaptable to automated, high-throughput screening of compounds. A decrease in the amount of product formed in comparison to a control is indicative of an agent capable of inhibiting at least one enzymatic activity of the PSMA enzyme. An increase in the amount of product formed in comparison to a control is indicative of an agent capable of enhancing at least one enzymatic activity of the PSMA enzyme. The PSMA enzyme can be NAALADase, folate hydrolase, dipeptidyl dipeptidase IV and/or γ-glutamyl hydrolase. The PSMA enzyme preferably is a PSMA multimer that includes recombinant soluble PSMA, most preferably a noncovalently associated dimer of PSMA in a native conformation.

The reaction mixture comprises a candidate agent. The candidate agent is preferably an antibody, a small organic compound, or a peptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random peptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing reaction materials is incubated under conditions whereby, the candidate agent interacts with the PSMA enzyme. The order of addition of components, incubation temperature, time of incubation, and other parameters of the assay may be readily determined Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of PSMA enzyme activity is detected by any convenient method available to the user. For example, the reaction mixture can contain a substrate for the PSMA enzyme. Preferably the substrate and/or the product formed by the action of the PSMA enzyme are detectable. The substrate usually comprises, or is coupled to, a detectable label. A wide variety of labels can be used, such as those that provide direct detection (e.g., radioactivity, luminescence, optical, or electron density, etc) or indirect detection (e.g., epitope tag such as the FLAG epitope, enzyme tag such as horseradish peroxidase, etc.). The label may be bound to the substrate, or incorporated into the structure of the substrate.

A variety of methods may be used to detect the label, depending on the nature of the label and other assay components. For example, the label may be detected while bound to the substrate or subsequent to separation from the substrate. Labels may be directly detected through optical or electron density, radioactive emissions, nonradiative energy transfers, etc. or indirectly detected with antibody conjugates, strepavidin-biotin conjugates, etc. Methods for detecting a variety of labels are well known in the art.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

DNA Constructs. All secreted PSMA constructs were derived from the original human PSMA clone p55A provided by Dr. W. D. W. Heston (Israeli et al., *Cancer Res.* 53: 227-230, 1993). The constructs were subcloned into expression vector PPI4 (Trkola et al., *Nature* 384: 184-187, 1996) for high-level expression and secretion in mammalian cells. Recombinant soluble PSMA (rsPSMA) corresponds to the entire extracellular domain of PSMA (amino acids 44-750 of SEQ ID NO:1 (GENBANK Protein Accession number AAA60209)).

pcDNA Plasmid Constructs: Nucleic acid molecules encoding the anti-PSMA antibodies 10.3, 006, 026, 051, 069 and 077 were cloned into plasmid pcDNA. The cloning protocol is given in FIG. 13. Primers (SEQ ID NOs: 33-36, sense and anti-sense) used for the variable region amplifications are also shown. The plasmids constructed for anti-PSMA antibodies 006, 026, 051, 069, 077 and 10.3 contain nucleotide sequences encoding the heavy chain of the antibodies (SEQ ID NOs: 2-7; PTA-4403, PTA-4405, PTA-4407, PTA-4409, PTA-4411, PTA-4413, respectively) or contain nucleotide sequences encoding light chain of the antibodies (SEQ ID NOs: 8-13; PTA-4404, PTA-4406, PTA-4408, PTA-4410, PTA-4412 and PTA-4414, respectively). Plasmid maps are given in FIGS. 14-25.

Western Blots. Cells were lysed in PBS containing 1 mM EDTA, 1% NP-40, 1% Triton X-100, and 5 mg/ml aprotinin and cell debris was removed by centrifugation at 3000 g for 30 min at 4° C. Lysates were separated on a 5-20% gradient gel before transfer to nitrocellulose membranes. The resulting blots were blocked in PBS containing 5% milk, 0.02% SDS and 0.1% Triton X-100 before incubation with MAB544 primary antibody (Maine Biotechnologies) at a concentration of 2 mg/ml. After three washes, blots were incubated with a goat anti-mouse HRP-conjugated secondary antibody at a concentration of 0.2 mg/ml. Blots are visualized using the Renaissance chemiluminescence system (Perkin-Elmer Life Sciences, Boston, Mass.).

ELISA. Cells were lysed in PBS containing 1 mM EDTA, 1% NP-40, 1% Triton X-100, and 5 mg/ml aprotinin. The resulting cell membranes were plated onto 96-well plates and dried in a sterile hood overnight. The plates were then blocked with PBS containing casein and TWEEN-20 before addition of mouse sera or hybridoma supernatants, using purified MAB544 (Maine Biotechnologies) or 7E11 (Cytogen) as a standard. After washing in PBS, an alkaline phosphatase conjugated secondary antibody (subclass specific) was incubated and subsequently washed in PBS. The pNPP substrate was then added for colorimetric detection at a wavelength of 405 nm.

Flow Cytometry. Wild-type 3T3 or PSMA-expressing 3T3 cells ($10^6$ cells per condition) were washed in PBS containing 0.1% $NaN_3$. Antibodies or sera were then added (1:100 dilution in PBS) and incubated on ice for 30 minutes. After washing in PBS+0.1% $NaN_3$, the cells were incubated with anti-mouse IgG+IgM (Calbiotech) for 30 minutes on ice. Cells were washed again in PBS+0.1% $NaN_3$ and analyzed by flow cytometry.

Example 1

Generation of a Panel of Monoclonal Antibodies (mAbs) to Conformational Epitopes on PSMA A panel of anti-PSMA mAbs that represent promising candidates for therapy was created. Briefly, the mAbs were generated as follows: BALB/c mice were immunized subcutaneously with recombinant PSMA at approximately three-week intervals. After a total of 4 injections, mice were sacrificed and their splenocytes fused with a myeloma cell line using standard techniques in order to create hybridomas. Individual hybridoma supernatants were screened by ELISA for reactivity with PSMA derived from either LNCaP human prostate tumor cells or from 3T3 cells engineered to express full-length human PSMA (3T3-PSMA cells). Positive clones were secondarily screened by flow cytometry for specific reactivity with intact 3T3-PSMA and LNCaP cells so as to select antibodies that recognize native, cell-surface PSMA and thus have the greatest therapeutic potential.

Mice having the ability to produce human antibodies (XE-NOMOUSE, Abgenix; Mendez et al., *Nature Genetics* 15:146, 1997) were immunized subcutaneously once or twice weekly with $5\times10^6$ LNCaP cells adjuvanted with alum or TITERMAX Gold (Sigma Chemical Co., St. Louis, Mo.). Animals were boosted twice with 10 ng of recombinant PSMA protein immunoaffinity captured onto protein G magnetic microbeads (Miltenyi Biotec, Auburn, Calif.). PSMA mAb 3.11 was used for capture. Splenocytes were fused with NSO myeloma cells and the hybridomas that resulted were screened as above by flow cytometry to detect clones producing antibodies reactive with the extracellular portion of PSMA. One clone, 10.3 (PTA-3347), produced such antibodies.

Figure 2:
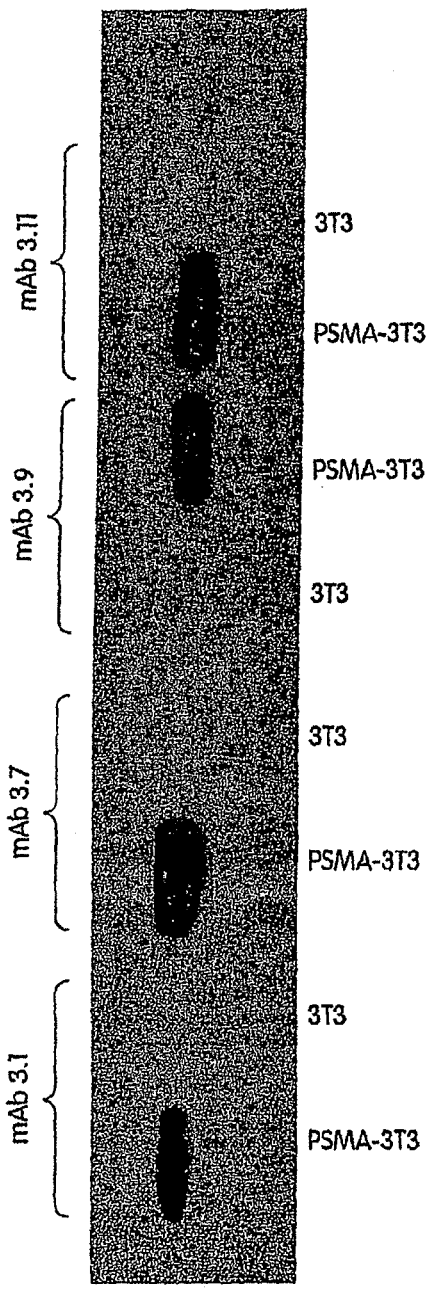
FIG. 2 shows a digitized image of immunoprecipitation of PSMA by mAbs. Lysates from 3T3-PSMA cells or parental 3T3 cells were incubated with each mAb and then precipitated using Protein A/G agarose beads. After washing, proteins were resolved on a polyacrylamide gel, blotted onto nitrocellulose membranes and visualized using the MAB544 anti-PSMA mAb.
Figure 3:
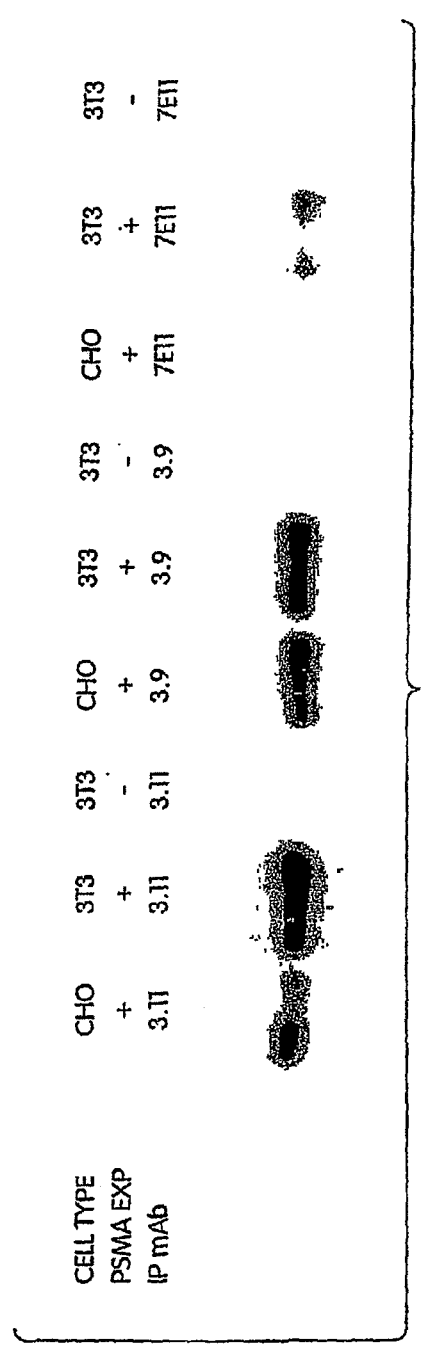
FIG. 3 shows the recognition of non-denatured PSMA by several PSMA antibodies that recognize PSMA conformation.

These methods have yielded a high proportion of mAbs that react exclusively with conformation-specific epitopes on cell-surface PSMA. As shown in FIG. 1, several (mAbs 3.7, 3.9, 3.11, 5.4, and 10.3) but not all (mAb 3.12) mAbs specifically bind viable PSMA-expressing cells. Using recombinant soluble PSMA proteins expressed in Chinese hamster ovary (CHO) cell lines, it further was demonstrated that the mAbs bind epitopes in the extracellular region of PSMA. The mAbs were also tested for their ability to immunoprecipitate native PSMA from 3T3-PSMA cell lysates. The mAbs positive in flow cytometry (FIG. 1) were also effective in immunoprecipitation (FIG. 2), whereas mAb 3.12 was unreactive. FIG. 3 shows the recognition of non-denatured full-length PSMA and recombinant soluble PSMA by several PSMA antibodies that recognize PSMA conformation. This further confirms that these methods yield a preponderance of mAbs that efficiently recognize native PSMA.

Figure 4:
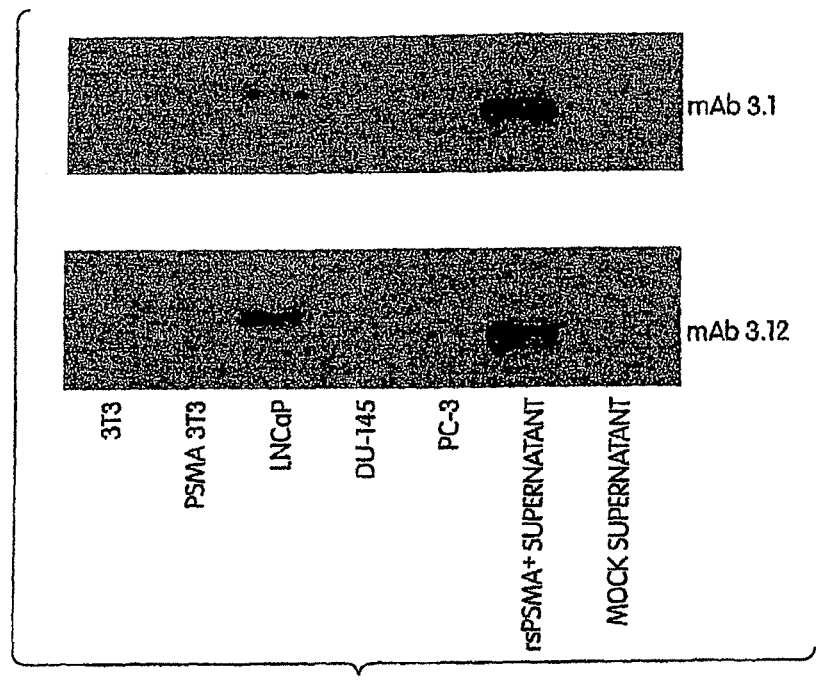
FIG. 4 is a digitized image of a Western blot that shows the recognition of denatured PSMA by two PSMA antibodies and shows that antibodies that recognize PSMA conformation do not recognize denatured PSMA.

The mAbs were tested for reactivity with denatured PSMA by Western blot analysis (FIG. 4). Lysates from the indicated cells and samples (controls: 3T3 cells, PSMA-negative human prostate cell lines PC-3 and DU145, mock supernatant; PSMA-positive samples: PSMA-expressing 3T3 cells, PSMA-positive human prostate cell line LNCaP, rsPSMA-positive supernatant) were resolved by SDS-PAGE, electroblotted, and probed with anti-PSMA mAbs 3.1 and 3.12 (ATCC Patent Deposit Designations PTA-3639 and PTA-3640, respectively). Four mAbs tested in parallel (3.7, 3.8, 3.9, 3.11) showed no reactivity to either full-length or secreted rsPSMA proteins. 7E11 mAb immunoprecipitated full-length but not secreted rsPSMA.

The mAbs reactive in flow cytometry and immunoprecipitation (mAbs 3.7, 3.9, 3.11, 5.4, and 10.3) were all unreactive in Western blot analysis, indicating that the mAbs do not recognize linear epitopes. Taken together, the data strongly suggest that these 5 mAbs recognize conformation-specific epitopes located in the extracellular domain of PSMA. Since mAbs to conformational epitopes typically possess the greatest affinity and specificity for antigen, they represent preferred candidates for therapy.

The reactivities of certain anti-PSMA antibodies are described in Table 2:

TABLE 2

Anti-PSMA Antibody Properties

| mAb | ELISA | Flow Cytometry | IP | Western | Epitope |
|---|---|---|---|---|---|
| 3.1 | + | + | + | + | Linear, Extracellular, exposed on native PSMA |
| 3.7 | + | + | + | − | Conformational, extracellular |
| 3.8 | + | + | + | − | Conformational, extracellular |
| 3.9 | + | + | + | − | Conformational, extracellular |
| 3.11 | + | + | + | − | Conformational, extracellular |
| 3.12 | + | − | − | + | Linear, Extracellular, not exposed on native PSMA |
| 5.4 | + | + | + | − | Conformational, extracellular |
| 7.1 | + | − | − | + | Linear, Extracellular, not exposed on native PSMA |
| 7.3 | + | + | + | − | Conformational, extracellular |
| 10.3 | + | + | + | − | Conformational, extracellular |
| 1.8.3 | + | + | | − | Extracellular |
| A3.1.3 | + | + | | − | Extracellular |
| A3.3.1 | + | + | | − | Extracellular |

The mAbs were determined by ELISA to be primarily of the mouse IgG2a, mouse IgG2b and human IgG1 isotypes, which mediate potent effector functions. Although a number of anti-PSMA mAbs have been described over the years and evaluated for therapeutic potential (see, e.g., Liu, H. et al. *Cancer Res.* 57: 3629-3634, 1997; Chang, S. S. et al. *Cancer Res.* 59: 3192-3198, 1999; Murphy, G. P. et al. *J Urology* 160: 2396-2401, 1998), none inhibit the enzymatic activity of PSMA and few recognize conformational determinants on PSMA.

Example 2

Production of Anti-PSMA mAbs

To accurately and quantitatively assess the therapeutic potential of these mAbs, the mAbs are produced in a quantity and quality suitable for extensive in vitro and in vivo characterization. Briefly, the mAb-secreting hybridomas are cultured in roller bottles in DMEM/F12 medium supplemented with 10% FBS that has been depleted of bovine IgG (Life Technologies). During the production phase of the culture, cells are maintained at ~5×10$^6$ cells/mL via twice-weekly exchanges of media. Collected media are clarified by filtration through a 0.22 micron filter and stored at −95° C. prior to purification. Given an average antibody expression levels of ~25 mg/L, approximately 3 L of roller bottle supernatants are required for each antibody to allow for losses in purification.

Culture supernatants from a given hybridoma are pooled and loaded onto a Protein A SEPHAROSE affinity column. Mouse IgG2a, mouse IgG2b and human IgG1 antibodies are loaded directly, but supernatants containing mouse IgG1 antibodies are adjusted to pH 8.5 and 1M NaCl prior to loading in order to promote binding. After washing the column, the mAb is eluted with low pH buffer into fractions using 1M Tris, pH 8.0. Elution peak fractions are pooled, dialyzed against PBS buffer, concentrated to 5 mg/mL and stored in sterile aliquots at −95° C. All purification procedures are carried out using endotoxin-free buffers and sanitized chromatography columns Purified mAbs are tested for purity by reducing and nonreducing SDS-PAGE, for PSMA binding affinity by ELISA, and for endotoxin levels by the *limulus amebocyte* lysate assay. These procedures routinely yield "animal-grade" antibody at >95% purity and <0.5 endotoxin units per milligram of protein.

Example 3

Evaluation of the Therapeutic Potential of the Unlabeled mAbs In Vitro

Purified mAbs are tested in a battery of assays for therapeutically relevant properties, including affinity, specificity, enzyme inhibitory activity and effector functions. The ideal product candidate binds and inhibits PSMA activity at sub-nanomolar concentrations and mediates potent cell-killing through Fc-related effector functions.

First, the mAbs' affinity for cell-surface and secreted forms of PSMA is measured by flow cytometry and ELISA, respectively. In the flow cytometry assay, varying amounts of mAbs are incubated with 5×10$^5$ 3T3-PSMA cells in FACS buffer (PBS containing 1% FBS and 0.1% NaN$_3$) for 2 hr to allow for saturation binding. Cells are washed and incubated with a phycoerythrin-coupled goat antibody to mouse IgG (ICN/Cappel) for detection of bound mAb by flow cytometry. Specific binding is calculated by subtracting the fluorescence intensity observed with parental 3T3 cells.

For ELISA, CHO cell-derived recombinant soluble PSMA protein (rsPSMA, Progenics, Tarrytown, N.Y.) is diluted to 1 µg/ml in 50 mM carbonate buffer, pH 9.4, and coated overnight at 4° C. onto 96-well IMMULON II microtiter plates at 100 µl/well. The plates are then blocked for 2 hr with PBS buffer containing 5% BSA. mAbs are added in a range of concentrations in ELISA buffer (PBS buffer containing 2% BSA, 1% FBS and 0.5% TWEEN 20) for 2 hours at room temperature. The plates are washed, and horseradish peroxidase conjugated goat antibody to mouse IgG is added for 1 hr at room temperature. The plates are washed again and 3,3',5, 5'-tetramethylbenzidine dihydrochloride (TMB) substrate (Pierce, Rockford, Ill.) is added for colorimetric readout at 450 nm using an ELISA plate reader (Molecular Devices, Sunnyvale, Calif.).

Example 4 mAb Cross-Competition Binding Assay

To identify whether a given group of mAbs recognize distinct or overlapping epitopes on PSMA, cross-competition binding assays are performed (Liu, H. et al. Cancer Res 57: 3629-3634, 1997). In this flow cytometry assay, a biotinylated test mAb is incubated with 3T3-PSMA cells in the presence or absence of varying concentrations of unlabeled competitor mAbs as described above. Following washing, phycoerythrin-conjugated streptavidin is added to determine the amount of bound biotinylated mAb. The percent inhibition is defined relative to that observed in the presence of an isotype-matched mAb of irrelevant specificity (0% inhibition) and to that observed using excess unlabeled test mAb (100% inhibition).

Example 5

Effects of mAbs on PSMA Enzymatic Activity

PSMA has been shown to possess both folate hydrolase (pteroyl-glutamyl carboxypeptidase) and N-acetylated α-linked acidic dipeptidase (NAALADase) enzymatic activities, which may influence the proliferation and malignancies of the tumor cell (Heston, W. D. W. *Prostate: Basic and Clinical Aspects* (R. K. Naz, ed.). CRC Press, New York: 219-243, 1997). A first set of mAbs described above (mAb 3.9, mAb 5.4 and mAb 7.3) and mAb J591 (ATCC #HB-12126) were tested for folate hydrolase modulating activity using previously described assays for measuring PSMA enzymatic activity (Pinto, J. T. et al. *Clinical Cancer Res* 2: 1445-1451, 1996).

Briefly, folate hydrolase activity was measured as follows. Fifty μM methotrexate di-gamma glutamate and 10 μg/ml rsPSMA (premixed with anti-PSMA or irrelevant mAb) was incubated in pH 4.5 acetate buffer in a volume of 100 μl for 2 hr at 37° C. Reactions were terminated by boiling for 5 minutes prior to separation of free, mono- and di-gamma glutamate forms of methotrexate by capillary electrophoresis on a Spectra Phoresis 1000 (Thermo Separation, San Jose, Calif.). The various methotrexate derivatives were quantified based on their retention times and absorbance at 300 nm.

Figure 8:
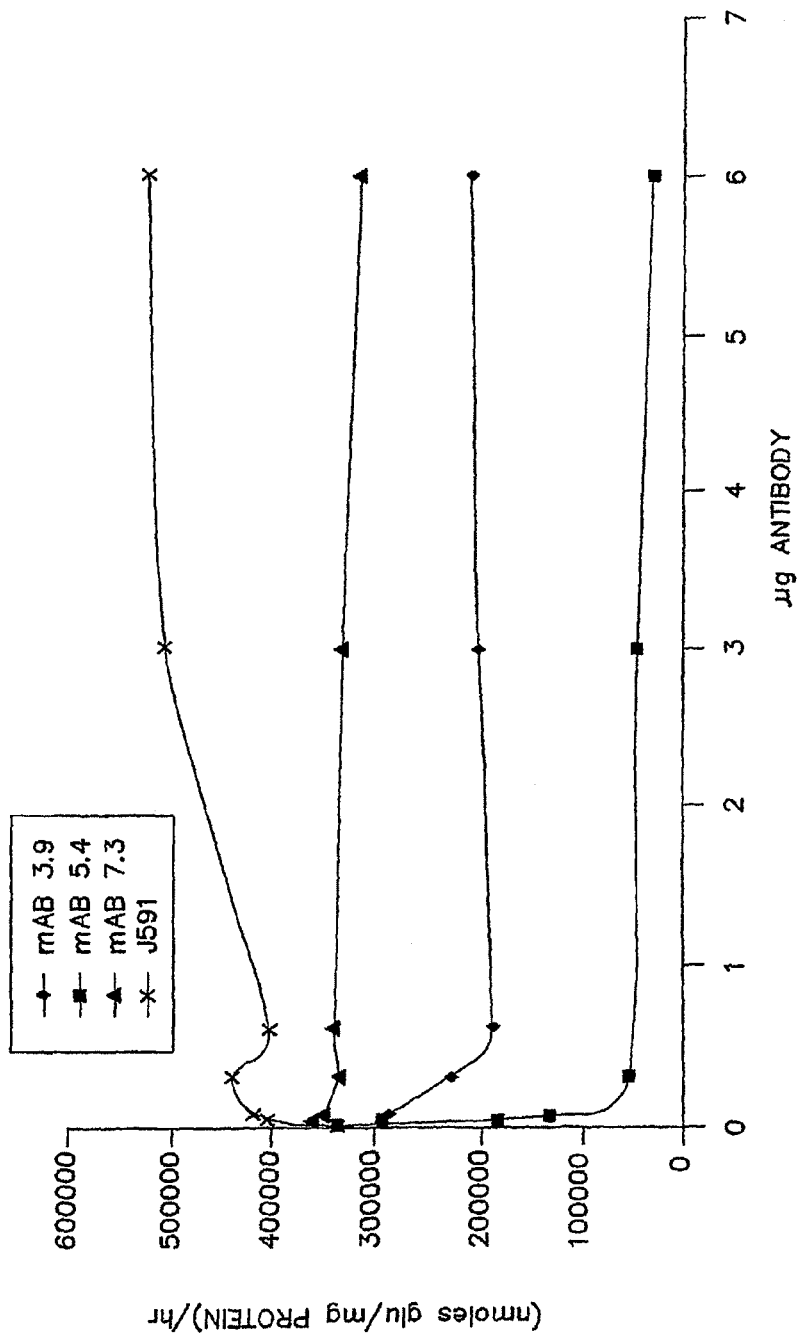
FIG. 8 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in 0.0002 µg rsPSMA #7.
Figure 9:
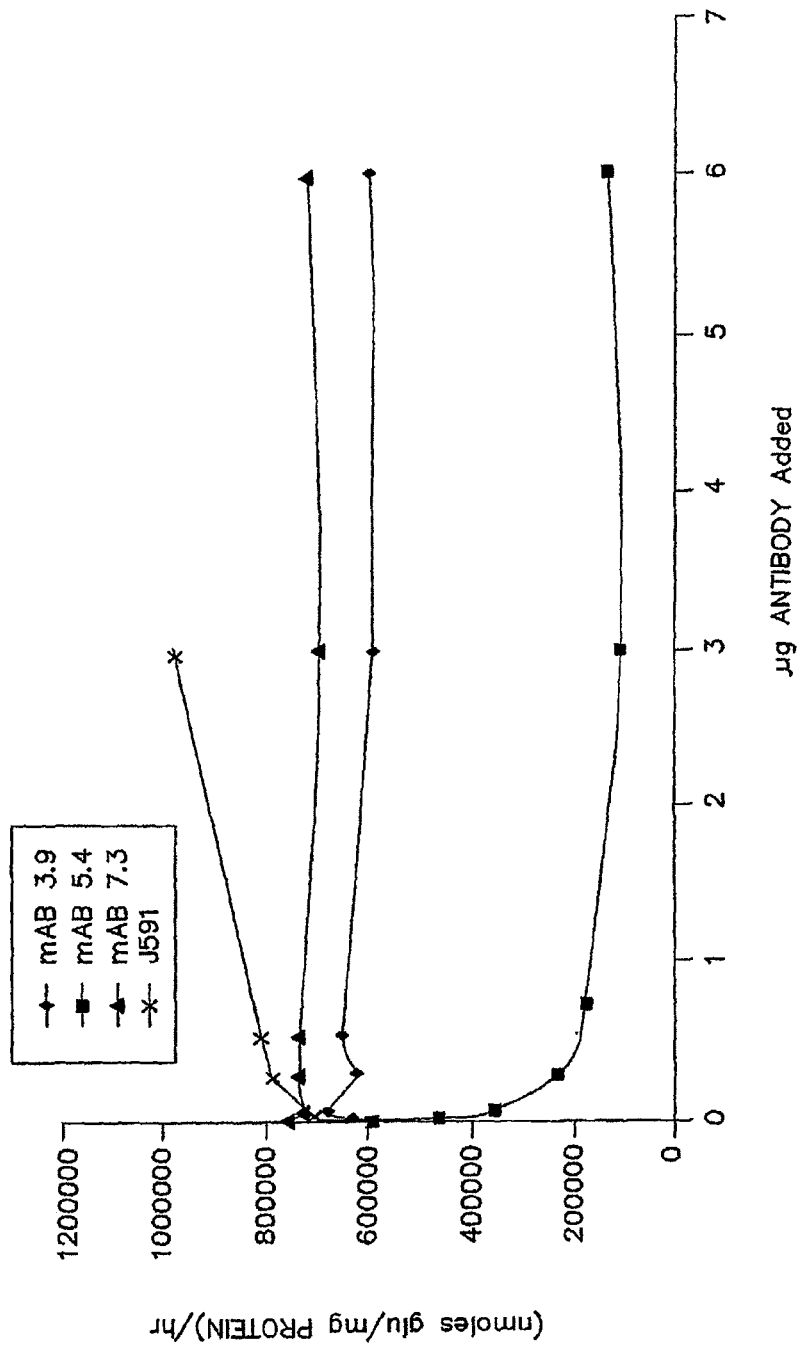
FIG. 9 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in 0.0002 µg rsPSMA #8.
Figure 10:
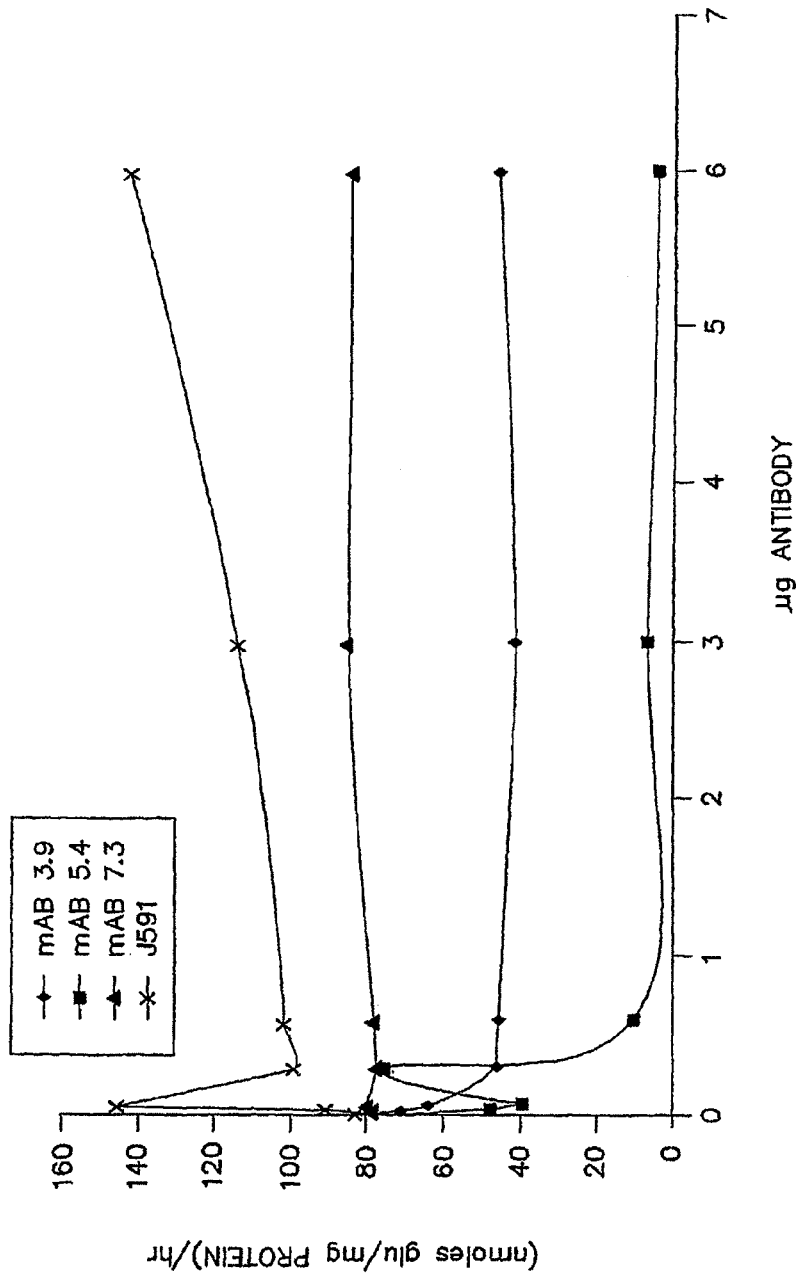
FIG. 10 shows the effect of four antibodies (mAb 3.9, mAb 5.4, mAb 7.3 and mAb J591) on the enzymatic activity of folate hydrolase through measuring the rate of cleavage of glutamate from methotrexate di-gamma glutamate by folate hydrolase present in lysates of C4-2 cells.
Figure 11A:
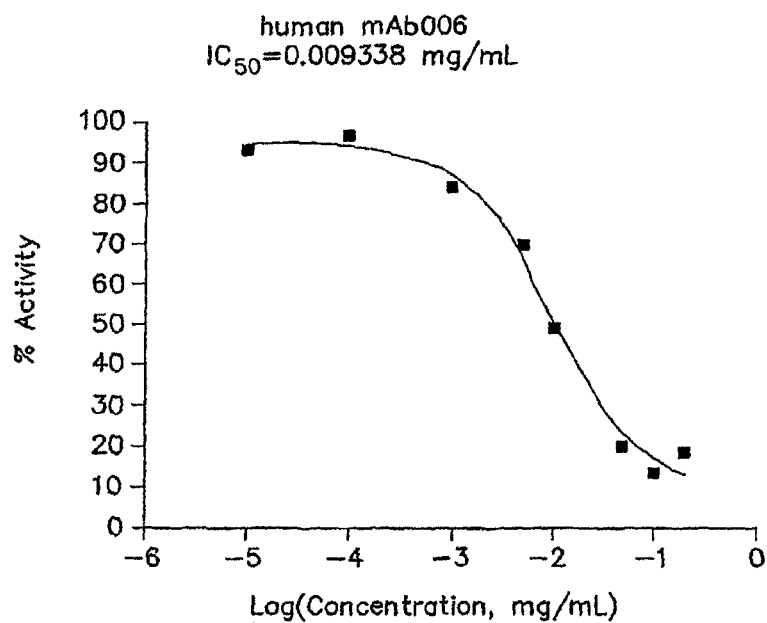
FIG. 11 shows the impact of four antibodies (human mAbs 006, 026 and 4.40.2 as well as murine mAb 5.4) on PSMA folate hydrolase activity.
Figure 11B:
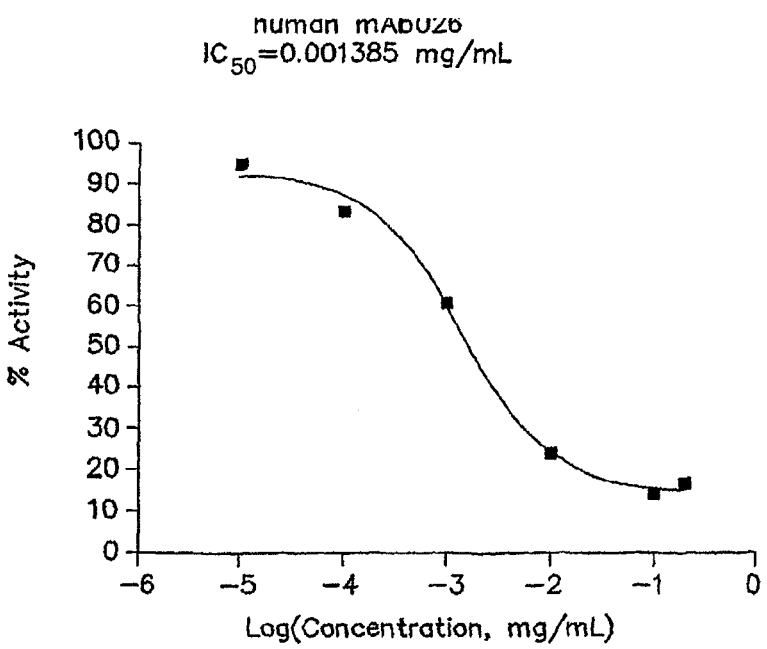
Figure 11C:
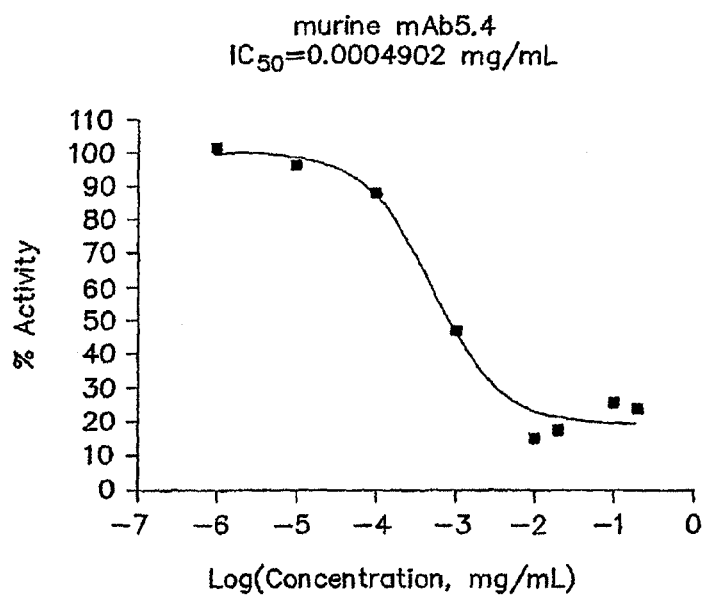
Figure 11D:
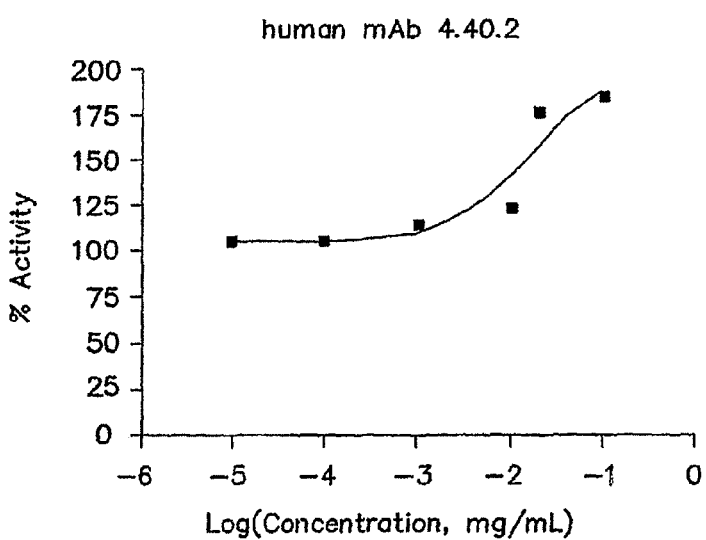

The data show that mAb 5.4 potently blocks the enzymatic activity of purified rsPSMA protein and in lysates of C4-2 cells. C4-2 is an androgen independent derivative of the LNaCP cell line (human prostate cancer line) which expresses endogenous PSMA. More details regarding the C4-2 cell line may be found in O'Keefe D. S. et al. *Prostate* 45: 149-157, 2000). FIGS. 8 and 9 provide the results for two production lots of rsPSMA (rsPSMA #7 and rsPSMA #8). The results for the C4-2 cell lysates are shown in FIG. 10. The figures illustrate the effect of four antibodies (mAb 3.9, mAb 5.4, mAb 7.3 and mAb J591) on the enzymatic activity of folate hydrolase by way of the rate of cleavage of glutamate from methotrexate di-gamma glutamate (MTXGlu2) by folate hydrolase present in the two production lots of rsPSMA and in the C4-2 cell lysates. In addition to the inhibitory effects of mAb 5.4, mAb 3.9 was also found to inhibit folate hydrolase activity.

Another set of mAbs (mAb 4.40.2, mAb 006, mAb 026 and mAb 5.4) was also tested for folate hydrolase modulating activity. The data confirm that mAb 5.4 potently blocks folate hydrolase activity of PSMA (FIG. 11). The concentration of mAb 5.4 which inhibited PSMA enzymatic activity by 50% (IC50, also referred to as EC50 or "effective concentration") was determined to be $4.902 \times 10^{-4}$ mg/mL. The data further show that mAb 006 and mAb 026 also block PSMA folate hydrolase activity, while mAb 4.40.2 did not (FIG. 11). The IC50 values for mAb 006 and mAb 026 were $9.338 \times 10^{-3}$ mg/mL and $1.385 \times 10^{-3}$ mg/mL, respectively.

For NAALADase activity assays, rsPSMA protein is incubated with varying amounts of anti-PSMA or control mAbs in 50 mM Tris pH 7.4, 1 mM $CoCl_2$ for 10 minutes at 37° C. before adding 50 μl of 0.6 μM N-acetylaspartyl-[$^3$H] glutamate. After 15 minutes, the reaction is stopped by adding 1 ml of 100 mM $NaPO_4$. Cleaved glutamate is separated from the substrate by ion exchange chromatography and detected by scintillation counting. Each measurement is performed in triplicate.

Example 6

Reactivity with Normal and Malignant Human Tissues by Immunohistochemistry

Anti-PSMA mAbs are tested by immunohistochemistry for reactivity with both normal and malignant human tissues using an avidin-biotin peroxidase method (Silver, D. A. et al. *Clin Cancer Res* 3: 81-85, 1997). Frozen or paraffin-embedded tissues can be used. Paraffin-embedded tissue sections are deparaffinized and endogenous peroxidase activity is blocked by incubation with 1% $H_2O_2$ for 15 minutes. Sections are blocked in a 1:10 dilution of horse serum in 2% PBS-BSA (Sigma Chemical, St Louis, Mo.) for 30 minutes before overnight incubation with 2 μg/ml anti-PSMA mAb in 2% PBS-BSA. After washing, sections are incubated with biotinylated secondary antibody, washed, and incubated with avidin:biotin peroxidase complexes (Vector Laboratories, Burlingame, Calif.) diluted 1:25 in PBS for 30 minutes. After washing, sections are visualized by immersion in PBS containing 0.05% diaminobenzidine tetrachloride, 0.01% $H_2O_2$, and 0.5% Triton X-100. Negative control sections are incubated with isotype-matched mAbs of irrelevant specificity. As a positive control, 7E11 (Cytogen, Princeton, N.J.), a well-characterized anti-PSMA mAb, is used.

Example 7

Antibody-Dependent Cellular Cytotoxicity (ADCC)

In the ADCC assay, mAbs are serially diluted and combined with $^{51}$Cr-labeled 3T3-PSMA cells or human prostate PC-3 cells that have been engineered to express human PSMA (PC-3-PSMA cells). NK effector cells are purified from lymph nodes or spleens using anti-NK microbeads (Miltenyi Biotec). Sera, NK effector cells, and $^{51}$Cr-loaded target cells are co-incubated at effector:target cell ratios of 10:1, 20:1, and 40:1, with each condition performed in triplicate. Cells are incubated 4-5 hours at 37° C. before supernatants are collected for measurement of $^{51}$Cr release by gamma counting. The percent specific lysis is determined relative to that observed in the presence of isotype-matched non-specific mAb (0% lysis) to that obtained using 10% sodium dodecyl sulfate (100% lysis).

Example 8

Complement-Mediated Lysis (CML)

For CML, $^{51}$Cr-loaded 3T3-PSMA or PC-3-PSMA cells serve as target cells. Serial dilutions of mAbs are co-incubated with rabbit complement and target cells for 4-5 hours at 37° C., with each condition being performed in triplicate. Supernatants are then collected and counted with a gamma counter. Specific lysis is computed as previously done with the ADCC assay data.

Example 9

Anti-Proliferative Effects

To test anti-proliferative effects of these antibodies, anti-PSMA mAbs are serially diluted and incubated with LNCaP, PC-3-PSMA and parental PC-3 cells in log-phase growth. At 4 hr, 24 hr, and 72 hr intervals, cells are removed and analyzed for density and viability by trypan blue staining and WST-1 assay (Roche Biochemicals).

Example 10

Optimization of Chelation and Radiolabeling Procedures

The most promising mAbs identified using the procedures described in the foregoing examples will be optimized for biochemical and biological stability and activity after labeling prior to evaluation in animals. Success in in vitro experiments is defined as identification of a radiolabeled mAb that specifically kills PSMA-expressing tumor cells at >10-fold lower concentrations than unlabeled or similarly labeled isotype control mAb.

Because the preferred α- and β-emitting isotopes are all radiometals, each of the mAbs is first conjugated with an appropriate metal chelating agent. Based on the favorable in vivo stability data and its proven use in human clinical trials, the bifunctional chelating agent C-functionalized trans cyclohexyldiethylenetriaminepentaacetic acid (p-SCN-CHX-A"-DTPA) is the preferred agent for attaching either $^{90}$Y or $^{213}$Bi to the antibody (Brechbiel, M. W. et al. *J. Chem. Soc. Chem. Commun.* 1169-1170, 1991). A form of this chelate has previously been tested in more than 70 doses in humans in ongoing trials at Memorial-Sloan Kettering Cancer Center (McDevitt, M. R. et al. *J. Nucl. Med.* 40:1722-1727, 1999). For $^{225}$Ac, our initial studies will examine a novel bifunctional chelating agent termed p-SCN-Bz-HEHA (1,4,7,10,13,16-hexaazacyclooctadecane-N,N',N",N''',N'''',N'''''-hexaacetic acid) (Deal, K. A. et al. *J. Med. Chem.* 42:2988-2992, 1999). The objective is to optimize the antibody conjugation and chelation ratios to maximize labeling yield and activity while maintaining suitable stability for in vivo utilization. Additional chelating agents also are used as they become available from the N.I.H. and other sources.

Initially, the antibody is rendered metal-free by incubation with a large molar excess of EDTA at pH=5. The EDTA and any metals scavenged from the antibody preparation are removed via continuous buffer exchange/dialysis so as to replace the pH=5 buffer with the conjugation buffer (Nikula, T. K. et al. *Nucl. Med. Biol.* 22:387-390, 1995). Conditions that yield optimal chelator to antibody ratio but still remain immunoreactive are identified by systematically varying the chelator:antibody ratio, reaction time, temperature, and/or buffer systems about initial conditions that employ a 40-fold molar excess of chelator to antibody in HEPES buffer, pH 8.5. The number of chelates bound per antibody is determined using an established spectrophotometric method (Pippin, C. G. et al. *Bioconjugate Chemistry* 3: 342-345, 1992).

For $^{90}$Y and $^{225}$Ac constructs, labeling efficiency is measured directly. For $^{213}$Bi, initial antibody constructs are tested for chelation efficiency using which has similar chelation chemistry as $^{213}$Bi but possesses the advantages of a longer half life ($t_{1/2}$=3 days), ready availability, and traceable γ-emission. Once optimized using $^{111}$In, labeling efficiency is determined for $^{213}$Bi.

Radiolabeled mAb is purified over a BioRad 10DG desalting column using 1% HSA as the mobile phase and evaluated by instant thin layer liquid chromatography (ITLC) and/or high performance liquid chromatography (HPLC) to determine the percent incorporation of radionuclide (Zamora, P. O. et al. *Biotechniques* 16: 306-311, 1994). ITLC and HPLC provide a means of establishing purity and identifying the percent of low molecular weight radiochemical impurities (i.e., metal chelates, colloids, and free metal). Duplicate ITLC strips for each mobile phase are developed, dried, and cut at the $R_f$ of 0.5 mark and counted in a gamma counter. The HPLC system is equipped with both an online UV absorption detector and radioactivity detector. The HPLC elution profile directly correlates radioactivity with protein and low molecular weight species as a function of the elution time. A TSK SW3000$_{XL}$ column (TosoHaas, Montgomeryville, Pa.) is used and calibrated using a range of protein molecular weight standards.

Example 11

Affinity and Immunoreactivity of Radiolabeled mAbs

Once radiolabeled constructs are obtained, purified, and assessed for biochemical and radiochemical purity, biological activity is determined. Binding activity of the radioconstruct is performed by Scatchard analysis of binding data obtained using whole LNCaP and 3T3-PSMA cells and/or membrane fractions as previously described (Scheinberg, D. A. et al. *Leukemia* 3: 440-445 (1991).

The immunoreactivity of the synthetic constructs is evaluated in order to correlate the chelate:antibody molar ratio with the biological activity. Briefly, 2 ng of labeled mAb is incubated with a ~25-fold excess of PSMA as expressed on 3T3-PSMA cells. After a 30 min incubation at 0° C., the cells are collected by centrifugation and the supernatant containing unbound mAb is added to fresh 3T3-PSMA cells for an additional 30 min at 0° C. Both sets of cells are centrifuged and washed twice with cold PBS. The cell pellets, supernatant and wash fractions are counted for radioactivity Immunoreactivity is defined as the amount of radioactivity in the cell pellets divided by the total radioactivity in the cell pellets, supernatant and wash fractions.

Example 12 mAb Internalization

Figure 12A:
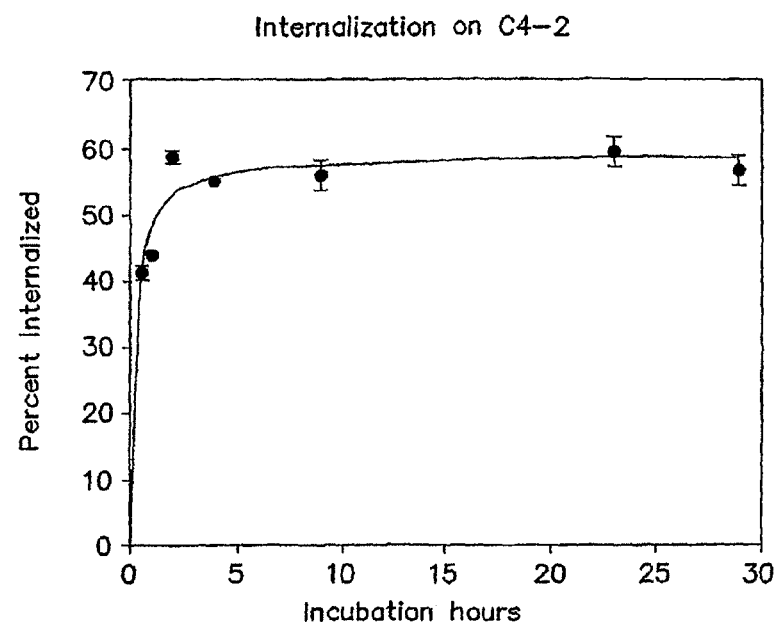
FIG. 12 illustrates the rapid and efficient internalization of $^{111}$In labeled mAb 026 incubated with C4-2 cells.
Figure 12B:
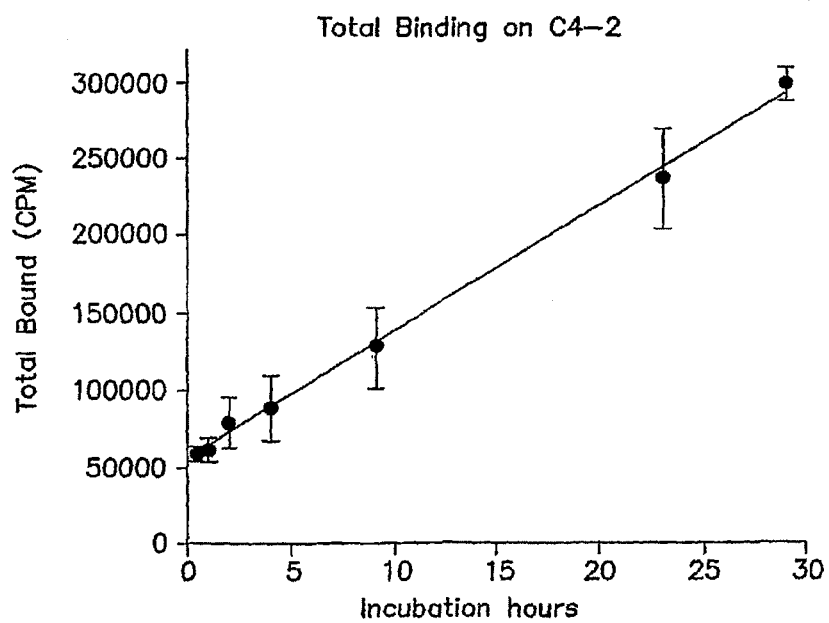
Figure 14:
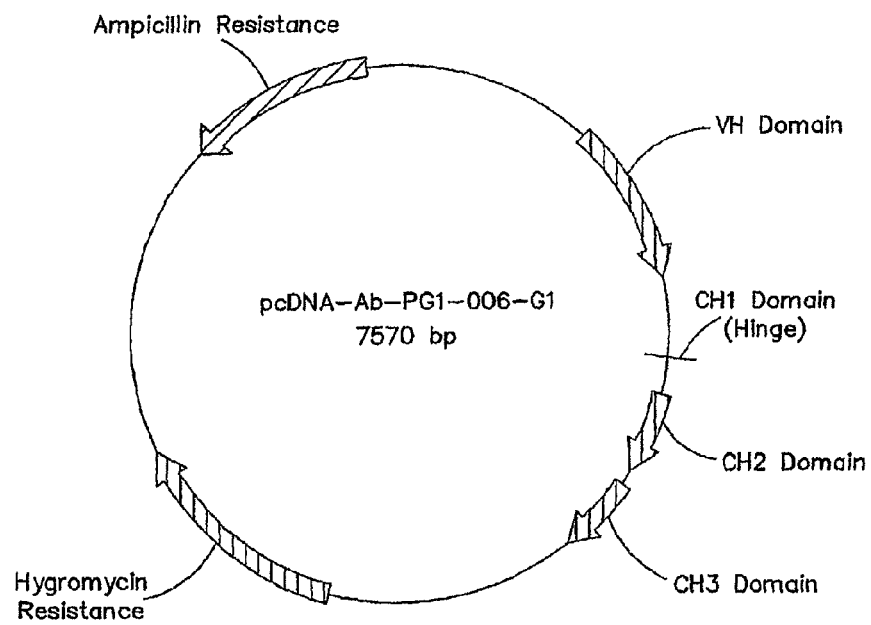
FIG. 14 provides the plasmid map of a nucleic acid molecule encoding the heavy chain of antibody AB-PG1-XG1-006.
Figure 15:
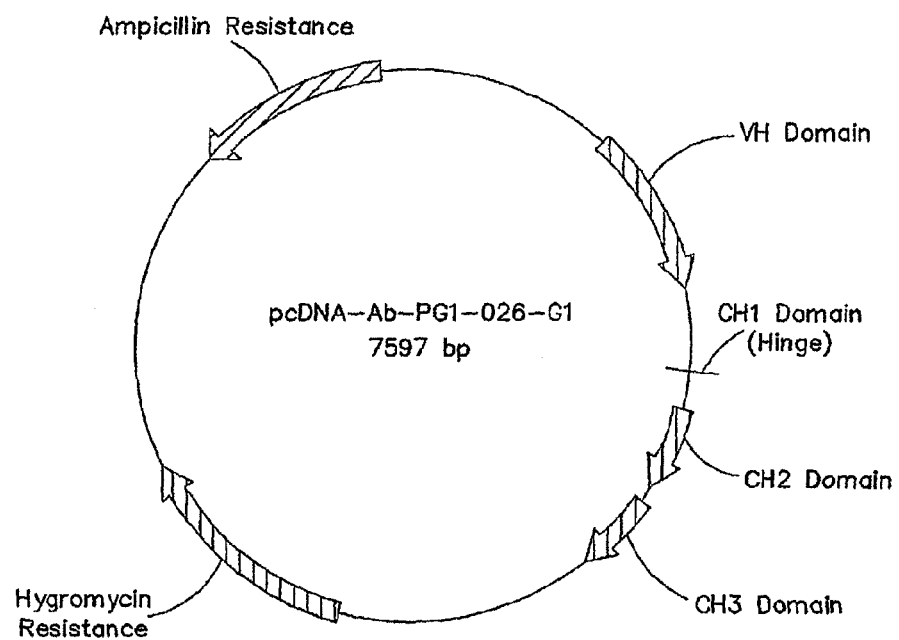
FIG. 15 provides the plasmid map of a nucleic acid molecule encoding the heavy chain of antibody AB-PG1-XG1-026.
Figure 16:
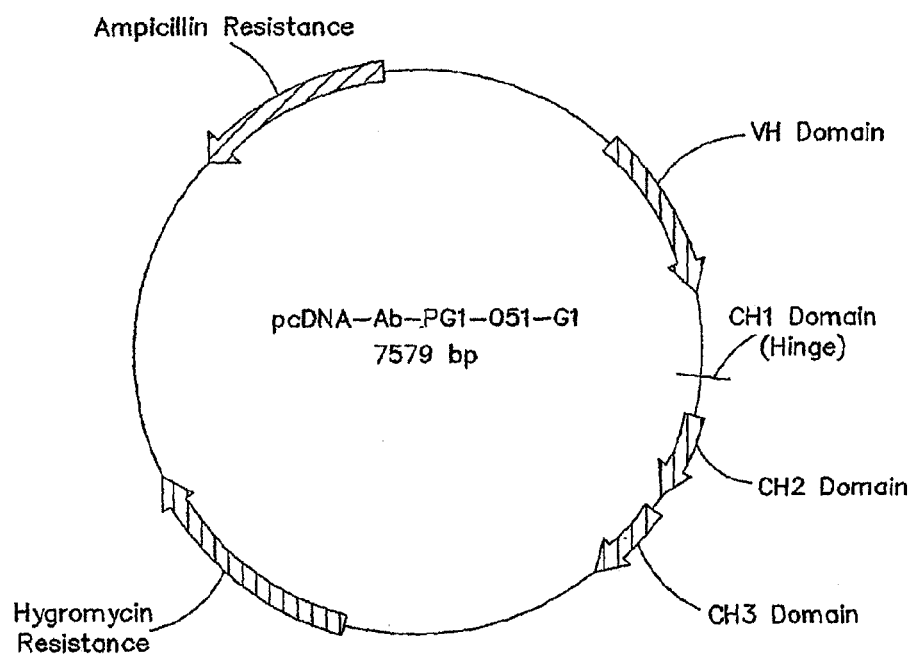
FIG. 16 provides the plasmid map of a nucleic acid molecule encoding the heavy chain of antibody AB-PG1-XG1-051.
Figure 17:
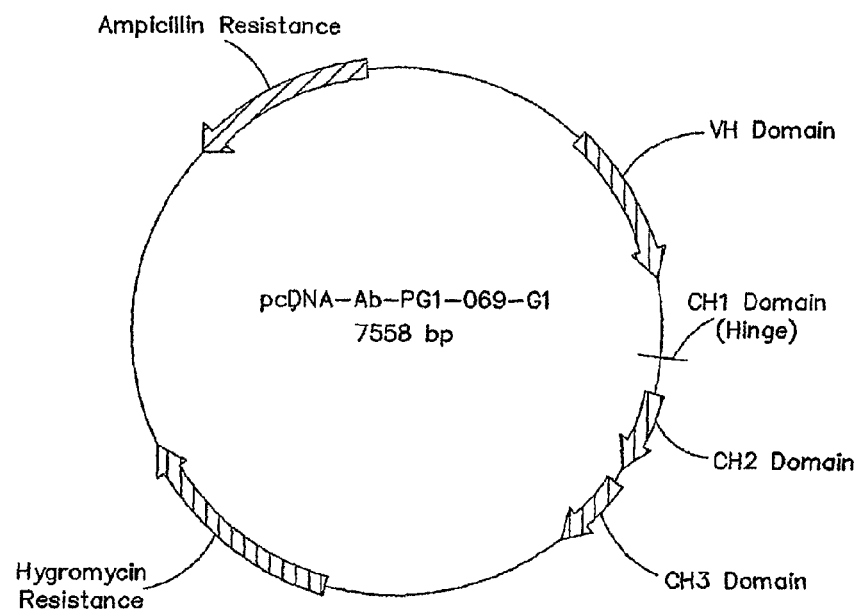
FIG. 17 provides the plasmid map of a nucleic acid molecule encoding the heavy chain of antibody AB-PG1-XG1-069.
Figure 18:
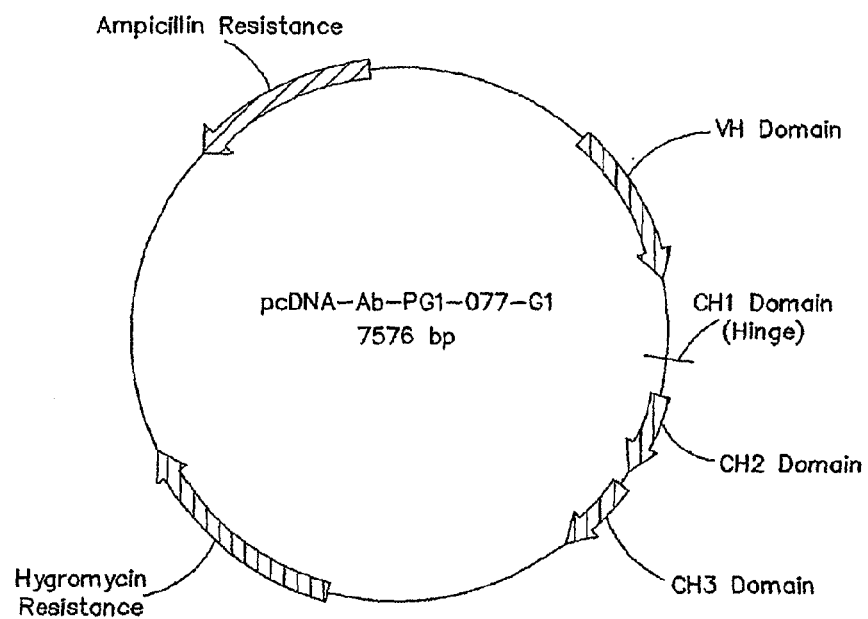
FIG. 18 provides the plasmid map of a nucleic acid molecule encoding the heavy chain of antibody AB-PG1-XG1-077.
Figure 19:
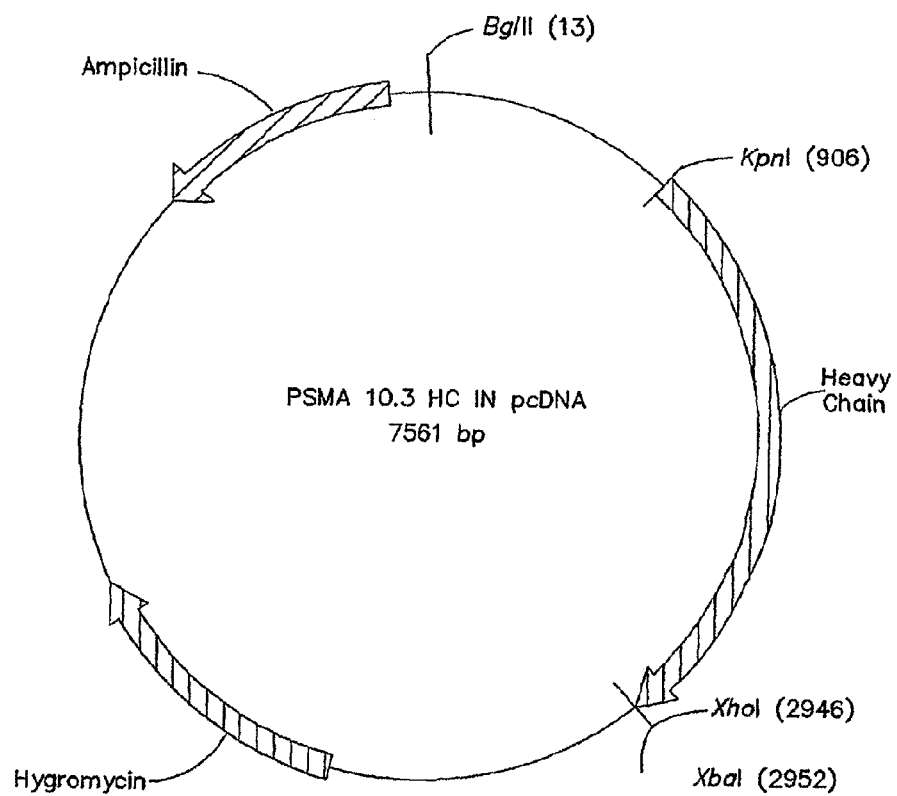
FIG. 19 provides the plasmid map of a nucleic acid molecule encoding the heavy chain of antibody PSMA 10.3.
Figure 20:
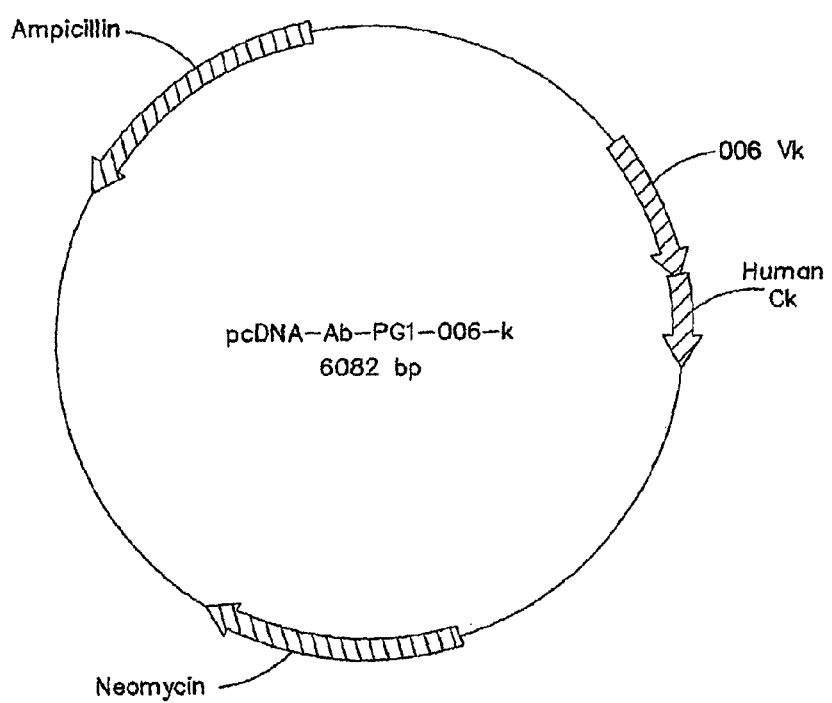
FIG. 20 provides the plasmid map of a nucleic acid molecule encoding the light chain of antibody AB-PG1-XG1-006.
Figure 21:
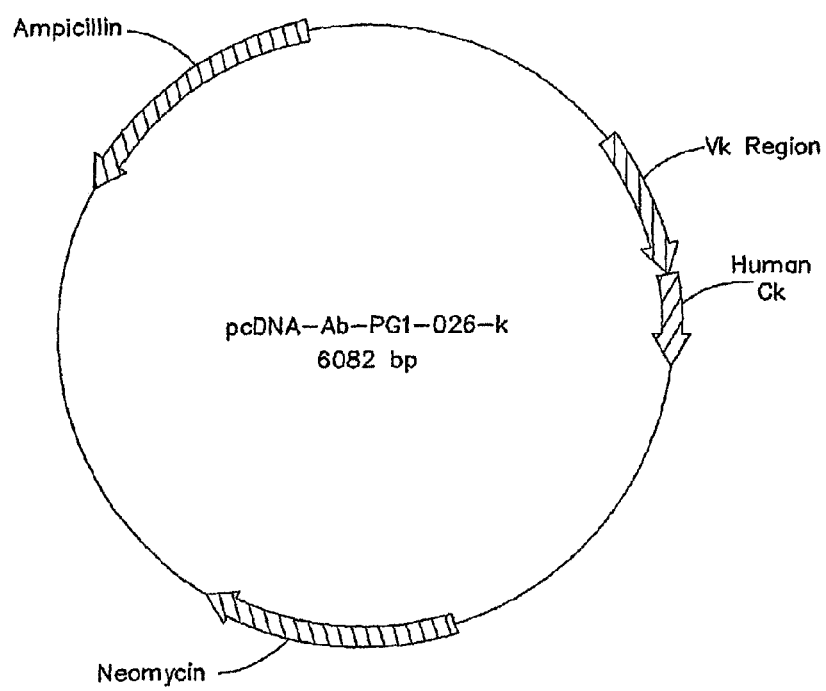
FIG. 21 provides the plasmid map of a nucleic acid molecule encoding the light chain of antibody AB-PG1-XG1-026.
Figure 22:
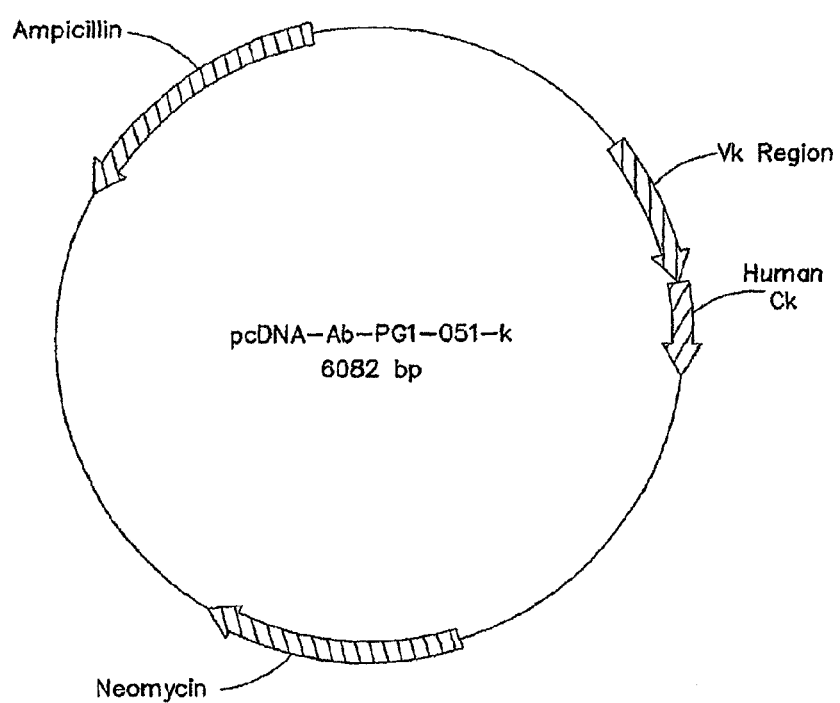
FIG. 22 provides the plasmid map of a nucleic acid molecule encoding the light chain of antibody AB-PG1-XG1-051.
Figure 23:
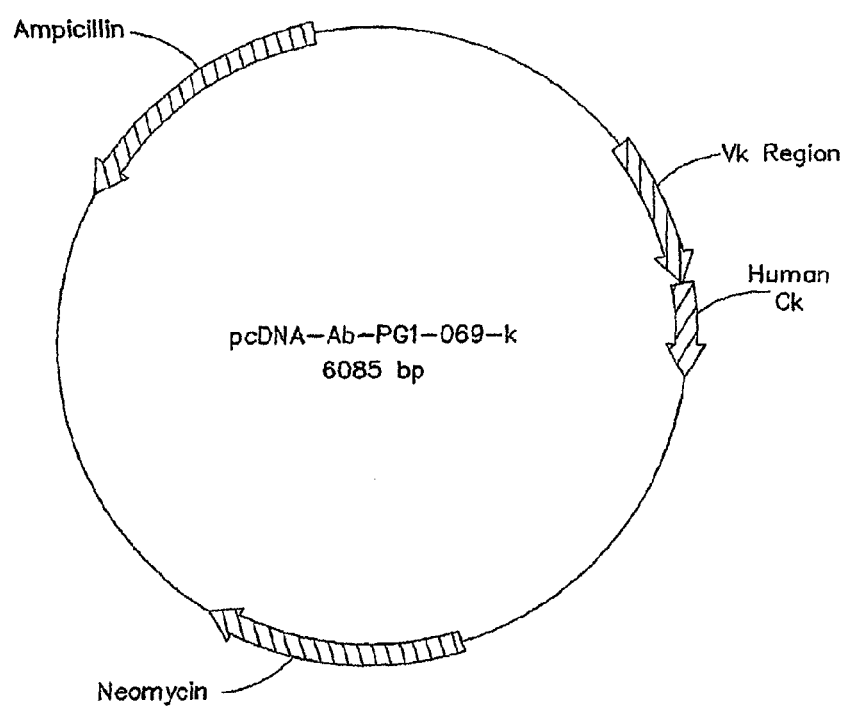
FIG. 23 provides the plasmid map of a nucleic acid molecule encoding the light chain of antibody AB-PG1-XG1-069.
Figure 24:
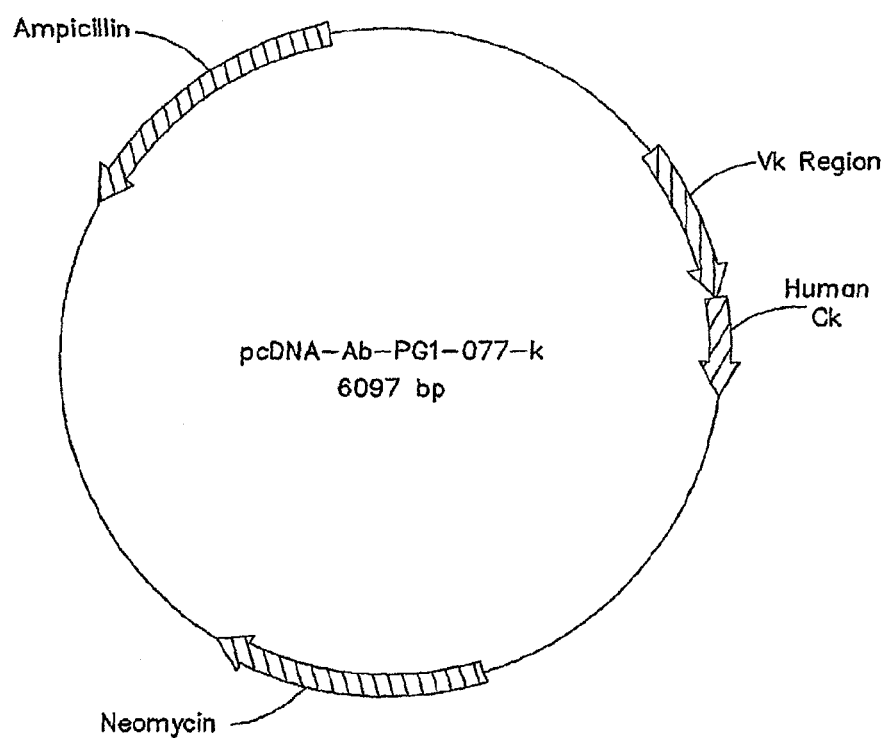
FIG. 24 provides the plasmid map of a nucleic acid molecule encoding the light chain of antibody AB-PG1-XG1-077.
Figure 25:
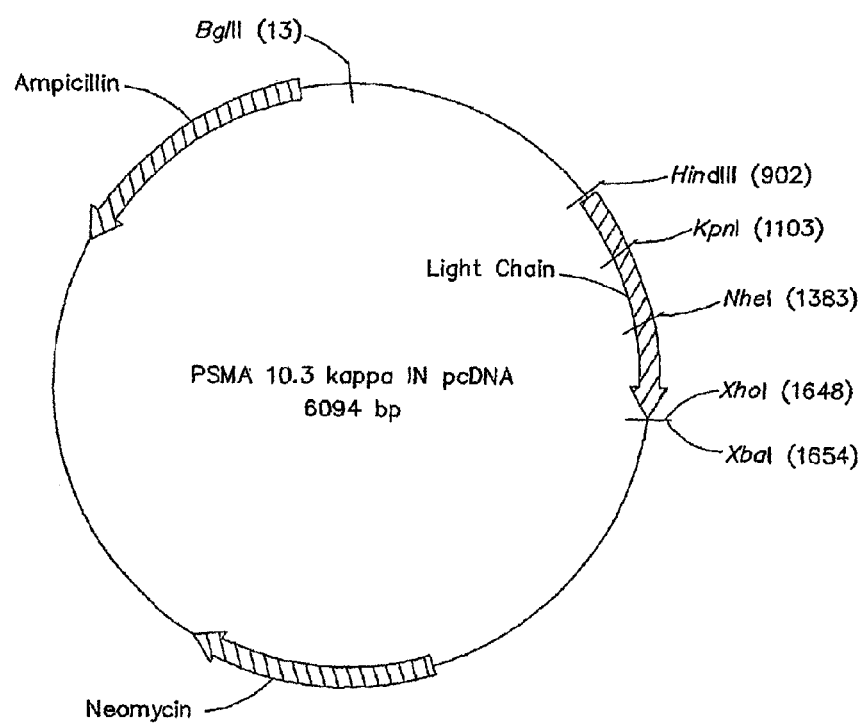
FIG. 25 provides the plasmid map of a nucleic acid molecule encoding the light chain of antibody PSMA 10.3.

The activity of radiolabeled mAbs can be significantly modulated by their internalization rates. Based upon previous results by other groups (Smith-Jones P. M. et al. *Cancer Res* 60: 5237-5243, 2000), significant internalization of PSMA after binding with one or more of the mAb constructs was expected. Internalization of the cell surface antibody-antigen complex was measured using $^{111}$In radiolabeled antibody (mAb 026) constructs (Caron, P. C. et al. *Cancer Res* 52: 6761-6767, 1992). Briefly, 5×10$^5$ C4-2 cells were incubated at 37° C. in 5% CO$_2$ with $^{111}$In radiolabeled antibody. At different times, cells were washed with PBS and cell-surface bound radiolabeled constructs were stripped with 1 ml of 50 mM glycine/150 mM NaCl, pH=2.8. Total cell-associated radioactivity and acid-resistant (internalized) radioactivity were determined by γ-counting. Percent internalization and total binding were calculated. $^{111}$In labeled mAb 026 was found to be rapidly and efficiently internalized. FIG. 12 shows the percent internalization and total binding of $^{111}$In labeled mAb 026 as a function of incubation time. Cells (such as parental 3T3 cells) that do not express PSMA can be used as a control to determine non-specific binding.

Example 13

In Vitro Cytotoxicity Studies

Assessment of in vitro cytotoxicity of a-labeled mAbs was undertaken once the immunoreactivity of the radioimmunoconjugate was established. Approximately 50,000 target cells (either LNCaP or 3T3-PSMA cells) were treated in 96 well plates and analyzed 24-96 hours later. Quantification of cell death due to $^{225}$Ac-labeled constructs (or $^{213}$Bi) was accomplished by determining the uptake of $^3$H-thymidine by surviving cells (Nikula, T. K. et al. *J. Nucl. Med.* 40: 166-176, 1999). Specificity was determined by use of control cells (PSMA-negative human prostate cell lines PC-3 and DU-145, as well as control 3T3 cells), blocking with excess unlabeled antibody, and control radioconjugates.

The cytotoxic effects of antibody conjugate concentration, specific activity, and time of exposure were then assessed. Cytotoxicity was expressed relative to that seen with 1M HCl (100% cell death) and media (background cell death). LD$_{50}$ values were calculated by plotting cell viability as a function of the number of $^{225}$Ac atoms bound on the cells (McDevitt, M. R. et al. (1998) *Eur. J. Nucl. Med.* 25: 1341-1351 (1998).

Figure 26:
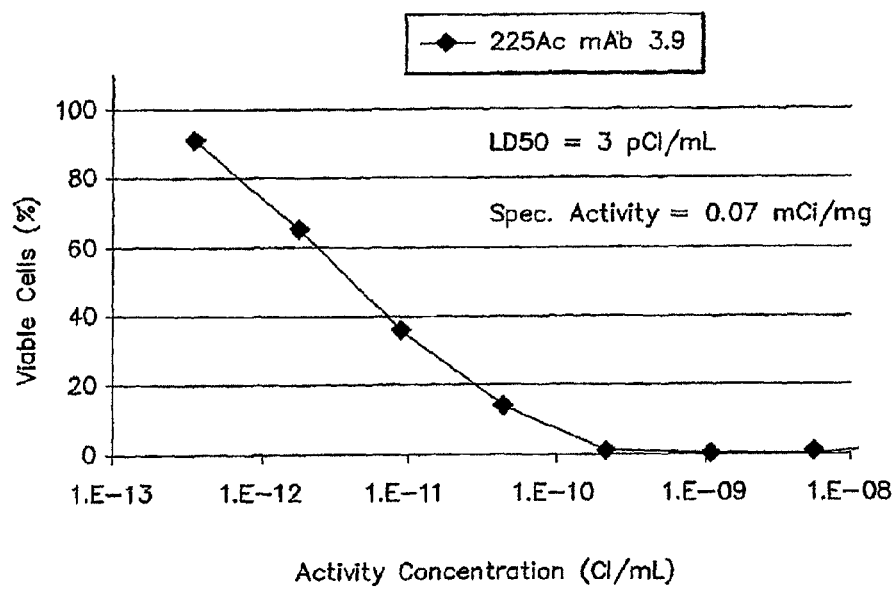
FIG. 26 depicts the cytotoxicity of $^{225}$Ac-3.9 on LNCaP target cells.
Figure 27A:
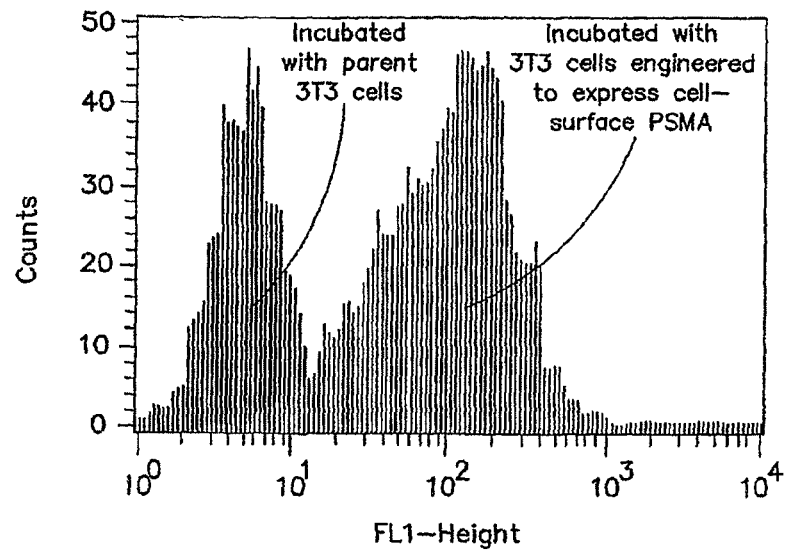
FIG. 27 illustrates the reactivity of anti-PSMA monoclonal antibodies XG-006, XG-051, 4.40.1, 4.49.1, 4.292.1 and 4.304.1 incubated with either parent 3T3 cells (black histogram) or 3T3 cells engineered to express cell-surface human PSMA (red histogram) and analyzed by flow cytometry.
Figure 27B:
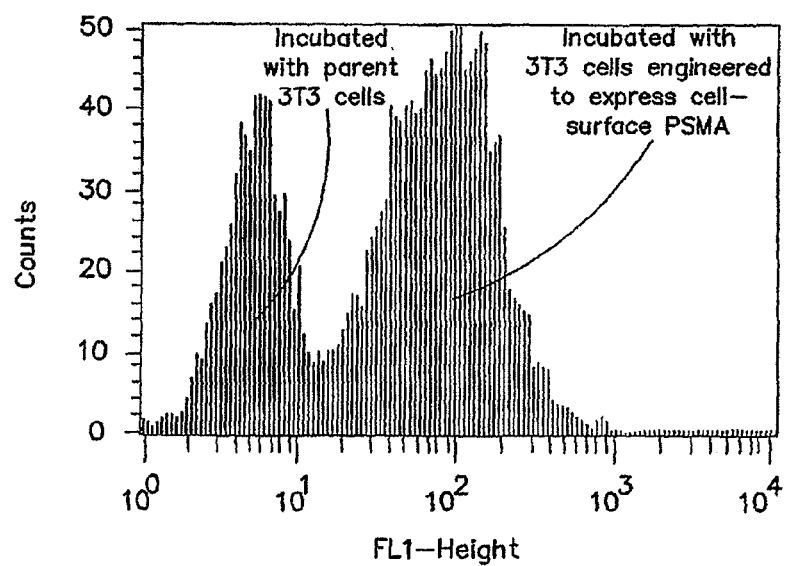
Figure 27C:
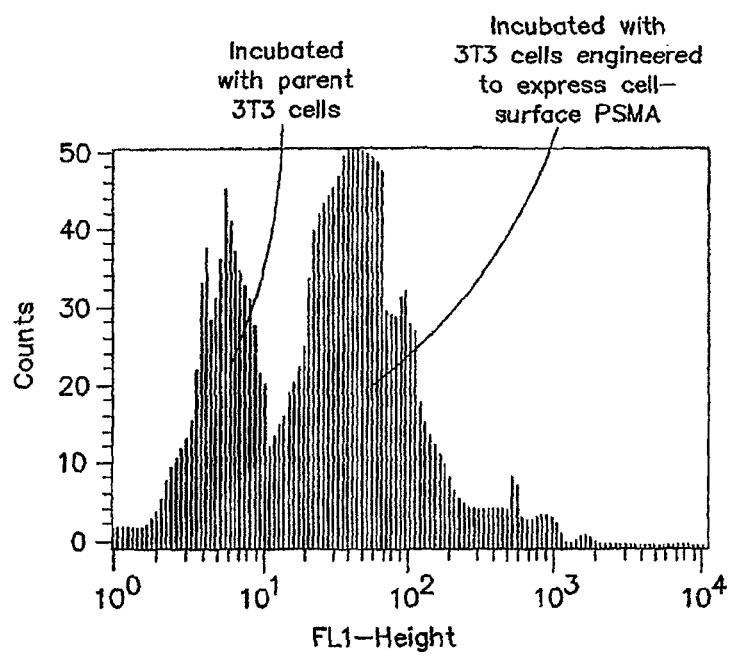
Figure 27D:
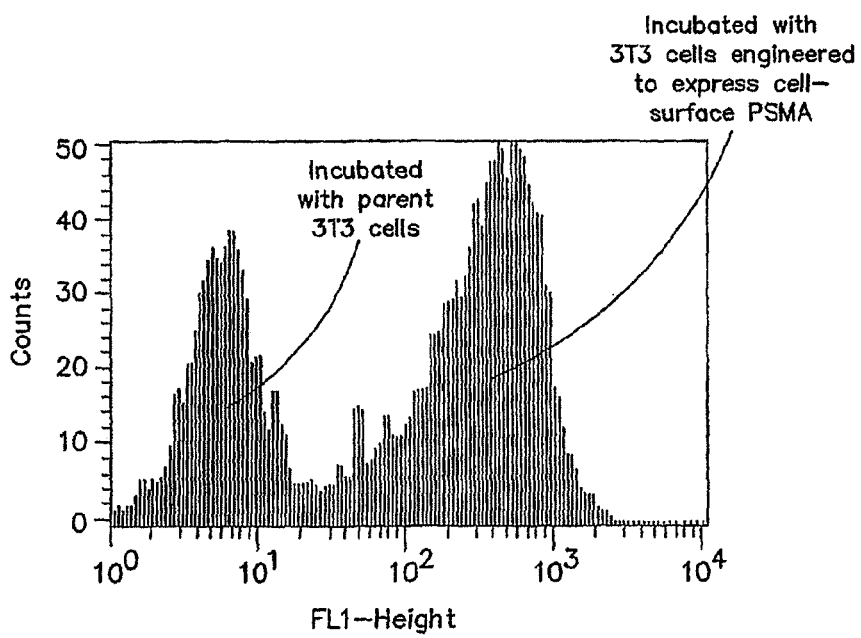
Figure 27E:
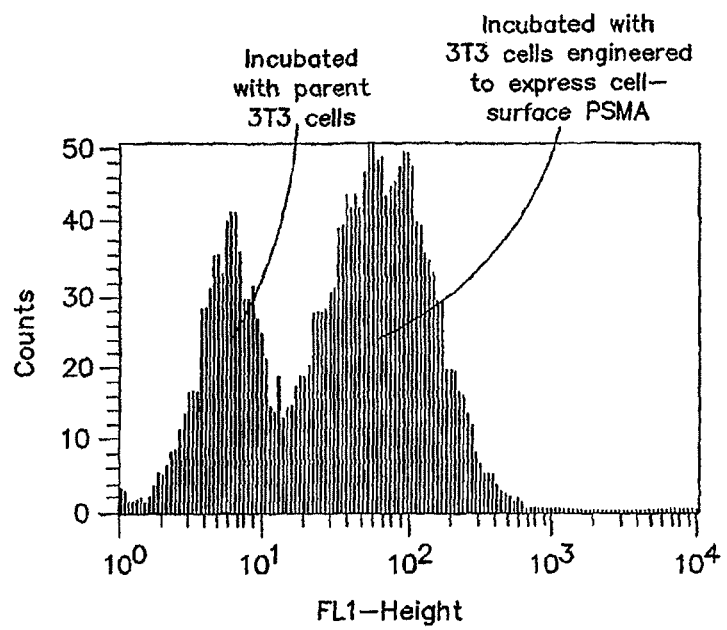
Figure 27F:
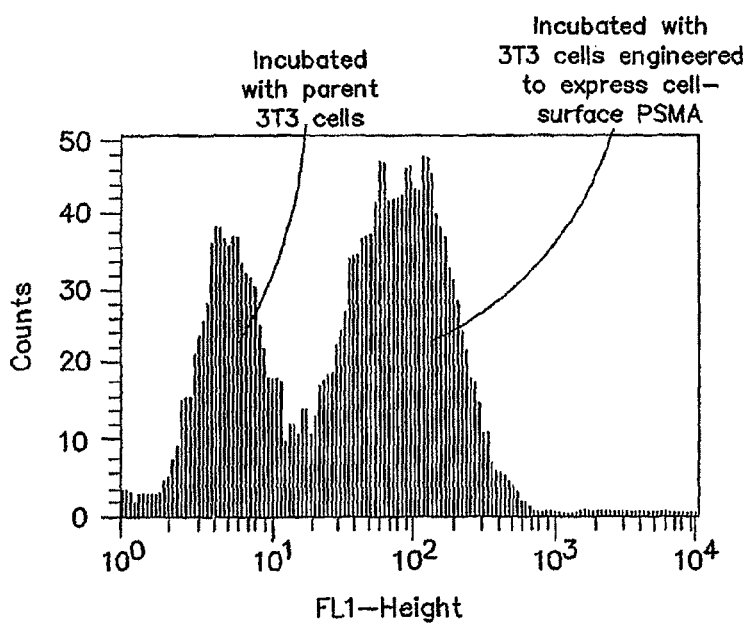

Multicellular spheroids of LNCaP-FGC cells had been established and were used to investigate the potential of radioimmunotherapy (RIT) to eradicate minimal disease in vitro. These three-dimensional spheroids mimic tissue structures more accurately than monolayer cultures and thus provide a more relevant model of solid tumors (O'Connor, K. C. *Pharm. Res.* 16: 486-493, 1999). LNCaP-FGC is a fast growing clone of the original LNCaP cell line, and the cells were grown using a liquid overlay technique to a size of 200-600 μm (Ballangrud, A. M. et al. *Clin. Cancer Res.* 5: 3171s-3176s, 1999). In larger spheroids, the inner mass of cells becomes necrotic, while the outer rim consists of proliferating tumor cells. Antibody penetration was measured by confocal microscopy, and prior results suggested that an anti-PSMA antibody should penetrate to a depth of 40-50 μm (Ballangrud, A. M. et al. 7th Conference on Radioimmunodetection and Radioimmunotherapy of Cancer, Princeton N.J., 1998). The in vitro cytotoxicity of $^{225}$Ac-3.9 on LNCaP target cells is shown in FIG. 26. The percentage of viable PSMA$^+$ LNCaP cells was plotted as a function of activity of the radioconjugate. Addition of a 100-fold excess of unlabeled antibody was used as a control for specificity.

Example 14

Evaluation of the In Vivo Efficacy of Unlabeled and Radiolabeled mAbs in Mouse Xenograft Models of Human Prostate Cancer Antibodies that are successful in the foregoing assays demonstrate significant specificity and functional properties that suggest they will be useful for therapeutic use. The most promising of these radiolabeled and "naked" mAb constructs are evaluated in the best available mouse models of prostate cancer. The studies employ an established xenograft model in which the LNCaP human prostate tumor cell line is injected into immunocompromised nude mice and allowed to form solid tumors (Ellis, W. J. et al. *Clin Cancer Res* 2: 1039-1048 (1996), which then are treated with both radiolabeled and unlabeled anti-PSMA mAb constructs. Follow-on studies also utilize a mouse xenograft model, CWR22, which reproduces many of the key biological features of human prostate cancer.

Lncap Tumor Cell Xenograft Model

A construct showing high affinity and high specificity is taken into the LNCaP tumor cell xenograft in vivo model for biodistribution and pharmacokinetic analysis. $^{111}$In labeled anti-PSMA antibody is used for these studies due to its favorable chelation chemistry, radioactive half-life and traceable gamma emission. Timepoints are evaluated as appropriate for the half-lives of $^{213}$Bi, $^{225}$Ac, $^{177}$Lu and $^{90}$Y, which are the nuclides of therapeutic interest. Labeled radioconstructs (1-5 μg) are injected i.v. into nude mice (normal and tumor bearing) and the mice are sacrificed at 5 min, 15 min, 30 min, 60 min, 2 hrs, 4 hrs, 18 hrs, and 24 hrs post-injection. Blood and major organs are taken from animals, weighed, and the percent radioactivity injected per gram of tissue is determined (Nikula, T. K. et al. *J. Nucl. Med.* 40: 166-176, 1999). Specificity is addressed by pre-injection with excess unlabeled construct. Macroscopic tumor volume and animal survival rates is recorded throughout the experiments.

A dose-ranging study is also conducted to determine the toxicity of the constructs when administered via i.v. or i.p. injection to normal and tumor-bearing mice. These animals are routinely examined for toxic side effects during the course of the studies by blood chemistry and physical examination. Animals are sacrificed during and at the conclusion of the study in order to collect blood and body tissues for further evaluation. Previous data has demonstrated an approximate maximum tolerated dose of 250 μCi/mouse, so total doses are kept below that level.

Once i.v. biodistribution and toxicity is documented, radiotherapy of tumors is assessed. Groups of five mice are injected with <1 μg radiolabeled anti-PSMA mAb construct both pre- and post-tumor challenge to assess anti-tumor activity. Antigen negative (RAJI or RAMOS) xenografted tumors are also used as a control. Other controls include (1) treatment with unlabeled anti-PSMA mAb only and (2) excess unlabeled anti-PSMA mAb pretreatment before $^{213}$Bi, $^{225}$Ac, $^{177}$Lu and/or $^{90}$Y-labeled anti-PSMA to block specific targeting.

Groups of tumor bearing mice are injected with unlabeled anti-PSMA mAbs (at equimolar concentrations) and several dose levels of radiolabeled anti-PSMA or a similarly labeled isotype control antibody. The effect on tumor growth is assessed over time. Statistical differences between therapy groups is determined using an analysis of variance (ANOVA) method and animal survival is illustrated using Kaplan-Meier plots. The efficacy of $^{213}$Bi, $^{225}$Ac, $^{177}$Lu and/or $^{90}$Y-labeled anti-PSMA constructs is correlated to the data obtained in vitro. Success in these experiments is defined as the ability to significantly (p<0.05) increase life-span and/or decrease tumor volume as compared to a radiolabeled isotype control mAb.

Furthermore, the tumor models are used to test whether predosing with unlabeled antibody prior to injection of radiolabeled antibody improves delivery of the radiolabeled antibody to the tumor. The tumor-bearing mice are injected with <1 µg radiolabeled anti-PSMA antibody with or without a prior single injection of 5-100 µg of unlabeled antibody. After several days, animals are sacrificed for evaluation of the distribution of radioactivity in the tumor, normal tissue, and blood. If predosing with unlabeled antibody improves delivery and targeting of radiolabeled antibody to the tumors, this approach is applied and optimized in toxicity and therapeutic studies.

In addition to overall survival, the role of timing of the injection after tumor transplantation (Day 1 vs 3 vs 7), the role of dosage (dose-response curves using 3-4 dose levels), the role of schedule (single vs multiple divided daily injections) and the specificity of the treatment (pre-treatment with unlabeled anti-PSMA to block targeting) is examined.

These in vivo studies are designed to address the maximum tolerated dose of radiolabeled antibody, the activity of the antibody, the optimal dosing schedule (single or multiple injections), and the effect on tumor size. Successful completion of this work enables determination of the feasibility of PSMA-targeted alpha particle radioimmunotherapy (RIT) of prostate cancer and identifies the optimal $^{213}$Bi and/or $^{225}$Ac-labeled constructs to enter into clinical development.

CWR22Mouse Xenograft Model

The most promising anti-PSMA mAbs in unlabeled, toxin-labeled and/or radiolabeled form are tested in the CWR22 human prostate cancer xenograft mouse model, (Wainstein, M. A. et al. *Cancer Res* 54:6049-6052 (1994); Nagabhushan, M. et al. *Cancer Res* 56:3042-3046 (1996); Pretlow, T. G. et al. *J Natl Cancer Inst* 85:394-398 (1993)). This model has many features of the human condition including a dependence on androgens, a correlation between measured levels of PSA in serum and tumor size, and high-level expression of PSMA. Following androgen withdrawal, PSA levels decrease to nearly undetectable levels and tumor volume decreases. Later, the tumor regrows as an androgen-independent neoplasm, manifest initially by a rise in PSA and later, measurable tumor growth. After androgen withdrawal, tumors regrow at variable time periods.

Four to six week old nude athymic BALB/c male mice are obtained from the National Cancer Institute-Frederick Cancer Center and maintained in pressurized ventilated caging. While immunodeficient in many respects, these mice mediate wild-type levels of ADCC and CML. The CWR22 tumor line is propagated in the animals by the injection of minced tumor tissue from an established tumor into the subcutaneous tissue of the flanks of athymic nude mice together with reconstituted basement membrane (MATRIGEL, Collaborative Research, Bedford, Mass.). To maintain serum androgen levels, the mice are administered 12.5-mg sustained-release testosterone pellets (Innovative Research of America, Sarasota, Fla.) subcutaneously before receiving tumors. Three to four weeks after inoculation, tumors of approximately 1.5×1.0×1.0 cm are measured. Androgens are withdrawn by surgical castration under pentobarbital anesthesia and removal of the sustained-release testosterone pellets. Tumor size is determined by caliper measurements of height, width and depth. PSA values are performed on the serum of the mice after tail bleeding using a Tandem-R PSA immuno-radiometric assay (Hybritech, San Diego, Calif.).

Groups of five mice are injected with anti-PSMA mAb or a similar isotype control mAb at dosages from 5-100 µg to assess anti-tumor activity. The effect of scheduling single doses vs. multiple divided daily injections is also examined Macroscopic tumor volume and animal survival rates are recorded throughout the experiments. Statistical differences between therapy groups are determined using an analysis of variance (ANOVA) method and animal survival are illustrated using Kaplan-Meier plots, with success defined as a difference of p<0.05. Similarly, the efficacy of "naked" mAbs is compared to that seen with $^{90}$Y, $^{177}$Lu, $^{213}$Bi and/or $^{225}$Ac-labeled anti-PSMA constructs.

These in vivo studies are designed to address the maximum tolerated dose of mAb, the activity of the antibody, the optimal dosage and dosing schedule (single or multiple divided injections), and the effect of treatment on tumor size. Successful completion of this work will enable determination of the feasibility of PSMA-targeted immunotherapy of prostate cancer and identification of the optimal constructs to enter into clinical development.

Example 15

Investigation of Native PSMA Protein Conformation

Extraction of PSMA from the Cell Surface of LNCaP and 3T3 Cells

LNCaP or 3T3 cells were grown to confluency in a T150 cell culture flask, detached using cell dissociation solution (Mediatech, Herndon, Va.) and transferred to a 15 ml conical tube. The cells were washed twice with PBS and resuspended with 2 ml of M-PER™ Mammalian Protein Extraction Reagent (Pierce, Rockford, Ill.). Following incubation for 10 min at 4° C., cell debris and insoluble aggregates were removed by centrifugation at 15,000 rpm for 30 min at 4° C. The supernatant was transferred to a cryogenic vial and stored at −80° C. until further use.

Production of Recombinant, Soluble PSMA (rsPSMA)

The extracellular domain of PSMA (amino acids 44-750 of the full-length protein, SEQ ID NO:1) was obtained as a secreted protein from a DXB11 Chinese hamster ovary (CHO) cell line, stably transfected with a rsPSMA expression vector. The cells were grown in a Celligen Plus 2.2 L Packed Bed Bioreactor (New Brunswick Scientific, Edison, N.J.) in protein-free media. The Bioreactor was operated in perfusion mode, and supernatant was collected aseptically into collection bags maintained at 4° C. The protease inhibitor aprotinin was added to the harvest supernatant, which was concentrated 25-fold prior to storage at −90° C. In some instances for purification, the concentrate was thawed and purified using subsequent steps of Concanavalin A lectin affinity chromatography and Butyl-SEPHAROSE hydrophobic interaction chromatography or according to the steps shown below.

The purified rsPSMA protein is dimeric, and possesses folate hydrolase enzymatic activity when tested according to published procedures (Pinto et al., *Clinical Cancer Research* 2:1445, 1996) and reacts with each of a panel of conformation-specific monoclonal antibodies, indicating that rsPSMA adopts a native conformation.

Purification of Recombinant, Soluble PSMA (rsPSMA)

Cell culture supernatants were concentrated 25-fold by tangential flow ultrafiltration and adjusted to 35% saturation with ammonium sulfate. Under these conditions, rsPSMA remains in the supernatant. Precipitated proteins were removed by centrifugation (20,000×g for 30 min, SS-34, Sorvall, Inc.) and the clarified supernatant was applied to a Butyl-SEPHAROSE resin (BioRad, Hercules, Calif.) followed by a wash with 35% ammonium sulfate in neutral phosphate-buffered saline containing 1 mM $Ca^{2+}$ and 0.5 mM $Mg^{2+}$ (PBS+). rsPSMA eluted in the flow-through and wash fractions of the column The fractions containing the rsPSMA protein were pooled, dialyzed into 10 mM sodium phosphate, pH 7.0, and loaded onto a Ceramic Hydroxyapatite column (BioRad, Hercules, Calif.). rsPSMA was eluted from the resin using 2M sodium chloride in 10 mM sodium phosphate, pH 7.0. The fractions containing the protein were pooled, dialyzed into 20 mM Tris, pH 7.5 containing 1 mM $Ca^{2+}$ and 0.5 mM $Mg^{2+}$, and applied to a Q650-SEPHAROSE column (TosoHaas, Montgomeryville, Pa.). rsPSMA was eluted from the resin with 150 mM NaCl in 20 mM Tris, pH 7.5 containing 1 mM $Ca^{2+}$ and 0.5 mM $Mg^{2+}$. Monomeric and dimeric forms of rsPSMA present after this step were separated using preparative size exclusion chromatography on a SUPERDEX 200 resin (Amersham Biosciences, Piscataway, N.J.) and PBS+(containing 1 mM $Ca^{2+}$ and 0.5 mM $Mg^{2+}$) as the running buffer. Purified rsPSMA was stored at −80° C. in PBS+. Unless otherwise indicated, PSMA monomers represent spontaneously dissociated protein recovered over SEC rather than forcibly denatured material.

Polyacrylamide Gel Electrophoresis (PAGE) and Western Blotting of the Different PSMA Proteins For each individual PAGE analysis, 15 µl of each cell lysate and 5 µl of the purified rsPSMA were used.

SDS-PAGE was performed using standard procedures. Samples were prepared by boiling for 5 minutes in the presence of Laemmli sample buffer (with or without the reducing agent dithiothreitol [DTT]). Samples were then applied on a 4-15% Tris-Glycine gel (BioRad, Hercules, Calif.). After electrophoresis for 1 h at 200V, the proteins were transferred onto nitrocellulose (BioRad) and analyzed by Western blotting.

The oligomeric nature of the different PSMA proteins was analyzed using Blue Native PAGE (BN-PAGE). Each sample was diluted with an equal volume of 2×BN-PAGE sample buffer (0.1M MOPS/0.1M Tris/40% glycerol/0.1% Coomassie G-250) prior to loading onto the gel. BN-PAGE was performed using 4-12% BisTris gels (Invitrogen, Carlsbad, Calif.) and 50 mM MOPS/50 mM Tris, pH 7.7 as running buffer. Coomassie Blue was omitted from the cathode buffer to avoid interference with protein binding during the transfer of the proteins onto nitrocellulose. Following electrophoresis for 2.5 hrs at 125V, the proteins were transferred onto a nitrocellulose membrane (BioRad) and analyzed by Western blotting.

Western blotting was performed as follows: Subsequent to transfer, the nitrocellulose membrane was blocked with 5% milk in PBS/0.1% Triton X-100/0.02% SDS, which was also used for the subsequent wash and antibody incubation steps. PSMA proteins were detected using the anti-PSMA mAbs 3.1 or 3.9 (Progenics Pharmaceuticals) as primary antibody and HRP-labeled anti-mouse IgG as secondary antibody and 1 h incubation at room temperature. The membranes were colorimetrically developed using chemiluminescence (NEN Plus, Perkin Elmer Life Sciences, Boston, Mass.).

Analytical size exclusion chromatography (SEC) was performed using a TSK $G3000SW_{XL}$ (TosoHaas, Montgomeryville, Pa.) column equilibrated in PBS+. The column was calibrated using bovine serum albumin (67 kDa), immunoglobulin G (150 kDa), ferritin (440 kDa) and thyroglobulin (670 kDa) as standards.

Results

Figure 5:
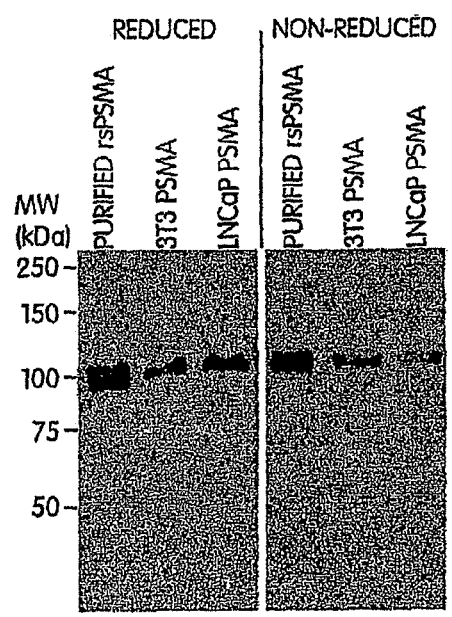
FIG. 5 is a digitized image of a polyacrylamide gel that shows an analysis of purified recombinant, soluble PSMA (rsPSMA) and of full-length PSMA from 3T3 cells T3 PSMA) or LNCaP cells (LNCaP PSMA) by reduced and non-reduced SDS-PAGE.

Both full-length PSMA and recombinant, soluble PSMA (rsPSMA) migrated on reducing and non-reducing SDS-PAGE with a molecular weight of ~100 kDa (FIG. 5). Thus, like full-length PSMA, rsPSMA is a monomer in the presence of denaturing agents, and no disulfide or other covalent bonds are present to mediate oligomerization. The result for full-length PSMA is in accordance with prior observations (Israeli et al., U.S. Pat. No. 5,538,866; Murphy et al., U.S. Pat. No. 6,158,508; Israeli, et al., *Cancer Research* 54:1807, 1994; Troyer et al. *Int. J. Cancer* 62:552, 1995; Troyer et al., *The Prostate* 30:233, 1997; Grauer et al., *Cancer Research* 58:4787, 1998). In each of these reports, full-length PSMA migrated as a major band of 100-120 kDa, with a minor (typically <5% of the total PSMA protein) 180-200 kDa band observed in a subset of reports (U.S. Pat. No. 6,158,508; Troyer et al., 1995; Troyer et al., 1997). Troyer et al. (1995) describe the 180-200 kDa species as being a noncovalently associated PSMA dimer that can be disrupted with increasing concentrations of SDS detergent.

rsPSMA contains 94% (707 of 750) of the amino acids present in full-length PSMA, and the two proteins were not clearly resolved in this analysis, as expected.

SDS-PAGE allows the analysis of denatured proteins only. In order to examine native proteins in their native state, other techniques have to be employed, such as Blue Native PAGE (BN-PAGE). BN-PAGE is used to determine the native molecular weight of proteins and their noncovalent complexes (Schägger & v. Jagow, *Anal. Biochem.* 199:223-231, 1991; Schagger et al., *Anal. Biochem.* 217:220-230, 1994). The dye Coomassie Blue G-250 binds to the hydrophobic domains on the surface of most proteins, enhances solubility, and introduces a charge shift on the native proteins resulting in migration towards the anode at pH 7.5 irrespective of the isoelectric point of the protein. Although the migration velocity of proteins in BN-PAGE varies somewhat, the molecular mass of proteins can be determined by their respective end points of migration due to the decreasing pore size of the acrylamide gradient present in the gels.

Figure 6A:
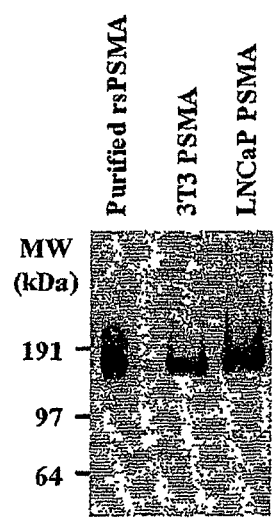
FIG. 6A is a digitized image of a polyacrylamide gel that depicts a Blue Native PAGE analysis of purified recombinant, soluble PSMA (Purified rsPSMA) and of full-length PSMA extracted from 3T3 cells (3T3 PSMA) or LNCaP cells (LNCaP PSMA).

When analyzed by BN-PAGE, full-length PSMA (extracted from LNCaP or 3T3 cells with nonionic detergents) as well as purified rsPSMA migrate with a molecular weight of ~190 kDa (FIG. 6A). This surprising observation for full-length PSMA indicates that the predominant form of cell-surface PSMA is a noncovalently associated dimer. This unexpected result can be contrasted with that of previous reports (U.S. Pat. No. 6,158,508; Troyer et al. 1995; Troyer et al., 1997), where the PSMA dimer represents a minor species in SDS-PAGE analyses. Presumably, the noncovalent PSMA dimer is largely dissociated by boiling in the presence of the denaturing detergent SDS.

Figure 6B:
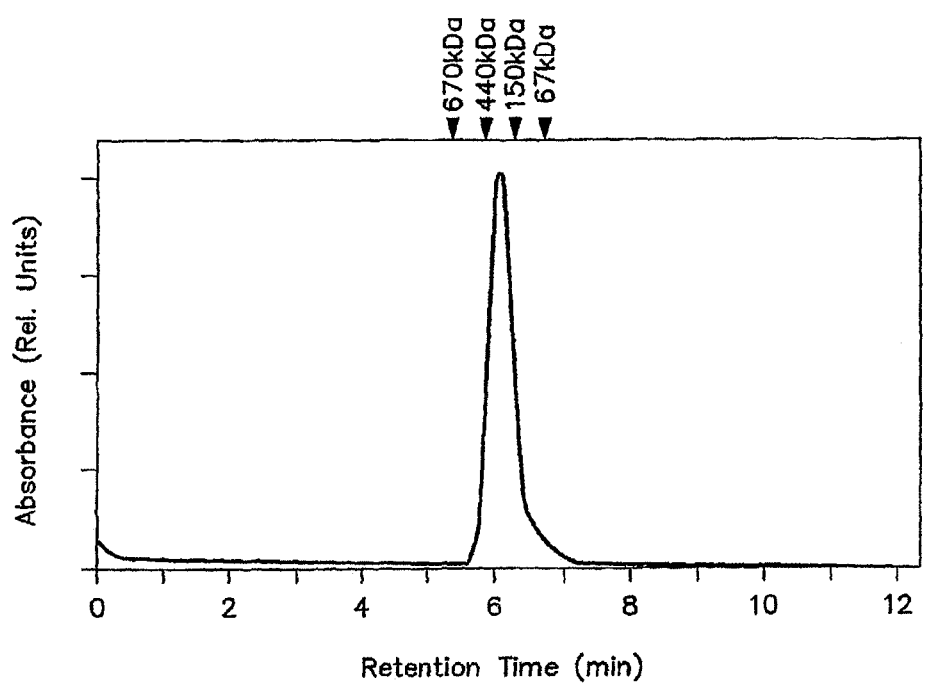
FIG. 6B shows the results of the analytical size exclusion chromatography (SEC) of purified rsPSMA in neutral PBS buffer. The arrows indicate the retention times of protein standards. The retention time of 260 kDa for rsPSMA is consistent with that of a homodimer.

Moreover, the result for the purified rsPSMA protein indicates that the dimer is stabilized via interactions between extracellular amino acids in addition to or exclusive of amino acids in the transmembrane or intracellular segments, which are not present in rsPSMA.

rsPSMA was subjected to analytical size exclusion chromatography (SEC) as a second sizing method. When analyzed in neutral PBS+ buffer, purified rsPSMA eluted as a single major peak with an apparent molecular mass of 260 kDa (FIG. 6B), slightly higher than expected. However, glycoproteins (such as rsPSMA) are typically nonglobular in shape and run at higher apparent molecular mass than standard SEC calibration proteins (Schulke, N., et al. (2002) *J. Virol.* 76, 7760-7776). Therefore, an apparent molecular mass of 260 kDa is consistent with the proposed homodimeric structure of rsPSMA. In contrast, purified monomeric rsPSMA eluted with an apparent molecular mass of 130 kDa. The studies demonstrate that the extracellular domain of PSMA is sufficient for dimerization, and the similarities between rsPSMA (amino acids 44-750) and PSM' (amino acids 58-750) suggest that the latter protein is likely to dimerize as well.

Example 16

Homodimerization is Required for Enzymatic Activity

Enzyme Assays

Pteroyl γ-glutamyl carboxypeptidase (folate hydrolase) activity was determined by monitoring the cleavage of poly γ-glutamylated methotrexate as described (Pinto, J. T., et al. (1996) Clin. Cancer Res. 2, 1445-1451) with the following exceptions. Di-γ-glutamylated methotrexate (MTXglu2) was used as substrate and HPLC was used rather than capillary electrophoresis. At the completion of the incubation (50 µM methotrexate di-gamma glutamate and 10 µg/ml rsPSMA in pH 4.5 acetate buffer in a volume of 100 µl for 2 hr at 37° C.), 100 µl of 0.5 M $Na_2HPO_4$ was added to stop the reaction. Samples were loaded at a flow rate of 1.25 ml/min through a 50×4 6 mm, 3 µm PRISM reversed-phase column (Thermo Hypersil-Keystone, Bellefonte, Pa.) with a PRISM 10×4-mm guard column, eluted with 15% methanol in 85% 0.5M $K_2HPO_4$, pH 7.0, and quantitated based on relative peak area observed at a wavelength of 313 nm.

For NAALADase assays, rsPSMA was incubated with N-acetyl-α-L-aspartyl-L-glutamate for 22 h at 37° C. in the presence of 20 mM sodium phosphate, 50 mM NaCl, 10 mM $ZnCl_2$, pH 7.1. Released L-glutamic acid was quantitated by using a commercial kit (R-Biopharm, Marshall, Mich.); 2-(phosphonomethyl) pentanedioic acid and Gly-Pro-7-amido-4-methylcoumarin were purchased from Sigma. Porcine kidney dipeptidyl peptidase IV (DPP IV) was used according to the manufacturer's instructions (Sigma).

Results

Figure 7A:
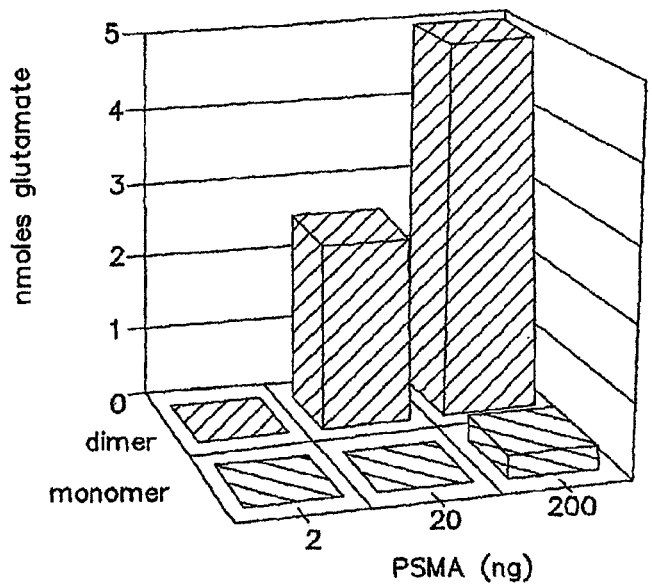
FIG. 7 illustrates that the dimeric but not monomeric rsPSMA (also referred to as $PSMA_{ECTO}$) is enzymatically active. Dimeric and monomeric PSMA were tested for folate hydrolase activity (FIG. 7A) and NAALADase activity (FIG. 7B). The background activity observed for PSMA monomer is consistent with residual amount (approximately 4%) of dimer present in the preparation.
Figure 7B:
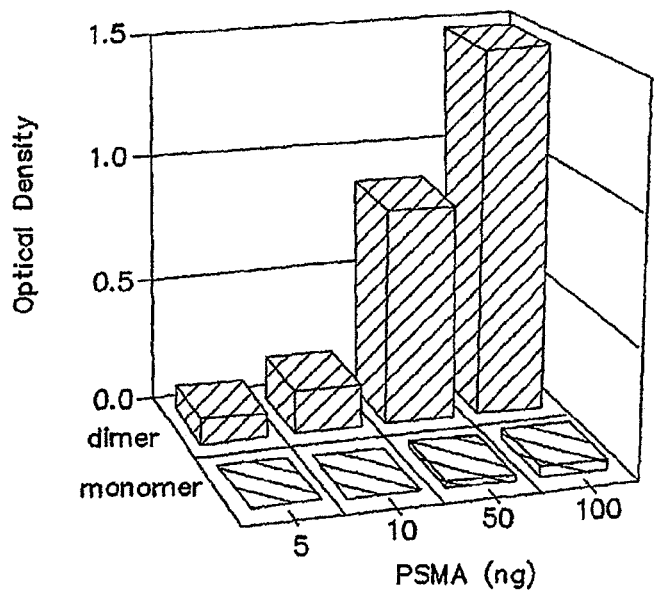

PSMA has been reported to possess folate hydrolase, NAALADase, and DPP IV activities (Pinto, J. T., et al. (1996) Clin. Cancer Res. 2, 1445-1451; Carter, R. E., et al. (1996) Proc. Natl. Acad. Sci. USA 93, 749-753; Pangalos, M. N., et al. (1999) J. Biol. Chem. 274, 8470-8483). The first two activities involve the hydrolysis of a carboxyl-terminal peptide bond to liberate a glutamic acid residue, whereas DPP IV cleaves downstream of an amino-terminal Aaa-Pro dipeptide sequence. The folate hydrolase activities of purified monomeric and dimeric forms of rsPSMA were evaluated. Whereas the dimer demonstrated high-level folate hydrolase activity, the monomer was essentially inactive (FIG. 7A). In fact, the residual activity of the monomer could be attributed to the residual amount (approximately 4%) of dimeric rsPSMA present in the preparation. High-level folate hydrolase activity was also observed for LNCaP cell lysates, consistent with prior observations (Pinto, J. T., et al. (1996) Clin. Cancer Res. 2, 1445-1451). Similarly, dimeric but not monomeric forms of rsPSMA possessed high-level NAALADase activity (FIG. 7B), which was abrogated by using 5 nM of the inhibitor 2-(phosphonomethyl)pentanedioic acid. Neither monomer nor dimer demonstrated DPP IV activity under conditions where porcine DPP IV efficiently hydrolyzed the substrate Gly-Pro-7-amido-4-methylcoumarin. This is consistent with the results reported by Barinka et al. (Barinka, C., et al. (2002) J. Neurochem. 80, 477-487), who similarly failed to confirm the DPP IV activity previously reported for PSMA (Pangalos, M. N., et al. (1999) J. Biol. Chem. 274, 8470-8483).

Example 16

Dissociation of PSMA Multimers

PSMA is a putative zinc metalloprotease, and site-directed mutagenesis of amino acids implicated in zinc binding results in a profound loss of enzymatic activity (Speno et al., *Molecular Pharmacology*, 55:179, 1999). These amino acids include His-377, Asp-387, Glu-425, Asp-453 and His-553. Ethylenediaminetetraacetic acid (EDTA) is a strong chelating agent for $Zn^{2+}$ and other divalent cations, and thus has the potential to remove $Zn^{2+}$ or other coordinate divalent cations from PSMA. We have determined that EDTA treatment causes the PSMA homodimer to dissociate into monomeric subunits. Similar results can be expected for other agents that possess similar chelating properties, such as ethyleneglycol-bis(beta-aminoethyl ether) (EGTA).

The purified rsPSMA protein was incubated with or without 10 mM EDTA for 16 hr at 4° C. and then analyzed by BN-PAGE. Under these conditions, the EDTA-treated protein was monomeric, whereas rsPSMA remained dimeric in the absence of EDTA. Although the dissociation of the PSMA dimer into monomer was essentially complete, any residual dimeric protein can be removed if desired by gel filtration, ultracentrifugation or other size-based separation methods that are well-known to those skilled in the art.

Example 17

Methods for Identifying Promoters of PSMA Dissociation

Compounds are screened for the ability to promote dissociation of PSMA dimers using a method that includes:

(a) contacting a PSMA dimer with a compound under conditions that do not promote dissociation of the PSMA dimer in the absence of the compound;

(b) measuring the amount of PSMA monomer; and (c) comparing the amount of PSMA monomer measured in the presence of the compound with that observed in the absence of the compound.

An increase in the amount of PSMA monomer measured in the presence of the compound indicates that the compound is capable of promoting dissociation of the PSMA dimer.

In a further embodiment, compounds are screened for the ability to promote dissociation of PSMA dimers using a method that includes:

(a) contacting a PSMA dimer with a compound under conditions that do not promote dissociation of the PSMA dimer in the absence of the compound;

(b) measuring the amount of PSMA dimer; and (c) comparing the amount of PSMA dimer measured in the presence of the compound with that observed in the absence of the compound.

A decrease in the amount of PSMA dimer measured in the presence of the compound indicates that the compound is capable of promoting dissociation of the PSMA dimer.

In a further embodiment, compounds are screened for the ability to promote dissociation of PSMA dimers using a method that includes:

(a) contacting a PSMA dimer with a compound under conditions that do not promote dissociation of the PSMA dimer in the absence of the compound;

(b) measuring the amounts of PSMA monomer and PSMA dimer;

(c) calculating a ratio of PSMA monomer to PSMA dimer; and (d) comparing the ratio obtained in (c) with that obtained in the absence of the compound.

An increase in the ratio measured in the presence of the compound indicates that the compound is capable of promoting dissociation of the PSMA dimer.

Example 18

Cell Surface PSMA Binding Studies

Flow Cytometry

Parent 3T3 cells or PSMA-expressing 3T3 cells ($2 \times 10^5$ cells per condition) were washed in PBS and incubated with PBS containing goat serum (10% v/v) for 20 minutes on ice to block non-specific binding sites. Anti-PSMA monoclonal antibodies (unpurified form in supernatants or purified mAbs) were added in serial dilutions to cells in 100 µl PBS and incubated on ice for 30 minutes. Control anti-human IgG (Caltag, Burlingame, Calif.) was used to establish background binding. After two washes in PBS, the cells were incubated with anti-human IgG (BD Pharmingen, San Diego, Calif.) for 30 minutes on ice. Cells were washed twice in PBS, resuspended in 250 µl PBS and analyzed by flow cytometry using a FACScan machine (Becton Dickinson, Franklin Lakes, N.J.) and CellQuest software. Viable cells were gated by forward scatter and side scatter parameters, and binding was quantified using histogram plots of mean fluorescence intensity (MFI) levels.

Anti-PSMA mAbs XG-006 (PTA-4403 and PTA-4404, heavy and light chain plasmids), XG-051 (PTA-4407 and PTA-4408), 4.4-0.1 (PTA-4360; 4.40, 4.40.1 and 4.40.2 are the same antibody that represent different stages of subcloning the hybridoma), 4.49.1, 4.292.1 (PTA-4390) and 4.304.1 were found to avidly bind to cell surface PSMA (FIG. 27).

Maximal Binding

Figure 28A:
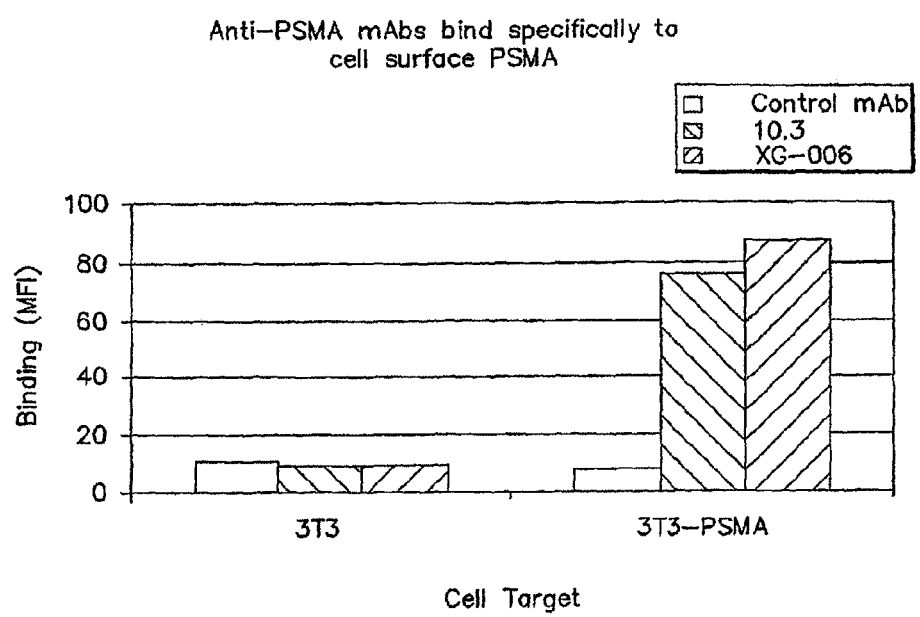
FIG. 28A shows that anti-PSMA mAbs bind to 3T3-PSMA cells and not 3T3 cells. One representative experiment from at least ten determinations is shown.
Figure 28B:
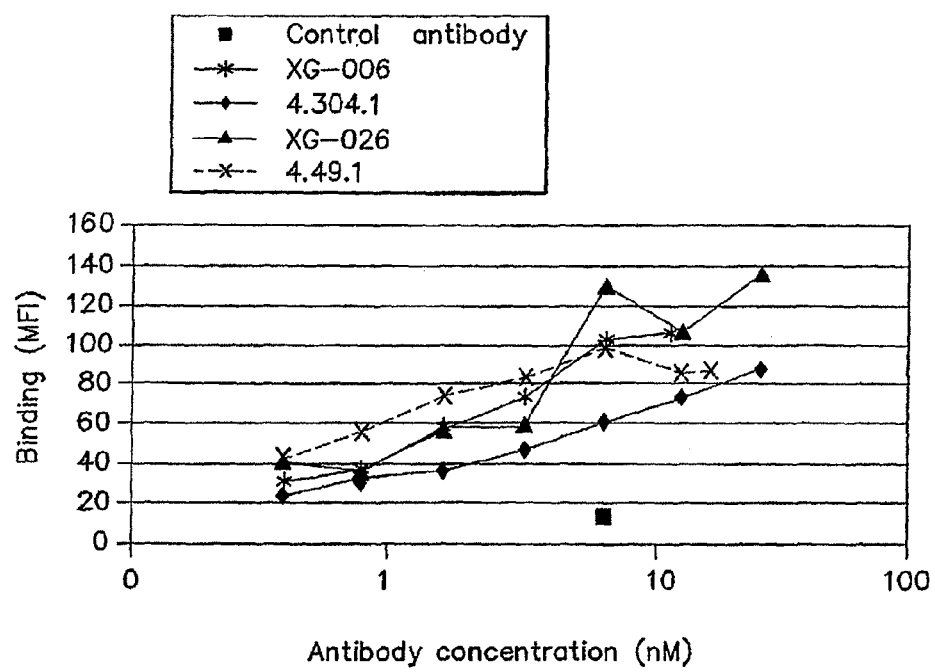
FIG. 28B illustrates that binding to cell-surface PSMA using serial dilutions of anti-PSMA mAb-containing culture supernatants occurred. One representative experiment from five is shown.
Figure 28C:
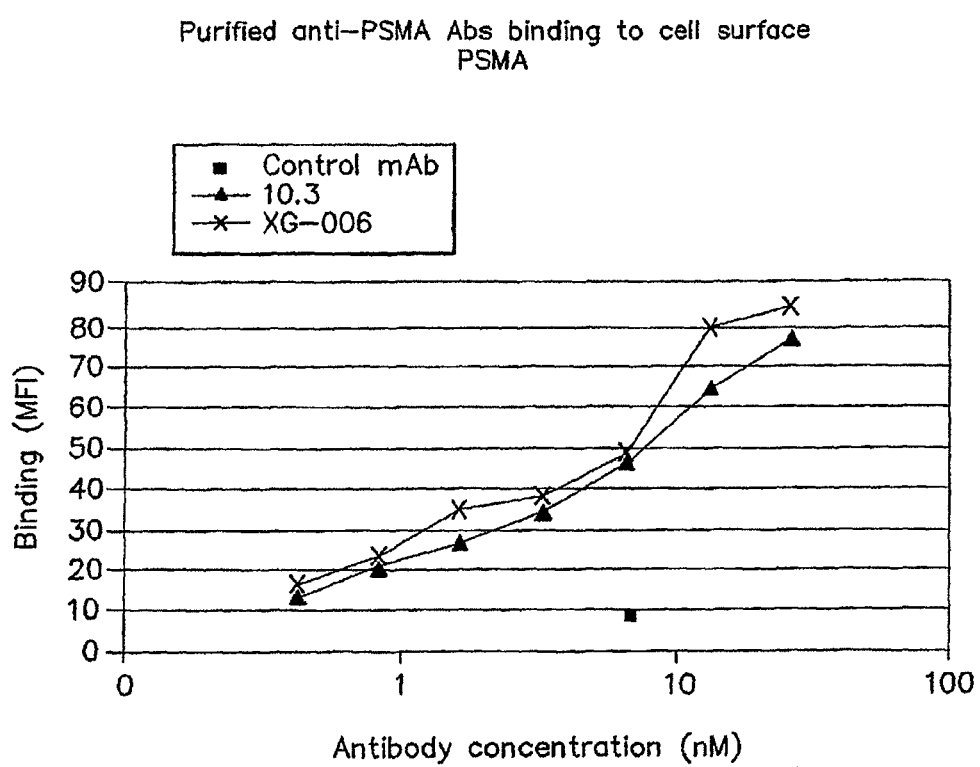
FIG. 28C shows binding to cell-surface PSMA using serial dilutions of purified anti-PSMA mAbs, XG-006 and 10.3 One representative experiment is shown.

Flow cytometry data (mean fluorescence intensity v. antibody concentration) were transposed and plotted using EXCEL software (Microsoft, Redmond, Wash.). Results from representative experiments of at least three determinations are depicted in FIGS. 28A-28C. Binding was compared by calculation of 50% effective concentration (EC50) using the Forecast function in EXCEL. The EC50 value represents the concentration of antibody required for half-maximal binding.

Anti-PSMA mAbs 10.3 (PSMA 10.3) and XG-006 were found to bind to 3T3-PSMA cells and not 3T3 cells (FIG. 28A). Antibody (26 nM) was added to cells, which were analyzed by flow cytometry. Binding to cell-surface PSMA using serial dilutions of anti-PSMA mAb-containing culture supernatants of XG-006, 4.304.1, XG-026 (PTA-4405 and PTA-4406) and 4.49.1 also was demonstrated (FIG. 28B). Binding to cell-surface PSMA using serial dilutions of purified anti-PSMA mAbs XG-006 and 10.3 is represented by FIG. 28C.

Example 19

Cytotoxicity of Toxin-Labeled Antibody

PSMA-3T3, LNCaP, and/or C4-2 cells (and control cell lines 3T3 and PC3 that do not express PSMA) were plated at 2,500 cells/100 µL/well in 96-well microplates (Falcon) and were incubated overnight at 37° C. in the presence of 5% $CO_2$. The media used for PSMA-3T3 (and 3T3) and LNCaP (and C4-2 and PC3) was DMEM or RMPI 1640, respectively, containing 2 mM L-glutamine, 10% FBS, and 1% penicillin-streptomycin. 50 ng (in 50 µL) of Mab-Zap or Hum-ZAP (Advanced Targeting Systems, San Diego, Calif.) in medium was added in each well. Mab-Zap and Hum-Zap are goat anti-mouse IgG antibody or goat anti-human IgG antibody covalently linked to saporin, the most potent of the plant ribosome-inactivating proteins (RIP) from the seeds of the plant *Saponaria officinalis*. Saporin induces cell death by apoptosis (Bergamaschi, G., Perfetti, V., Tonon, L., Novella, A., Lucotti, C., Danova, M., Glennie, M. J., Merlini, G., Cazzola, M. Saporin, a ribosome-inactivating protein used to prepare immunotoxins, induces cell death via apoptosis. *Br J Haematol* 93, 789-94. (1996)). The Mab-Zap did not bind to or internalize in cells in the absence of an appropriate primary antibody.

Figure 29A:
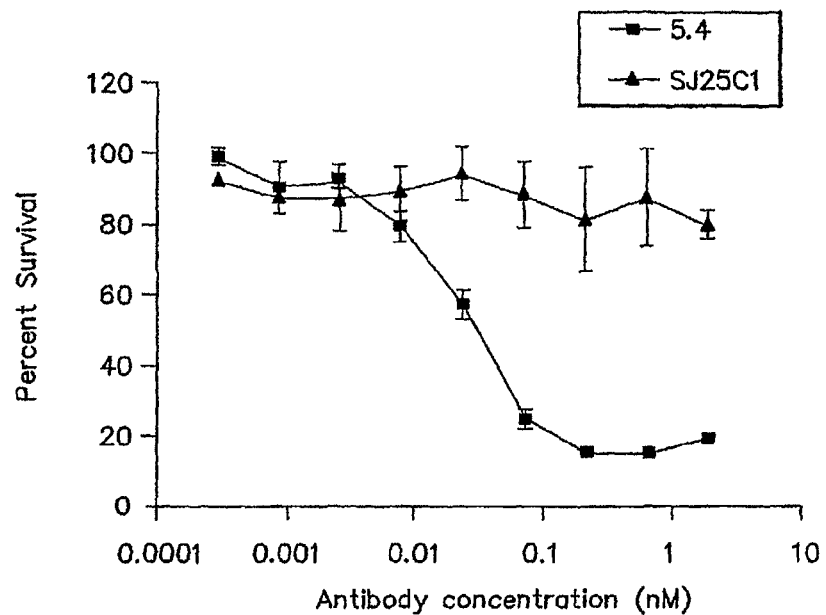
FIG. 29 illustrates the immunotoxin cytotoxicity of murine anti-PSMA antibodies on C4-2 prostate cancer cells. SJ25C-1 as a control antibody is a murine anti-CD19 IgG. The LD 50 s (M) for 5.4, 3.9, and mJ591 antibodies were $2.27 \times 10^{-11}$, $2.29 \times 10^{-11}$ and $8.82 \times 10^{-11}$, respectively.
Figure 29B:
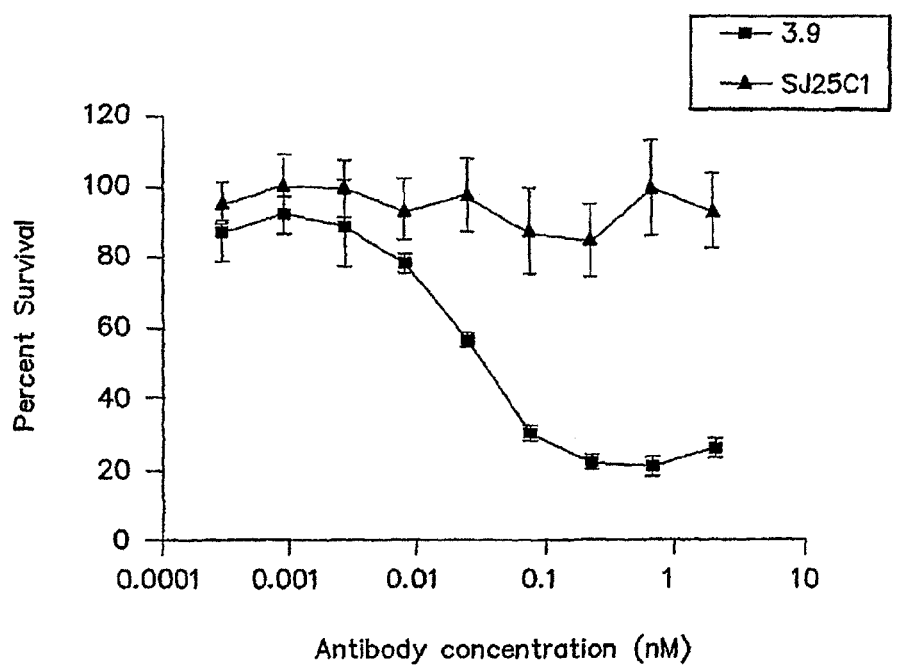
Figure 29C:
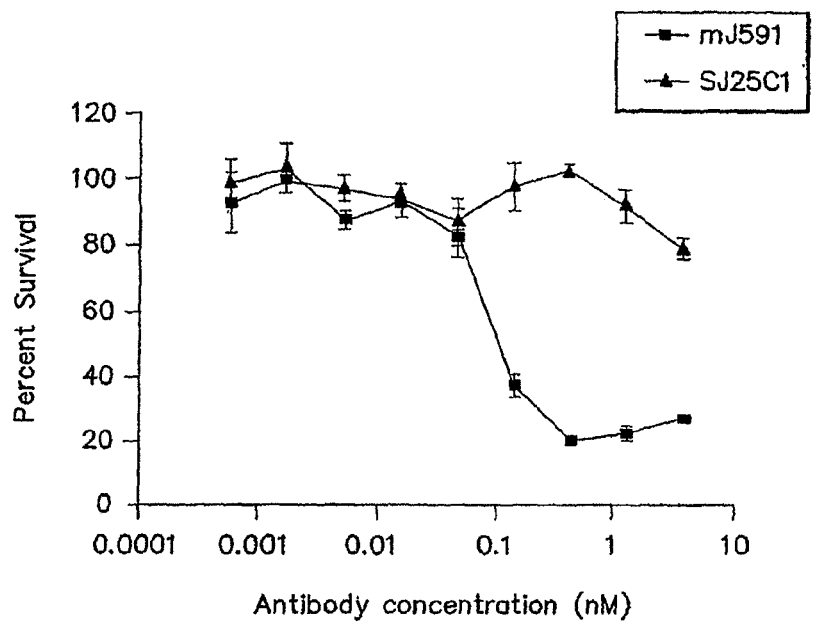
Figure 30A:
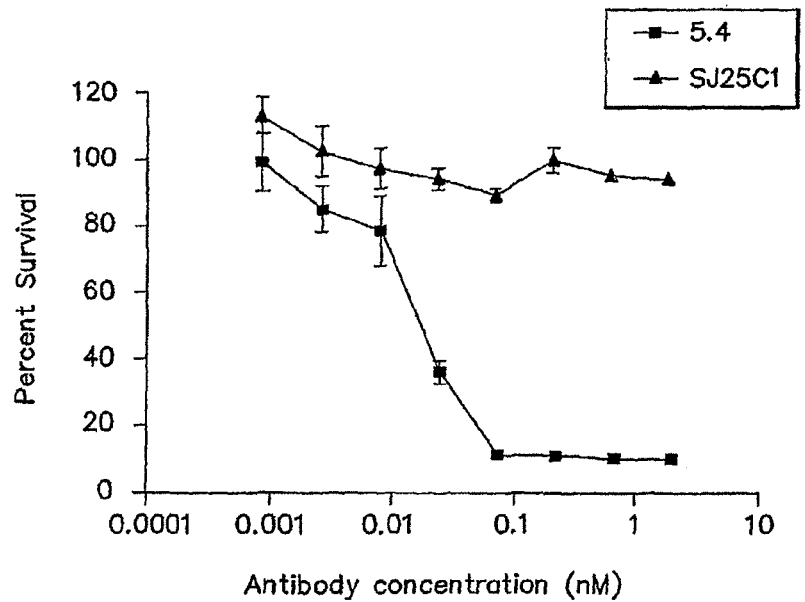
FIG. 30 illustrates the immunotoxin cytotoxicity of murine anti-PSMA antibodies on PSMA-3T3 cells. SJ25C-1 as a control antibody is a murine anti-CD19 IgG. The LD 50 s (M) for 5.4, 3.9, and mJ591 antibodies were $1.64 \times 10^{-11}$, $1.96 \times 10^{-11}$ and $8.90 \times 10^{-11}$, respectively.
Figure 30B:
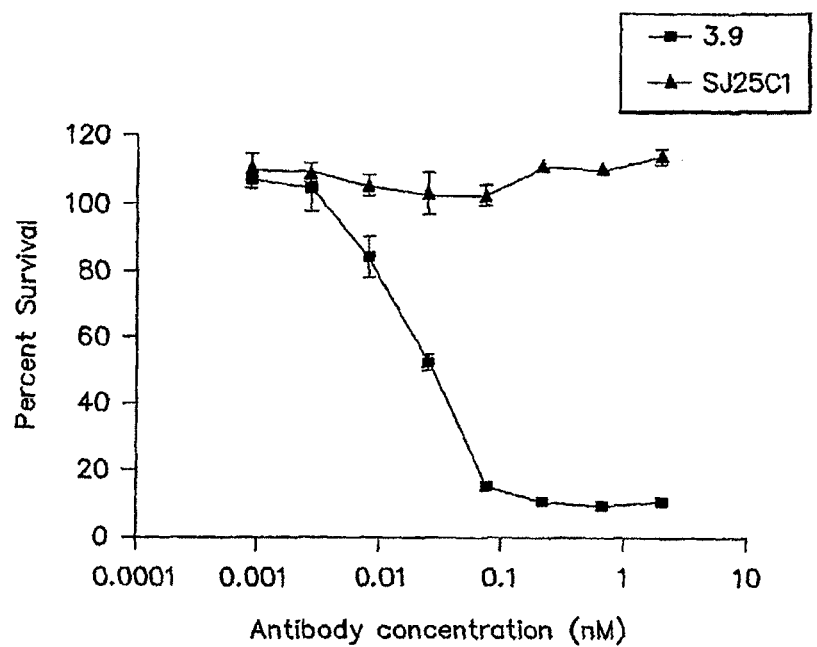
Figure 30C:
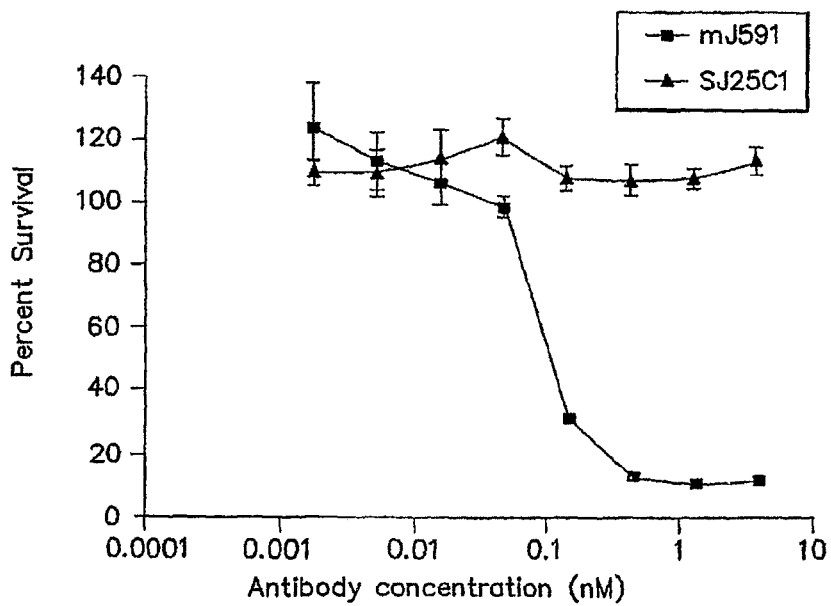

Murine 3.9, 5.4, mJ591 (ATCC #HB-12126) and human 006, 4.40, 4.304 anti-PSMA antibodies (and control IgG antibodies) were added into plates at different concentrations to bring the total volume to 200 µL in triplicate. The plates were kept cold on ice for at least 30 min to maximize Map-Zap or Hum-Zap binding to PSMA antibodies before internalization. The plates were incubated for 2 days and then the medium was changed and incubated for another 2 days. After 4 days incubation, the medium was withdrawn and fresh medium containing 10% Alamar Blue (20 µL, Bioscience, Camarillo, Calif.) was added into each well and incubated for 2 hrs. A CYTOFLUOR plate reader was used to measure fluorescence in 96-well plates at wavelengths of 530 nm excitation and 590 nm emission. Internalization of toxin was mediated by anti-PSMA antibodies. The cell kill is illustrated in FIG. 29 on C4-2 cells and in FIG. 30 on PSMA-3T3 cells.

Figure 31:
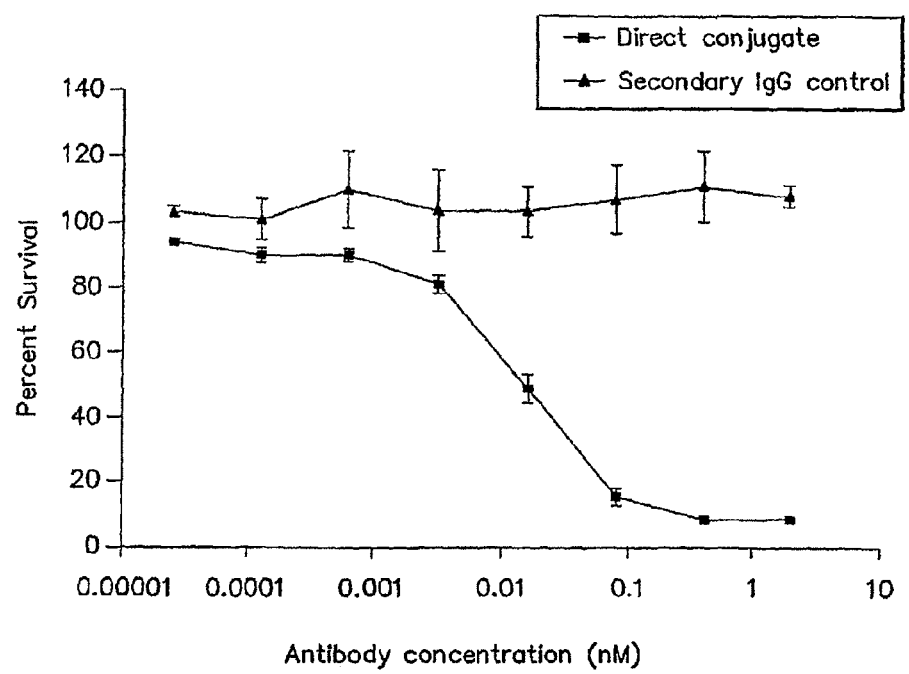
FIG. 31 provides the cytotoxicity of direct conjugated human 4.304 anti-PSMA antibodies with saporin on PSMA-3T3. The LD50 was $1.48 \times 10^{-11}$ M for direct conjugated 4.304 anti-PSMA antibodies with saporin.

Human 4.304 anti-PSMA antibody was directly conjugated with saporin (Wrenn et al., *Brain Res.* 740:175-184, 1996), and its cytotoxicity was demonstrated using a similar protocol as described above (see FIG. 31).

Example 20

Immunoreactivity

PSMA-3T3, LNCaP and C4-2 were used as PSMA expressing cell lines and 3T3 was used as a control cell line not expressing PSMA. The cells were blocked with 10% goat serum on ice to reduce non-specific binding in this assay.

A small amount (1-5 ng) of labeled mAb was added into a cell pellet of 10 million cells and incubated at 0° C. (on ice) with gentle mixing. After a 1 hour incubation, the cells were collected by centrifugation and the supernatant containing unbound mAb was transferred to a fresh cell pellet for an additional 1 hour incubation at 0° C. Both sets of cells were centrifuged and washed twice with cold PBS. The cell pellets, supernatant and wash fractions were counted for radioactivity. Immunoreactivity is defined as the amount of radioactivity in the cell pellets divided by the total radioactivity in the cell pellets, supernatant and wash fractions. These data are shown below in Table 3.

TABLE 3

Immunoreactivity of $^{111}$In Radiolabeled Antibody on PSMA Expressing Cells

| Radiolabeled mAb | Immunoreactivity (%) | Cell line |
|---|---|---|
| $^{111}$In 4.304 | 92.6 (1.4) | PSMA-3T3 (3T3) |
| | 92.6 | PSMA-3T3 |
| | 91.4 (1.7) | PSMA-3T3 (3T3) |
| | 89.1 | LNCaP |
| | 92.4 | C4-2 |

TABLE 3-continued

Immunoreactivity of $^{111}$In Radiolabeled Antibody on PSMA Expressing Cells

| Radiolabeled mAb | Immunoreactivity (%) | Cell line |
|---|---|---|
| Average = | 91.6 ± 1.5 | |
| $^{111}$In 4.40 | 87.7 (0.5) | PSMA-3T3 (3T3) |
| | 86.8 | PSMA-3T3 |
| | 89.4 (1.5) | PSMA-3T3 (3T3) |
| Average = | 88.0 ± 1.3 | |
| $^{111}$In mJ591 | 58.5 | PSMA-3T3 |
| | 54.9 (1.1) | PSMA-3T3 (3T3) |
| Average = | 56.7 ± 2.5 | |
| $^{111}$In 3.9 | 88 | LNCaP |
| | 87 | C4-2 |
| | 89 (2) | PSMA-3T3 (3T3) |
| | 95.3 (0.5) | PSMA-3T3 (3T3) |
| | 88.6 | PSMA-3T3 |
| | 84.8 | C4-2 |
| | 89.3 | PSMA-3T3 |
| Average = | 88.6 ± 3.2 | |

Antibodies 4.40, 4.304 and mJ591 were conjugated to the bifunctional chelate CHX-A"-DTPA and antibody 3.9 was conjugated to C-DOTA.

Immunoreactivity of $^{225}$Ac radiolabeled antibody (026 and 4.40) was also assessed with a methodology similar to that described above for the $^{111}$In labeled antibodies. $^{225}$Ac was chelated with the bifunctional DOTA at 50° C. for 30 minutes. The chelated $^{225}$Ac was then conjugated to antibodies 026 and 4.40 at 35° C. for 30 minutes. Unconjugated $^{225}$Ac was removed by a PD10 column (Amersham Biosciences, Picataway, N.J.). The immunoreactivity of the radiolabeled antibodies was then determined. The data are presented below in Table 4. In addition to the assessment of the immunoreactivity of these antibodies, the yield of the labeling procedure was also assessed, and these data are also provided below in Table 4.

TABLE 4

Yield and Immunoreactivity of $^{225}$Ac Radiolabeled Antibody

| Antibody | Yield | Immunoreactivity |
|---|---|---|
| 026 | 9.3 +/− 0.8 (n = 2) | 61.3 +/− 1.1 (n = 2) |
| 4.40 | 14.3 +/− 0.6 (n = 2) | 78.1 +/− 0.1 (n = 2) |

Example 21

Competitive Binding Assay to Identify Binding Epitopes

To identify whether a given group of mAbs recognize distinct or overlapping epitopes on PSMA, competition binding assays were performed with $^{111}$In radiolabeled antibodies. $2\times10^5$ cells (100 µL) of PSMA-3T3 were plated into 96-well microplates, and antibodies 4.40, 4.304 and mJ591 (100 µL) at different concentrations (series dilution) were added. The cells were incubated at 0° C. for 30 min. 20 µL of In-111 radiolabeled CHX-A"-DTPA antibody constructs were added into each well. After a 2 hour incubation on ice for competition binding, the cells were washed 5 times using cold PBS. The cells containing bound $^{111}$In antibodies were recovered from microplates into test tubes and counted in a gamma counter.

Figure 32:
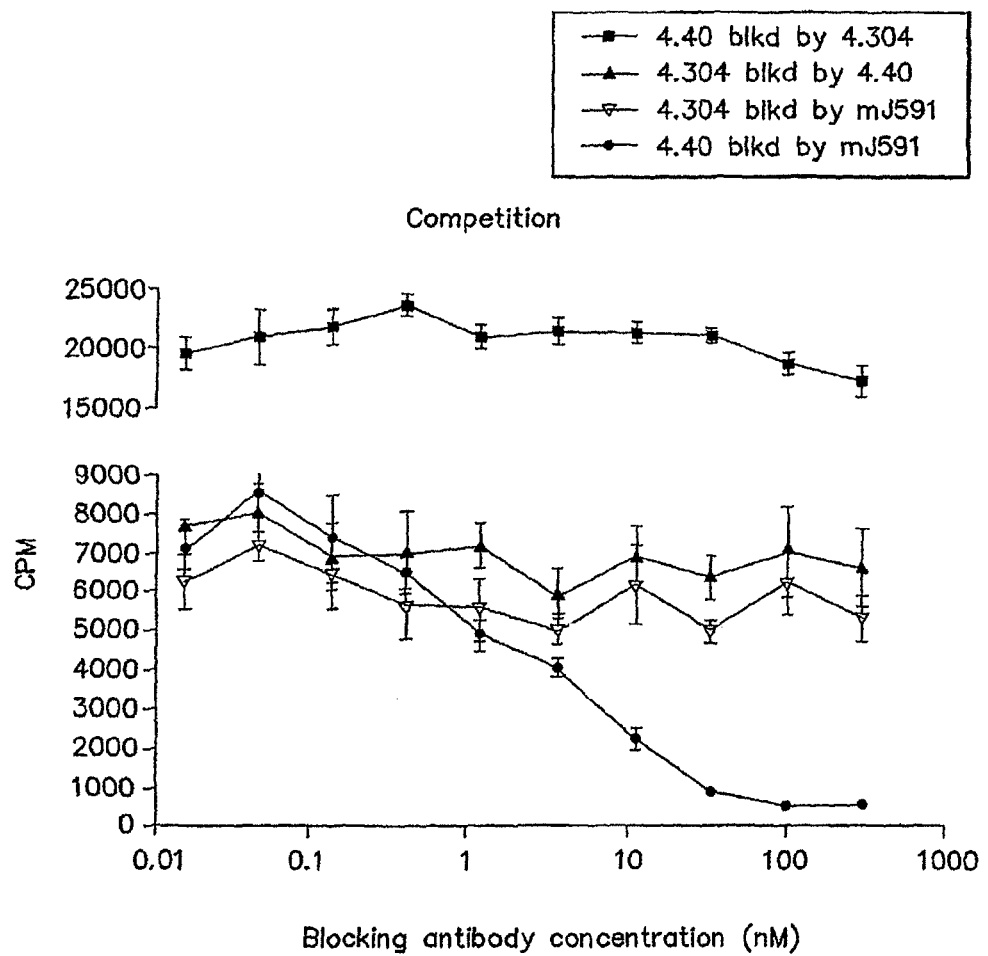
FIG. 32 illustrates the results of the competition assay of unmodified 4.304, 4.40, mJ591 anti-PSMA antibodies used to compete with In-111 radiolabeled 4.40 and 4.304 anti-PSMA antibodies.
Figure 33:
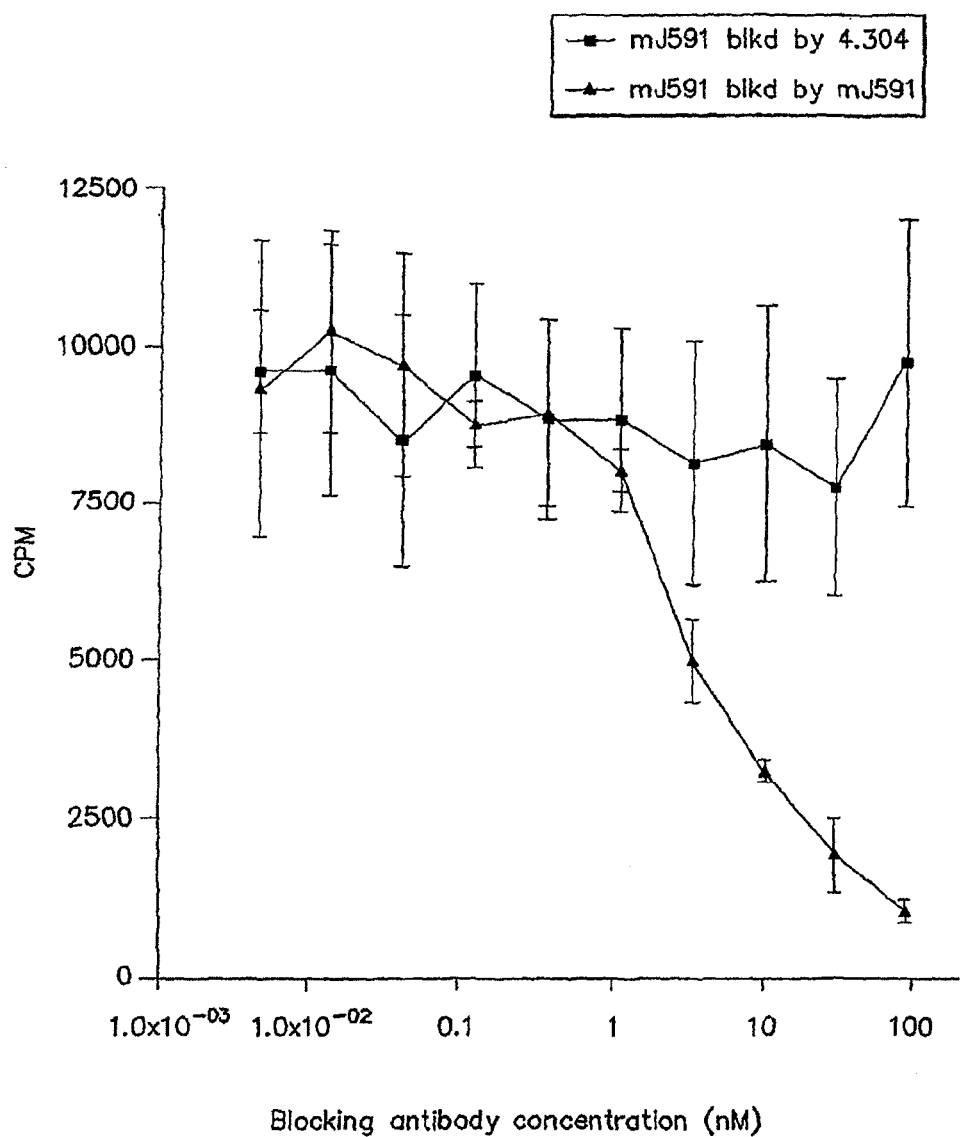
FIG. 33 illustrates the results of the competition assay of unmodified 4.304, mJ591 anti-PSMA antibodies used to compete with In-111 radiolabeled mJ591 anti-PSMA antibodies.

Results detailed in FIG. 32 show that mJ591 blocked $^{111}$In 4.40 binding to PSMA-3T3 cells and did not block $^{111}$In 4.304. In addition, 4.40 and 4.304 did not block each other. Unmodified antibodies 4.304 and mJ591 were also used to compete with $^{111}$In radiolabeled mJ591. Human 4.304 did not compete with $^{111}$In mJ591 for binding to PSMA-3T3 (FIG. 33).

Example 22

Binding Affinity Using BIACORE 3000

To determine the kinetics and affinity of the antibodies, the antibodies in crude supernatants, in purified form and in bifunctional chelate modified forms were analyzed using a BIACORE 3000 instrument (Biacore Inc., Piscataway, N.J.). BIACORE 3000 is a fully automated surface plasmon resonance (SPR)-based biosensor system that is designed to provide real-time kinetic data from assay formats that require no tags or labeling of compounds for biomolecular interactions. It is ideal for screening crude supernatants.

Figure 34:
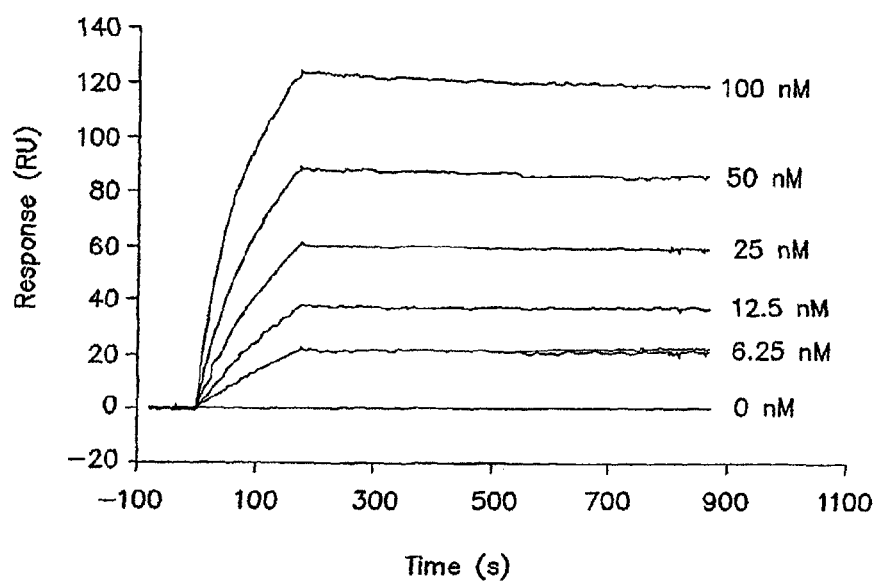
FIG. 34 shows an analysis of antibody PRGX1-XG-006 in association phase and dissociation phase at different concentrations of rsPSMA from 100 nM to 6.25 nM.

The streptavidin-coated sensor chips (SA chips, Biacore, Inc.) were used to capture biotinylated anti-human IgG antibody (Sigma, St. Louis, Mo.). The entire sensor chip surface was conditioned with five injections of conditioning solution (1 M NaCl, 50 mM NaOH) and equilibrated with PBS buffer containing 0.005% polysorbate 20. Two to three thousand resonance units (RU) of biotinylated anti-human IgG antibody (Sigma) were immobilized onto the SA chip followed by an injection of regeneration buffer (glycine-HCl, pH 2.2). Antibodies in supernatants were diluted to 2 µg/mL in PBS buffer and captured onto one anti-human IgG flow cell, while isotype-matched control human antibody (Sigma) was similarly captured on a second flow cell. rsPSMA at different concentrations in PBS buffer was flowed over the cells at 30 µL/min for 3 min in an "association phase" followed by a "dissociation phase" for 10 min SPR was monitored and displayed as a function of time. For each antibody at one concentration, the chip was regenerated and equilibrated. Examples of the analysis of antibody PRGX1-XG-006 in association phase and dissociation phase at different concentrations of rsPSMA from 100 nM to 6.25 nM are shown in FIG. 34. Thermodynamic and kinetic rate constants of binding were calculated using the BIACOREEvaluation software. For example, the affinity of XG-006 antibodies in a supernatant to rsPSMA was determined to be $4.92\times10^{-10}$ M with a $K_a$ of $1.3\times10^5$ M$^{-1}$ s$^{-1}$ and a $K_d$ of $6.4\times10^{-5}$ s$^{-1}$. Selective data for several human PSMA antibodies in crude supernatant, purified form, and modified with bifunctional chelate is listed in Table 5 for comparison.

Binding activity of $^{111}$In radiolabeled antibodies was determined by Scatchard analysis of binding data obtained using PSMA-expressing cells (LNCaP, C4-2, PSMA-3T3 and parental 3T3 as a control). The experimental procedures and methods of data analysis have been described previously (Scheinberg, D. A. et al. *Leukemia* 3: 440-445 (1991)).

TABLE 5

Kinetic Rate Constants of Antibodies in Crude Supernatant, Purified, Bifunctional Chelate Modified Forms along with KD Determined Using $^{111}$In Radiolabeled Scatchard Analysis

| Antibodies | Ka (M$^{-1}$, s$^{-1}$) | Kd (s$^{-1}$) | KD (M$^{-1}$) | AVG KD |
|---|---|---|---|---|
| 006 Supernatant | 1.30E+05 | 6.40E−05 | 4.92E−10 | 4.92E−10 |
| Purified 006-1 | 2.94E+05 | 1.37E−04 | 4.66E−10 | |
| Purified 006-2 | 2.26E+05 | 1.27E−04 | 5.62E−10 | 5.14E−10 |
| 4.40 Supernatant | 2.10E+05 | 1.25E−04 | 5.95E−10 | 5.95E−10 |
| Purified 4.40-1 | 2.54E+05 | 1.52E−04 | 5.98E−10 | |
| Purified 4.40-2 | 2.43E+05 | 2.37E−04 | 9.75E−10 | 7.87E−10 |
| CHX-4.40-1 | 2.57E+05 | 1.60E−04 | 6.23E−10 | |
| CHX-4.40-2 | 2.47E+05 | 1.55E−04 | 6.28E−10 | 6.25E−10 |
| IN-111CHX-4.40-1 | | | 4.44E−09 | |

TABLE 5-continued

Kinetic Rate Constants of Antibodies in Crude Supernatant, Purified, Bifunctional Chelate Modified Forms along with KD Determined Using $^{111}$In Radiolabeled Scatchard Analysis

| Antibodies | Ka (M$^{-1}$, s$^{-1}$) | Kd (s$^{-1}$) | KD (M$^{-1}$) | AVG KD |
|---|---|---|---|---|
| IN-111CHX-4.40-2 | | | 4.95E−09 | 4.70E−09 |
| 4.304 Supernatant | 1.40E+05 | 1.25E−04 | 8.93E−10 | 8.93E−10 |
| Purified 4.304-1 | 8.31E+04 | 1.20E−04 | 1.44E−09 | |
| Purified 4.304-2 | 1.06E+05 | 6.33E−05 | 5.97E−10 | 1.02E−09 |
| CHX-4.304-1 | 6.19E+04 | 1.21E−04 | 1.95E−09 | |
| CHX-4.304-2 | 6.79E+04 | 1.49E−04 | 2.19E−09 | 2.07E−09 |
| IN-111CHX-4.304-1 | | | 9.63E−09 | |
| IN-111CHX-4.304-2 | | | 5.97E−09 | 7.80E−09 |
| 10.3 Supernatant | 1.90E+05 | 3.63E−04 | 1.91E−09 | 1.91E−09 |
| Purified 10.3-1 | 3.28E+05 | 6.32E−05 | 1.93E−10 | |
| Purified 10.3-2 | 2.96E+05 | 6.43E−05 | 2.17E−10 | 2.05E−10 |

Figure 35:
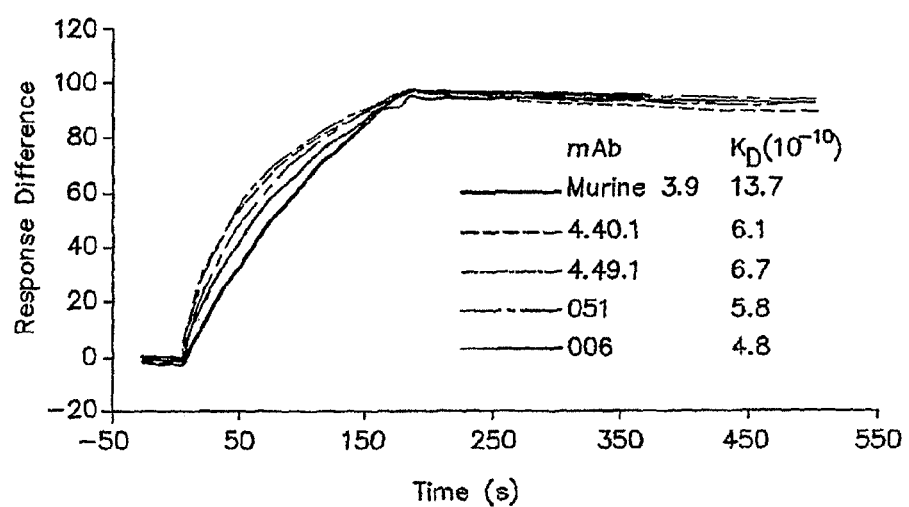
FIG. 35 shows the results of the comparison of the fully human anti-PSMA antibodies 4.40.1, 4.49.1, 051 and 006 and the murine anti-PSMA antibody 3.9 performed using BIA-CORE analysis.

A comparison of the fully human antibodies 4.40.1, 4.49.1, 051 and 006 and the murine antibody 3.9 was performed by BIACORE. For each antibody for comparison, response was normalized to 100 RU. The graph of time vs. response difference for these antibodies is given in FIG. 35. The binding affinities for these antibodies were determined to be 6.1, 6.7, 5.8, 4.8 and 13.7×10$^{-10}$M, respectively.

Example 23

Characterization of Cell Lines for In Vitro and in Vivo Studies

Figure 36:
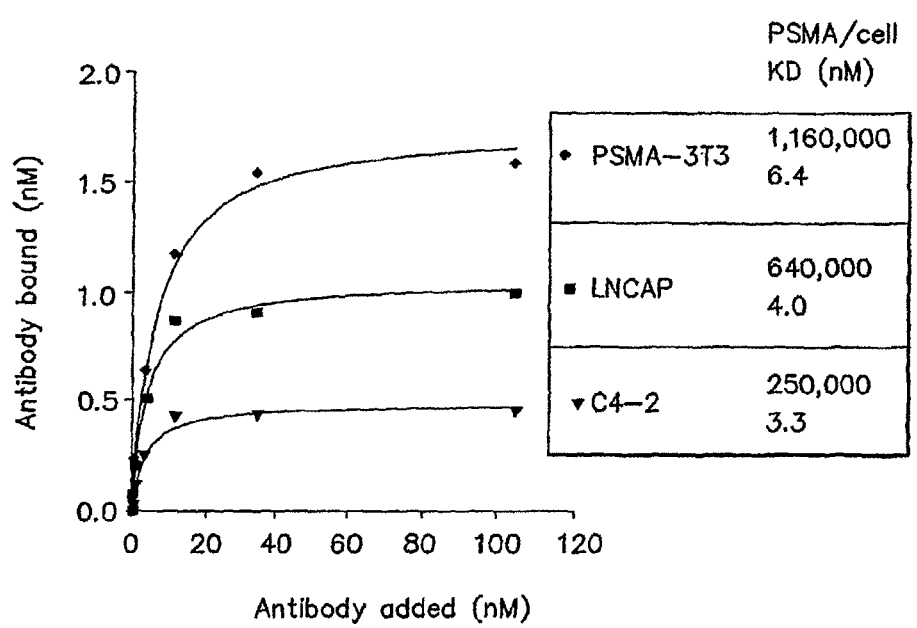
FIG. 36 provides results from the Scatchard analysis using In-111 labeled anti-PSMA antibody 3.9 of the PSMA-3T3, LNCaP and C4-2 cell lines.

Results from a Scatchard analysis using $^{111}$In labeled anti-PSMA antibody 3.9 are represented in FIG. 36. Transfected murine 3T3 cells express >1 million copies of PSMA per cell, LNCAP cells (androgen dependent human prostate cancer cell line) express 0.64 million copies, while C4-2 cells (androgen independent) express 0.25 million copies per cell. The affinity of 3.9 for cell surface PSMA is 6.4 nM for PSMA-3T3, 4.0 nM for LNCAP and 3.3 nM for C4-2 (4.6 nM is the average of these data).

A summary of the analyses of crude supernatants for the human anti-PSMA antibodies is given in Table 6 below.

TABLE 6

Characterization of Anti-PSMA Monoclonal Antibodies

| Supernatant | Ab Conc (μg/mL) | | Binding to 3T3-PSMA (FACS) | | | | Anti-PSMA Western | Biacore studies | | |
|---|---|---|---|---|---|---|---|---|---|---|
| | PGNX | Lysate EIA | PGNX FACS | Max binding | AVG EC50 | C4.2 FACS | | KD, M-1 (× 10$^{-10}$) | Ka, M-1s-1 (× 10$^5$) | Kd, s-1 (× 10$^{-5}$) |
| PRGX1-XG1-026 | 4.7 | ND$^1$ | ND | 148 | 2.4 | ND | Conf.$^2$ | 2.0 | 1.5 | 2.9 |
| 4.4.1 | 4.7 | 0.08 | 7 | 8 | ND | 5.2 | Conf. | 4.2 | 2.3 | 9.7 |
| PRGX1-XG1-006 | 1.8 | 0.39 | 114 | 183 | 3.4 | 9.5 | Conf. | 4.8 | 1.3 | 6.4 |
| PRGX1-XG1-051 | 3.5 | 0.48 | 83 | 202 | 2.0 | 9.9 | Conf. | 5.8 | 1.4 | 8.2 |
| 4.40.1 | 4.3 | 0.33 | 53 | 163 | 2.3 | 10.8 | Conf. | 6.1 | 2.1 | 12.5 |
| 4.49.1 | 2.6 | 0.36 | 362 | 162 | 0.9 | 16.2 | Conf. | 6.7 | 3.1 | 20.7 |
| 4.292.1 | 2.7 | 0.18 | 75 | 195 | 6.0 | 9.2 | Conf. | 6.8 | 1.2 | 8.5 |
| 4.304.1 | 4.1 | 0.39 | 92 | 184 | 9.1 | 8.4 | Conf. | 8.7 | 1.4 | 12.5 |
| 4.232.1 | 2.4 | 0.49 | 97 | 138 | 2.7 | 6.0 | Linear$^3$ | 9.4 | 1.5 | 13.8 |
| 4.153.1 | 5.9 | 0.29 | 279 | 182 | 5.3 | 14.8 | Conf. | 9.5 | 1.2 | 11.8 |
| 4.333.1 | 2.9 | 0.18 | 82 | 168 | 3.1 | 6.6 | Conf. | 11 | 0.7 | 8.5 |
| PRGX1-XG1-077 | 3.9 | 0.45 | 392 | 227 | 6.0 | 12.4 | Conf. | 16 | 0.6 | 10.4 |
| 10.3 | 8.5 | 1.06 | ND | ND | ND | ND | ND | 19 | 1.9 | 36.4 |
| pure 10.3 | | 0.44 | 130 | 181 | 7.5 | ND | Conf. | ND | | |
| | | | | | | 4.7 | | | | |
| 4.22.1 | 2.8 | 0.08 | 7 | ND | ND | 4.7 | ND | 20 | 1.7 | 33 |
| 4.248.1 | 3.5 | 0.37 | 7 | ND | ND | 4.1 | Conf. | 27 | 1.0 | 28 |
| 4.54.1 | 10 | 0.14 | 267 | 162 | 3.9 | 13.6 | ND | 30 | 1.9 | 56 |
| 4.7.1 | 5 | 0.23 | 156 | 141 | 1.6 | 10.2 | Conf. | 32 | 1.7 | 56 |
| 4.78.1 | 5.3 | 0.00 | 205 | 118 | 1.0 | 7.9 | Conf. | 53 | 2.4 | 125 |
| 4.48.1 | 4.9 | 0.06 | 14 | ND | ND | 7.7 | ND | 62 | 0.9 | 59 |
| 4.209.1 | 3.5 | 0.22 | 60 | ND | ND | 6.7 | ND | 142 | 0.9 | 125 |
| 4.177.1 | 1.1 | 0.15 | 236 | 174 | 2.4 | 10.6 | ND | 155 | 0.6 | 93 |
| 4.152.1 | 3.4 | 0.38 | 81 | 85 | 4.0 | 7.5 | ND | 163 | 0.8 | 126 |
| 4.28.1 | 4.2 | 0.04 | 112 | 155 | 4.2 | 11.3 | ND | 167 | 1.2 | 192 |
| 4.16.1 | 5.3 | 0.00 | 8 | ND | ND | 7.8 | ND | 177 | 1.8 | 313 |
| 4.360.1 | 1.5 | 0.02 | 112 | 130 | 2.2 | 7.9 | ND | 197 | 1.0 | 201 |
| 4.288.1 | 15.4 | 0.02 | 67 | 141 | 4.1 | 6.5 | ND | 198 | 1.3 | 257 |
| 4.219.2 | 0.5 | 0.34 | 69 | ND | ND | 5.9 | ND | ND | | |
| PRGX1-XG1-069 | 6.5 | ND | ND | 71 | 7.9 | ND | ND | No Binding | | |
| Murine 3.9 | | | | | | | | 13.7 | 0.7 | 9.7 |
| Control | | | | | | | | 6.34 | 2.24 | 14.2 |

$^1$ND = not determined
$^2$conf. = conformational epitope
$^3$linear = linear epitope

Example 24

Cytotoxicity of Radiolabeled Antibody

The in vitro cytotoxicity of $^{225}$Ac labeled anti-PSMA antibody (4.40 and 026) was determined using methodology similar to that used in Example 19. Prostate cancer cells (100 µL of C4-2, LNCaP, and PC3 cells at a concentration of 2×10$^4$ cells/mL) were placed into separate wells of a 96 well microplate. For tests with the 026 antibody, C4-2 and PC3 cells were placed into separate wells of a 96 well microplate. After overnight incubation, the cells were treated with $^{225}$Ac labeled human anti-PSMA antibody at different concentrations for over 4 days. Cell cytotoxicity was quantified using Alamar Blue (Biosource International, Camarillo, Calif.).

Figure 37:
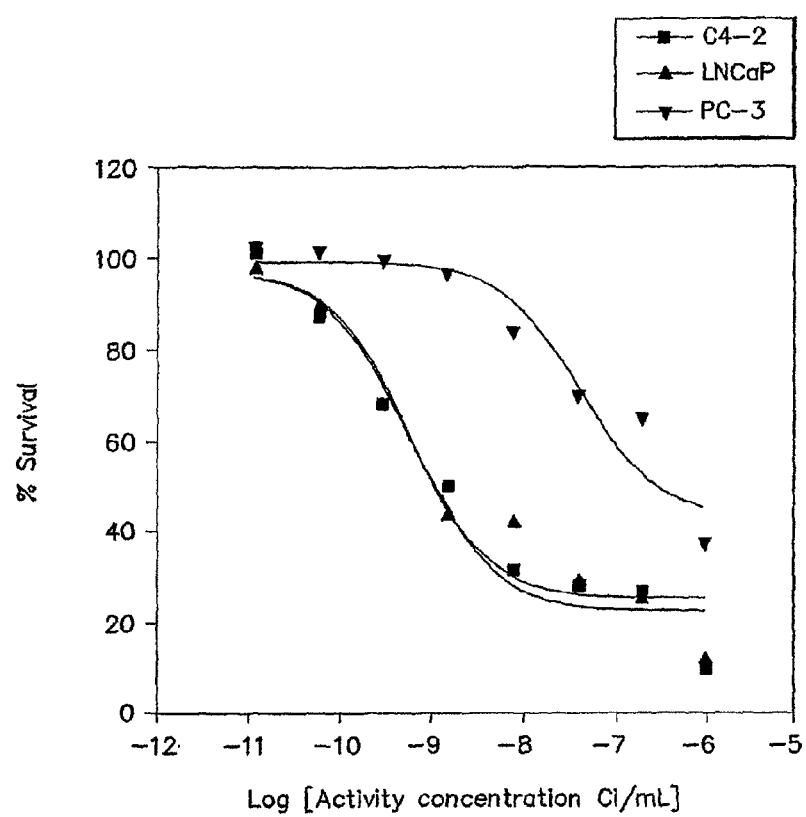
FIG. 37 shows in vitro cytotoxicity of Ac-225 labeled human anti-PSMA antibody 4.40 on prostate cancer cells.

FIG. 37 shows a plot of cell survival vs. $^{225}$Ac activity concentration using $^{225}$Ac labeled 4.40 antibody. The EC50 for PSMA expressing cells (C4-2 and LNCaP) was <2 nCi/mL. However, the EC50 was 420 nCi/mL for PC3 cells, which do not express PSMA on the cell surface. Therefore, the $^{225}$Ac labeled human anti-PSMA 4.40 antibody shows >200-fold selectivity in killing PSMA expressing prostate cancer cells (C4-2 and LNCaP) vs. control cells (PC3).

Figure 38:
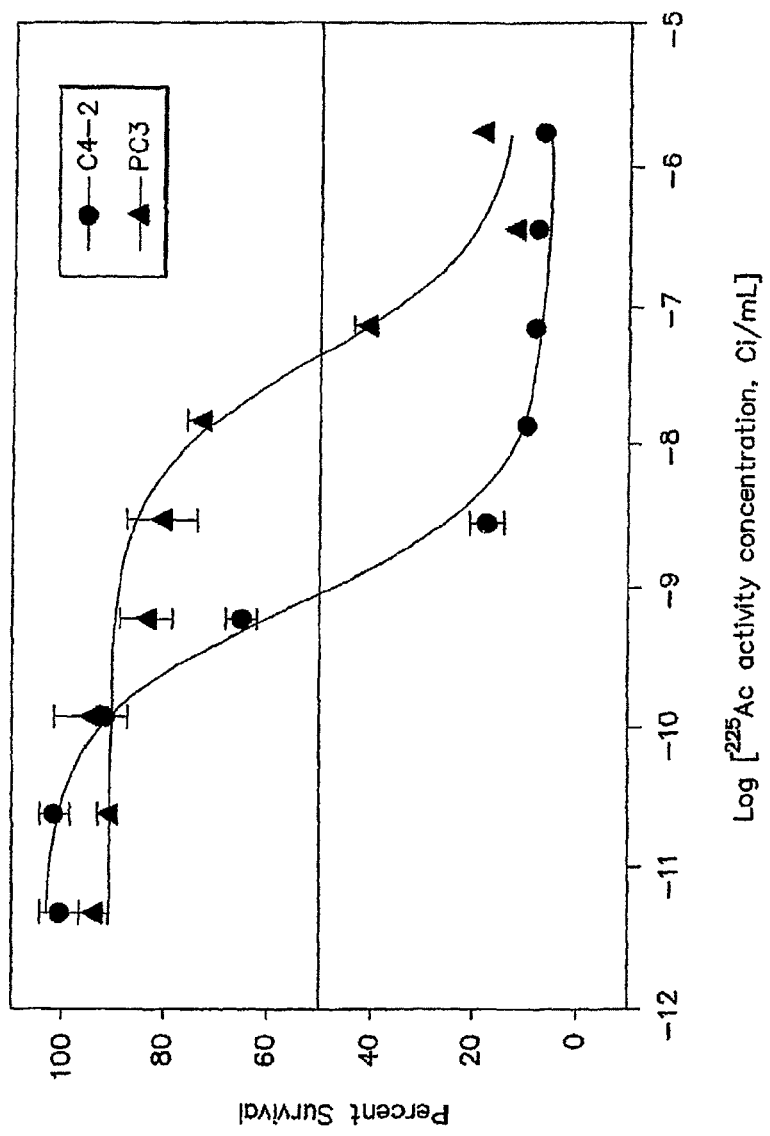
FIG. 38 shows the specific killing of PSMA expressing cells (C4-2) vs. PSMA non-expressing cells (PC-3) treated with $^{225}$Ac labeled mAb 026.

FIG. 38 shows a plot of cell survival vs. $^{225}$Ac activity concentration using $^{225}$Ac labeled 026 antibody. The $^{225}$Ac labeled human anti-PSMA 026 antibody shows >50-fold selectivity in killing PSMA expressing prostate cancer cells (C4-2) vs. control cells (PC3).

Example 25

Cytotoxicity of $^{225}$Ac Labeled Antibody vs. Control Antibody

The in vitro cytotoxicity of $^{225}$Ac labeled anti-PSMA antibody was determined using methodology similar to that used in Example 19 and Example 24 above. Human prostate cancer cells (100 µL of C4-2 and LNCaP cells at a concentration of 2×10$^4$ cells/mL) were placed into separate wells of a 96 well microplate. After overnight incubation, the cells were treated with $^{225}$Ac labeled human anti-PSMA 026 antibody at different concentrations for 4 days. Cell cytotoxicity was quantified using Alamar Blue (Biosource International, Camarillo, Calif.). Human IgG (HuIgG) was used as a control. The cytotoxicity of an anti-PSMA mAb 026 "2 hour wash" was also determined. A 2 hour wash means that the cells were incubated with $^{225}$Ac labeled antibody for 2 hours. After 2 hours, the media was removed and fresh media was added for the 4 day incubation.

Figures 39A, 39B:
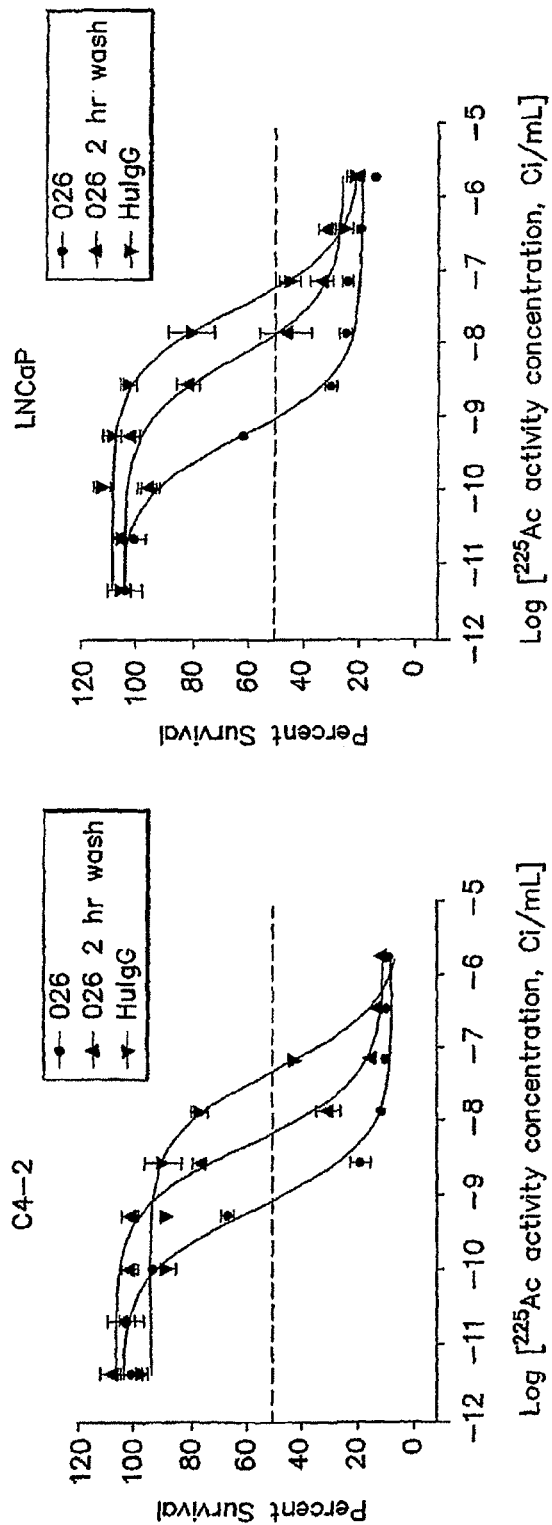
FIG. 39 shows the in vitro cytotoxicity of $^{225}$Ac labeled mAb 026 on human prostate cancer cell lines (C4-2 and LNCaP).

FIG. 39 shows a plot of cell survival vs. the $^{225}$Ac activity concentration for both C4-2 and LNCaP cells using radiolabeled mAb 026, mAb 026 2 hour wash and HuIgG. $^{225}$Ac labeled mAb 026 showed an IC50 of <1 nCi/mL. Therefore, the $^{225}$Ac labeled human anti-PSMA 026 antibody showed >50-fold selectivity in killing the prostate cancer cells vs. the control antibody.

Example 26

Cytotoxicity of $^{225}$Ac Labeled Antibody vs. Control Antibody Evaluated by $^3$H Thymidine Incorporation Human prostate cancer cells (C4-2) in a 96 microplate were treated with $^{225}$Ac labeled mAbs at different concentrations for 4 days. Cell survival was assessed using $^3$H thymidine incorporation (Nikula, T. K, et al. *J. Nucl. Med.* 40: 166-176, 1999).

Figure 40:
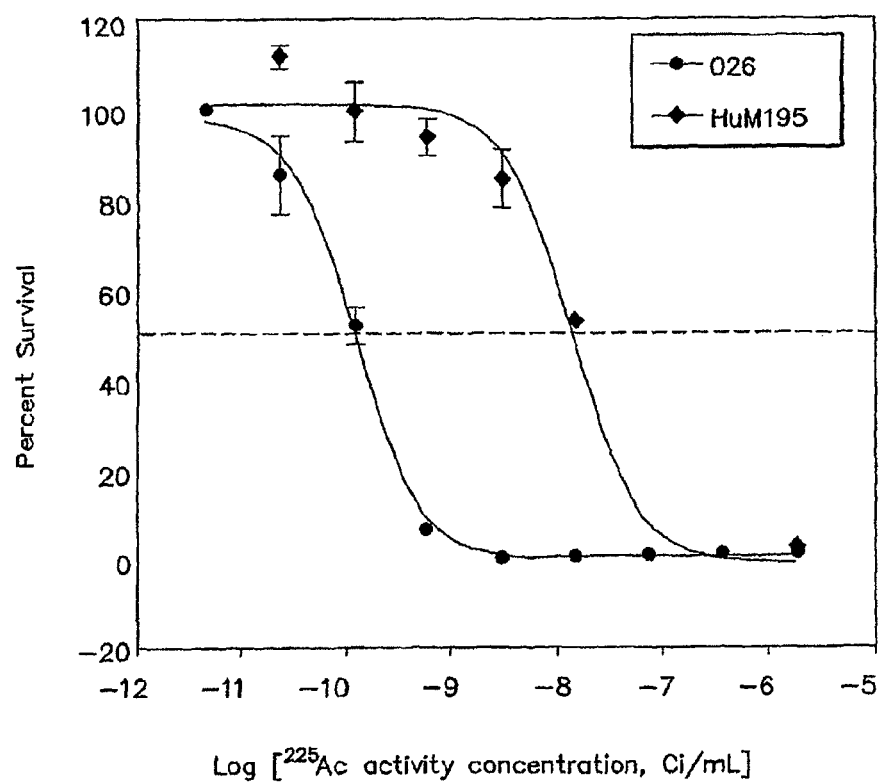
FIG. 40 shows the in vitro cytotoxicity of $^{225}$Ac labeled mAb 026 on human prostate cancer cell line, C4-2, evaluated by $^{3}$H thymidine incorporation.

FIG. 40 shows a plot of cell survival vs. the $^{225}$Ac activity concentration for C4-2 cells using radiolabeled mAb 026 and control mAb (HuM195). The IC50 was 0.12 nCi/mL using $^{225}$Ac labeled 026 vs. 13 nCi/ml with the control mAb (HuM195). The radiolabeled 026 antibody, therefore, showed >100-fold selectivity in killing the PSMA expressing C4-2 cells vs. the control antibody.

Example 27

In Vivo Radioimmunotherapy with $^{177}$Lu Labeled Antibodies

Figure 41:
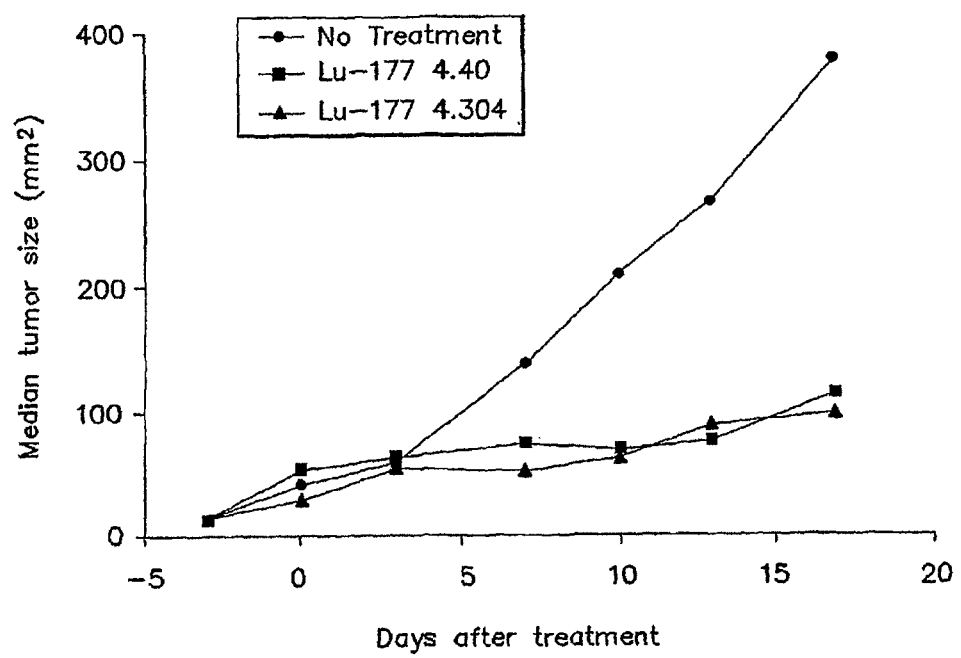
FIG. 41 shows the results of in vivo radioimmunotherapy with Lu-177 labeled human anti-PSMA antibodies.

Athymic nude mice from the National Cancer Institute were implanted subcutaneously with 2×10$^6$ PSMA-3T3 cells. After measurable tumors appeared at day 7 post implantation, the mice were treated by injection with either a single 250 µCi dose human anti-PSMA antibody 4.40 or 4.304 labeled with $^{177}$Lu (University of Missouri Research Reactor), or were injected with buffer only as control. The tumor size of individual animals was measured using an electronic caliper. FIG. 41 shows a plot of the median tumor size in each group over time. Tumor growths were substantially reduced in $^{177}$Lu antibody treated groups compared to the control group.

Example 28

In Vivo Biodistribution Study with $^{177}$Lu Labeled Antibodies

Figure 42A:
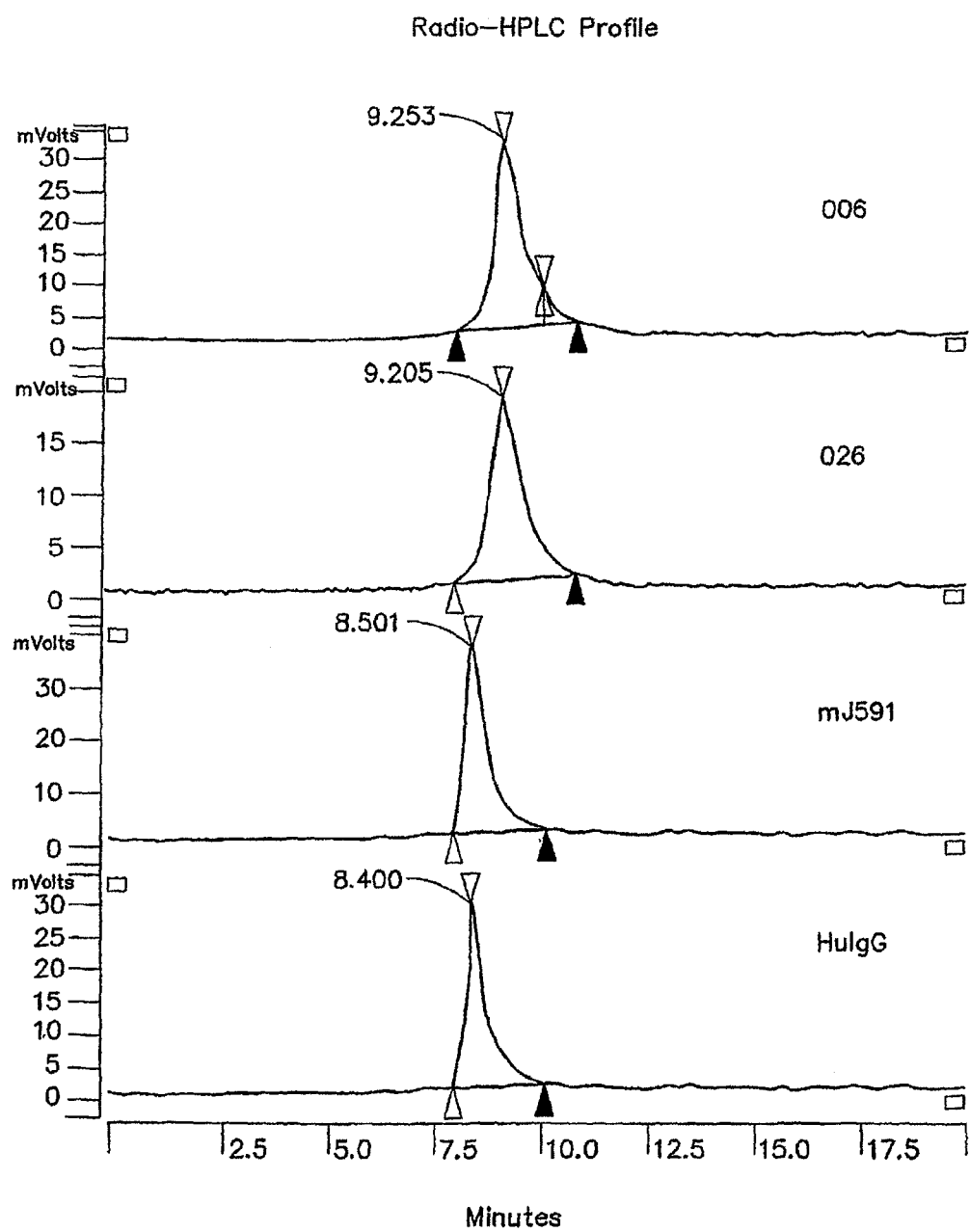
FIG. 42 provides the radio-HPLC profile and cell-based immunoreactivity of $^{177}$Lu labeled antibodies (006, 026, mJ591 and HuIgG (control)).

Athymic nude mice from the National Cancer Institute (male, approximately 6 weeks old) were injected subcutaneously with 4×10$^6$ PSMA-3T3 cells and 2.8×10$^6$ 3T3 cells in 0.2 mL in the right and left flank of each animal, respectively. Anti-PSMA antibodies 006, 026, mJ591 and HuIgG (control) modified with CHX-A"-DTPA were labeled with $^{177}$Lu. FIG. 42 shows the radio-HPLC profile of the radiolabeled antibodies as well as the cell-based immunoreactivity performed as quality control. On day 6 after tumor implantation, $^{177}$Lu labeled antibodies (10 µCi and 1 ng in 0.15 mL) were injected retro-orbitally. The animals were randomized before antibody injection. Mice (30 per antibody, 5 per time point) were sacrificed at different times (days 0.17, 1, 2, 4, 7 and 12). Tumors and individual organs (PSMA+ tumor, PSMA– tumor, blood, liver, kidneys, spleen, lungs, heart, bone, muscle, carcass) were taken and weighed. Activity in each organ along with standards prepared from injection solutions were counted using a multi-channel gamma counter.

Figure 43A:
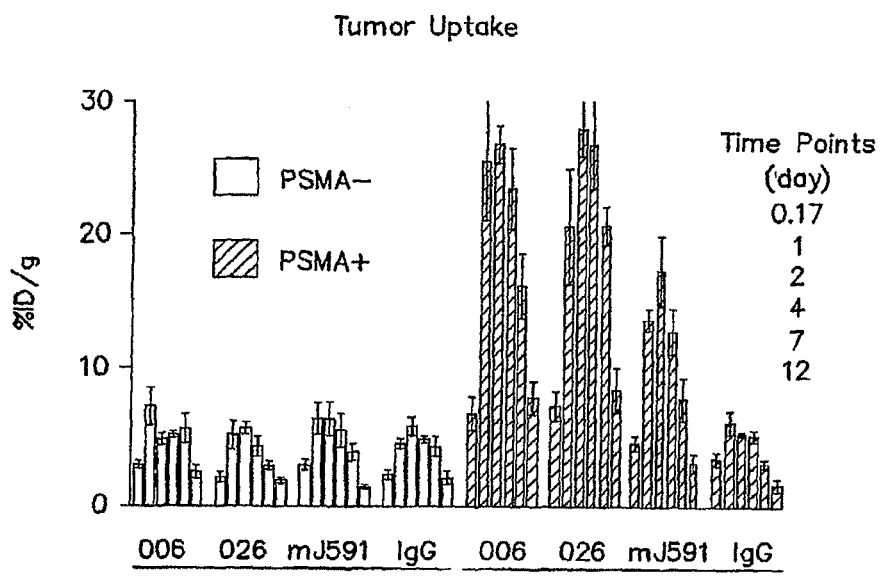
FIG. 43 shows the specific binding of $^{177}$Lu labeled antibodies (006, 026, mJ591 and IgG (control)) to PSMA positive tumors in vivo.
Figure 43B:
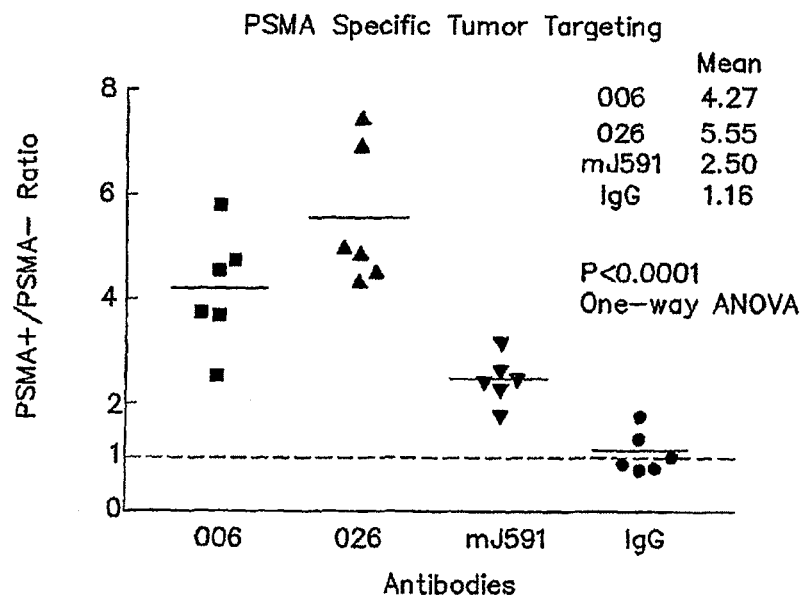

Results of this study show that $^{177}$Lu labeled antibodies specifically bound to tumors expressing PSMA in vivo in the animal model. The percent injected dose per gram of tissue (% ID/g) was calculated and plotted over time for the different antibodies in the PSMA+ and PSMA– tumors (FIG. 43A). PSMA specific tumor targeting (ratio of PSMA+/PSMA– tumor uptake) is provided in FIG. 43B.

Figure 44A:
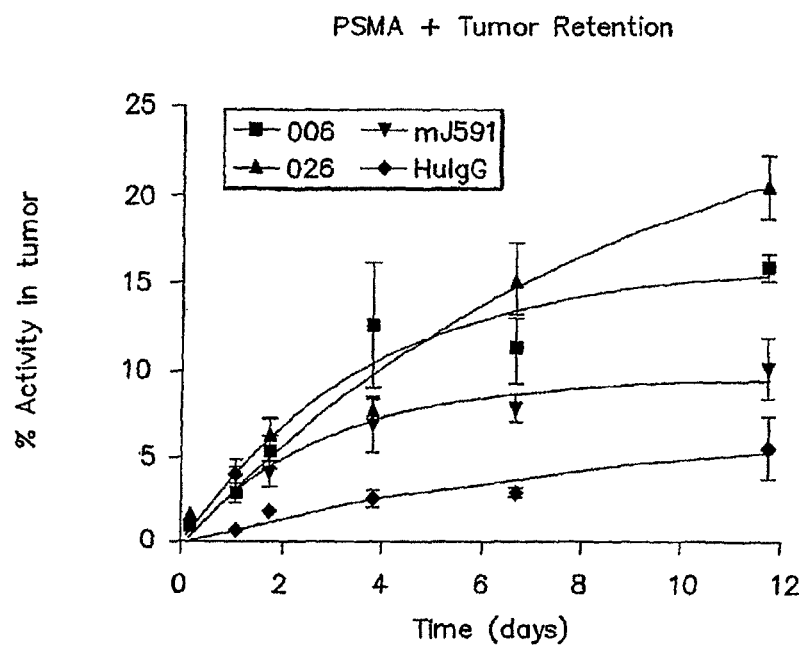
FIG. 44 shows the preferential retention of radiolabeled antibodies (006, 026, mJ591 and HuIgG) in PSMA+ tumors vs. PSMA– tumors as assessed by the percent activity in the tumors.
Figure 44B:
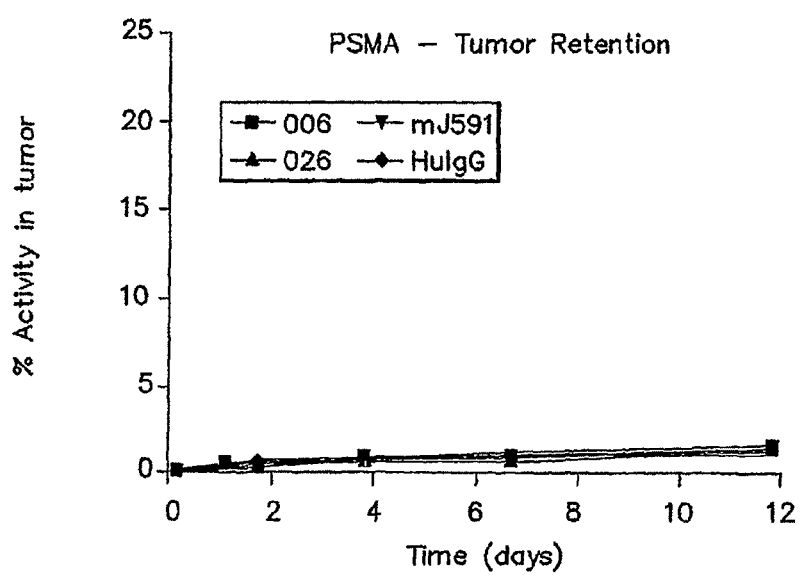
Figures 45A, 45B:
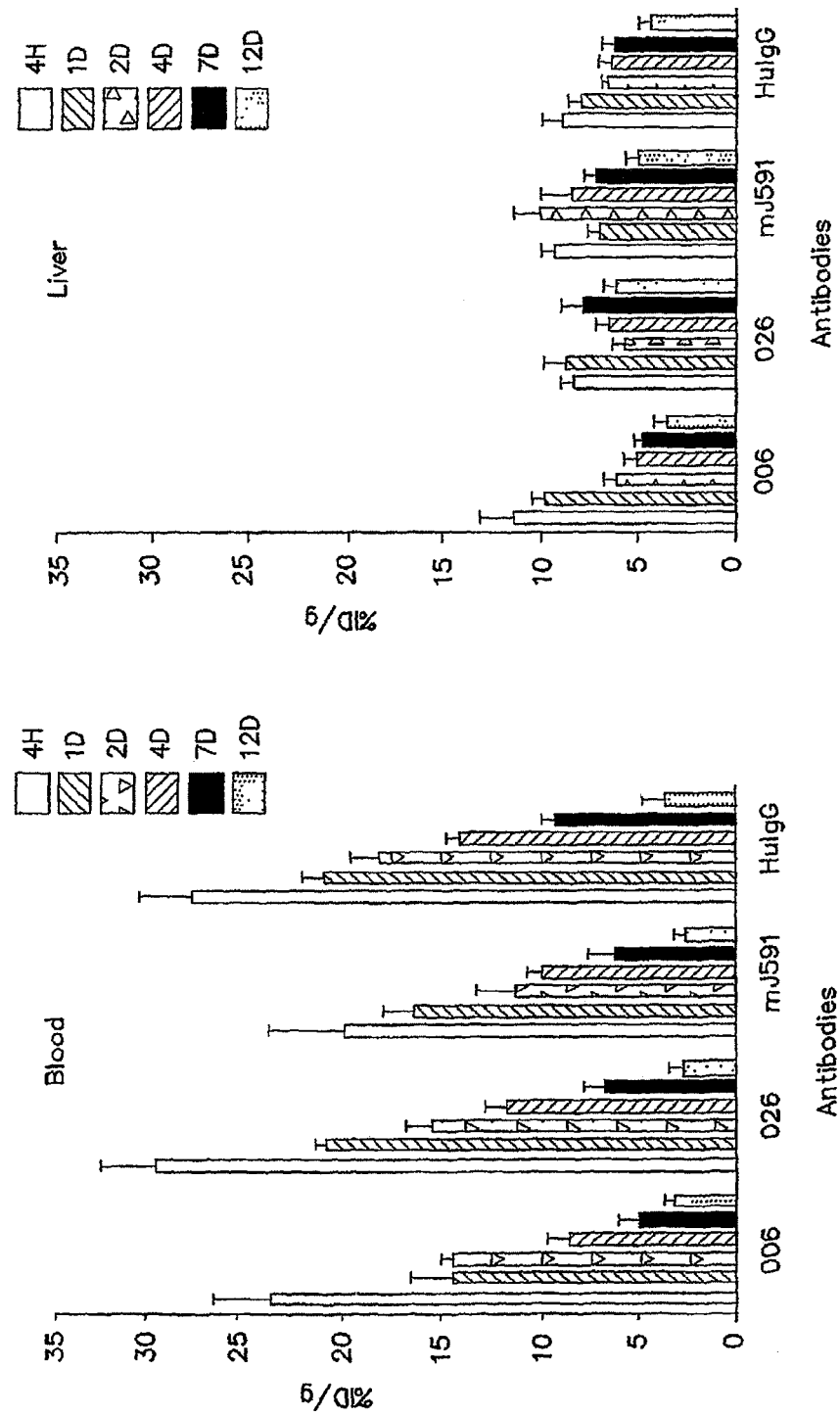
FIG. 45 provides data for normal organ (blood, liver, spleen, lungs, bone, heart and muscle) uptake (injected dose per gram of tissue, % ID/g) for the antibodies (006, 026, mJ591 and HuIgG).
Figures 45C, 45D:
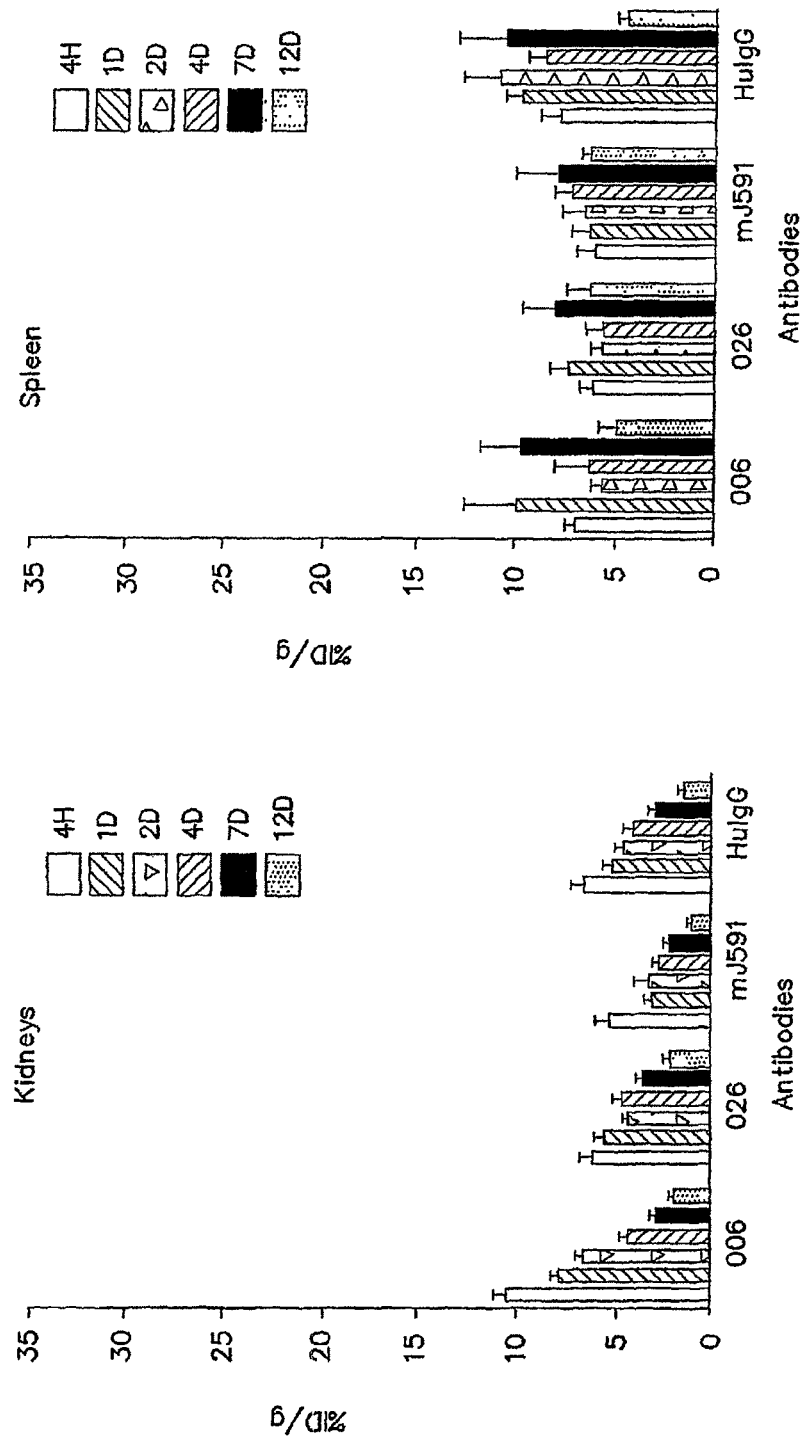
Figures 45E, 45F:
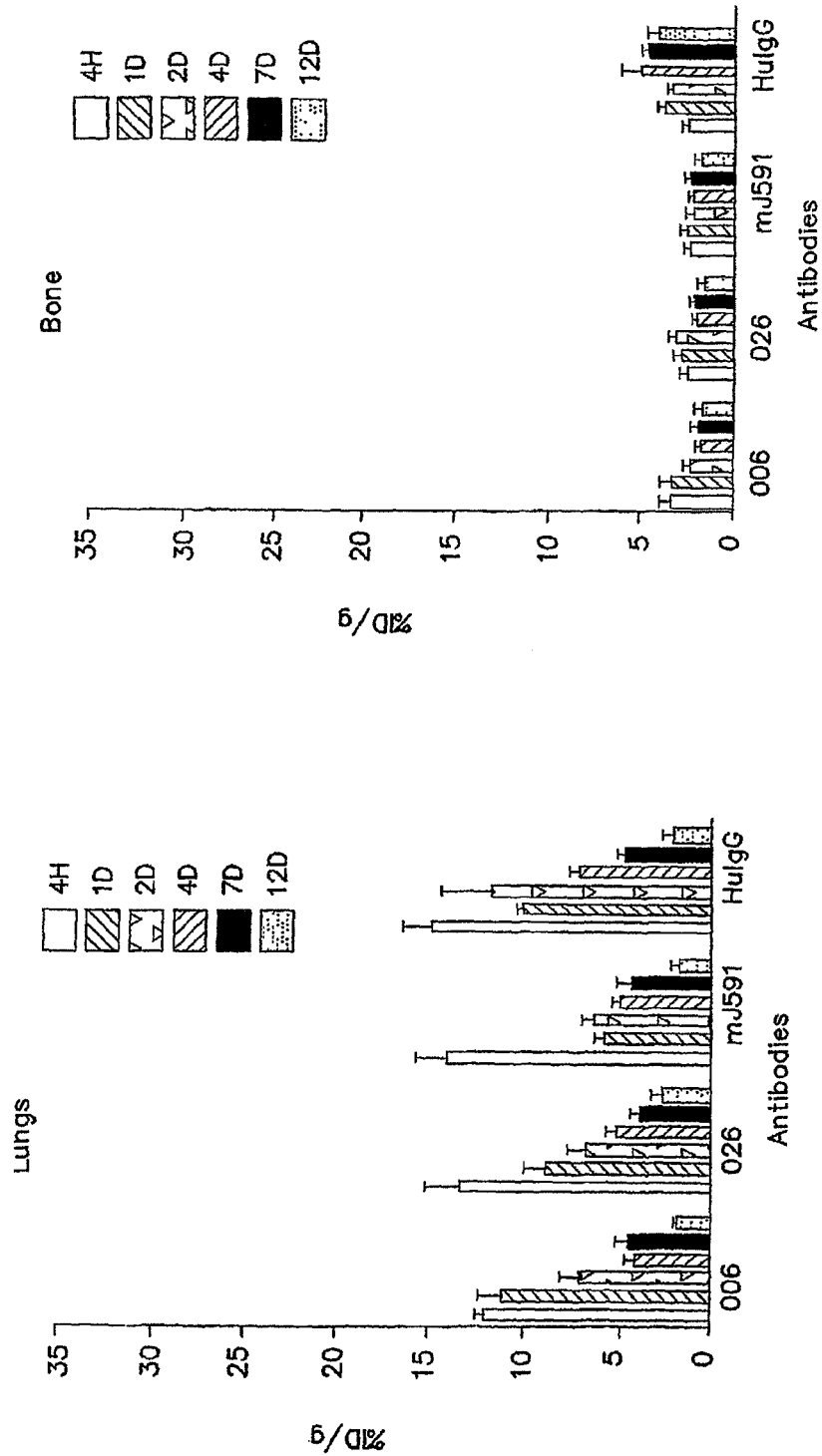
Figures 45G, 45H:
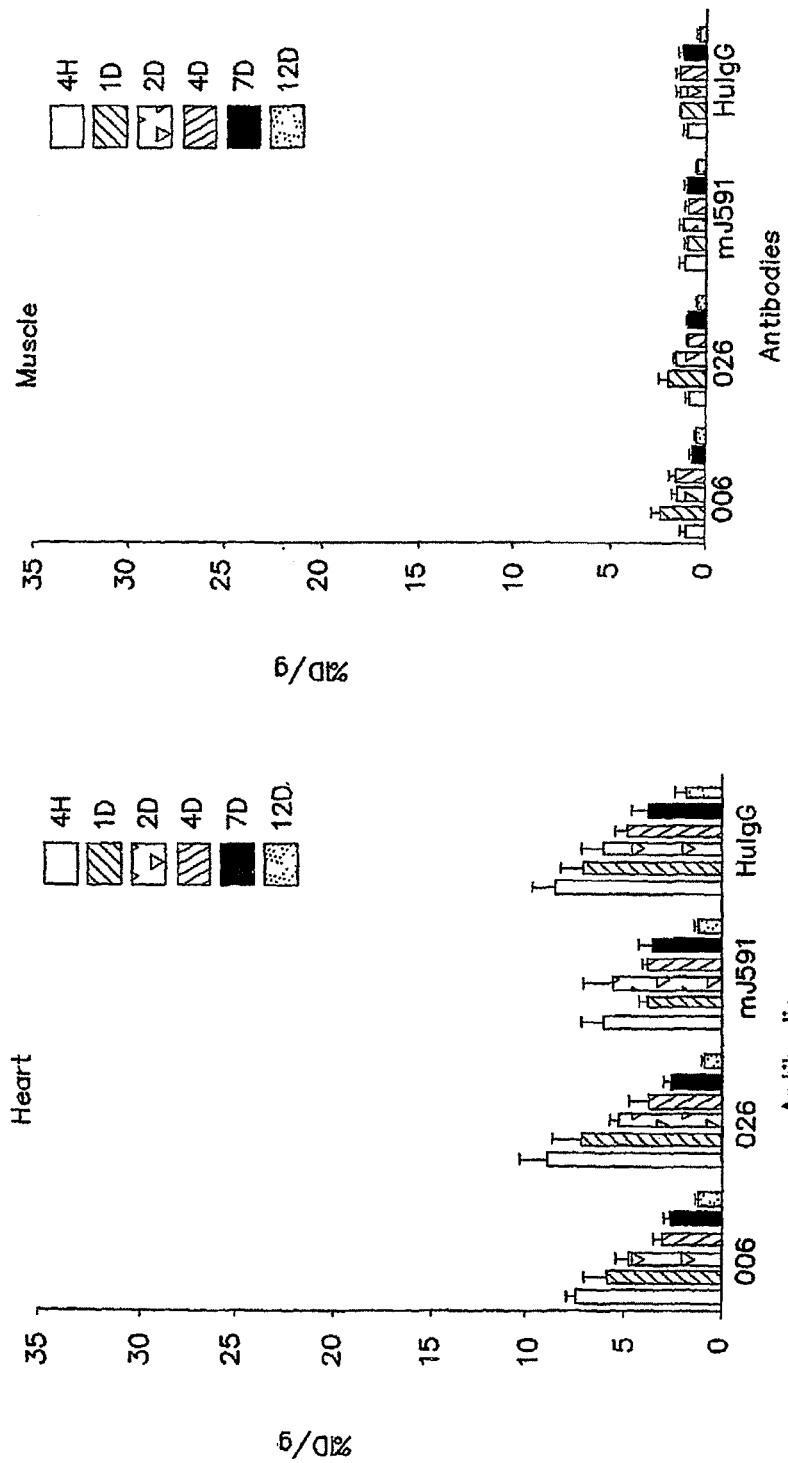

FIG. 44 shows the percent activity in the tumors with the various radiolabeled antibodies (006, 026, mJ591 and HuIgG) over time (% tumor retention vs. total body retention). The data again illustrate the specificity by which the radiolabeled antibodies target the PSMA expressing tumors. FIG. 44A shows the activity over time in the PSMA+ tumors while FIG. 44B shows the percent activity over time in the PSMA– tumors for the different antibodies. FIG. 45 shows the data for normal organ (blood, liver, kidneys, spleen, lungs, bone, heart and muscle) uptake (% ID/g) plotted over time.

Example 29

In Vivo Therapeutic Efficacy of $^{177}$Lu Radiolabeled Antibodies

Athymic nude mice from the National Cancer Institute (male, approximately 6 weeks old) were injected subcutaneously with 4×10$^6$ PSMA-3T3 cells and 2.8×10$^6$ 3T3 cells in 0.2 mL in the right and left flank of each animal, respectively. $^{177}$Lu labeled mAb 026 (0 µCi, n=5; 300 µCi and 10 µg, n=9; and 400 µCi and 13.5 µg, n=5) were injected into the mice on day 6 after tumor implantation. Animals were weighed and tumors were measured over time. Tumor size (mm$^3$) was calculated using the formula: length×(width)$^2$/2. Mice were sacrificed if tumor size reached 1000 mm$^3$ Animal survival was also assessed, and the Kaplan-Meier plot was created.

Figure 46A:
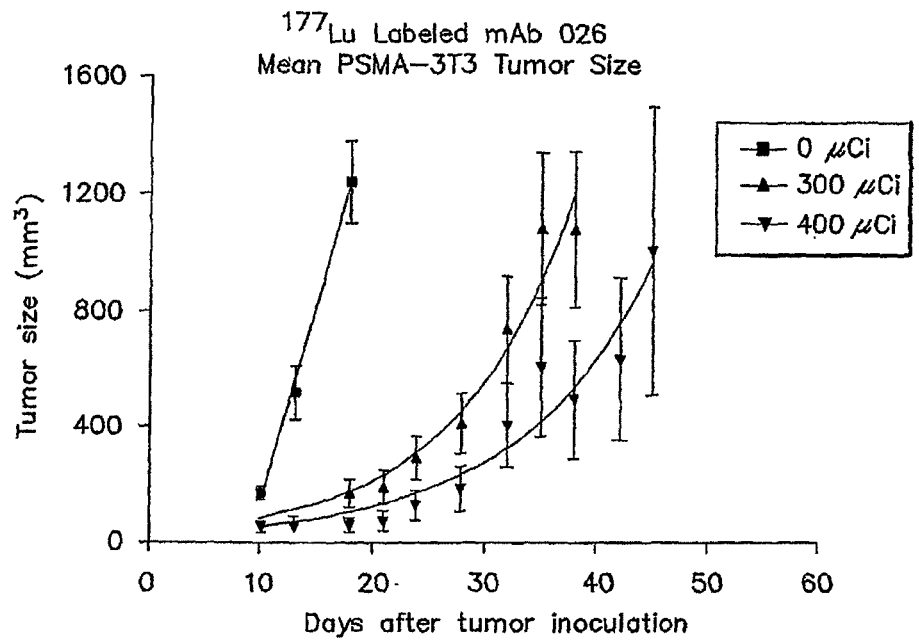
FIG. 46 illustrates the therapeutic efficacy of $^{177}$Lu labeled mAb 026 in PSMA-3T3 and 3T3 tumor-bearing mice.
Figure 46B:
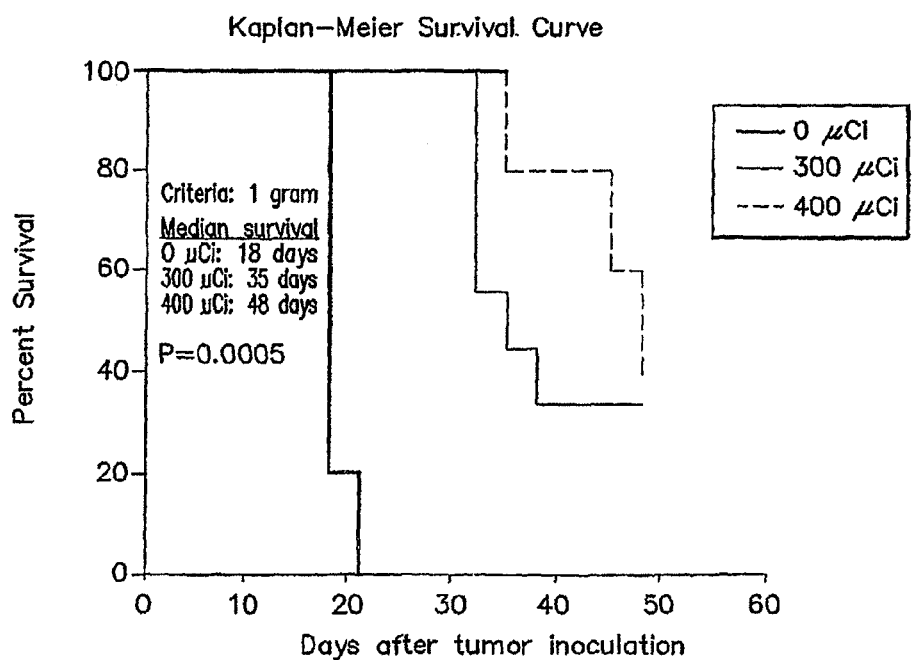

The results of the study show that treatment decreased tumor size and increased survival in the mice. FIG. 46A shows the tumor size in the mice treated with the radiolabeled antibodies ($^{177}$Lu labeled mAb 026) at all three dose levels. The mice treated with 300 µCi and 400 µCi had consistently smaller tumors than the mice in the control group (0 µCi). FIG. 46B shows that the mice treated with 300 µCi and 400 µCi had increased survival relative to the control mice. Median survival was increased by 2.4-fold in mice treated with 300 µCi and 3.5-fold in mice treated with 400 µCi using time after treatment. Treatment with 400 µCi was found to be non-toxic. Additionally, at the end of the experiment (48 days after tumor implantation), one animal from each treated group remained PSMA-3T3 tumor free but had large 3T3 tumors.

Example 30

Binding of Antibodies to rsPSMA Dimer and Monomer

A Biacore 3000 instrument was used to monitor, in real time, binding of rsPSMA dimer and monomer to anti-PSMA mAbs. Antibodies were immobilized at approximately 10,000 resonance units to CM5 sensor chips according to the manufacturer's instructions for amine coupling (Biacore, Inc., Piscataway, N.J.). A reference surface of isotype-matched antibody of irrelevant specificity was used as a background control. Binding experiments were performed at 25° C. in PBS buffer with 0.005% [vol/vol] Surfactant P20. Purified rsPSMA dimer (50 nM) or monomer (100 nM) was passed over control and test flow cells at a flow rate of 5 µL/min. The sensor surface was regenerated with two pulses of 20 nM HCl.

Figure 47:
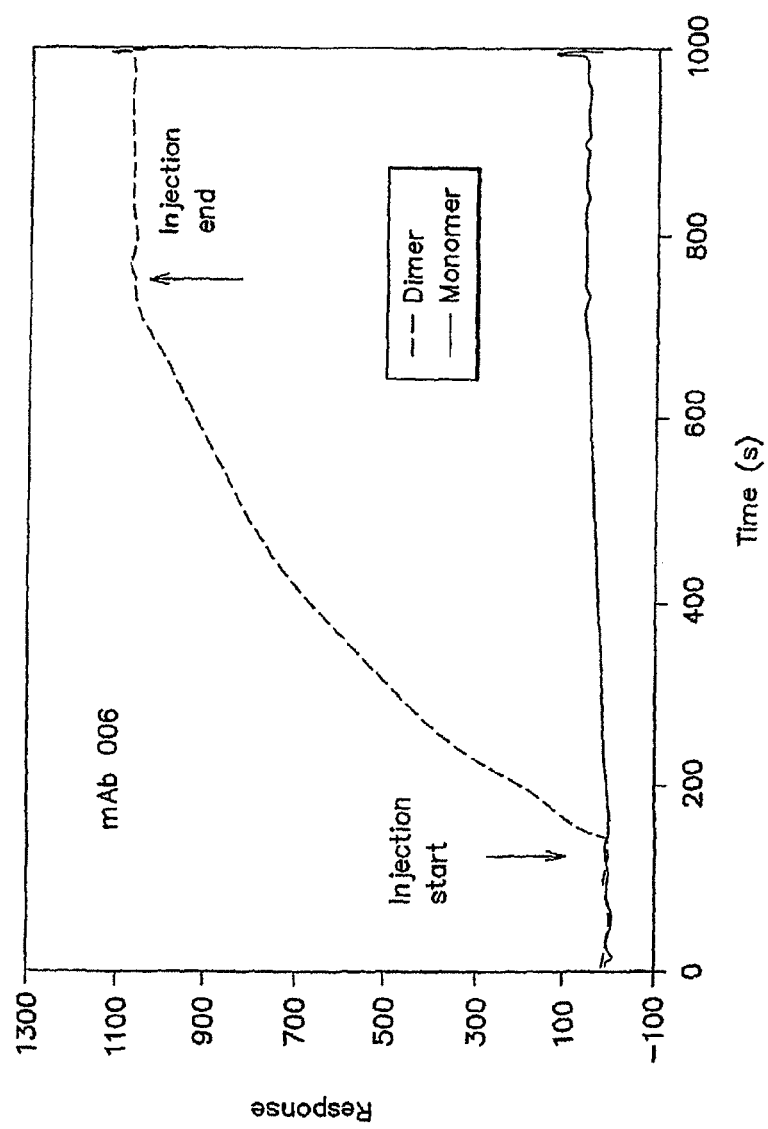
FIG. 47 shows the preferential binding of mAb 006 to rsPSMA dimer.
Figure 48:
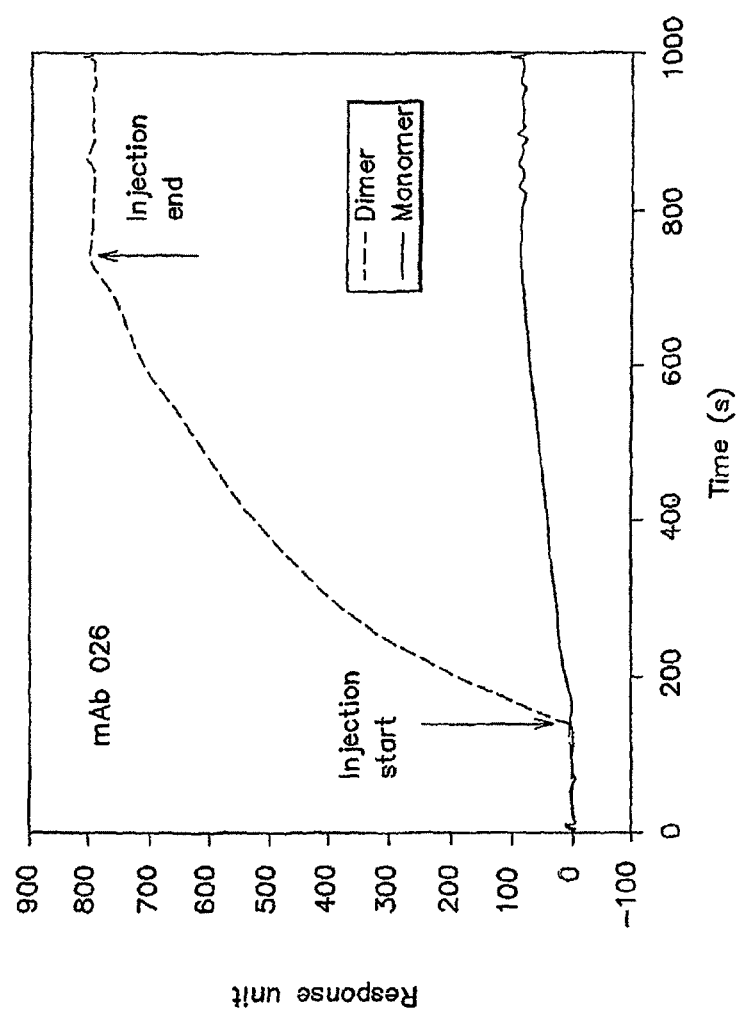
FIG. 48 shows the preferential binding of mAb 026 to rsPSMA dimer.
Figure 49:
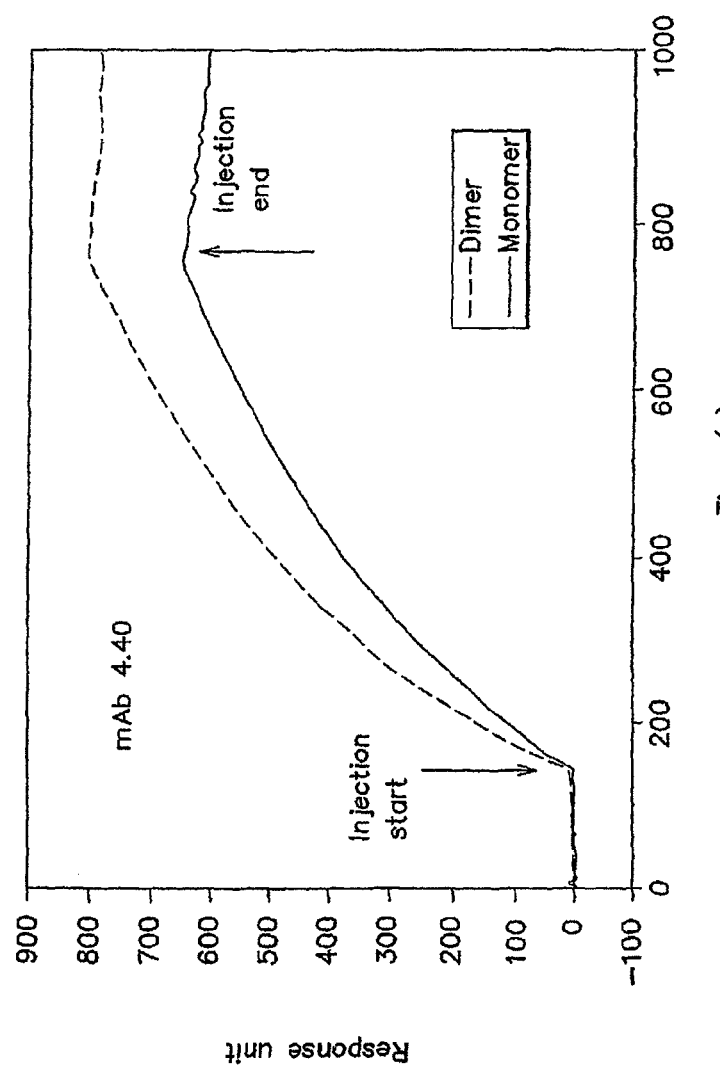
FIG. 49 shows the binding of mAb 4.40 to rsPSMA dimer and monomer.
Figure 50:
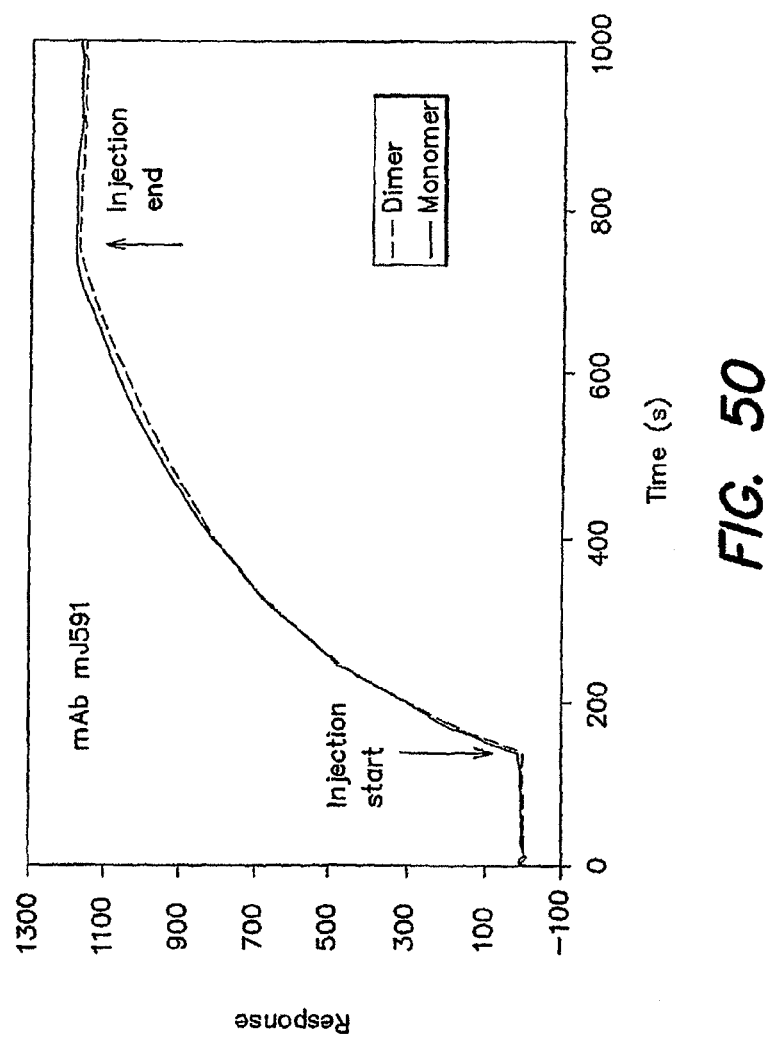
FIG. 50 shows the binding of mAb mJ591 to rsPSMA dimer and monomer.

FIGS. 47 and 48, respectively, show that anti-PSMA mAbs 006 and 026 bind preferentially to the rsPSMA dimer rather than the rsPSMA monomer. Anti-PSMA antibodies 4.40 and mJ591, however, were shown to bind both the rsPSMA dimer and monomer at significant levels (FIGS. 49 and 50, respectively). This study illustrates that anti-PSMA mAbs 006 and 026 are PSMA dimer-specific antibodies and bind dimer-specific epitopes on PSMA. The results also indicate that the native conformation of PSMA is a homodimer, and that the monomer possesses a partially denatured conformation or exposes epitopes located at the dimer surface and/or dimer interface that are not accessible in the dimer.

Example 31

Immunization with rsPSMA Dimer Preparations

Immunization

BALB/c mice were immunized by subcutaneous injection at days 0, 7, 14, and 42 with either 5 µg clinical rsPSMA lot #4019-0001 (75% dimer/25% monomer) or 5 µg rsPSMA batch #TD045-003 run 1/peak 2 (100% monomer) on alum (250 µg per dose, Sigma) or adjuvanted with 50 µg alhydrogel per dose. Serum was drawn 10 days after the fourth immunization and analyzed by enzyme-linked immunoassay (EIA) and flow cytometry.

EIA rsPSMA lot #4019-0001 or rsPSMA batch #TD045-003 run 1/peak 2 was passively adsorbed to 96-well microtiter plates. Remaining binding sites on the plate were blocked with a PBS/Casein/Tween 20 buffer. Serially diluted mouse serum or controls were added and bound antibody was detected using a goat anti-mouse IgG antibody conjugated to alkaline phosphatase. The EIA was developed with the substrate pNPP which produces a color change that is directly proportional to the amount of anti-PSMA antibody bound. Absorbance was read at 405 nm with a correction of 620 nm Antibody titer was defined as the highest dilution of mouse serum yielding a blank corrected absorbance of 0.1. Immune mouse serum with a known anti-PSMA titer or normal mouse serum with no anti-PSMA reactivity was used as controls.

Flow Cytometry Analysis

PSMA-3T3 cells were incubated with 200 µL of immune serum at a dilution of 1/50 in PBS with 0.1% sodium azide on ice for 30 minutes Immune mouse serum with known anti-PSMA titer or normal mouse serum with no anti-PSMA reactivity was used as controls. The cells were washed twice with PBS with 0.1% sodium azide and incubated for 30 minutes on ice with FITC-conjugated goat anti-mouse IgG. Cells were washed once, resuspended in PBS with 0.1% sodium azide and subjected to flow cytometric analysis on FACScaliber (Becton Dickinson).

Results

5/5 mice immunized with rsPSMA lot #4019-0001 showed an anti-PSMA antibody response by EIA. Antibody titer was similar for assay plates coated with rsPSMA lot #4019-0001 (75% dimer/25% monomer) and assay plates coated with rsPSMA batch #TD045-003 run 1/peak 2 (100% monomer). Median response for the group was 1/6400.

4/5 mice immunized with rsPSMA batch #TD045-003 run 1/peak 2 showed an anti-PSMA antibody response by EIA. One mouse was negative. Antibody titer was similar for assay plates coated with rsPSMA lot #4019-0001 (75% dimer/25% monomer) and assay plates coated with rsPSMA batch #TD045-003 run 1/peak 2 (100% monomer). Median response for the group was 1/6400.

The results of the EIA analysis are provided in Table 7.

Figure 51:
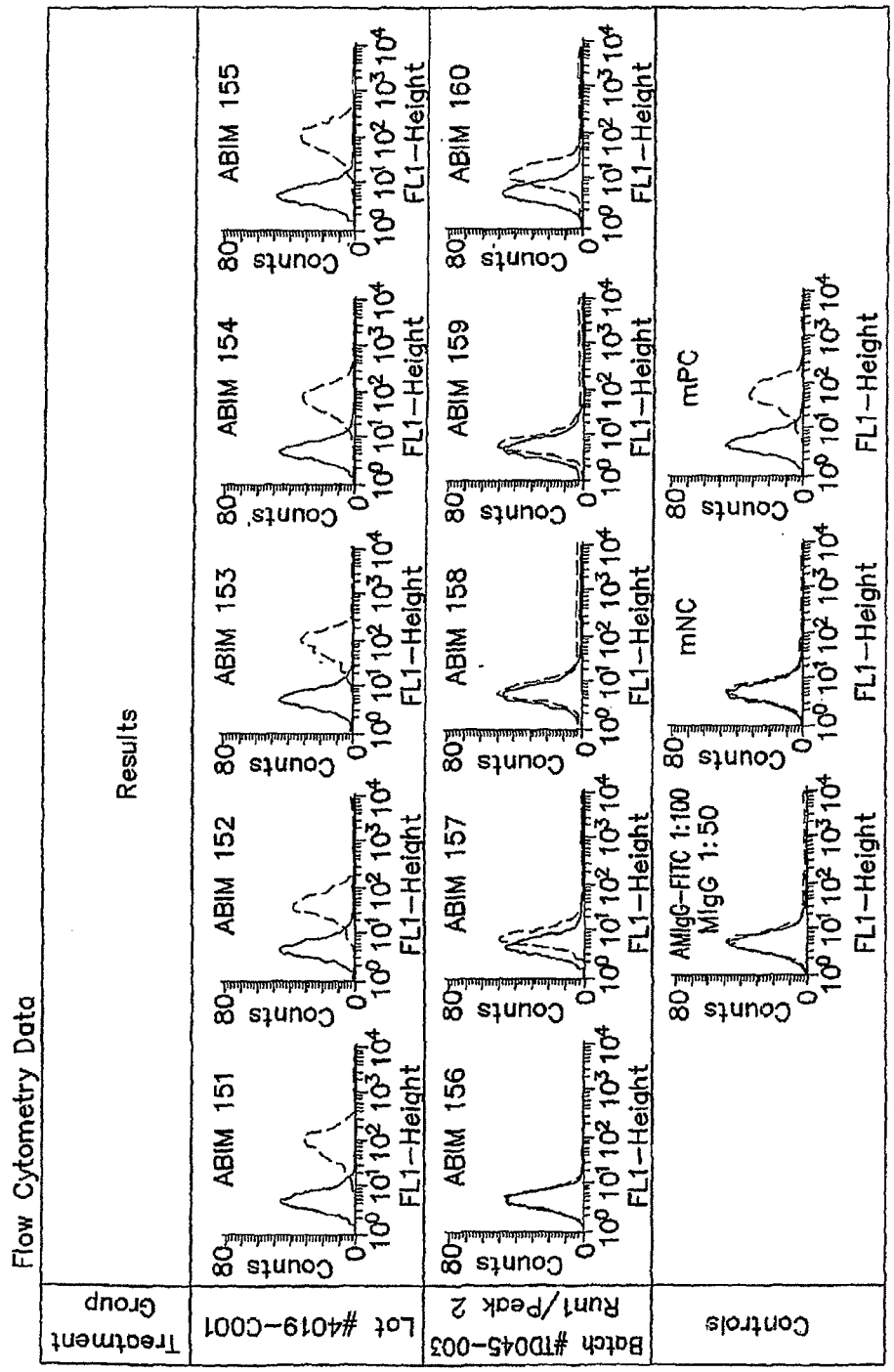
FIG. 51 is a series of graphs that show flow cytometry data for the binding of anti-PSMA antisera to PSMA-3T3 cells. Antisera from mice immunized with a rsPSMA dimer preparation (ABIM151, ABIM152, ABIM153, ABIM154 and ABIM155) exhibited strong binding to PSMA-expressing cells. Antisera from mice immunized with a rsPSMA monomer preparation (ABIM156, ABIM157, ABIM158, ABIM159 and ABIM160) exhibited little or no binding to PSMA-expressing cells.

The results of the flow cytometry analysis are provided in FIG. 51.

TABLE 7

Specificity of the Anti-PSMA Antibody Response in Mice Vaccinated 4 Times with rsPSMA 5 µg/dose and 50 µg/dose Alhydrogel

| Mouse ID # | Immunogen | EIA Titer vs. Lot 4019-C001 | EIA Titer vs. Batch TD045-003 run1/peak 2 | Median RFI vs. PSMA-3T3 cells |
|---|---|---|---|---|
| ABIM151 | 4019-C001 Dimer | 1/3200 | 1/3200 | 84 |

TABLE 7-continued

Specificity of the Anti-PSMA Antibody Response in Mice Vaccinated
4 Times with rsPSMA 5 μg/dose and 50 μg/dose Alhydrogel

| Mouse ID # | Immunogen | EIA Titer vs. Lot 4019-C001 | EIA Titer vs. Batch TD045-003 run1/peak 2 | Median RFI vs. PSMA-3T3 cells |
|---|---|---|---|---|
| ABIM152 | 4019-C001 Dimer | 1/3200 | 1/3200 | 41 |
| ABIM153 | 4019-C001 Dimer | 1/25600 | 1/25600 | 76 |
| ABIM154 | 4019-C001 Dimer | 1/12800 | 1/12800 | 63 |
| ABIM155 | 4019-C001 Dimer | 1/6400 | 1/6400 | 74 |
| ABIM156 | Monomer | 1/1600 | 1/1600 | 5 |
| ABIM157 | Monomer | 1/6400 | 1/12800 | 8 |
| ABIM158 | Monomer | 0 | 0 | 6 |
| ABIM159 | Monomer | 1/6400 | 1/6400 | 6 |
| ABIM160 | Monomer | 1/6400 | 1/6400 | 12 |

When tested by ELISA, sera from both monomer and dimer immunized animals showed similar levels of anti-PSMA antibodies, indicating that each protein was immunogenic when formulated on alum. For dimer immunized animals, the median endpoint titers were 1/6,400 (range 1/3,200 to 1/12,800) regardless of whether rsPSMA monomer or dimer was used as the coating antigen. Similarly, monomer-immunized animals had median endpoint titers of 1/6,400 in both assay formats, although the range varied depending on whether the monomer (range <1/400 to 1/12,800) or dimer (range <1/400 to 1/6,400) was used for coating.

However, a difference between sera was observed with cell-based flow cytometry (FIG. 51). Anti-PSMA antibody in the serum of mice immunized with a dimer preparation of rsPSMA (lot #4019-0001) showed strong binding to PSMA-3T3 cells. Anti-PSMA antibody in the serum of mice immunized with a 100% monomer preparation of rsPSMA (batch #TD045-003 run 1/peak 2) showed no binding to PSMA-3T3 cells.

Each dimer immunized animal elicited high-titered antibodies to PSMA-3T3 cells (median mean fluorescence intensity (MFI)=74, range 41-84), but such antibodies were very weak to absent in monomer-immunized animals (median MFI=6, range 5-12). The level of binding observed for monomer immunized animals was comparable to that for naïve animals. Similar background levels of binding to parental 3T3 cells were observed for all sera (median MFI=6 in all cases).

An identical pattern of reactivity was observed with human prostate cancer cell lines. Consistent, high-level reactivity with PSMA-expressing C4-2 cells was observed for sera from dimer immunized animals (median MFI=28.0, range 23.1-28.8) but not monomer immunized (median MFI=12.8, range 11.2-14.5) or control animals (median MFI=12.3, range 8.6-16.0). Background levels of binding to PSMA-negative PC-3 cells were observed for all sera (median MFI=7 in all cases).

Thus, while it is possible to elicit the production of antibodies that recognize native PSMA using monomeric forms of the PSMA protein or fragments thereof, these results speak to the relative efficiency of eliciting an immune response to native PSMA using dimeric forms of PSMA protein. Additionally, flow cytometry but not ELISA was able to reveal the differences in the humoral immune responses elicited by monomeric and dimeric forms of PSMA. The inability of the ELISA to uncover such differences suggests that rsPSMA adopts a partially denatured conformation upon adsorption to plastic.

Figure 52:
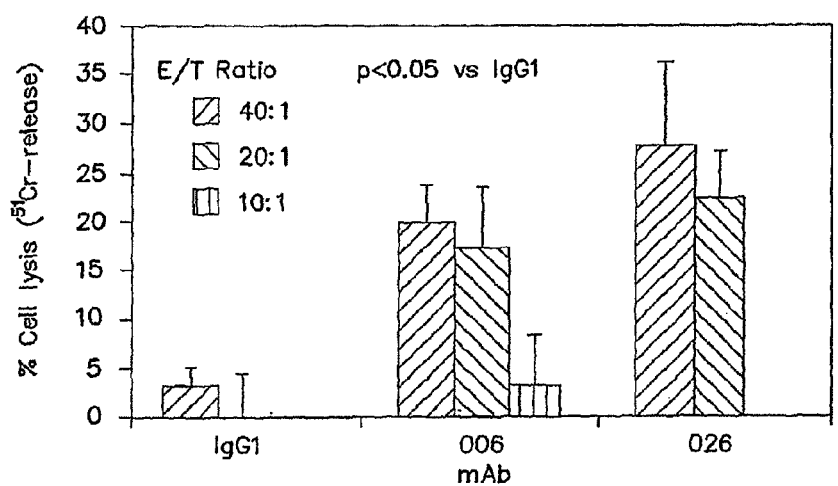
FIG. 52 provides the results showing antibody dependent cell-mediated cytotoxicity (ADCC) of human prostate cancer cells mediated by mAbs 006 and 026.

Example 32 mAbs 006 and 026 Mediate Efficient ADCC of Human Prostate Cancer Cells $^{51}$Cr labeled C4-2 cells ($1 \times 10^4$/well, target cells) were incubated in triplicates with 10 μg/mL mAb at 4° C. for 1 hour. Fresh human PBMCs (effector cells) were added to washed target cells at effector to target (E/T) ratios of 40:1, 20:1, and 10:1 and incubated at 37° C. overnight. $^{51}$Cr in harvested supernatants was measured using a γ-scintillation counter and % cell lysis was calculated. mAbs 006 and 026 demonstrated statistically significant antibody dependent cell-mediated cytotoxicity (ADCC) of C4-2 cells compared to isotype matched human IgG1 mAb control (FIG. 52). No effect was observed when PSMA-negative human prostate tumor cells (PC-3) were used.

Example 33

Monomer-Dimer Equilibrium

Figure 53A:
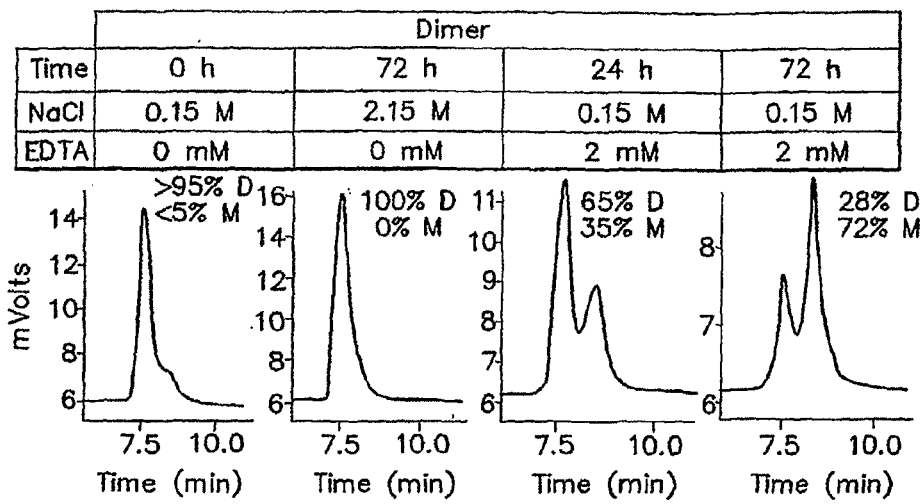
FIG. 53 shows the results of PSMA monomer-dimer equilibrium analysis. Purified dimeric (FIG. 53A) and monomeric (FIG. 53B) rsPSMA were subjected to various buffer conditions and analyzed for size by analytical size exclusion chromatography (SEC). The percentages of monomer (M) and dimer (D) are indicated. The monomer and dimer were initially contained in PBS+ buffer at a concentration of 0.2 mg/ml. The buffer conditions were adjusted as indicated, and the proteins were incubated at ambient temperature for the indicated time periods before SEC analysis.

Purified dimeric and monomeric forms of rsPSMA were resolved by preparative size exclusion chromatography (SEC) in PBS+ buffer and collected in separate fractions. To assess whether dimer and monomer exist in a reversible equilibrium, the buffer conditions were perturbed, and the monomer-dimer ratio was analyzed by SEC. As indicated in FIG. 53A, a dimer preparation that contained approximately 5% monomer initially was converted to 100% dimer upon incubation for 72 h at ambient temperature in PBS+supplemented with 2M sodium chloride (FIG. 53A). Conversely, the addition of 2 mM of the metal-chelating agent EDTA converted the dimer into monomer with a half-life of approximately 2 days (FIG. 53A), indicating that dimer stability is dependent upon the presence of metal ions, such as $Zn^{2+}$ in the active site of PSMA.

Figure 53B:
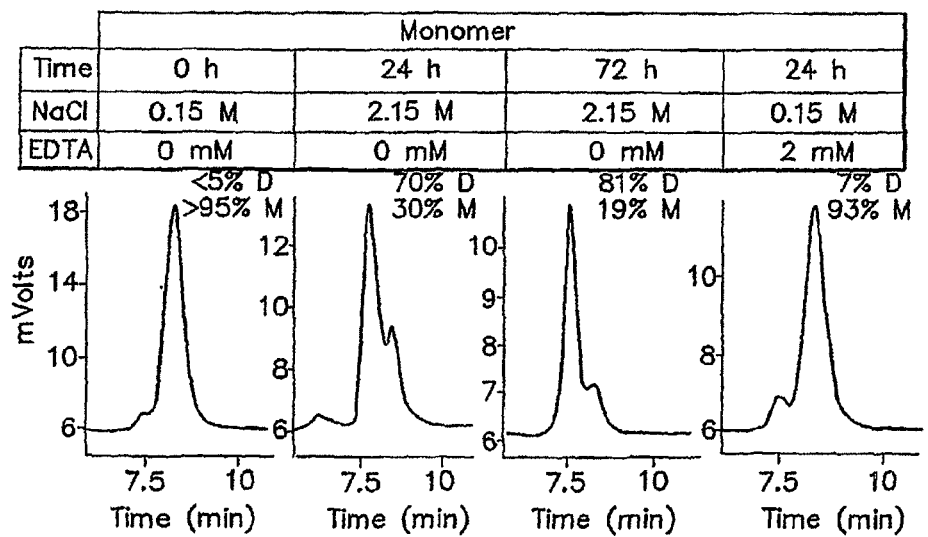

For a preparation that initially comprised >95% monomer, high salt similarly drove the equilibrium to mostly (81%) dimer within 72 h (FIG. 53B). EDTA had little influence on the oligomeric state of the monomer. Thus, regardless of the initial oligomeric state of the protein, high salt concentrations promoted dimerization, whereas metal-chelating agents dissociated dimers into monomers.

PSMA shares modest sequence and structural homology with human transferrin receptor (TfR), which contains a vestigial catalytic domain but lacks enzymatic activity. TfR is expressed as a type II membrane protein that forms a disulfide-linked homodimer, but the intermolecular disulfides are not required for dimerization (Alvarez, E., et al. (1989) EMBO J. 8, 2231-2240.0). The high-resolution crystal structure of the TfR ectodomain reveals that the protein is organized into three distinct domains known as the protease-like, apical, and helical domains, with the last domain being principally responsible for dimerization (Lawrence, C. M., et al. (1999) Science 286, 779-782). PSMA and TfR share 30%, 30%, and 24% sequence identity within these domains, respectively. The helical dimerization domain of PSMA are amino acids 601-750 of SEQ ID NO: 1.

Example 34 rsPSMA Formulation Studies pH Stability of rsPSMA

Dimeric rsPSMA (2 mg/ml in PBS+) was diluted 10-fold into a broad-range base buffer solution (2 mM glycine, 2 mM citric acid, 2 mM Hepes, 2 mM MES, 2 mM Tris Base) that was adjusted to cover pH 4 to pH 8.5 in steps of 0.5 pH units. Following incubation for 4 days at 45° C., the individual samples were subjected to analytical TSK gel filtration chromatography (run at pH 7.5) and analyzed for protein recovery and the preservation of the dimeric structure of rsPSMA. The findings are summarized in Table 8.

TABLE 8

Recovery and Structure of rsPSMA at Various pHs

| pH | Dimer Content[1] | Monomer Content[1] | Aggregate Content[1] | Recovery from column[2] |
|---|---|---|---|---|
| 4.0 | +++++ | – | – | + |
| 4.5 | – | – | – | – |
| 5.0 | ++ | – | +++ | ++ |
| 5.5 | ++++ | + | – | +++ |
| 6.0 | +++++ | – | – | +++++ |
| 6.5 | ++++ | + | – | ++++ |
| 7.0 | ++++ | + | – | ++++ |
| 7.5 | ++++ | + | – | + |
| 8.0 | +++ | + | + | + |
| 8.5 | – | – | – | – |

[1] of recovered protein
[2] of total protein at t = 0
– <5%
+ 5%-25%
++ 25-50%
+++ 50-75%
++++ 75-95%
+++++ >95%

Base Buffer Evaluation

Dimeric rsPSMA (2 mg/ml in PBS+) was diluted 10-fold into the following buffer solutions:
- PBS+
- 20 mM Hepes, pH 7.0
- 20 mM sodium phosphate +150 mM NaCl, pH 6.5
- 20 mM histidine +150 mM NaCl, pH 6.0
- 20 mM sodium phosphate +150 mM NaCl, pH 6.0
- 20 mM sodium acetate+150 mM NaCl, pH 6.0
- 20 mM sodium citrate+150 mM NaCl, pH 6.0

Each sample was incubated for 3 or 4 days at 45° C. and subsequently analyzed by analytical TSK gel filtration chromatography for protein recovery and the preservation of the dimeric structure of rsPSMA. The findings are summarized in Table 9.

TABLE 9

Recovery and Structure of rsPSMA with Various Buffers

| Base Buffer | Dimer Content[1] | Monomer Content[1] | Aggregate Content[1] | Recovery from column[2] |
|---|---|---|---|---|
| PBS+ | +++ | – | + | ++ |
| Phosphate | +++++ | – | – | +++++ |
| Acetate | +++++ | – | – | +++++ |
| Citrate | N/A | N/A | N/A | – |
| Histidine | +++ | + | ++ | + |

[1] of recovered protein
[2] of total protein at t = 0

TABLE 9-continued

Recovery and Structure of rsPSMA with Various Buffers

| Base Buffer | Dimer Content[1] | Monomer Content[1] | Aggregate Content[1] | Recovery from column[2] |
|---|---|---|---|---|

– <5%
+ 5%-25%
++ 25-50%
+++ 50-75%
++++ 75-95%
+++++ >95%

Excipients

Dimeric rsPSMA (2 mg/ml in PBS+) was dialyzed over night into 20 mM sodium acetate, pH 6.0 and 150 mM NaCl. To evaluate the effect of the individual amino acids, the protein was diluted 8-fold into 20 mM sodium acetate, pH 6.0 and 150 mM NaCl containing 50 mM of either glycine, histidine, proline, isoleucine, leucine, alanine, lysine, arginine, threonine, glutamic acid, or aspartic acid as excipients. Following incubation for 5 days at 45° C., each sample was analyzed by analytical TSK gel filtration chromatography for protein recovery and the preservation of the dimeric structure of the protein. The findings are summarized in Table 10.

TABLE 10

Recovery and Structure of rsPSMA with Various Amino Acids

| Amino Acid | Dimer Content[1] | Monomer Content[1] | Aggregate Content[1] | Recovery from column[2] |
|---|---|---|---|---|
| Glycine | ++++ | + | – | ++++ |
| Histidine | N/A | N/A | N/A | + |
| Proline | ++++ | + | – | ++++ |
| Isoleucine | ++++ | + | – | ++++ |
| Leucine | ++++ | + | – | ++++ |
| Alanine | ++++ | + | – | ++++ |
| Arginine | ++++ | + | – | ++++ |
| Threonine | ++ | N/A | +++ | ++++ |
| Glutamic Acid | – | – | +++++ | ++++ |
| Aspartic Acid | – | – | +++++ | +++ |

[1] of recovered protein
[2] of total protein at t = 0
– <5%
+ 5%-25%
++ 25-50%
+++ 50-75%
++++ 75-95%
+++++ >95%

Surfactants

Dimeric rsPSMA (2 mg/ml in PBS+) was diluted 10-fold into PBS+containing 0.5% (w/v) of either Triton X-100, dodecylmaltoside, cholic acid, or CHAPS and incubated for 4 days at 4° C. Each sample was subsequently analyzed by analytical TSK gel filtration chromatography for protein recovery and the preservation of the dimeric structure of the protein. The findings are summarized in Table 11.

TABLE 11

Recovery and Structure of rsPSMA with Various Surfactants

| Surfactant | Dimer Content[1] | Monomer Content[1] | Aggregate Content[1] | Recovery from column[2] |
|---|---|---|---|---|
| Triton X-100 | ++++ | + | + | ++++ |
| Dodecylmaltoside | ++++ | – | + | +++++ |

TABLE 11-continued

Recovery and Structure of rsPSMA with Various Surfactants

| Surfactant | Dimer Content[1] | Monomer Content[1] | Aggregate Content[1] | Recovery from column[2] |
|---|---|---|---|---|
| Cholic Acid | ++++ | − | + | +++++ |
| CHAPS | ++++ | + | − | +++++ |

[1] of recovered protein
[2] of total protein at t = 0
− <5%
+ 5%-25%
++ 25-50%
+++ 50-75%
++++ 75-95%
+++++ >95%

Other Excipients

Dimeric rsPSMA (2 mg/ml in PBS+) was diluted 10-fold into PBS+containing either 1.4 M (35% saturation) ammonium sulfate, 5 mM EDTA, 1 mM DTT, or 10% glycerol and incubated for 4 days at 4° C. Each sample was subsequently analyzed by analytical TSK gel filtration chromatography for protein recovery and the preservation of the dimeric structure of the protein. The findings are summarized in Table 12.

TABLE 12

Recovery and Structure of rsPSMA with Various Excipients

| Excipient | Dimer Content[1] | Monomer Content[1] | Aggregate Content[1] | Recovery from column[2] |
|---|---|---|---|---|
| Ammonium Sulfate | ++++ | − | + | +++++ |
| EDTA | ++ | ++++ | − | +++++ |
| DTT | ++++ | + | − | +++++ |
| Glycerol | ++++ | + | − | +++++ |

[1] of recovered protein
[2] of total protein at t = 0
− <5%
+ 5%-25%
++ 25-50%
+++ 50-75%
++++ 75-95%
+++++ >95%

Conversion of Monomers into Dimers

To evaluate the potential of reversing monomeric rsPSMA into dimers, monomeric rsPSMA (2 mg/ml in PBS+) was diluted 10-fold into PBS+ containing either 1.4 M (35% saturation) ammonium sulfate, 2 M NaCl, 1 mM DTT, 5 mM EDTA, or 10% glycerol and incubated for up to 4 days at 4° C. Each sample was subsequently analyzed by analytical TSK gel filtration chromatography for protein recovery and the formation of the dimeric structure of the protein. The findings are summarized in Table 13.

TABLE 13

Conversion of rsPSMA Monomers

| Excipient | Dimer Content[1] | Monomer Content[1] | Aggregate Content[1] | Recovery from column[2] |
|---|---|---|---|---|
| Ammonium Sulfate | ++ | +++ | + | +++++ |
| NaCl | +++ | ++ | + | +++++ |
| DTT | + | ++++ | − | +++++ |
| EDTA | − | +++++ | − | +++++ |
| Glycerol | + | ++++ | − | +++++ |

[1] of recovered protein
[2] of total protein at t = 0
− <5%
+ 5%-25%
++ 25-50%
+++ 50-75%
++++ 75-95%
+++++ >95%

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference.

The invention claimed is:

1. A method for inhibiting the growth of cells expressing prostate specific membrane antigen (PSMA) protein dimer, comprising:
    contacting the cells with a composition comprising a monoclonal antibody that binds PSMA protein dimer, PSMA protein dimer being a homodimer of PSMA protein monomer having the sequence of SEQ ID NO: 1, or an antigen-binding fragment thereof, in an amount effective to inhibit the growth of the cells expressing PSMA protein dimer,
    wherein the antibody, or the antigen-binding fragment, i) binds live cells, ii) binds with at least a two-fold greater affinity to PSMA protein dimer than to PSMA protein monomer, and iii) is conjugated to a cytotoxic agent.

2. A method for treating a PSMA-expressing cancer in a subject, comprising:
    administering to the subject having the PSMA-expressing cancer a composition comprising a monoclonal antibody that binds PSMA protein dimer, PSMA protein dimer being a homodimer of PSMA protein monomer having the sequence of SEQ ID NO: 1, or an antigen-binding fragment thereof, in an amount effective to treat the PSMA-expressing cancer,
    wherein the antibody, or the antigen-binding fragment, i) binds live cells, ii) binds with at least a two-fold greater affinity to PSMA protein dimer than to PSMA protein monomer, and iii) is conjugated to a cytotoxic agent.

3. A method of specific delivery of at least one therapeutic agent to cells expressing PSMA protein dimer, comprising:
    administering to a subject having cells expressing PSMA protein dimer a composition comprising a monoclonal antibody that binds PSMA protein dimer, PSMA protein dimer being a homodimer of PSMA protein monomer having the sequence of SEQ ID NO: 1, or an antigen-binding fragment thereof, in an amount effective to deliver the at least one therapeutic agent to the cells,
    wherein the antibody, or the antigen-binding fragment, i) binds live cells, ii) binds with at least a two-fold greater affinity to PSMA protein dimer than to PSMA protein monomer, and iii) is conjugated to the at least one therapeutic agent.

4. The method of any of claims 1-3, wherein the antibody or antigen-binding fragment binds with at least a four-fold greater affinity.

5. The method of claim 4, wherein the antibody or antigen-binding fragment binds with at least a five-fold greater affinity.

6. The method of claim 5, wherein the antibody or antigen-binding fragment binds with at least a ten-fold greater affinity.

7. The method of claim 6, wherein the antibody or antigen-binding fragment binds with at least a twenty-fold greater affinity.

8. The method of any of claims 1-3, wherein the antibody or antigen-binding fragment specifically binds PSMA protein dimer without substantial binding to PSMA protein monomer.

9. The method of any of claims 1-3, wherein the antibody or antigen-binding fragment inhibits an enzymatic activity of PSMA protein dimer.

10. The method of any of claims 1-3, wherein the antibody is a humanized antibody.

11. The method of any of claims 1-3, wherein the antibody is a human antibody.

12. The method of any of claims 1-3, wherein the antibody is a chimeric antibody.

13. The method of any of claims 1-3, wherein the antigen-binding fragment is a Fab fragment, a F(ab')$_2$ fragment or a Fv fragment.

14. The method of any of claims 1-3, wherein the antibody is a single chain antibody Fv (scFv).

15. The method of any of claims 1-3, wherein the antibody comprises a heavy chain variable region comprising the three complementarity determining regions (CDRs) of the heavy chain variable region of the amino acid sequence of SEQ ID NO: 15 and a light chain variable region comprising the three CDRs of the light chain variable region of the amino acid sequence of SEQ ID NO: 17.

16. The method of claim 15, wherein the antibody is mAb AB-PG1-XG1-006, the heavy chain and light chain of which are encoded by plasmids having the ATCC accession numbers PTA-4403 and PTA-4404, respectively.

17. The method of any of claims 1-3, wherein the antibody comprises a heavy chain variable region comprising the three complementarity determining regions (CDRs) of the heavy chain variable region of the amino acid sequence of SEQ ID NO: 19 and a light chain variable region comprising the three CDRs of the light chain variable region of the amino acid sequence of SEQ ID NO: 21.

18. The method of claim 17, wherein the antibody is mAb AB-PG1-XG1-026, the heavy chain and light chain of which are encoded by plasmids having the ATCC accession numbers PTA-4405 and PTA-4406, respectively.

19. The method of claim 3, wherein the at least one therapeutic agent is a cytotoxic agent, an immunostimulatory agent or an immunomodulator.

20. The method of any of claims 1, 2 and 19, wherein the cytotoxic agent is a radionuclide, a chemical toxin or a protein toxin.

21. The method of claim 20, wherein the radionuclide emits α radiation.

22. The method of claim 20, wherein the radionuclide emits β radiation.

23. The method of claim 20, wherein the radionuclide emits γ radiation.

24. The method of claim 20, wherein the radionuclide is $^{225}$Ac, $^{211}$At, $^{212}$Bi, $^{213}$Bi, $^{212}$Pb, $^{224}$Ra, $^{223}$Ra, $^{186}$Rh, $^{188}$Rh, $^{177}$Lu, $^{90}$Y, $^{131}$I, $^{67}$Cu, $^{64}$Cu, $^{153}$Sm, $^{166}$Ho, $^{125}$I, $^{123}$I, or $^{77}$Br.

25. The method of any of claims 1, 2 and 19, wherein the cytotoxic agent is an enediyne, a dolastatin, or a plant toxin.

26. The method of any of claims 1, 2 and 19, wherein the cytotoxic agent is calicheamicin, esperamicin, methotrexate, doxorubicin, melphalan, chlorambucil, ARA-C, vindesine, mitomycin C, cis-platinum, etoposide, bleomycin, 5-fluorouracil, estramustine, vincristine, etoposide, doxorubicin, paclitaxel, docetaxel, dolastatin 10, auristatin E, auristatin PHE, ricin, abrin, modeccin, botulinum toxin, diphtheria toxin, combrestatin A4, angiostatin, endostatin, interferon inducible protein 10, 2ME2, angiostatin, anti-VEGF RhuMAb, Apra (CT-2584), benefin, BMS275291, carboxyamidotriazole, CC4047, CC5013, CC7085, CDC801, CGP-41251 (PKC 412), CM101, combretastatin A-4 Prodrug, EMD 121974, endostatin, flavopiridol, genistein (GCP), IM-862, ImmTher, interferon alpha, interleukin-12, ZD1839, marimastat, Col-3, octreotide, penicillamine, PI-88, prinomastat (AG-3340), PTK787 (ZK22584), RO317453, solimastat, squalamine, SU 101, SU 5416, SU-6668, suradista (FCE 26644), suramin (metaret), tetrathiomolybdate, thalidomide, or TNP-470.

27. The method of any of claims 1-3, wherein the composition further comprises a pharmaceutically acceptable carrier, excipient or stabilizer.

28. The method of any of claims 1-3, wherein the cells are prostate cancer cells or the cancer is prostate cancer.

29. The method of any of claims 1-3, wherein the cells are non-prostate cancer cells or the cancer is non-prostate cancer.

30. The method of claim 29, wherein the non-prostate cancer cells are from bladder cancer, pancreatic cancer, lung cancer, kidney cancer, sarcoma, breast cancer, brain cancer, neuroendocrine carcinoma, colon cancer, testicular cancer, or melanoma.

31. The method of claim 29, wherein the non-prostate cancer is bladder cancer, pancreatic cancer, lung cancer, kidney cancer, sarcoma, breast cancer, brain cancer, neuroendocrine carcinoma, colon cancer, testicular cancer, or melanoma.

* * * * *

SEQUENCE LISTING

```
<160> NUMBER OF SEQ ID NOS: 39

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80
```

```
Pro His Leu Ala Gly Thr Glu Gln Asn Phe Gln Leu Ala Lys Gln Ile
                85                  90                  95
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
        115                 120                 125
Ser Ile Ile Asn Glu Asp Gly Asn Glu Ile Phe Asn Thr Ser Leu Phe
    130                 135                 140
Glu Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
Lys Ile Asn Cys Ser Gly Lys Ile Val Ile Ala Arg Tyr Gly Lys Val
        195                 200                 205
Phe Arg Gly Asn Lys Val Lys Asn Ala Gln Leu Ala Gly Ala Lys Gly
    210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
        275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
        355                 360                 365
Asp Arg Tyr Val Ile Leu Gly Gly His Arg Asp Ser Trp Val Phe Gly
    370                 375                 380
Gly Ile Asp Pro Gln Ser Gly Ala Ala Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
        435                 440                 445
Tyr Ile Asn Ala Asp Ser Ser Ile Glu Gly Asn Tyr Thr Leu Arg Val
    450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
            500                 505                 510
```

Ser Lys Leu Gly Ser Gly Asn Asp Phe Glu Val Phe Gln Arg Leu
    515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
                595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 2
<211> LENGTH: 7570
<212> TYPE: DNA
<213> ORGANISM: Artificial Sequence
<220> FEATURE:
<223> OTHER INFORMATION: Synthetic Oligonucleotide

<400> SEQUENCE: 2
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatggagtt ggggctgcgc tggggcttcc tcgttgctct    960
tttaagaggt gtccagtgtc aggtgcaatt ggtggagtct ggggggaggcg tggtccagcc   1020 tgggaggtcc ctgagactct cctgtgcagc gtctggattc gccttcagta gatatggcat   1080
gcactgggtc cgccaggctc caggcaaggg gctggagtgg gtggcagtta tggtatga     1140 tggaagtaat aaatactatg cagactccgt gaagggccga ttcaccatct ccagagacaa   1200
ttccaagaac acgcagtatc tgcaaatgaa cagcctgaga gccgaggaca cggctgtgta   1260
ttactgtgcg agaggcggtg acttcctcta ctactactat tacggtatgg acgtctgggg   1320
ccaagggacc acggtcaccg tctcctcagc ctccaccaag ggcccatcgg tcttccccct   1380
ggcaccctct agcaagagca cctctggggg cacagcggcc ctgggctgcc tggtcaagga   1440
ctacttcccc gaaccggtga cggtgtcgtg gaactcaggc gccctgacca gcggcgtgca   1500
caccttcccg gctgtcctac agtcctcagg actctactcc ctcagcagcg tggtgaccgt   1560
gccctccagc agcttgggca cccagaccta catctgcaac gtgaatcaca agcccagcaa   1620
caccaaggtg gacaagagag ttggtgagag gccagcacag ggagggaggg tgtctgctgg   1680
aagccaggct cagcgctcct gcctggacgc atcccggcta tgcagtccca gtccagggca   1740
gcaaggcagg cccgtctgc ctcttcaccc ggaggcctct gcccgcccca ctcatgctca    1800
gggagagggt cttctggctt ttccccagg ctctgggcag gcacaggcta ggtgccccta    1860
acccaggccc tgcacacaaa ggggcaggtg ctgggctcag acctgccaag agccatatcc   1920
gggaggaccc tgcccctgac ctaagcccac cccaaaggcc aaactctcca ctccctcagc   1980
tcggacacct tctctcctcc cagattccag taactcccaa tcttctctct gcagagccca   2040
aatcttgtga caaaactcac acatgcccac cgtgcccagg taagccagcc caggcctcgc   2100
cctccagctc aaggcgggac aggtgcccta gagtagcctg catccaggga caggccccag   2160
ccgggtgctg acacgtccac ctccatctct tcctcagcac ctgaactcct ggggggaccg   2220
tcagtcttcc tcttcccccc aaaacccaag gacaccctca tgatctcccg gacccctgag   2280
gtcacatgcg tggtggtgga cgtgagccac gaagaccctg aggtcaagtt caactggtac   2340
gtggacggcg tggaggtgca taatgccaag acaaagccgc gggaggagca gtacaacagc   2400
acgtaccgtg tggtcagcgt cctcaccgtc ctgcaccagg actggctgaa tggcaaggag   2460
tacaagtgca aggtctccaa caaagccctc ccagccccca tcgagaaaac catctccaaa   2520
gccaaaggtg ggacccgtgg ggtgcgaggg ccacatggac agaggccggc tcggcccacc   2580
ctctgccctg agagtgaccg ctgtaccaac ctctgtccct acagggcagc cccgagaacc   2640
acaggtgtac accctgcccc catcccggga ggagatgacc aagaaccagg tcagcctgac   2700
ctgcctggtc aaaggcttct atcccagcga catcgccgtg gagtgggaga gcaatgggca   2760
gccggagaac aactacaaga ccacgcctcc cgtgctggac tccgacggct ccttcttcct   2820
ctatagcaag ctcaccgtgg acaagagcag gtggcagcag gggaacgtct tctcatgctc   2880
cgtgatgcat gaggctctgc acaaccacta cacgcagaag agcctctccc tgtctccggg   2940
taaatgagaa ttcctcgagt ctagagggcc cgtttaaacc cgctgatcag cctcgactgt   3000
gccttctagt tgccagccat ctgttgtttg ccctcccccc gtgccttcct tgaccctgga   3060
aggtgccact cccactgtcc tttcctaata aaatgaggaa attgcatcgc attgtctgag   3120
```

```
taggtgtcat tctattctgg ggggtggggt ggggcaggac agcaaggggg aggattggga    3180
agacaatagc aggcatgctg gggatgcggt gggctctatg gcttctgagg cggaaagaac    3240
cagctggggc tctaggggt  atccccacgc gccctgtagc ggcgcattaa gcgcggcggg    3300
tgtggtggtt acgcgcagcg tgaccgctac acttgccagc gccctagcgc ccgctccttt    3360
cgctttcttc ccttcctttc tcgccacgtt cgccggcttt cccgtcaag  ctctaaatcg    3420
gggcatccct ttagggttcc gattagtgc  tttacggcac ctcgacccca aaaaacttga    3480
ttagggtgat ggttcacgta gtgggccatc gccctgatag acggttttc  gcccttgac    3540
gttggagtcc acgttctta  atagtggact cttgttccaa actggaacaa cactcaaccc    3600
tatctcggtc tattcttttg atttataagg gattttgggg atttcggcct attggttaaa    3660
aaatgagctg atttaacaaa aatttaacgc gaattaattc tgtggaatgt gtgtcagtta    3720
gggtgtggaa agtccccagg ctccccaggc aggcagaagt atgcaaagca tgcatctcaa    3780
ttagtcagca accaggtgtg gaaagtcccc aggctcccca gcaggcagaa gtatgcaaag    3840
catgcatctc aattagtcag caaccatagt cccgcccta  actccgccca tcccgcccct    3900
aactccgccc agttccgccc attctccgcc ccatggctga ctaattttt  ttatttatgc    3960
agaggccgag gccgcctctg cctctgagct attccagaag tagtgaggag gcttttttgg    4020
aggcctaggc ttttgcaaaa agctcccggg agcttgtata tccatttcg  gatctgatca    4080
gcacgtgatg aaaaagcctg aactcaccgc gacgtctgtc gagaagtttc tgatcgaaaa    4140
gttcgacagc gtctccgacc tgatgcagct ctcggagggc gaagaatctc gtgctttcag    4200
cttcgatgta ggagggcgtg gatatgtcct gcgggtaaat agctgcgccg atggtttcta    4260
caaagatcgt tatgtttatc ggcactttgc atcggccgcg ctcccgattc cggaagtgct    4320
tgacattggg gaattcagcg agagcctgac ctattgcatc tcccgccgtg cacagggtgt    4380
cacgttgcaa gacctgcctg aaaccgaact gcccgctgtt ctgcagccgg tcgcggaggc    4440
catggatgcg atcgctgcgg ccgatcttag ccagacgagc gggttcggcc cattcggacc    4500
gcaaggaatc ggtcaataca ctacatggcg tgatttcata tgcgcgattg ctgatcccca    4560
tgtgtatcac tggcaaactg tgatggacga caccgtcagt gcgtccgtcg cgcaggctct    4620
cgatgagctg atgctttggg ccgaggactg ccccgaagtc cggcacctcg tgcacgcgga    4680
tttcggctcc aacaatgtcc tgacggacaa tggccgcata acagcggtca ttgactggag    4740
cgaggcgatg ttcggggatt cccaatacga ggtcgccaac atcttcttct ggaggccgtg    4800
gttggcttgt atggagcagc agacgcgcta cttgagcgg  aggcatccgg agcttgcagg    4860
atcgccgcgg ctccgggcgt atatgctccg cattggtctt gaccaactct atcagagctt    4920
ggttgacggc aatttcgatg atgcagcttg ggcgcagggt cgatgcgacg caatcgtccg    4980
atccggagcc gggactgtcg ggcgtacaca atcgcccgc  agaagcgcgg ccgtctggac    5040
cgatggctgt gtagaagtac tcgccgatag tggaaaccga cgccccagca ctcgtccgag    5100
ggcaaaggaa tagcacgtgc tacgagattt cgattccacc gccgccttct atgaaaggtt    5160
gggcttcgga atcgttttcc gggacgccgg ctggatgatc ctccagcgcg ggatctcat    5220
gctggagttc ttcgcccacc ccaacttgtt tattgcagct tataatggtt acaaataaag    5280
caatagcatc acaaatttca caaataaagc atttttttca ctgcattcta gttgtggttt    5340
gtccaaactc atcaatgtat cttatcatgt ctgtataccg tcgacctcta gctagagctt    5400
ggcgtaatca tggtcatagc tgtttcctgt gtgaaattgt tatccgctca caattccaca    5460
caacatacga gccggaagca taaagtgtaa agcctggggt gcctaatgag tgagctaact    5520
```

```
cacattaatt gcgttgcgct cactgcccgc tttccagtcg ggaaacctgt cgtgccagct    5580
gcattaatga atcggccaac gcgcgggag aggcggtttg cgtattgggc gctcttccgc    5640
ttcctcgctc actgactcgc tgcgctcggt cgttcggctg cggcgagcgg tatcagctca    5700
ctcaaaggcg gtaatacggt tatccacaga atcaggggat aacgcaggaa agaacatgtg    5760
agcaaaaggc cagcaaaagg ccaggaaccg taaaaaggcc gcgttgctgg cgttttttcca   5820 taggctccgc cccctgacg agcatcacaa aaatcgacgc tcaagtcaga ggtggcgaaa    5880
cccgacagga ctataaagat accaggcgtt tccccctgga agctccctcg tgcgctctcc    5940
tgttccgacc ctgccgctta ccggatacct gtccgccttt ctcccttcgg aagcgtggc    6000 gctttctcaa tgctcacgct gtaggtatct cagttcggtg taggtcgttc gctccaagct    6060
gggctgtgtg cacgaacccc ccgttcagcc cgaccgctgc gccttatccg gtaactatcg    6120
tcttgagtcc aacccggtaa gacacgactt atcgccactg gcagcagcca ctggtaacag    6180
gattagcaga gcgaggtatg taggcggtgc tacagagttc ttgaagtggt ggcctaacta    6240
cggctacact agaaggacag tatttggtat ctgcgctctg ctgaagccag ttaccttcgg    6300
aaaaagagtt ggtagctctt gatccggcaa acaaaccacc gctggtagcg gtggtttttt    6360
tgtttgcaag cagcagatta cgcgcagaaa aaaaggatct caagaagatc ctttgatctt    6420
ttctacgggg tctgacgctc agtggaacga aaactcacgt taagggattt tggtcatgag    6480
attatcaaaa aggatcttca cctagatcct tttaaattaa aaatgaagtt ttaaatcaat    6540
ctaaagtata tatgagtaaa cttggtctga cagttaccaa tgcttaatca gtgaggcacc    6600
tatctcagcg atctgtctat ttcgttcatc catagttgcc tgactccccg tcgtgtagat    6660
aactacgata cgggagggct taccatctgg ccccagtgct gcaatgatac cgcgagaccc    6720
acgctcaccg gctccagatt tatcagcaat aaaccagcca gccggaaggg ccgagcgcag    6780
aagtggtcct gcaactttat ccgcctccat ccagtctatt aattgttgcc gggaagctag    6840
agtaagtagt tcgccagtta atagtttgcg caacgttgtt gccattgcta caggcatcgt    6900
ggtgtcacgc tcgtcgtttg gtatggcttc attcagctcc ggttcccaac gatcaaggcg    6960
agttacatga tcccccatgt tgtgcaaaaa agcggttagc tccttcggtc ctccgatcgt    7020
tgtcagaagt aagttggccg cagtgttatc actcatggtt atggcagcac tgcataattc    7080
tcttactgtc atgccatccg taagatgctt ttctgtgact ggtgagtact caaccaagtc    7140
attctgagaa tagtgtatgc ggcgaccgag ttgctcttgc ccggcgtcaa tacgggataa    7200
taccgcgcca catagcagaa ctttaaaagt gctcatcatt ggaaaacgtt cttcggggcg    7260
aaaactctca aggatcttac cgctgttgag atccagttcg atgtaaccca ctcgtgcacc    7320
caactgatct tcagcatctt ttactttcac cagcgtttct gggtgagcaa aaacaggaag    7380
gcaaaatgcc gcaaaaaagg gaataagggc gacacggaaa tgttgaatac tcatactctt    7440 ccttttttcaa tattattgaa gcatttatca gggttattgt ctcatgagcg gatacatatt    7500
tgaatgtatt tagaaaaata acaaataggg gttccgcgc acatttcccc gaaaagtgcc    7560
acctgacgtc                                                          7570
```

<210> SEQ ID NO 3
<211> LENGTH: 7597
<212> TYPE: DNA
<213> ORGANISM: Artificial Sequence
<220> FEATURE:
<223> OTHER INFORMATION: Synthetic Oligonucleotide

<400> SEQUENCE: 3

```
gacggatcgg gagatctccc gatccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata     300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttgatctca ccatgggtc aaccgccatc ctcaccatgg agttgggct      960
gcgctgggtt ctcctcgttg ctcttttaag aggtgtccag tgtcaggtgc agctggtgga   1020
gtctggggga ggcgtggtcc agcctgggag gtccctgaga ctctcctgtg cagcgtctgg   1080
attcaccttc agtaactatg tcatgcactg ggtccgccag gctccaggca aggggctgga   1140
gtgggtggca attatatggt atgatggaag taataaatac tatgcagact ccgtgaaggg   1200
ccgattcacc atctccagag acaattccaa gaacacgctg tatctgcaaa tgaacagcct   1260
gagagccgag gacacggctg tgtattactg tgcgggtgga tataactgga actacgagta   1320
ccactactac ggtatggacg tctggggcca agggaccacg gtcaccgtct cctcagcctc   1380
caccaagggc ccatcggtct tccccctggc accctctagc aagagcacct ctggggggcac   1440
agcggccctg ggctgcctgg tcaaggacta cttccccgaa ccggtgacgg tgtcgtggaa   1500
ctcaggcgcc ctgaccagcg gcgtgcacac cttcccggct gtcctacagt cctcaggact   1560
ctactccctc agcagcgtgg tgaccgtgcc ctccagcagc ttgggcaccc agacctacat   1620
ctgcaacgtg aatcacaagc ccagcaacac caaggtggac aagagagttg gtgagaggcc   1680
agcacaggga gggagggtgt ctgctggaag ccaggctcag cgctcctgcc tggacgcatc   1740
ccggctatgc agtcccagtc cagggcagca aggcaggccc cgtctgcctc ttcacccgga   1800
ggcctctgcc cgccccactc atgctcaggg agagggtctt ctggcttttt ccccaggctc   1860
tgggcaggca caggctaggt gcccctaacc caggccctgc acacaaaggg gcaggtgctg   1920
ggctcagacc tgccaagagc catatccggg aggaccctgc ccctgaccta gcccaccccc   1980
aaaggccaaa ctctccactc cctcagctcg acaccttct ctcctcccag attccagtaa   2040
ctcccaatct tctctctgca gagcccaaat cttgtgacaa aactcacaca tgcccaccgt   2100
gcccaggtaa gccagcccag gcctcgccct ccagctcaag gcgggacagg tgccctagag   2160
tagcctgcat ccaggacag gccccagccg ggtgctgaca cgtccacctc catctcttcc   2220
tcagcacctg aactcctggg gggaccgtca gtcttcctct tccccccaaa acccaaggac   2280
accctcatga tctcccggac ccctgaggtc acatgcgtgg tggtggacgt gagccacgaa   2340
gaccctgagg tcaagttcaa ctggtacgtg gacggcgtgg aggtgcataa tgccaagaca   2400
```

-continued

```
aagccgcggg aggagcagta caacagcacg taccgtgtgg tcagcgtcct caccgtcctg    2460
caccaggact ggctgaatgg caaggagtac aagtgcaagg tctccaacaa agccctccca    2520
gcccccatcg agaaaccat ctccaaagcc aaggtggga cccgtggggt gcgagggcca     2580 catgacaga ggccggctcg gcccaccctc tgccctgaga gtgaccgctg taccaacctc    2640
tgtccctaca gggcagcccc gagaaccaca ggtgtacacc ctgcccccat cccgggagga   2700
gatgaccaag aaccaggtca gcctgacctg cctggtcaaa ggcttctatc ccagcgacat   2760
cgccgtggag tgggagagca atgggcagcc ggagaacaac tacaagacca cgcctcccgt   2820
gctggactcc gacggctcct tcttcctcta tagcaagctc accgtggaca gagcaggtg    2880 gcagcagggg aacgtcttct catgctccgt gatgcatgag gctctgcaca accactacac   2940
gcagaagagc ctctccctgt ctccgggtaa atgagaattc ctcgagtcta gagggcccgt   3000
ttaaacccgc tgatcagcct cgactgtgcc ttctagttgc cagccatctg ttgtttgccc   3060
ctcccccgtg ccttccttga ccctggaagg tgccactccc actgtccttt cctaataaaa   3120
tgaggaaatt gcatcgcatt gtctgagtag gtgtcattct attctggggg gtggggtggg   3180
gcaggacagc aagggggagg attgggaaga caatagcagg catgctgggg atgcggtggg   3240
ctctatggct tctgaggcgg aaagaaccag ctggggctct aggggggtatc cccacgcgcc   3300 ctgtagcggc gcattaagcg cggcgggtgt ggtggttacg cgcagcgtga ccgctacact   3360
tgccagcgcc ctagcgcccg ctcctttcgc tttcttccct cctttctcg ccacgttcgc    3420 cggctttccc cgtcaagctc taaatcgggg catcccttta gggttccgat ttagtgcttt   3480
acggcacctc gaccccaaaa aacttgatta gggtgatggt tcacgtagtg gccatcgcc    3540 ctgatagacg gttttcgcc ctttgacgtt ggagtccacg ttctttaata gtggactctt   3600
gttccaaact ggaacaacac tcaaccctat ctcggtctat tcttttgatt tataagggat   3660 tttgggatt tcggcctatt ggttaaaaaa tgagctgatt taacaaaaat ttaacgcgaa   3720
ttaattctgt ggaatgtgtg tcagttaggg tgtggaaagt ccccaggctc cccaggcagg   3780
cagaagtatg caaagcatgc atctcaatta gtcagcaacc aggtgtggaa agtccccagg   3840
ctccccagca ggcagaagta tgcaaagcat gcatctcaat tagtcagcaa ccatagtccc   3900
gcccctaact ccgcccatcc cgcccctaac tccgcccagt tccgcccatt ctccgcccca   3960
tggctgacta attttttta tttatgcaga ggccgaggcc gcctctgcct ctgagctatt    4020
ccagaagtag tgaggaggct ttttggagg cctaggcttt tgcaaaaagc tcccgggagc    4080
ttgtatatcc attttcggat ctgatcagca cgtgatgaaa aagcctgaac tcaccgcgac   4140
gtctgtcgag aagtttctga tcgaaaagtt cgacagcgtc tccgacctga tgcagctctc   4200
ggagggcgaa gaatctcgtg ctttcagctt cgatgtagga gggcgtggat atgtcctgcg   4260
ggtaaatagc tgcgccgatg gtttctacaa agatcgttat gtttatcggc actttgcatc   4320
ggccgcgctc ccgattccgg aagtgcttga cattggggaa ttcagcgaga gcctgaccta   4380
ttgcatctcc cgccgtgcac agggtgtcac gttgcaagac ctgcctgaaa ccgaactgcc   4440
cgctgttctg cagccggtcg cggaggccat ggatgcgatc gctgcggccg atcttagcca   4500
gacgagcggg ttcggcccat tcggaccgca aggaatcggt caatacacta catggcgtga   4560
tttcatatgc gcgattgctg atccccatgt gtatcactgg caaactgtga tggacgacac   4620
cgtcagtgcg tccgtcgcgc aggctctcga tgagctgatg ctttgggccg aggactgccc   4680
cgaagtccgg cacctcgtgc acgcggattt cggctccaac aatgtcctga cggacaatgg   4740
ccgcataaca gcggtcattg actggagcga ggcgatgttc ggggattccc aatacgaggt   4800
```

```
cgccaacatc ttcttctgga ggccgtggtt ggcttgtatg gagcagcaga cgcgctactt    4860
cgagcggagg catccggagc ttgcaggatc gccgcggctc cgggcgtata tgctccgcat    4920
tggtcttgac caactctatc agagcttggt tgacggcaat ttcgatgatg cagcttgggc    4980
gcagggtcga tgcgacgcaa tcgtccgatc cggagccggg actgtcgggc gtacacaaat    5040
cgcccgcaga agcgcggccg tctggaccga tggctgtgta gaagtactcg ccgatagtgg    5100
aaaccgacgc cccagcactc gtccgagggc aaaggaatag cacgtgctac gagatttcga    5160
ttccaccgcc gccttctatg aaaggttggg cttcggaatc gttttccggg acgccggctg    5220
gatgatcctc cagcgcgggg atctcatgct ggagttcttc gcccacccca acttgtttat    5280
tgcagcttat aatggttaca ataaagcaa tagcatcaca aatttcacaa ataaagcatt    5340 ttttcactg cattctagtt gtggtttgtc caaactcatc aatgtatctt atcatgtctg    5400
tataccgtcg acctctagct agagcttggc gtaatcatgg tcatagctgt ttcctgtgtg    5460
aaattgttat ccgctcacaa ttccacacaa catacgagcc ggaagcataa agtgtaaagc    5520
ctggggtgcc taatgagtga gctaactcac attaattgcg ttgcgctcac tgcccgcttt    5580
ccagtcggga aacctgtcgt gccagctgca ttaatgaatc ggccaacgcg cggggagagg    5640
cggtttgcgt attgggcgct cttccgcttc ctcgctcact gactcgctgc gctcggtcgt    5700
tcggctgcgg cgagcggtat cagctcactc aaaggcggta atacggttat ccacagaatc    5760
aggggataac gcaggaaaga acatgtgagc aaaaggccag caaaaggcca ggaaccgtaa    5820
aaaggccgcg ttgctggcgt ttttccatag gctccgcccc cctgacgagc atcacaaaaa    5880
tcgacgctca agtcagaggt ggcgaaaccc gacaggacta taaagatacc aggcgtttcc    5940
ccctggaagc tccctcgtgc gctctcctgt tccgaccctg ccgcttaccg gatacctgtc    6000
cgcctttctc ccttcgggaa gcgtggcgct ttctcaatgc tcacgctgta ggtatctcag    6060
ttcggtgtag tcgttcgct ccaagctggg ctgtgtgcac gaaccccccg ttcagcccga    6120
ccgctgcgcc ttatccggta actatcgtct tgagtccaac ccggtaagac acgacttatc    6180
gccactggca gcagccactg gtaacaggat tagcagagcg aggtatgtag gcggtgctac    6240
agagttcttg aagtggtggc ctaactacgg ctacactaga aggacagtat ttggtatctg    6300
cgctctgctg aagccagtta ccttcggaaa aagagttggt agctcttgat ccggcaaaca    6360
aaccaccgct ggtagcggtg gtttttttgt ttgcaagcag cagattacgc gcagaaaaaa    6420
aggatctcaa gaagatcctt tgatcttttc tacggggtct gacgctcagt ggaacgaaaa    6480
ctcacgttaa gggattttgg tcatgagatt atcaaaaagg atcttcacct agatcctttt    6540
aaattaaaaa tgaagtttta atcaatcta aagtatatat gagtaaactt ggtctgacag    6600
ttaccaatgc ttaatcagtg aggcacctat ctcagcgatc tgtctatttc gttcatccat    6660
agttgcctga ctccccgtcg tgtagataac tacgatacgg gagggcttac catctggccc    6720
cagtgctgca atgataccgc gagacccacg ctcaccggct ccagatttat cagcaataaa    6780
ccagccagcc ggaagggccg agcgcagaag tggtcctgca actttatccg cctccatcca    6840
gtctattaat tgttgccggg aagctagagt aagtagttcg ccagttaata gtttgcgcaa    6900
cgttgttgcc attgctacag gcatcgtggt gtcacgctcg tctttggta tggcttcatt    6960 cagctccggt tcccaacgat caaggcgagt tacatgatcc cccatgttgt gcaaaaaagc    7020
ggttagctcc ttcggtcctc cgatcgttgt cagaagtaag ttggccgcag tgttatcact    7080
catggttatg gcagcactgc ataattctct tactgtcatg ccatccgtaa gatgcttttc    7140
tgtgactggt gagtactcaa ccaagtcatt ctgagaatag tgtatgcggc gaccgagttg    7200
```

```
ctcttgcccg gcgtcaatac gggataaatac cgcgccacat agcagaactt taaaagtgct   7260
catcattgga aaacgttctt cggggcgaaa actctcaagg atcttaccgc tgttgagatc   7320
cagttcgatg taacccactc gtgcacccaa ctgatcttca gcatctttta ctttcaccag   7380
cgtttctggg tgagcaaaaa caggaaggca aaatgccgca aaaaagggaa taagggcgac   7440
acggaaatgt tgaatactca tactcttcct ttttcaatat tattgaagca tttatcaggg   7500
ttattgtctc atgagcggat acatatttga atgtatttag aaaaataaac aaatagggt   7560 tccgcgcaca tttccccgaa aagtgccacc tgacgtc   7597

<210> SEQ ID NO 4
<211> LENGTH: 7579
<212> TYPE: DNA
<213> ORGANISM: Artificial Sequence
<220> FEATURE:
<223> OTHER INFORMATION: Synthetic Oligonucleotide

<400> SEQUENCE: 4
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatggagtt gggacttagc tgggttttcc tcgttgctct    960
tttaagaggt gtccagtgtc aggtccagct ggtggagtct ggggaggcg tggtccagcc   1020 tgggaggtcc ctgagactct cctgtgcagc gtctggattc accttcagta gctatggcat   1080
gcactgggtc cgccaggctc aggcaaggg gctggactgg gtggcaatta tttggcatga   1140
tggaagtaat aaatactatg cagactccgt gaagggccga ttcaccatct ccagagacaa   1200
ttccaagaag acgctgtacc tgcaaatgaa cagtttgaga gccgaggaca cggctgtgta   1260
ttactgtgcg agagcttggg cctatgacta cggtgactat gaatactact cggtatggga   1320
cgtctggggc aagggaccac cggtcaccgt ctcctcagcc tccaccaagg gcccatcggt   1380
cttccccctg gcaccctcta gcaagagcac ctctggggc acagcggccc tgggctgcct   1440
ggtcaaggac tacttccccg aaccggtgac ggtgtcgtgg aactcaggcg ccctgaccag   1500
cggcgtgcac accttcccgg ctgtcctaca gtcctcagga ctctactccc tcagcagcgt   1560
ggtgaccgtg ccctcagca gcttgggcac ccagacctac atctgcaacg tgaatcacaa   1620
gcccagcaac accaaggtgg acaagagagt tggtgagagg ccagcacagg gagggaggt   1680
```

-continued

```
gtctgctgga agccaggctc agcgctcctg cctggacgca tcccggctat gcagtcccag      1740
tccagggcag caaggcaggc cccgtctgcc tcttcacccg gaggcctctg cccgccccac      1800
tcatgctcag ggagagggtc ttctggcttt ttccccaggc tctgggcagg cacaggctag      1860
gtgcccctaa cccaggccct gcacacaaag gggcaggtgc tgggctcaga cctgccaaga      1920
gccatatccg ggaggaccct gccctgacc taagcccacc ccaaaggcca aactctccac       1980
tccctcagct cggacacctt ctctcctccc agattccagt aactcccaat cttctctctg      2040
cagagcccaa atcttgtgac aaaactcaca catgcccacc gtgcccaggt aagccagccc      2100
aggcctcgcc ctccagctca aggcgggaca gtgccctag agtagcctgc atccagggac       2160
aggccccagc cgggtgctga cacgtccacc tccatctctt cctcagcacc tgaactcctg      2220
gggggaccgt cagtcttcct cttccccca aacccaagg acaccctcat gatctcccgg        2280
acccctgagg tcacatgcgt ggtggtggac gtgagccacg aagaccctga ggtcaagttc      2340
aactggtacg tggacggcgt ggaggtgcat aatgccaaga caaagccgcg ggaggagcag      2400
tacaacagca cgtaccgtgt ggtcagcgtc ctcaccgtcc tgcaccagga ctggctgaat      2460
ggcaaggagt acaagtgcaa ggtctccaac aaagccctcc cagcccccat cgagaaaacc      2520
atctccaaag ccaaaggtgg gacccgtggg gtgcgagggc cacatggaca gaggccggct      2580
cggcccaccc tctgccctga gagtgaccgc tgtaccaacc tctgtcccta cagggcagcc      2640
ccgagaacca caggtgtaca ccctgccccc atcccgggag gagatgacca gaaccaggt     2700 cagcctgacc tgcctggtca aaggcttcta tcccagcgac atcgccgtgg agtgggagag     2760
caatgggcag ccggagaaca actacaagac cacgcctccc gtgctggact ccgacggctc     2820
cttcttcctc tatagcaagc tcaccgtgga caagagcagg tggcagcagg gaacgtctt      2880 ctcatgctcc gtgatgcatg aggctctgca caaccactac acgcagaaga gcctctccct     2940
gtctccgggt aaatgagaat tcctcgagtc tagagggccc gtttaaaccc gctgatcagc     3000
ctcgactgtg ccttctagtt gccagccatc tgttgtttgc ccctcccccg tgccttcctt     3060
gaccctggaa ggtgccactc ccactgtcct ttcctaataa aatgaggaaa ttgcatcgca     3120
ttgtctgagt aggtgtcatt ctattctggg ggtgggggtg gggcaggaca gcaaggggga     3180
ggattgggaa gacaatagca ggcatgctgg ggatgcggtg gctctatgg cttctgaggc      3240 ggaaagaacc agctggggct ctaggggta tccccacgcg ccctgtagcg cgcattaag       3300 cgcggcgggt gtggtggtta cgcgcagcgt gaccgctaca cttgccagcg ccctagcgcc     3360
cgctcctttc gctttcttcc cttccttct cgccacgttc gccggctttc ccgtcaagc       3420 tctaaatcgg ggcatccctt tagggttccg atttagtgct ttacggcacc tcgaccccaa     3480
aaaacttgat tagggtgatg gttcacgtag tgggccatcg ccctgataga cggttttcg      3540 ccctttgacg ttggagtcca cgttctttaa tagtggactc ttgttccaaa ctggaacaac     3600
actcaaccct atctcggtct attcttttga tttataaggg attttgggga tttcggccta     3660
ttggttaaaa aatgagctga tttaacaaaa atttaacgcg aattaattct gtggaatgtg     3720
tgtcagttag ggtgtggaaa gtccccaggc tccccaggca ggcagaagta tgcaaagcat     3780
gcatctcaat tagtcagcaa ccaggtgtgg aaagtcccca ggctcccag caggcagaag      3840 tatgcaaagc atgcatctca attagtcagc aaccatagtc cgcccctaa ctccgcccat      3900 cccgccccta actccgccca gttccgccca ttctccgccc catggctgac taattttttt     3960
tatttatgca gaggccgagg ccgcctctgc ctctgagcta ttccagaagt agtgaggagg     4020
cttttttgga ggcctaggct tttgcaaaaa gctcccggga gcttgtatat ccattttcgg     4080
```

-continued

```
atctgatcag cacgtgatga aaaagcctga actcaccgcg acgtctgtcg agaagtttct   4140
gatcgaaaag ttcgacagcg tctccgacct gatgcagctc tcggagggcg aagaatctcg   4200
tgctttcagc ttcgatgtag gagggcgtgg atatgtcctg cgggtaaata gctgcgccga   4260
tggtttctac aaagatcgtt atgtttatcg gcactttgca tcggccgcgc tcccgattcc   4320
ggaagtgctt gacattgggg aattcagcga gagcctgacc tattgcatct cccgccgtgc   4380
acagggtgtc acgttgcaag acctgcctga aaccgaactg cccgctgttc tgcagccggt   4440
cgcggaggcc atgatgcga tcgctgcggc cgatcttagc cagacgagcg ggttcggccc   4500
attcggaccg caaggaatcg gtcaatacac tacatggcgt gatttcatat gcgcgattgc   4560
tgatccccat gtgtatcact ggcaaactgt gatggacgac accgtcagtg cgtccgtcgc   4620
gcaggctctc gatgagctga tgcttttgggc cgaggactgc cccgaagtcc ggcacctcgt   4680
gcacgcggat ttcggctcca caatgtcct gacggacaat ggccgcataa cagcggtcat   4740
tgactggagc gaggcgatgt tcggggattc ccaatacgag gtcgccaaca tcttcttctg   4800
gaggccgtgg ttggcttgta tggagcagca gacgcgctac ttcgagcgga ggcatccgga   4860
gcttgcagga tcgccgcggc tccgggcgta tatgctccgc attggtcttg accaactcta   4920
tcagagcttg gttgacggca atttcgatga tgcagcttgg gcgcagggtc gatgcgacgc   4980
aatcgtccga tccggagccg ggactgtcgg gcgtacacaa atcgcccgca gaagcgcggc   5040
cgtctggacc gatggctgtg tagaagtact cgccgatagt ggaaaccgac gccccagcac   5100
tcgtccgagg gcaaaggaat agcacgtgct acgagatttc gattccaccg ccgccttcta   5160
tgaaaggttg ggcttcggaa tcgttttccg ggacgccggc tggatgatcc tccagcgcgg   5220
ggatctcatg ctggagttct tcgcccaccc caacttgttt attgcagctt ataatggtta   5280
caaataaagc aatagcatca caaatttcac aaataaagca ttttttttcac tgcattctag   5340
ttgtggtttg tccaaaactca tcaatgtatc ttatcatgtc tgtataccgt cgacctctag   5400
ctagagcttg gcgtaatcat ggtcatagct gtttcctgtg tgaaattgtt atccgctcac   5460
aattccacac aacatacgag ccggaagcat aaagtgtaaa gcctggggtg cctaatgagt   5520
gagctaactc acattaattg cgttgcgctc actgcccgct ttccagtcgg gaaacctgtc   5580
gtgccagctg cattaatgaa tcggccaacg cgcggggaga ggcggtttgc gtattgggcg   5640
ctcttccgct tcctcgctca ctgactcgct gcgctcggtc gttcggctgc ggcgagcggt   5700
atcagctcac tcaaaggcgg taatacggtt atccacagaa tcaggggata acgcaggaaa   5760
gaacatgtga gcaaaaggcc agcaaaaggc caggaaccgt aaaaaggccg cgttgctggc   5820
gttttttccat aggctccgcc cccctgacga gcatcacaaa aatcgacgct caagtcagag   5880
gtggcgaaac ccgacaggac tataaagata ccaggcgttt cccccctggaa gctccctcgt   5940
gcgctctcct gttccgaccc tgccgcttac cggatacctg tccgcctttc tcccttcggg   6000
aagcgtggcg ctttctcaat gctcacgctg taggtatctc agttcggtgt aggtcgttcg   6060
ctccaagctg ggctgtgtgc acgaaccccc cgttcagccc gaccgctgcg ccttatccgg   6120
taactatcgt cttgagtcca acccggtaag acacgactta tcgccactgg cagcagccac   6180
tggtaacagg attagcagag cgaggtatgt aggcggtgct acagagttct tgaagtggtg   6240
gcctaactac ggctacacta aaggacagt atttggtatc tgcgctctgc tgaagccagt   6300
taccttcgga aaaagagttg gtagctcttg atccggcaaa caaaccaccg ctggtagcgg   6360
tggtttttttt gtttgcaagc agcagattac gcgcagaaaa aaaggatctc aagaagatcc   6420
tttgatcttt tctacggggt ctgacgctca gtggaacgaa aactcacgtt aagggatttt   6480
```

| | | |
|---|---|---|
| ggtcatgaga ttatcaaaaa ggatcttcac ctagatcctt ttaaattaaa aatgaagttt | 6540 |
| taaatcaatc taaagtatat atgagtaaac ttggtctgac agttaccaat gcttaatcag | 6600 |
| tgaggcacct atctcagcga tctgtctatt tcgttcatcc atagttgcct gactccccgt | 6660 |
| cgtgtagata actacgatac gggagggctt accatctggc cccagtgctg caatgatacc | 6720 |
| gcgagaccca cgctcaccgg ctccagattt atcagcaata aaccagccag ccggaagggc | 6780 |
| cgagcgcaga gtggtcctg caactttatc cgcctccatc cagtctatta attgttgccg | 6840 |
| ggaagctaga gtaagtagtt cgccagttaa tagtttgcgc aacgttgttg ccattgctac | 6900 |
| aggcatcgtg gtgtcacgct cgtcgtttgg tatggcttca ttcagctccg gttcccaacg | 6960 |
| atcaaggcga gttacatgat cccccatgtt gtgcaaaaaa gcggttagct ccttcggtcc | 7020 |
| tccgatcgtt gtcagaagta agttggccgc agtgttatca ctcatggtta tggcagcact | 7080 |
| gcataattct cttactgtca tgccatccgt aagatgcttt tctgtgactg gtgagtactc | 7140 |
| aaccaagtca ttctgagaat agtgtatgcg gcgaccgagt tgctcttgcc cggcgtcaat | 7200 |
| acgggataat accgcgccac atagcagaac tttaaaagtg ctcatcattg gaaaacgttc | 7260 |
| ttcggggcga aaactctcaa ggatcttacc gctgttgaga tccagttcga tgtaacccac | 7320 |
| tcgtgcaccc aactgatctt cagcatcttt tactttcacc agcgtttctg ggtgagcaaa | 7380 |
| aacaggaagg caaaatgccg caaaaaaggg aataagggcg acacggaaat gttgaatact | 7440 |
| catactcttc cttttcaat attattgaag catttatcag ggttattgtc tcatgagcgg | 7500 |
| atacatattt gaatgtattt agaaaaataa acaaataggg gttccgcgca catttccccg | 7560 |
| aaaagtgcca cctgacgtc | 7579 |

<210> SEQ ID NO 5
<211> LENGTH: 7558
<212> TYPE: DNA
<213> ORGANISM: Artificial Sequence
<220> FEATURE:
<223> OTHER INFORMATION: Synthetic Oligonucleotide

<400> SEQUENCE: 5

| | | |
|---|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca tgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| ggtaccaagc ttggatccca ccatggggtc aaccgtcatc ctcgccctcc tcctggctgt | 960 |

```
tctccaagga gtctgtgccg aggtgcagct ggtgcagtct ggagcagagg tgaaaaagcc    1020
cggggagtct ctgaagatct cctgtaaggg ttctggatac agctttacca gttactggat    1080
cggctgggtg cgccagatgc ccgggaaagg cctggagtgg atgggatca tctatcctgg    1140 tgactctgat accagataca gcccgtcctt ccaaggccag gtcaccatct cagccgacaa    1200
gtccatcagc accgcctacc tgcagtggag cagcctgaag gcctcggaca ccgccatgta    1260
ttactgtgcg agacggatgg cagcagctgg ccccttttgac tactgggcc agggaaccct    1320 ggtcaccgtc tcctcagcct ccaccaaggg cccatcggtc ttccccctgg cacccctctag    1380 caagagcacc tctgggggca gcggccct gggctgcctg gtcaaggact acttccccga    1440
accggtgacg gtgtcgtgga actcaggcgc cctgaccagc ggcgtgcaca ccttcccggc    1500
tgtcctacag tcctcaggac tctactccct cagcagcgtg gtgaccgtgc cctccagcag    1560
cttgggcacc cagacctaca tctgcaacgt gaatcacaag cccagcaaca ccaaggtgga    1620
caagagagtt ggtgagaggc cagcacaggg agggagggtg tctgctggaa gccaggctca    1680
gcgctcctgc ctggacgcat cccggctatg cagtcccagt ccagggcagc aaggcaggcc    1740
ccgtctgcct cttcacccgg aggcctctgc ccgccccact catgctcagg gagagggtct    1800
tctggctttt tccccaggct ctgggcaggc acaggctagg tgcccctaac ccaggccctg    1860
cacacaaagg ggcaggtgct gggctcagac ctgccaagag ccatatccgg gaggaccctg    1920
cccctgacct aagcccaccc caaaggccaa actctccact ccctcagctc ggacaccttc    1980
tctcctccca gattccagta actcccaatc ttctctctgc agagcccaaa tcttgtgaca    2040
aaactcacac atgcccaccg tgcccaggta agccagccca ggcctcgccc tccagctcaa    2100
ggcgggacag tgccctaga gtagcctgca tccaggaca ggccccagcc gggtgctgac    2160
acgtccacct ccatctcttc ctcagcacct gaactcctgg ggggaccgtc agtcttcctc    2220
ttccccccaa aacccaagga caccctcatg atctcccgga cccctgaggt cacatgcgtg    2280
gtggtggacg tgagccacga agaccctgag gtcaagttca actggtacgt ggacggcgtg    2340
gaggtgcata atgccaagac aaagccgcgg gaggagcagt acaacagcac gtaccgtgtg    2400
gtcagcgtcc tcaccgtcct gcaccaggac tggctgaatg gcaaggagta caagtgcaag    2460
gtctccaaca aagccctccc agcccccatc gagaaaacca tctccaaagc caaaggtggg    2520
acccgtgggg tgcgagggcc acatggacag aggccggctc ggcccaccct ctgccctgag    2580
agtgaccgct gtaccaacct ctgtccctac agggcagccc cgagaaccac aggtgtacac    2640
cctgccccca tcccgggagg agatgaccaa gaaccaggtc agcctgacct gcctggtcaa    2700
aggcttctat cccagcgaca tcgccgtgga gtgggagagc aatgggcagc cggagaacaa    2760
ctacaagacc acgcctcccg tgctggactc cgacggctcc ttcttcctct atagcaagct    2820
caccgtggac aagagcaggt ggcagcaggg gaacgtcttc tcatgctccg tgatgcatga    2880
ggctctgcac aaccactaca cgcagaagag cctctccctg tctccgggta atgagaatt    2940 cctcgagtct agagggcccg tttaaacccg ctgatcagcc tcgactgtgc cttctagttg    3000
ccagccatct gttgtttgcc cctccccgt gccttccttg accctggaag gtgccactcc    3060
cactgtcctt tcctaataaa atgaggaaat tgcatcgcat tgtctgagta ggtgtcattc    3120
tattctgggg ggtggggtgg ggcaggacag caaggggag gattgggaag acaatagcag    3180
gcatgctggg gatgcggtgg gctctatggc ttctgaggcg gaaagaacca gctggggctc    3240
tagggggtat ccccacgcgc cctgtagcgg cgcattaagc gcggcgggtg tggtggttac    3300
gcgcagcgtg accgctacac ttgccagcgc cctagcgccc gctcctttcg ctttcttccc    3360
```

-continued

| | | |
|---|---|---|
| ttcctttctc gccacgttcg ccggctttcc ccgtcaagct ctaaatcggg gcatccctttt | 3420 | |
| agggttccga tttagtgctt tacggcacct cgacccccaaa aaacttgatt agggtgatgg | 3480 | |
| ttcacgtagt gggccatcgc cctgatagac ggttttttcgc cctttgacgt tggagtccac | 3540 | |
| gttctttaat agtggactct tgttccaaac tggaacaaca ctcaacccta tctcggtcta | 3600 | |
| ttcttttgat ttataaggga ttttggggat ttcggcctat tggttaaaaa atgagctgat | 3660 | |
| ttaacaaaaa tttaacgcga attaattctg tggaatgtgt gtcagttagg gtgtggaaag | 3720 | |
| tccccaggct ccccaggcag gcagaagtat gcaaagcatg catctcaatt agtcagcaac | 3780 | |
| caggtgtgga aagtccccag gctccccagc aggcagaagt atgcaaagca tgcatctcaa | 3840 | |
| ttagtcagca accatagtcc cgcccctaac tccgcccatc ccgcccctaa ctccgcccag | 3900 | |
| ttccgcccat tctccgcccc atggctgact aattttttttt atttatgcag aggccgaggc | 3960 | |
| cgcctctgcc tctgagctat tccagaagta gtgaggaggc ttttttggag gcctaggctt | 4020 | |
| ttgcaaaaag ctcccgggag cttgtatatc cattttcgga tctgatcagc acgtgatgaa | 4080 | |
| aaagcctgaa ctcaccgcga cgtctgtcga gaagtttctg atcgaaaagt tcgacagcgt | 4140 | |
| ctccgacctg atgcagctct cggagggcga agaatctcgt gctttcagct tcgatgtagg | 4200 | |
| agggcgtgga tatgtcctgc gggtaaatag ctgcgccgat ggtttctaca aagatcgtta | 4260 | |
| tgtttatcgg cactttgcat cggccgcgct cccgattccg gaagtgcttg acattgggga | 4320 | |
| attcagcgag agcctgacct attgcatctc ccgccgtgca cagggtgtca cgttgcaaga | 4380 | |
| cctgcctgaa accgaactgc ccgctgttct gcagccggtc gcggaggcca tggatgcgat | 4440 | |
| cgctgcggcc gatcttagcc agacgagcgg gttcggccca ttcggaccgc aaggaatcgg | 4500 | |
| tcaatacact acatggcgtg atttcatatg cgcgattgct gatccccatg tgtatcactg | 4560 | |
| gcaaactgtg atggacgaca ccgtcagtgc gtccgtcgcg caggctctcg atgagctgat | 4620 | |
| gctttgggcc gaggactgcc ccgaagtccg gcacctcgtg cacgcggatt tcggctccaa | 4680 | |
| caatgtcctg acggacaatg gccgcataac agcggtcatt gactgagcg aggcgatgtt | 4740 | |
| cggggattcc caatacgagg tcgccaacat cttcttctgg aggccgtggt tggcttgtat | 4800 | |
| ggagcagcag acgcgctact tcgagcggag gcatccggag cttgcaggat cgccgcggct | 4860 | |
| ccgggcgtat atgctccgca ttggtcttga ccaactctat cagagcttgg ttgacggcaa | 4920 | |
| tttcgatgat gcagcttggg cgcagggtcg atgcgacgca atcgtccgat ccggagccgg | 4980 | |
| gactgtcggg cgtacacaaa tcgcccgcag aagcgcggcc gtctggaccg atggctgtgt | 5040 | |
| agaagtactc gccgatagtg gaaaccgacg ccccagcact cgtccgaggg caaaggaata | 5100 | |
| gcacgtgcta cgagatttcg attccaccgc cgccttctat gaaaggttgg gcttcggaat | 5160 | |
| cgttttccgg gacgccggct ggatgatcct ccagcgcggg gatctcatgc tggagttctt | 5220 | |
| cgcccacccc aacttgttta ttgcagctta taatggttac aaataaagca atagcatcac | 5280 | |
| aaatttcaca aataaagcat ttttttcact gcattctagt tgtggtttgt ccaaactcat | 5340 | |
| caatgtatct tatcatgtct gtataccgtc gacctctagc tagagcttgg cgtaatcatg | 5400 | |
| gtcatagctg tttcctgtgt gaaattgtta tccgctcaca attccacaca acatacgagc | 5460 | |
| cggaagcata aagtgtaaag cctggggtgc ctaatgagtg agctaactca cattaattgc | 5520 | |
| gttgcgctca ctgcccgctt tccagtcggg aaacctgtcg tgccagctgc attaatgaat | 5580 | |
| cggccaacgc gcggggagag gcggtttgcg tattgggcgc tcttccgctt cctcgctcac | 5640 | |
| tgactcgctg cgctcggtcg ttcggctgcg gcgagcggta tcagctcact caaaggcggt | 5700 | |
| aatacggtta tccacagaat caggggataa cgcaggaaag aacatgtgag caaaaggcca | 5760 | |

-continued

```
gcaaaaggcc aggaaccgta aaaaggccgc gttgctggcg ttttcccata ggctccgccc    5820
ccctgacgag catcacaaaa atcgacgctc aagtcagagg tggcgaaacc cgacaggact    5880
ataaagatac caggcgtttc ccctggaag ctccctcgtg cgctctcctg ttccgaccct     5940
gccgcttacc ggatacctgt ccgcctttct cccttcggga agcgtggcgc tttctcaatg    6000
ctcacgctgt aggtatctca gttcggtgta ggtcgttcgc tccaagctgg gctgtgtgca    6060 cgaaccccc gttcagcccg accgctgcgc cttatccggt aactatcgtc ttgagtccaa     6120
cccggtaaga cacgacttat cgccactggc agcagccact ggtaacagga ttagcagagc    6180
gaggtatgta ggcggtgcta cagagttctt gaagtggtgg cctaactacg gctacactag    6240
aaggacagta tttggtatct gcgctctgct gaagccagtt accttcggaa aaagagttgg    6300
tagctcttga tccggcaaac aaaccaccgc tggtagcggt ggtttttttg tttgcaagca    6360
gcagattacg cgcagaaaaa aaggatctca agaagatcct ttgatctttt ctacggggtc    6420
tgacgctcag tggaacgaaa actcacgtta agggattttg gtcatgagat tatcaaaaag    6480
gatcttcacc tagatccttt taaattaaaa atgaagtttt aaatcaatct aaagtatata    6540
tgagtaaact tggtctgaca gttaccaatg cttaatcagt gaggcaccta tctcagcgat    6600
ctgtctattt cgttcatcca tagttgcctg actccccgtc gtgtagataa ctacgatacg    6660
ggagggctta ccatctggcc ccagtgctgc aatgatacccg cgagacccac gctcaccggc   6720
tccagattta tcagcaataa accagccagc cggaagggcc gagcgcagaa gtggtcctgc    6780
aactttatcc gcctccatcc agtctattaa ttgttgccgg gaagctagag taagtagttc    6840
gccagttaat agtttgcgca acgttgttgc cattgctaca ggcatcgtgg tgtcacgctc    6900
gtcgtttggt atggcttcat tcagctccgg ttcccaacga tcaaggcgag ttacatgatc    6960
ccccatgttg tgcaaaaaag cggttagctc cttcggtcct ccgatcgttg tcagaagtaa    7020
gttggccgca gtgttatcac tcatggttat ggcagcactg cataattctc ttactgtcat    7080
gccatccgta agatgctttt ctgtgactgg tgagtactca accaagtcat tctgagaata    7140
gtgtatgcgg cgaccgagtt gctcttgccc ggcgtcaata cgggataata ccgcgccaca    7200
tagcagaact ttaaaagtgc tcatcattgg aaaacgttct cggggcgaa aactctcaag      7260 gatcttaccg ctgttgagat ccagttcgat gtaacccact cgtgcaccca actgatcttc    7320
agcatctttt actttcacca gcgtttctgg gtgagcaaaa acaggaaggc aaaatgccgc    7380
aaaaaaggga ataagggcga cacggaaatg ttgaatactc atactcttcc ttttcaata     7440 ttattgaagc atttatcagg gttattgtct catgagcgga tacatatttg aatgtattta    7500
gaaaaataaa caatagggg ttccgcgcac atttccccga aaagtgccac ctgacgtc       7558
```

<210> SEQ ID NO 6
<211> LENGTH: 7576
<212> TYPE: DNA
<213> ORGANISM: Artificial Sequence
<220> FEATURE:
<223> OTHER INFORMATION: Synthetic Oligonucleotide

<400> SEQUENCE: 6

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
```

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatggagtt tgggctgtgc tggattttcc tcgttgctct    960
tttaagaggt gtccagtgtc aggtgcagct ggtggagtct gggggaggcg tggtccagcc   1020
tgggaggtcc ctgagactct cctgtgcagc ctctggattc accttcatta gctatggcat   1080
gcactgggtc cgccaggctc caggcaaggg gctggagtgg gtggcagtta tatcatatga   1140
tggaagtaat aaatactatg cagactccgt gaagggccga ttcaccatct ccagagacaa   1200
ttccaagaac acgctgtatc tgcaaatgaa cagcctgaga gctgaggaca cggctgtgta   1260
ttactgtgcg agagtattag tgggagcttt atattattat aactactacg ggatggacgt   1320
ctggggccaa gggaccacgg tcaccgtctc ctcagcctcc accaagggcc catcggtctt   1380
ccccctggca ccctctagca agagcacctc tgggggcaca gcggccctgg gctgcctggt   1440
caaggactac ttccccgaac cggtgacggt gtcgtggaac tcaggcgccc tgaccagcgg   1500
cgtgcacacc ttcccggctg tcctacagtc ctcaggactc tactccctca gcagcgtggt   1560
gaccgtgccc tccagcagct tgggcaccca gacctacatc tgcaacgtga atcacaagcc   1620
cagcaacacc aaggtggaca agagagttgg tgagaggcca gcacagggag ggagggtgtc   1680
tgctggaagc caggctcagc gctcctgcct ggacgcatcc cggctatgca gtcccagtcc   1740
agggcagcaa ggcaggcccc gtctgcctct tcacccggag gcctctgccc gccccactca   1800
tgctcaggga gagggtcttc tggctttttc cccaggctct gggcaggcac aggctaggtg   1860
cccctaaccc aggccctgca cacaaagggg caggtgctgg gctcagacct gccaagagcc   1920
atatccggga ggaccctgcc cctgacctaa gcccacccca aaggccaaac tctccactcc   1980
ctcagctcgg acaccttctc tcctcccaga ttccagtaac tcccaatctt ctctctgcag   2040
agcccaaatc ttgtgacaaa actcacacat gcccaccgtg cccaggtaag ccagcccagg   2100
cctcgccctc cagctcaagg cgggacaggt gccctagagt agcctgcatc caggacagg   2160 ccccagccgg gtgctgacac gtccacctcc atctcttcct cagcacctga actcctgggg   2220
ggaccgtcag tcttcctctt ccccccaaaa cccaaggaca ccctcatgat ctcccggacc   2280
cctgaggtca catgcgtggt ggtggacgtg agccacgaag accctgaggt caagttcaac   2340
tggtacgtgg acggcgtgga ggtgcataat gccaagacaa agccgcggga ggagcagtac   2400
aacagcacgt accgtgtggt cagcgtcctc accgtcctgc accaggactg gctgaatggc   2460
aaggagtaca agtgcaaggt ctccaacaaa gccctcccag cccccatcga gaaaaccatc   2520
tccaaagcca aggtgggac ccgtggggtg cgagggccac atggacagag gccggctcgg   2580 cccacccctct gccctgagag tgaccgctgt accaacctct gtccctacag gcagccccg   2640 agaaccacag gtgtacaccc tgcccccatc ccggaggag atgaccaaga accaggtcag   2700
```

```
cctgacctgc ctggtcaaag gcttctatcc cagcgacatc gccgtggagt gggagagcaa    2760
tgggcagccg gagaacaact acaagaccac gcctcccgtg ctggactccg acggctcctt    2820
cttcctctat agcaagctca ccgtggacaa gagcaggtgg cagcagggga acgtcttctc    2880
atgctccgtg atgcatgagg ctctgcacaa ccactacacg cagaagagcc tctccctgtc    2940
tccgggtaaa tgagaattcc tcgagtctag agggcccgtt taaacccgct gatcagcctc    3000
gactgtgcct tctagttgcc agccatctgt tgtttgcccc tcccccgtgc cttccttgac    3060
cctggaaggt gccactccca ctgtcctttc ctaataaaat gaggaaattg catcgcattg    3120
tctgagtagg tgtcattcta ttctgggggg tggggtgggg caggacagca agggggagga    3180
ttgggaagac aatagcaggc atgctgggga tgcggtgggc tctatggctt ctgaggcgga    3240
aagaaccagc tggggctcta gggggtatcc ccacgcgccc tgtagcggcg cattaagcgc    3300
ggcgggtgtg gtggttacgc gcagcgtgac cgctacactt gccagcgccc tagcgcccgc    3360
tcctttcgct ttcttccctt cctttctcgc cacgttcgcc ggctttcccc gtcaagctct    3420
aaatcggggc atccctttag ggttccgatt tagtgcttta cggcacctcg accccaaaaa    3480
acttgattag ggtgatggtt cacgtagtgg gccatcgccc tgatagacgg ttttcgccc    3540 tttgacgttg gagtccacgt tctttaatag tggactcttg ttccaaactg gaacaacact    3600
caaccctatc tcggtctatt cttttgattt ataagggatt tgggggattt cggcctattg    3660
gttaaaaaat gagctgattt aacaaaaatt taacgcgaat taattctgtg aatgtgtgt    3720 cagttagggt gtggaaagtc cccaggctcc ccaggcaggc agaagtatgc aaagcatgca    3780
tctcaattag tcagcaacca ggtgtggaaa gtccccaggc tccccagcag gcagaagtat    3840
gcaaagcatg catctcaatt agtcagcaac catagtcccg cccctaactc cgcccatccc    3900
gcccctaact ccgcccagtt ccgcccattc tccgccccat ggctgactaa ttttttttat    3960
ttatgcagag gccgaggccg cctctgcctc tgagctattc cagaagtagt gaggaggctt    4020
ttttggaggc ctaggctttt gcaaaaagct cccgggagct gtatatcca ttttcggatc    4080 tgatcagcac gtgatgaaaa agcctgaact caccgcgacg tctgtcgaga agtttctgat    4140
cgaaaagttc gacagcgtct ccgacctgat gcagctctcg gagggcgaag aatctcgtgc    4200
tttcagcttc gatgtaggag ggcgtggata tgtcctgcgg gtaaatagct gcgccgatgg    4260
tttctacaaa gatcgttatg tttatcggca ctttgcatcg gccgcgctcc cgattccgga    4320
agtgcttgac attggggaat tcagcgagag cctgacctat tgcatctccc gccgtgcaca    4380
gggtgtcacg ttgcaagacc tgcctgaaac cgaactgccc gctgttctgc agccggtcgc    4440
ggaggccatg gatgcgatcg ctgcggccga tcttagccag acgagcgggt tcggcccatt    4500
cggaccgcaa ggaatcggtc aatacactac atggcgtgat ttcatatgcg cgattgctga    4560
tccccatgtg tatcactggc aaactgtgat ggacgacacc gtcagtgcgt ccgtcgcgca    4620
ggctctcgat gagctgatgc tttgggccga ggactgcccc gaagtccggc acctcgtgca    4680
cgcggatttc ggctccaaca atgtcctgac ggacaatggc cgcataacag cggtcattga    4740
ctggagcgag gcgatgttcg gggattccca atacgaggtc gccaacatct tcttctggag    4800
gccgtggttg gcttgtatgg agcagcagac gcgctacttc gagcggaggc atccggagct    4860
tgcaggatcg ccgcggctcc gggcgtatat gctccgcatt ggtcttgacc aactctatca    4920
gagcttggtt gacggcaatt tcgatgatgc agcttgggcg cagggtcgat gcgacgcaat    4980
cgtccgatcc ggagccggga ctgtcgggcg tacacaaatc gcccgcagaa gcgcggccgt    5040
ctggaccgat ggctgtgtag aagtactcgc cgatagtgga aaccgacgcc ccagcactcg    5100
```

```
tccgagggca aaggaatagc acgtgctacg agatttcgat tccaccgccg ccttctatga   5160
aaggttgggc ttcggaatcg ttttccggga cgccggctgg atgatcctcc agcgcgggga   5220
tctcatgctg gagttcttcg cccaccccaa cttgtttatt gcagcttata atggttacaa   5280
ataaagcaat agcatcacaa atttcacaaa taaagcattt ttttcactgc attctagttg   5340
tggtttgtcc aaactcatca atgtatctta tcatgtctgt ataccgtcga cctctagcta   5400
gagcttggcg taatcatggt catagctgtt tcctgtgtga aattgttatc cgctcacaat   5460
tccacacaac atacgagccg gaagcataaa gtgtaaagcc tggggtgcct aatgagtgag   5520
ctaactcaca ttaattgcgt tgcgctcact gcccgctttc cagtcgggaa acctgtcgtg   5580
ccagctgcat taatgaatcg gccaacgcgc ggggagaggc ggtttgcgta ttgggcgctc   5640
ttccgcttcc tcgctcactg actcgctgcg ctcggtcgtt cggctgcggc gagcggtatc   5700
agctcactca aaggcggtaa tacggttatc cacagaatca ggggataacg caggaaagaa   5760
catgtgagca aaaggccagc aaaaggccag gaaccgtaaa aaggccgcgt tgctggcgtt   5820
tttccatagg ctccgccccc ctgacgagca tcacaaaaat cgacgctcaa gtcagaggtg   5880
gcgaaacccg acaggactat aaagatacca ggcgtttccc cctggaagct ccctcgtgcg   5940
ctctcctgtt ccgaccctgc cgcttaccgg atacctgtcc gcctttctcc cttcgggaag   6000
cgtggcgctt tctcaatgct cacgctgtag gtatctcagt tcggtgtagg tcgttcgctc   6060
caagctgggc tgtgtgcacg aaccccccgt tcagcccgac cgctgcgcct tatccggtaa   6120
ctatcgtctt gagtccaacc cggtaagaca cgacttatcg ccactggcag cagccactgg   6180
taacaggatt agcagagcga ggtatgtagg cggtgctaca gagttcttga agtggtggcc   6240
taactacggc tacactagaa ggacagtatt tggtatctgc gctctgctga agccagttac   6300
cttcggaaaa agagttggta gctcttgatc cggcaaacaa accaccgctg gtagcggtgg   6360
tttttttgtt tgcaagcagc agattacgcg cagaaaaaaa ggatctcaag aagatccttt   6420
gatcttttct acggggtctg acgctcagtg gaacgaaaac tcacgttaag ggattttggt   6480
catgagatta tcaaaaagga tcttcaccta gatcctttta aattaaaaat gaagttttaa   6540
atcaatctaa agtatatatg agtaaacttg gtctgacagt taccaatgct taatcagtga   6600
ggcacctatc tcagcgatct gtctatttcg ttcatccata gttgcctgac tccccgtcgt   6660
gtagataact acgatacggg agggcttacc atctggcccc agtgctgcaa tgataccgcg   6720
agacccacgc tcaccggctc cagatttatc agcaataaac cagccagccg aagggccga   6780
gcgcagaagt ggtcctgcaa ctttatccgc ctccatccag tctattaatt gttgccggga   6840
agctagagta agtagttcgc cagttaatag tttgcgcaac gttgttgcca ttgctacagg   6900
catcgtggtg tcacgctcgt cgtttggtat ggcttcattc agctccggtt cccaacgatc   6960
aaggcgagtt acatgatccc ccatgttgtg caaaaaagcg gttagctcct tcggtcctcc   7020
gatcgttgtc agaagtaagt tggccgcagt gttatcactc atggttatgg cagcactgca   7080
taattctctt actgtcatgc catccgtaag atgcttttct gtgactggtg agtactcaac   7140
caagtcattc tgagaatagt gtatgcggcg accgagttgc tcttgcccgg cgtcaatacg   7200
ggataatacc gcgccacata gcagaacttt aaaagtgctc atcattggaa aacgttcttc   7260
ggggcgaaaa ctctcaagga tcttaccgct gttgagatcc agttcgatgt aacccactcg   7320
tgcacccaac tgatcttcag catctttac tttcaccagc gtttctgggt gagcaaaaac   7380
aggaaggcaa aatgccgcaa aaaagggaat aagggcgaca cggaaatgtt gaatactcat   7440
actcttcctt tttcaatatt attgaagcat ttatcagggt tattgtctca tgagcggata   7500
```

```
catatttgaa tgtatttaga aaaataaaca aataggggtt ccgcgcacat tccccgaaa    7560 agtgccacct gacgtc                                                  7576

<210> SEQ ID NO 7
<211> LENGTH: 7561
<212> TYPE: DNA
<213> ORGANISM: Artificial Sequence
<220> FEATURE:
<223> OTHER INFORMATION: Synthetic Oligonucleotide

<400> SEQUENCE: 7
gacggatcgg gagatctccc gatccctat ggtcgactct cagtacaatc tgctctgatg     60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg    780
gtaggcgtgt acggtgggag gtctatataa gcagagctct ctggctaact agagaaccca   840
ctgcttactg gcttatcgaa attaatacga ctcactatag ggagacccaa gctggctaga   900
ggtaccggat ctcaccatgg agttgggct gagctgggtt ttcctcgttg ctctttttaag    960 aggtgtccag tgtcaggagc agctggtgga gtcgggggga ggcgtggtcc agcctgggag   1020
gtccctgaga ctctcctgtg cagcgtctgg attcaccttc agtacctatg gcatgcactg   1080
ggtccgccag gctccaggca aggggctgga gtgggtggca gttacatggc atgatggaag   1140
taataaatac tatgcagact ccgtgaaggg ccgattcacc atctccagag acaactccaa   1200
gaacacgctg tatctgcaaa tgaacagcct gagagccgag gacacggctg tgtattactg   1260
tgcgagagga ggagtgggag caacttacta ctactactac ggtatggacg tctgggccaa   1320
agggaccacg gtcaccgtct cctcagcctc caccaagggc ccatcggtct tccccctggc   1380
accctctagc aagagcacct ctgggggcac agcggccctg ggctgcctgg tcaaggacta   1440
cttccccgaa ccggtgacgg tgtcgtggaa ctcaggcgcc ctgaccagcg gcgtgcacac   1500
cttcccggct gtcctacagt cctcaggact ctactccctc agcagcgtgg tgaccgtgcc   1560
ctccagcagc ttgggcaccc agacctacat ctgcaacgtg aatcacaagc ccagcaacac   1620
caaggtggac aagagagttg gtgagaggcc agcacaggga gggagggtgt ctgctggaag   1680
ccaggctcag cgctcctgcc tggacgcatc ccggctatgc agtcccagtc cagggcagca   1740
aggcaggccc cgtctgcctc ttcacccgga ggcctctgcc cgccccactc atgctcaggg   1800
agagggtctt ctggcttttt cccaggctct gggcaggca caggctaggt gcccctaacc   1860
caggccctgc acacaaaggg gcaggtgctg ggctcagacc tgccaagagc catatccggg   1920
aggaccctgc ccctgaccta agcccacccc aaaggccaaa ctctccactc cctcagctcg   1980
```

```
gacaccttct ctcctcccag attccagtaa ctcccaatct tctctctgca gagcccaaat    2040
cttgtgacaa aactcacaca tgcccaccgt gcccaggtaa gccagcccag gcctcgccct    2100
ccagctcaag gcgggacagg tgccctagag tagcctgcat ccagggacag gccccagccg    2160
ggtgctgaca cgtccacctc catctcttcc tcagcacctg aactcctggg gggaccgtca    2220
gtcttcctct tcccccccaaa acccaaggac accctcatga tctcccggac ccctgaggtc   2280
acatgcgtgg tggtggacgt gagccacgaa gaccctgagg tcaagttcaa ctggtacgtg    2340
gacggcgtgg aggtgcataa tgccaagaca aagccgcggg aggagcagta acagcacg     2400 taccgtgtgg tcagcgtcct caccgtcctg caccaggact ggctgaatgg caaggagtac    2460
aagtgcaagg tctccaacaa agccctccca gcccccatcg agaaaaccat ctccaaagcc    2520
aaaggtggga cccgtggggt gcgagggcca catggacaga ggccggctcg gcccaccctc    2580
tgccctgaga gtgaccgctg taccaacctc tgtccctaca gggcagcccc gagaaccaca    2640
ggtgtacacc ctgcccccat cccgggagga gatgaccaag aaccaggtca gcctgacctg    2700
cctggtcaaa ggcttctatc ccagcgacat cgccgtggag tgggagagca atgggcagcc    2760
ggagaacaac tacaagacca cgcctcccgt gctggactcc gacggctcct tcttcctcta    2820
tagcaagctc accgtggaca agagcaggtg gcagcagggg aacgtcttct catgctccgt    2880
gatgcatgag gctctgcaca accactacac gcagaagagc ctctccctgt ctccgggtaa    2940
atgactcgag tctagagggc ccgtttaaac ccgctgatca gcctcgactg tgccttctag    3000
ttgccagcca tctgttgttt gcccctcccc cgtgccttcc ttgacctggg aaggtgccac    3060
tcccactgtc ctttcctaat aaaatgagga aattgcatcg cattgtctga gtaggtgtca    3120
ttctattctg gggggtgggg tggggcagga cagcaagggg gaggattggg aagacaatag    3180
caggcatgct ggggatgcgg tggctctat ggcttctgag gcggaaagaa ccagctgggg     3240
ctctaggggg tatccccacg cgccctgtag cggcgcatta gcgcggcgg gtgtggtggt     3300 tacgcgcagc gtgaccgcta cacttgccag cgccctagcg cccgctcctt tcgctttctt    3360
cccttccttt ctcgccacgt tcgccggctt tccccgtcaa gctctaaatc ggggcatccc    3420
tttagggttc cgatttagtg ctttacggca cctcgacccc aaaaaacttg attagggtga    3480
tggttcacgt agtgggccat cgccctgata cggggttttt cgccctttga cgttggagtc    3540
cacgttcttt aatagtggac tcttgttcca aactggaaca acactcaacc ctatctcggt    3600
ctattctttt gatttataag ggattttggg gatttcggcc tattggttaa aaaatgagct    3660
gatttaacaa aaatttaacg cgaattaatt ctgtggaatg tgtgtcagtt agggtgtgga    3720
aagtccccag gctccccagg caggcagaag tatgcaaagc atgcatctca attagtcagc    3780
aaccaggtgt ggaaagtccc caggctcccc agcaggcaga agtatgcaaa gcatgcatct    3840
caattagtca gcaaccatag tcccgcccct aactccgccc atcccgcccc taactccgcc    3900
cagttccgcc cattctccgc cccatggctg actaattttt tttatttatg cagaggccga    3960
ggccgcctct gcctctgagc tattccagaa gtagtgagga ggcttttttg gaggcctagg    4020
cttttgcaaa aagctcccgg gagcttgtat atccattttc ggatctgatc agcacgtgat    4080
gaaaaagcct gaactcaccg cgacgtctgt cgagaagttt ctgatcgaaa agttcgacag    4140
cgtctccgac ctgatgcagc tctcggaggg cgaagaatct cgtgctttca gcttcgatgt    4200
aggagggcgt ggatatgtcc tgcgggtaaa tagctgcgcc gatggtttct acaaagatcg    4260
ttatgtttat cggcactttg catcggccgc gctcccgatt ccggaagtgc ttgacattgg    4320
ggaattcagc gagagcctga cctattgcat ctcccgccgt gcacagggtg tcacgttgca    4380
```

```
agacctgcct gaaaccgaac tgcccgctgt tctgcagccg gtcgcggagg ccatggatgc    4440
gatcgctgcg gccgatctta gccagacgag cgggttcggc ccattcggac cgcaaggaat    4500
cggtcaatac actacatggc gtgatttcat atgcgcgatt gctgatcccc atgtgtatca    4560
ctggcaaact gtgatggacg acaccgtcag tgcgtccgtc gcgcaggctc tcgatgagct    4620
gatgctttgg gccgaggact gccccgaagt ccggcacctc gtgcacgcgg atttcggctc    4680
caacaatgtc ctgacggaca atggccgcat aacagcggtc attgactgga gcgaggcgat    4740
gttcggggat tcccaatacg aggtcgccaa catcttcttc tggaggccgt ggttggcttg    4800
tatggagcag cagacgcgct acttcgagcg gaggcatccg gagcttgcag gatcgccgcg    4860
gctccgggcg tatatgctcc gcattggtct tgaccaactc tatcagagct tggttgacgg    4920
caatttcgat gatgcagctt gggcgcaggg tcgatgcgac gcaatcgtcc gatccggagc    4980
cgggactgtc gggcgtacac aaatcgcccg cagaagcgcg gccgtctgga ccgatggctg    5040
tgtagaagta ctcgccgata gtggaaaccg acgcccagc actcgtccga gggcaaagga    5100
atagcacgtg ctacgagatt tcgattccac cgccgccttc tatgaaaggt tgggcttcgg    5160
aatcgttttc cgggacgccg gctggatgat cctccagcgc ggggatctca tgctggagtt    5220
cttcgcccac cccaacttgt ttattgcagc ttataatggt tacaaataaa gcaatagcat    5280
cacaaatttc acaaataaag cattttttc actgcattct agttgtggtt tgtccaaact    5340
catcaatgta tcttatcatg tctgtatacc gtcgacctct agctagagct tggcgtaatc    5400
atggtcatag ctgtttcctg tgtgaaattg ttatccgctc acaattccac acaacatacg    5460
agccggaagc ataaagtgta aagcctgggg tgcctaatga gtgagctaac tcacattaat    5520
tgcgttgcgc tcactgcccg ctttccagtc gggaaacctg tcgtgccagc tgcattaatg    5580
aatcggccaa cgcgcgggga gaggcggttt gcgtattggg cgctcttccg cttcctcgct    5640
cactgactcg ctgcgctcgg tcgttcggct gcggcgagcg gtatcagctc actcaaaggc    5700
ggtaatacgg ttatccacag aatcagggga taacgcagga aagaacatgt gagcaaaagg    5760
ccagcaaaag gccaggaacc gtaaaaaggc cgcgttgctg gcgttttcc ataggctccg    5820 cccccctgac gagcatcaca aaaatcgacg ctcaagtcag aggtggcgaa acccgacagg    5880
actataaaga taccaggcgt ttccccctgg aagctccctc gtgcgctctc ctgttccgac    5940
cctgccgctt accggatacc tgtccgcctt tctcccttcg ggaagcgtgg cgctttctca    6000
atgctcacgc tgtaggtatc tcagttcggt gtaggtcgtt cgctccaagc tgggctgtgt    6060
gcacgaaccc cccgttcagc ccgaccgctg cgccttatcc ggtaactatc gtcttgagtc    6120
caacccggta agacacgact tatcgccact ggcagcagcc actggtaaca ggattagcag    6180
agcgaggtat gtaggcggtg ctacagagtt cttgaagtgg tggcctaact acggctacac    6240
tagaaggaca gtatttggta tctgcgctct gctgaagcca gttaccttcg gaaaaagagt    6300
tggtagctct tgatccggca aacaaaccac cgctggtagc ggtggttttt ttgtttgcaa    6360
gcagcagatt acgcgcagaa aaaaaggatc tcaagaagat cctttgatct tttctacggg    6420
gtctgacgct cagtggaacg aaaactcacg ttaagggatt ttggtcatga gattatcaaa    6480
aaggatcttc acctagatcc ttttaaatta aaaatgaagt tttaaatcaa tctaaagtat    6540
atatgagtaa acttggtctg acagttacca atgcttaatc agtgaggcac ctatctcagc    6600
gatctgtcta tttcgttcat ccatagttgc ctgactcccc gtcgtgtaga taactacgat    6660
acgggagggc ttaccatctg gccccagtgc tgcaatgata ccgcgagacc cacgctcacc    6720
ggctccagat ttatcagcaa taaaccagcc agccggaagg gccgagcgca gaagtggtcc    6780
```

-continued

| | |
|---|---|
| tgcaacttta tccgcctcca tccagtctat taattgttgc cgggaagcta gagtaagtag | 6840 |
| ttcgccagtt aatagtttgc gcaacgttgt tgccattgct acaggcatcg tggtgtcacg | 6900 |
| ctcgtcgttt ggtatggctt cattcagctc cggttcccaa cgatcaaggc gagttacatg | 6960 |
| atcccccatg ttgtgcaaaa aagcggttag ctccttcgt cctccgatcg ttgtcagaag | 7020 |
| taagttggcc gcagtgttat cactcatggt tatggcagca ctgcataatt ctcttactgt | 7080 |
| catgccatcc gtaagatgct tttctgtgac tggtgagtac tcaaccaagt cattctgaga | 7140 |
| atagtgtatg cggcgaccga gttgctcttg cccggcgtca atacgggata taccgcgcc | 7200 |
| acatagcaga actttaaaag tgctcatcat tggaaaacgt tcttcgggc gaaaactctc | 7260 |
| aaggatctta ccgctgttga tccagttc gatgtaaccc actcgtgcac ccaactgatc | 7320 |
| ttcagcatct tttactttca ccagcgtttc tgggtgagca aaaacaggaa ggcaaaatgc | 7380 |
| cgcaaaaaag gaataagggg cgacacggaa atgttgaata ctcatactct ccttttttca | 7440 |
| atattattga agcatttatc agggttattg tctcatgagc ggatacatat ttgaatgtat | 7500 |
| ttagaaaaat aaacaaatag gggttccgcg cacatttccc cgaaaagtgc cacctgacgt | 7560 |
| c | 7561 |

<210> SEQ ID NO 8
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 8

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccaccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatga gggtccctgc tcagctcctg gactcctgc tgctctggct | 960 |
| cccagatacc agatgtgaca tccagatgac ccagtctcca tcctccctgt ctgcatctgt | 1020 |
| aggagacaga gtcaccatca cttgccgggc gagtcagggc attagcaatt atttagcctg | 1080 |
| gtatcagcag aaaacaggga agttcctaa gttcctgatc tatgaagcat ccactttgca | 1140 |
| atcaggggtc ccatctcggt tcagtggcgg tggatctggg acagatttca ctctcaccat | 1200 |
| cagcagcctg cagcctgaag atgttgcaac ttattactgt caaaattata acagtgcccc | 1260 |

```
attcactttc ggccctggga ccaaagtgga tatcaaacga actgtggctg caccctctgt    1320
cttcatcttc ccgccatctg atgagcagtt gaaatctgga actgctagcg ttgtgtgcct    1380
gctgaataac ttctatccca gagaggccaa agtacagtgg aaggtggata acgccctcca    1440
atcgggtaac tcccaggaga gtgtcacaga gcaggacagc aaggacagca cctacagcct    1500
cagcagcacc ctgacgctga gcaaagcaga ctacgagaaa cacaaagtct acgcctgcga    1560
agtcacccat cagggcctga gctcgcccgt cacaaagagc ttcaacaggg gagagtgtta    1620
ggaattcgcg gccgctcgag tctagagggc ccgtttaaac ccgctgatca gcctcgactg    1680
tgccttctag ttgccagcca tctgttgttt gcccctcccc cgtgccttcc ttgaccctgg    1740
aaggtgccac tcccactgtc ctttcctaat aaaatgagga aattgcatcg cattgtctga    1800
gtaggtgtca ttctattctg ggggtgggg tggggcagga cagcaagggg gaggattggg    1860
aagacaatag caggcatgct ggggatgcgg tgggctctat ggcttctgag gcggaaagaa    1920
ccagctgggg ctctagggg tatccccacg cgccctgtag cggcgcatta agcgcggcgg    1980
gtgtggtggt tacgcgcagc gtgaccgcta cacttgccag cgccctagcg cccgctcctt    2040
tcgctttctt cccttccttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata cggttttt cgcccttga    2220
cgttggagtc cacgttcttt aatagtggac tcttgttcca aactggaaca cactcaacc    2280
ctatctcggt ctattctttt gatttataag gattttggg gatttcggcc tattggttaa    2340
aaaatgagct gatttaacaa aaatttaacg cgaattaatt ctgtggaatg tgtgtcagtt    2400
agggtgtgga aagtccccag gctcccccag caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaattttt tttatttatg    2640
cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc aggggcgccc ggttcttttt gtcaagaccg    2940
acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg aagccggtc    3240
ttgtcgatca ggatgatctg gacgaagagc atcagggct cgcgccagcc gaactgttcg    3300
ccaggctcaa ggcgcgcatg cccgacggcg aggatctcgt cgtgacccat ggcgatgcct    3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat tcgattccca ccgccgcctt    3660
```

```
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcattttttt cactgcattc    3840
tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg gtcgttcggc tgcggcgagc    4200
ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
```

| | |
|---|---|
| ccgaaaagtg ccacctgacg tc | 6082 |

<210> SEQ ID NO 9
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 9

| | |
|---|---|
| gacggatcgg gagatctccc gatccsctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatga gggtccccgc tcagctcctg gggctcctgc tgctctgttt | 960 |
| cccaggtgcc agatgtgaca tccagatgac ccagtctcca tcctcactgt ctgcatctgt | 1020 |
| aggagacaga gtcaccatca cttgtcgggc gagtcaggsc attaccaatt atttagcctg | 1080 |
| gtttcagcag aaaccaggga aagcccctaa gtcccttatc tatgctgcat ccagtttgca | 1140 |
| aagtgggatc ccatcaaagt tcagcggcag tggatctggg acagatttca gtctcaccat | 1200 |
| cagcagcctg cagcctgaag attttgcaac ttattactgc caacagtata atagttaccc | 1260 |
| gatcaccttc ggccaaggga cacgactgga gattaaacga actgtggctg caccatctgt | 1320 |
| cttcatcttc ccgccatctg atgagcagtt gaaatctgga actgctagcg ttgtgtgcct | 1380 |
| gctgaataac ttctatccca gagaggccaa agtacagtgg aaggtggata acgccctcca | 1440 |
| atcgggtaac tcccaggaga gtgtcacaga gcaggacagc aaggacagca cctacagcct | 1500 |
| cagcagcacc ctgacgctga gcaaagcaga ctacgagaaa cacaaagtct acgcctgcga | 1560 |
| agtcacccat cagggcctga gctcgcccgt cacaaagagc ttcaacggg gagagtgtta | 1620 |
| ggaattcgcg gccgctcgag tctagagggc ccgtttaaac ccgctgatca gcctcgactg | 1680 |
| tgccttctag ttgccagcca tctgttgttt gcccctcccc cgtgccttcc ttgaccctgg | 1740 |
| aaggtgccac tcccactgtc ctttcctaat aaaatgagga attgcatcg cattgtctga | 1800 |
| gtaggtgtca ttctattctg gggggtgggg tgggcagga cagcaagggg gaggattggg | 1860 |
| aagacaatag caggcatgct ggggatgcgg tgggctctat ggcttctgag gcggaaagaa | 1920 |
| ccagctgggg ctctaggggg tatccccacg cgccctgtag cggcgcatta agcgcggcgg | 1980 |
| gtgtggtggt tacgcgcagc gtgaccgcta cacttgccag cgccctagcg cccgctcctt | 2040 |

```
tcgctttctt cccttcctttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata gacggttttt cgcccttgga    2220
cgttggagtc cacgttcttt aatagtggac tcttgttcca aactggaaca acactcaacc    2280
ctatctcggt ctattctttt gatttataag gattttggg gatttcggcc tattggttaa    2340
aaaatgagct gatttaacaa aaatttaacg cgaattaatt ctgtggaatg tgtgtcagtt    2400
agggtgtgga aagtccccag gctccccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaattttt tttatttatg    2640
cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc agggggcgccc ggttctttt gtcaagaccg    2940 acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg gaagccggtc    3240
ttgtcgatca ggatgatctg gacgaagagc atcaggggct cgcgccagcc gaactgttcg    3300
ccaggctcaa ggcgcgcatg cccgacggcg aggatctcgt cgtgacccat ggcgatgcct    3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcattttttt cactgcattc    3840
tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg gtcgttcggc tgcggcgagc    4200
ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
```

```
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatcccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                             6082
```

<210> SEQ ID NO 10
<211> LENGTH: 6082
<212> TYPE: DNA
<213> ORGANISM: Artificial Sequence
<220> FEATURE:
<223> OTHER INFORMATION: Synthetic Oligonucleotide

<400> SEQUENCE: 10

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
```

```
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatga gggtccctgc tcagctcctg gggctcctgc tgctctgttt    960
cccaggtgcc agatgtgaca tccagatgac ccagtctcca tcctcactgt ctgcatctgt   1020
aggagacaga gtcaccatca cttgtcgggc gagtcagggc attagccatt atttagcctg   1080
gtttcagcag aaaccaggga aagcccctaa gtccctgatc tatgctgcat ccagtttgca   1140
aagtggggtc ccatcaaagt tcagcggcag tggatctggg acagatttca ctctcaccat   1200
cagcagccta cagcctgaag attttgcaac ttattactgc caacagtata atagtttccc   1260
gctcactttc ggcggaggga ccaaggtgga gatcaaacga actgtggctg caccatctgt   1320
cttcatcttc ccgccatctg atgagcagtt gaaatctgga actgctagcg ttgtgtgcct   1380
gctgaataac ttctatccca gagaggccaa agtacagtgg aaggtggata acgccctcca   1440
atcgggtaac tcccaggaga gtgtcacaga gcaggacagc aaggacagca cctacagcct   1500
cagcagcacc ctgacgctga gcaaagcaga ctacgagaaa cacaaagtct acgcctgcga   1560
agtcacccat cagggcctga gctcgcccgt cacaaagagc ttcaacaggg gagagtgtta   1620
ggaattcgcg gccgctcgag tctagagggc ccgtttaaac ccgctgatca gcctcgactg   1680
tgccttctag ttgccagcca tctgttgttt gcccctcccc cgtgccttcc ttgaccctgg   1740
aaggtgccac tcccactgtc ctttcctaat aaaatgagga aattgcatcg cattgtctga   1800
gtaggtgtca ttctattctg gggggtgggg tggggcagga cagcaagggg gaggattggg   1860
aagacaatag caggcatgct ggggatgcgg tgggctctat ggcttctgag gcggaaagaa   1920
ccagctgggg ctctaggggg tatccccacg cgccctgtag cggcgcatta agcgcggcgg   1980
gtgtggtggt tacgcgcagc gtgaccgcta cacttgccag cgccctagcg cccgctcctt   2040
tcgctttctt cccttccttt ctcgccacgt tcgccggctt tccccgtcaa gctctaaatc   2100
ggggcatccc tttagggttc cgatttagtg ctttacggca cctcgacccc aaaaaacttg   2160
attagggtga tggttcacgt agtgggccat cgccctgata cggttttt cgccctttga   2220 cgttggagtc cacgttcttt aatagtggac tcttgttcca aactggaaca acactcaacc   2280
ctatctcggt ctattctttt gatttataag ggattttggg gatttcggcc tattggttaa   2340
aaaatgagct gatttaacaa aaatttaacg cgaattaatt ctgtggaatg tgtgtcagtt   2400
agggtgtgga agtccccag gctcccagg caggcagaag tatgcaaagc atgcatctca   2460
attagtcagc aaccaggtgt ggaaagtccc caggctcccc agcaggcaga agtatgcaaa   2520
gcatgcatct caattagtca gcaaccatag tcccgcccct aactccgccc atcccgcccc   2580
taactccgcc cagttccgcc cattctccgc cccatggctg actaatttt tttatttatg   2640 cagaggccga ggccgcctct gcctctgagc tattccagaa gtagtgagga ggcttttttg   2700
gaggcctagg cttttgcaaa aagctcccgg gagcttgtat atccatttc ggatctgatc   2760 aagagacagg atgaggatcg tttcgcatga ttgaacaaga tggattgcac gcaggttctc   2820
```

```
cggccgcttg ggtggagagg ctattcggct atgactgggc acaacagaca atcggctgct    2880
ctgatgccgc cgtgttccgg ctgtcagcgc aggggcgccc ggttctttt gtcaagaccg    2940 acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg ctacctgcc    3180 cattcgacca ccaagcgaaa catcgcatcg agcgagcacg tactcggatg aagccggtc    3240 ttgtcgatca ggatgatctg gacgaagagc atcaggggct cgcgccagcc gaactgttcg    3300
ccaggctcaa ggcgcgcatg cccgacggcg aggatctcgt cgtgacccat ggcgatgcct    3360
gcttgccgaa tatcatggtg gaaaatggcc gcttttctgg attcatcgac gtgccggc    3420 tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcattttttt cactgcattc    3840
tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg tcgttcggc tgcggcgagc    4200 ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
```

```
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                            6082

<210> SEQ ID NO 11
<211> LENGTH: 6085
<212> TYPE: DNA
<213> ORGANISM: Artificial Sequence
<220> FEATURE:
<223> OTHER INFORMATION: Synthetic Oligonucleotide

<400> SEQUENCE: 11
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatga gggtccccgc tcagcttctc ttccttctgc tactctggct    960
cccagatacc actggaggaa tagtgatgac gcagtctcca gccaccctgt ctgtgtctcc    1020
aggggaaaga gccaccctct cctgcaggac cagtcagagt attggctgga acttagcctg    1080
gtaccaacag aaacctggcc aggctcccag gctcctcatc tatggtgcat cttccaggac    1140
cactggtatc ccagccaggt tcagtggcag tgggtctggg acagagttca ctctcaccat    1200
```

-continued

```
cagcagcctg cagtctgaag attctgcagt ttattactgt cagcattatg ataactggcc    1260
catgtgcagt tttggccagg ggaccgagct ggagatcaaa cgaactgtgg ctgcaccatc    1320
tgtcttcatc ttcccgccat ctgatgagca gttgaaatct ggaactgcta gcgttgtgtg    1380
cctgctgaat aacttctatc ccagagaggc caaagtacag tggaaggtgg ataacgccct    1440
ccaatcgggt aactcccagg agagtgtcac agagcaggac agcaaggaca gcacctacag    1500
cctcagcagc accctgacgc tgagcaaagc agactacgag aaacacaaag tctacgcctg    1560
cgaagtcacc catcagggcc tgagctcgcc cgtcacaaag agcttcaaca ggggagagtg    1620
ttaggaattc gcggccgctc gagtctagag gcccgtttta aacccgctga tcagcctcga    1680
ctgtgccttc tagttgccag ccatctgttg tttgcccctc ccccgtgcct tccttgaccc    1740
tggaaggtgc cactcccact gtcctttcct aataaaatga ggaaattgca tcgcattgtc    1800
tgagtaggtg tcattctatt ctggggggtg gggtggggca ggacagcaag ggggaggatt    1860
gggaagacaa tagcaggcat gctggggatg cggtgggctc tatggcttct gaggcggaaa    1920
gaaccagctg gggctctagg gggtatcccc acgcgccctg tagcggcgca ttaagcgcgg    1980
cgggtgtggt ggttacgcgc agcgtgaccg ctacacttgc cagcgcccta gcgcccgctc    2040
ctttcgcttt cttcccttcc tttctcgcca cgttcgccgg ctttccccgt caagctctaa    2100
atcggggcat ccctttaggg ttccgattta gtgctttacg gcacctcgac cccaaaaaac    2160
ttgattaggg tgatggttca cgtagtgggc catcgccctg atagacggtt tttcgccctt    2220
tgacgttgga gtccacgttc tttaatagtg actcttgtt ccaaactgga caaacactca    2280
accctatctc ggtctattct tttgatttat aagggatttt ggggatttcg gcctattggt    2340
taaaaaatga gctgatttaa caaaaattta cgcgaatta attctgtgga atgtgtgtca    2400
gttagggtgt ggaaagtccc caggctcccc aggcaggcag aagtatgcaa agcatgcatc    2460
tcaattagtc agcaaccagg tgtggaaagt ccccaggctc cccagcaggc agaagtatgc    2520
aaagcatgca tctcaattag tcagcaacca tagtcccgcc cctaactccg cccatcccgc    2580
ccctaactcc gcccagttcc gcccattctc cgccccatgg ctgactaatt ttttttattt    2640
atgcagaggc cgaggccgcc tctgcctctg agctattcca gaagtagtga ggaggctttt    2700
ttggaggcct aggcttttgc aaaaagctcc cgggagcttg tatatccatt ttcggatctg    2760
atcaagagac aggatgagga tcgtttcgca tgattgaaca agatggattg cacgcaggtt    2820
ctccggccgc ttgggtggag aggctattcg gctatgactg ggcacaacag acaatcggct    2880
gctctgatgc cgccgtgttc cggctgtcag cgcaggggcg cccggttctt tttgtcaaga    2940
ccgacctgtc cggtgccctg aatgaactgc aggacgaggc agcgcggcta tcgtggctgg    3000
ccacgacggg cgttccttgc gcagctgtgc tcgacgttgt cactgaagcg ggaagggact    3060
ggctgctatt gggcgaagtg ccggggcagg atctcctgtc atctcacctt gctcctgccg    3120
agaaagtatc catcatggct gatgcaatgc ggcggctgca tacgcttgat ccggctacct    3180
gcccattcga ccaccaagcg aaacatcgca tcgagcgagc acgtactcgg atggaagccg    3240
gtcttgtcga tcaggatgat ctggacgaag agcatcaggg gctcgcgcca gccgaactgt    3300
tcgccaggct caaggcgcgc atgcccgacg gcgaggatct cgtcgtgacc catggcgatg    3360
cctgcttgcc gaatatcatg gtggaaaatg gccgcttttc tggattcatc gactgtggcc    3420
ggctgggtgt ggcggaccgc tatcaggaca tagcgttggc tacccgtgat attgctgaag    3480
agcttggcgg cgaatgggct gaccgcttcc tcgtgcttta cggtatcgcc gctcccgatt    3540
cgcagcgcat cgccttctat cgccttcttg acgagttctt ctgagcggga ctctggggtt    3600
```

```
cgaaatgacc gaccaagcga cgcccaacct gccatcacga gatttcgatt ccaccgccgc   3660
cttctatgaa aggttgggct tcggaatcgt tttccgggac gccggctgga tgatcctcca   3720
gcgcggggat ctcatgctgg agttcttcgc ccaccccaac ttgtttattg cagcttataa   3780
tggttacaaa taaagcaata gcatcacaaa tttcacaaat aaagcatttt tttcactgca   3840
ttctagttgt ggtttgtcca aactcatcaa tgtatcttat catgtctgta taccgtcgac   3900
ctctagctag agcttggcgt aatcatggtc atagctgttt cctgtgtgaa attgttatcc   3960
gctcacaatt ccacacaaca tacgagccgg aagcataaag tgtaaagcct ggggtgccta   4020
atgagtgagc taactcacat taattgcgtt gcgctcactg cccgctttcc agtcgggaaa   4080
cctgtcgtgc cagctgcatt aatgaatcgg ccaacgcgcg gggagaggcg gtttgcgtat   4140
tgggcgctct tccgcttcct cgctcactga ctcgctgcgc tcggtcgttc ggctgcggcg   4200
agcggtatca gctcactcaa aggcggtaat acggttatcc acagaatcag gggataacgc   4260
aggaaagaac atgtgagcaa aaggccagca aaaggccagg aaccgtaaaa aggccgcgtt   4320
gctggcgttt ttccataggc tccgcccccc tgacgagcat cacaaaaatc gacgctcaag   4380
tcagaggtgg cgaaacccga caggactata aagataccag gcgtttcccc ctggaagctc   4440
cctcgtgcgc tctcctgttc cgaccctgcc gcttaccgga tacctgtccg cctttctccc   4500
ttcgggaagc gtggcgcttt ctcaatgctc acgctgtagg tatctcagtt cggtgtaggt   4560
cgttcgctcc aagctgggct gtgtgcacga acccccccgtt cagcccgacc gctgcgcctt   4620
atccggtaac tatcgtcttg agtccaaccc ggtaagacac gacttatcgc cactggcagc   4680
agccactggt aacaggatta gcagagcgag gtatgtaggc ggtgctacag agttcttgaa   4740
gtggtggcct aactacggct acactagaag gacagtattt ggtatctgcg ctctgctgaa   4800
gccagttacc ttcggaaaaa gagttggtag ctcttgatcc ggcaaacaaa ccaccgctgg   4860
tagcggtggt ttttttgttt gcaagcagca gattacgcgc agaaaaaaag gatctcaaga   4920
agatcctttg atcttttcta cggggtctga cgctcagtgg aacgaaaact cacgttaagg   4980
gattttggtc atgagattat caaaaaggat cttcacctag atccttttaa attaaaaatg   5040
aagttttaaa tcaatctaaa gtatatatga gtaaacttgg tctgacagtt accaatgctt   5100
aatcagtgag gcacctatct cagcgatctg tctatttcgt tcatccatag ttgcctgact   5160
ccccgtcgtg tagataacta cgatacggga gggcttacca tctggcccca gtgctgcaat   5220
gataccgcga gacccacgct caccggctcc agatttatca gcaataaacc agccagccgg   5280
aagggccgag cgcagaagtg gtcctgcaac tttatccgcc tccatccagt ctattaattg   5340
ttgccgggaa gctagagtaa gtagttcgcc agttaatagt ttgcgcaacg ttgttgccat   5400
tgctacaggc atcgtggtgt cacgctcgtc gtttggtatg gcttcattca gctccggttc   5460
ccaacgatca aggcgagtta catgatcccc catgttgtgc aaaaaagcgg ttagctcctt   5520
cggtcctccg atcgttgtca gaagtaagtt ggccgcagtg ttatcactca tggttatggc   5580
agcactgcat aattctctta ctgtcatgcc atccgtaaga tgcttttctg tgactggtga   5640
gtactcaacc aagtcattct gagaatagtg tatgcggcga ccgagttgct cttgcccggc   5700
gtcaatacgg gataataccg cgccacatag cagaacttta aaagtgctca tcattggaaa   5760
acgttcttcg gggcgaaaac tctcaaggat cttaccgctg ttgagatcca gttcgatgta   5820
acccactcgt gcacccaact gatcttcagc atcttttact ttcaccagcg tttctgggtg   5880
agcaaaaaca ggaaggcaaa atgccgcaaa aaagggaata agggcgacac ggaaatgttg   5940
aatactcata ctcttccttt ttcaatatta ttgaagcatt tatcagggtt attgtctcat   6000
```

| | |
|---|---|
| gagcggatac atatttgaat gtatttagaa aaataaacaa ataggggttc cgcgcacatt | 6060 |
| tccccgaaaa gtgccacctg acgtc | 6085 |

<210> SEQ ID NO 12
<211> LENGTH: 6097
<212> TYPE: DNA
<213> ORGANISM: Artificial Sequence
<220> FEATURE:
<223> OTHER INFORMATION: Synthetic Oligonucleotide

<400> SEQUENCE: 12

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| aagcttggat ctcaccatga gggtccctgc tcagctcctg gggctgctaa tgctctggat | 960 |
| acctggatcc agtgcagata ttgtgatgac ccagactcca ctctctctgt ccgtcacccc | 1020 |
| tggacagccg gcctccatct cctgcaagtc tagtcagagc ctcctgcata gtgatggaaa | 1080 |
| gacctttttg tattggtatc tgcagaagcc aggccagcct ccacagctcc tgatctatga | 1140 |
| ggtttccaac cggttctctg gagtgccaga taggttcagt ggcagcgggt cagggacaga | 1200 |
| tttcacactg aaaatcagcc gggtggaggc tgaggatgtt gggctttatt actgcatgca | 1260 |
| aagtatacag cttccgctca cttcggcgg agggaccaag gtggagatca aacgaactgt | 1320 |
| ggctgcacca tctgtcttca tcttcccgcc atctgatgag cagttgaaat ctggaactgc | 1380 |
| tagcgttgtg tgcctgctga ataacttcta tcccagagag gccaaagtac agtggaaggt | 1440 |
| ggataacgcc ctccaatcgg gtaactccca ggagagtgtc acagagcagg acagcaagga | 1500 |
| cagcacctac agcctcagca gcaccctgac gctgagcaaa gcagactacg agaaacacaa | 1560 |
| agtctacgcc tgcgaagtca cccatcaggg cctgagctcg cccgtcacaa agagcttcaa | 1620 |
| caggggagag tgttaggaat tcgcggccgc tcgagtctag agggcccgtt taaacccgct | 1680 |
| gatcagcctc gactgtgcct tctagttgcc agccatctgt tgtttgcccc tcccccgtgc | 1740 |
| cttccttgac cctggaaggt gccactccca ctgtcctttc ctaataaaat gaggaaattg | 1800 |
| catcgcattg tctgagtagg tgtcattcta ttctgggggg tggggtgggg caggacagca | 1860 |
| agggggagga ttgggaagac aatagcaggc atgctgggga tgcggtgggc tctatggctt | 1920 |
| ctgaggcgga aagaaccagc tggggctcta ggggtatccc cacgcgcccc tgtagcggcg | 1980 |

```
cattaagcgc ggcgggtgtg gtggttacgc gcagcgtgac cgctacactt gccagcgccc    2040
tagcgcccgc tcctttcgct ttcttccctt cctttctcgc cacgttcgcc ggctttcccc    2100
gtcaagctct aaatcggggc atcccttttag ggttccgatt tagtgcttta cggcacctcg    2160
accccaaaaa acttgattag ggtgatggtt cacgtagtgg gccatcgccc tgatagacgg    2220 ttttttcgccc tttgacgttg gagtccacgt tctttaatag tggactcttg ttccaaactg    2280
gaacaacact caaccctatc tcggtctatt cttttgattt ataagggatt ttggggattt    2340
cggcctattg gttaaaaaat gagctgattt aacaaaaatt taacgcgaat taattctgtg    2400
gaatgtgtgt cagttagggt gtggaaagtc cccaggctcc ccaggcaggc agaagtatgc    2460
aaagcatgca tctcaattag tcagcaacca ggtgtggaaa gtccccaggc tccccagcag    2520
gcagaagtat gcaaagcatg catctcaatt agtcagcaac catagtcccg cccctaactc    2580
cgcccatccc gcccctaact ccgcccagtt ccgcccattc tccgcccat ggctgactaa     2640 tttttttat ttatgcagag gccgaggccg cctctgcctc tgagctattc cagaagtagt     2700
gaggaggctt ttttggaggc ctaggctttt gcaaaaagct cccgggagct tgtatatcca    2760
ttttcggatc tgatcaagag acaggatgag gatcgtttcg catgattgaa caagatggat    2820
tgcacgcagg ttctccggcc gcttgggtgg agaggctatt cggctatgac tgggcacaac    2880
agacaatcgg ctgctctgat gccgccgtgt tccggctgtc agcgcagggg cgcccggttc    2940
tttttgtcaa gaccgacctg tccggtgccc tgaatgaact gcaggacgag gcagcgcggc    3000
tatcgtggct ggccacgacg ggcgttcctt gcgcagctgt gctcgacgtt gtcactgaag    3060
cgggaaggga ctggctgcta ttgggcgaag tgccggggca ggatctcctg tcatctcacc    3120
ttgctcctgc cgagaaagta tccatcatgg ctgatgcaat gcggcggctg catacgcttg    3180
atccggctac ctgcccattc gaccaccaag cgaaacatcg catcgagcga gcacgtactc    3240
ggatggaagc cggtcttgtc gatcaggatg atctggacga agagcatcag gggctcgcgc    3300
cagccgaact gttcgccagg ctcaaggcgc gcatgcccga cggcgaggat ctcgtcgtga    3360
cccatggcga tgcctgcttg ccgaatatca tggtggaaaa tggccgcttt tctggattca    3420
tcgactgtgg ccgctgggt gtggcggacc gctatcagga catagcgttg gctacccgtg    3480
atattgctga gagcttggc ggcgaatggg ctgaccgctt cctcgtgctt tacggtatcg    3540
ccgctcccga ttcgcagcgc atcgccttct atcgccttct tgacgagttc ttctgagcgg    3600
gactctgggg ttcgaaatga ccgaccaagc gacgcccaac ctgccatcac gagatttcga    3660
ttccaccgcc gccttctatg aaaggttggg cttcggaatc gttttccggg acgccggctg    3720
gatgatcctc cagcgcgggg atctcatgct ggagttcttc gcccacccca acttgtttat    3780
tgcagcttat aatggttaca aataaagcaa tagcatcaca aatttcacaa ataaagcatt    3840
tttttcactg cattctagtt gtggtttgtc caaactcatc aatgtatctt atcatgtctg    3900
tataccgtcg acctctagct agagcttggc gtaatcatgg tcatagctgt ttcctgtgtg    3960
aaattgttat ccgctcacaa ttccacacaa catacgagcc ggaagcataa agtgtaaagc    4020
ctggggtgcc taatgagtga gctaactcac attaattgcg ttgcgctcac tgcccgcttt    4080
ccagtcggga aacctgtcgt gccagctgca ttaatgaatc ggccaacgcg cggggagagg    4140
cggtttgcgt attgggcgct cttccgcttc ctcgctcact gactcgctgc gctcggtcgt    4200
tcggctgcgg cgagcggtat cagctcactc aaaggcggta atacggttat ccacagaatc    4260 agggggataac gcaggaaaga acatgtgagc aaaaggccag caaaaggcca ggaaccgtaa    4320
aaaggccgcg ttgctggcgt ttttccatag gctccgcccc cctgacgagc atcacaaaaa    4380
```

```
tcgacgctca agtcagaggt ggcgaaaccc gacaggacta taaagatacc aggcgtttcc   4440
ccctggaagc tccctcgtgc gctctcctgt tccgaccctg ccgcttaccg gatacctgtc   4500
cgcctttctc ccttcgggaa gcgtggcgct ttctcaatgc tcacgctgta ggtatctcag   4560
ttcggtgtag gtcgttcgct ccaagctggg ctgtgtgcac gaaccccccg ttcagcccga   4620
ccgctgcgcc ttatccggta actatcgtct tgagtccaac ccggtaagac acgacttatc   4680
gccactggca gcagccactg gtaacaggat tagcagagcg aggtatgtag gcggtgctac   4740
agagttcttg aagtggtggc ctaactacgg ctacactaga aggacagtat ttggtatctg   4800
cgctctgctg aagccagtta ccttcggaaa aagagttggt agctcttgat ccggcaaaca   4860
aaccaccgct ggtagcggtg gtttttttgt ttgcaagcag cagattacgc gcagaaaaaa   4920
aggatctcaa gaagatcctt tgatcttttc tacggggtct gacgctcagt ggaacgaaaa   4980
ctcacgttaa gggattttgg tcatgagatt atcaaaaagg atcttcacct agatcctttt   5040
aaattaaaaa tgaagtttta atcaatcta agtatatat gagtaaactt ggtctgacag   5100
ttaccaatgc ttaatcagtg aggcacctat ctcagcgatc tgtctatttc gttcatccat   5160
agttgcctga ctccccgtcg tgtagataac tacgatacgg gagggcttac catctggccc   5220
cagtgctgca atgataccgc gagacccacg ctcaccggct ccagatttat cagcaataaa   5280
ccagccagcc ggaagggccg agcgcagaag tggtcctgca actttatccg cctccatcca   5340
gtctattaat tgttgccggg aagctagagt aagtagttcg ccagttaata gtttgcgcaa   5400
cgttgttgcc attgctacag gcatcgtggt gtcacgctcg tcgtttggta tggcttcatt   5460
cagctccggt tcccaacgat caaggcgagt tacatgatcc cccatgttgt gcaaaaaagc   5520
ggttagctcc ttcggtcctc cgatcgttgt cagaagtaag ttggccgcag tgttatcact   5580
catggttatg gcagcactgc ataattctct tactgtcatg ccatccgtaa gatgcttttc   5640
tgtgactggt gagtactcaa ccaagtcatt ctgagaatag tgtatgcggc gaccgagttg   5700
ctcttgcccg gcgtcaatac gggataatac cgcgccacat agcagaactt taaaagtgct   5760
catcattgga aaacgttctt cggggcgaaa actctcaagg atcttaccgc tgttgagatc   5820
cagttcgatg taacccactc gtgcacccaa ctgatcttca gcatctttta ctttcaccag   5880
cgtttctggg tgagcaaaaa caggaaggca aaatgccgca aaaagggaa taagggcgac   5940 acggaaatgt tgaatactca tactcttcct ttttcaatat tattgaagca tttatcaggg   6000
ttattgtctc atgagcggat acatatttga atgtatttag aaaaataaac aataggggt   6060 tccgcgcaca tttccccgaa aagtgccacc tgacgtc                             6097

<210> SEQ ID NO 13
<211> LENGTH: 6094
<212> TYPE: DNA
<213> ORGANISM: Artificial Sequence
<220> FEATURE:
<223> OTHER INFORMATION: Synthetic Oligonucleotide

<400> SEQUENCE: 13
gacggatcgg gagatctccc gatccccta t ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
```

-continued

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatgg tgttgcagac ccaggtcttc atttctctgt tactctggat    960
ctctggtgcc tacggggaca tcgtgatgac ccagtctcca gactccctgg ctgtgtctct   1020
gggcgagagg gccaccatca actgcaagtc caaccagagt gtcttacaca gctccaacaa   1080
taagaactat ttagcttggt accagcagaa accaggacag cctcctaaat tgctcattta   1140
ttgggcattc ctccgggaat ccggggtccc tgaccgcttc agtggcagcg ggtctgggac   1200
agatttcact ctcaccatca gcagcctgca ggctgaagat gtggcagttt attactgtca   1260
ccaatattat tctactttat atactttcgg cggagggacc aaggtagaga tcaaacgaac   1320
ygtggctgca ccatctgtct tcatcttccc gccatctgat gagcagttga aatctggaac   1380
tgctagcgtt gtgtgcctgc tgaataactt ctatcccaga gaggccaaag tacagtggaa   1440
ggtggataac gccctccaat cgggtaactc ccaggagagt gtcacagagc aggacagcaa   1500
ggacagcacc tacagcctca gcagcaccct gacgctgagc aaagcagact acgagaaaca   1560
caaagtctac gcctgcgaag tcacccatca gggcctgagc tcgcccgtca caaagagctt   1620
caacagggga gagtgttagg cggccgctcg agtctagagg gcccgtttaa acccgctgat   1680
cagcctcgac tgtgccttct agttgccagc catctgttgt ttgcccctcc cccgtgcctt   1740
ccttgaccct ggaaggtgcc actcccactg tcctttccta ataaaatgag gaaattgcat   1800
cgcattgtct gagtaggtgt cattctattc tggggggtgg ggtggggcag gacagcaagg   1860
gggaggattg ggaagacaat agcaggcatg ctggggatgc ggtgggctct atggcttctg   1920
aggcggaaag aaccagctgg ggctctaggg ggtatcccca cgcgccctgt agcggcgcat   1980
taagcgcggc gggtgtggtg gttacgcgca gcgtgaccgc tacacttgcc agcgccctag   2040
cgcccgctcc tttcgctttc ttcccttcct ttctcgccac gttcgccggc tttccccgtc   2100
aagctctaaa tcgggcatc cctttagggt tccgatttag tgctttacgg cacctcgacc   2160
ccaaaaaact tgattagggt gatggttcac gtagtgggcc atcgccctga tagacggttt   2220
ttcgcccttt gacgttggag tccacgttct ttaatagtgg actcttgttc caaactggaa   2280
caacactcaa ccctatctcg gtctattctt ttgatttata agggattttg gggatttcgg   2340
cctattggtt aaaaaatgag ctgatttaac aaaaatttaa cgcgaattaa ttctgtggaa   2400
tgtgtgtcag ttagggtgtg gaaagtcccc aggctcccca gcaggcaga agtatgcaaa   2460
gcatgcatct caattagtca gcaaccaggt gtggaaagtc cccaggctcc ccagcaggca   2520
gaagtatgca aagcatgcat ctcaattagt cagcaaccat agtcccgccc ctaactccgc   2580
ccatcccgcc cctaactccg cccagttccg cccattctcc gccccatggc tgactaattt   2640
ttttatttta tgcagaggcc gaggccgcct ctgcctctga gctattccag aagtagtgag   2700
gaggcttttt tggaggccta ggcttttgca aaaagctccc gggagcttgt atatccattt   2760
```

```
tcggatctga tcaagagaca ggatgaggat cgtttcgcat gattgaacaa gatggattgc    2820
acgcaggttc tccggccgct tgggtggaga ggctattcgg ctatgactgg gcacaacaga    2880
caatcggctg ctctgatgcc gccgtgttcc ggctgtcagc gcagggggcgc ccggttcttt   2940 ttgtcaagac cgacctgtcc ggtgccctga atgaactgca ggacgaggca gcgcggctat    3000
cgtggctggc cacgacgggc gttccttgcg cagctgtgct cgacgttgtc actgaagcgg    3060
gaagggactg gctgctattg ggcgaagtgc cggggcagga tctcctgtca tctcaccttg    3120
ctcctgccga gaaagtatcc atcatggctg atgcaatgcg gcggctgcat acgcttgatc    3180
cggctacctg cccattcgac caccaagcga acatcgcat cgagcgagca cgtactcgga    3240
tggaagccgg tcttgtcgat caggatgatc tggacgaaga gcatcagggg ctcgcgccag    3300
ccgaactgtt cgccaggctc aaggcgcgca tgcccgacgg cgaggatctc gtcgtgaccc    3360
atggcgatgc ctgcttgccg aatatcatgg tggaaaatgg ccgcttttct ggattcatcg    3420
actgtggccg gctgggtgtg gcggaccgct atcaggacat agcgttggct acccgtgata    3480
ttgctgaaga gcttggcggc gaatgggctg accgcttcct cgtgctttac ggtatcgccg    3540
ctcccgattc gcagcgcatc gccttctatc gccttcttga cgagttcttc tgagcgggac    3600
tctggggttc gaaatgaccg accaagcgac gcccaacctg ccatcacgag atttcgattc    3660
caccgccgcc ttctatgaaa ggttgggctt cggaatcgtt ttccgggacg ccggctggat    3720
gatcctccag cgcggggatc tcatgctgga gttcttcgcc cacccc aact tgtttattgc    3780 agcttataat ggttacaaat aaagcaatag catcacaaat ttcacaaata aagcattttt    3840
ttcactgcat tctagttgtg gtttgtccaa actcatcaat gtatcttatc atgtctgtat    3900
accgtcgacc tctagctaga gcttggcgta atcatggtca tagctgtttc ctgtgtgaaa    3960
ttgttatccg ctcacaattc cacacaacat acgagccgga agcataaagt gtaaagcctg    4020
gggtgcctaa tgagtgagct aactcacatt aattgcgttg cgctcactgc ccgctttcca    4080
gtcgggaaac ctgtcgtgcc agctgcatta atgaatcggc caacgcgcgg ggagaggcgg    4140
tttgcgtatt gggcgctctt ccgcttcctc gctcactgac tcgctgcgct cggtcgttcg    4200
gctgcggcga gcggtatcag ctcactcaaa ggcggtaata cggttatcca cagaatcagg    4260
ggataacgca ggaaagaaca tgtgagcaaa aggccagcaa aaggccagga accgtaaaaa    4320
ggccgcgttg ctggcgtttt tccataggct ccgcccccct gacgagcatc acaaaaatcg    4380
acgctcaagt cagaggtggc gaaacccgac aggactataa agataccagg cgtttccccc    4440
tggaagctcc ctcgtgcgct ctcctgttcc gaccctgccg cttaccggat acctgtccgc    4500
ctttctccct tcgggaagcg tggcgctttc tcaatgctca cgctgtaggt atctcagttc    4560
ggtgtaggtc gttcgctcca agctgggctg tgtgcacgaa ccccccgttc agcccgaccg    4620
ctgcgcctta tccggtaact atcgtcttga gtccaacccg gtaagacacg acttatcgcc    4680
actggcagca gccactggta acaggattag cagagcgagg tatgtaggcg gtgctacaga    4740
gttcttgaag tggtggccta actacggcta cactagaagg acagtatttg gtatctgcgc    4800
tctgctgaag ccagttacct tcggaaaaag agttggtagc tcttgatccg gcaaacaaac    4860
caccgctggt agcggtggtt tttttgtttg caagcagcag attacgcgca gaaaaaaagg    4920
atctcaagaa gatcctttga tcttttctac ggggtctgac gctcagtgga acgaaaactc    4980
acgttaaggg attttggtca tgagattatc aaaaaggatc ttcacctaga tccttttaaa    5040
ttaaaaatga agttttaaat caatctaaag tatatatgag taaacttggt ctgacagtta    5100
ccaatgctta atcagtgagg cacctatctc agcgatctgt ctatttcgtt catccatagt    5160
```

```
tgcctgactc cccgtcgtgt agataactac gatacgggag ggcttaccat ctggccccag    5220
tgctgcaatg ataccgcgag acccacgctc accggctcca gatttatcag caataaacca    5280
gccagccgga agggccgagc gcagaagtgg tcctgcaact ttatccgcct ccatccagtc    5340
tattaattgt tgccgggaag ctagagtaag tagttcgcca gttaatagtt tgcgcaacgt    5400
tgttgccatt gctacaggca tcgtggtgtc acgctcgtcg tttggtatgg cttcattcag    5460
ctccggttcc caacgatcaa ggcgagttac atgatccccc atgttgtgca aaaaagcggt    5520
tagctccttc ggtcctccga tcgttgtcag aagtaagttg gccgcagtgt tatcactcat    5580
ggttatggca gcactgcata attctcttac tgtcatgcca tccgtaagat gcttttctgt    5640
gactggtgag tactcaacca agtcattctg agaatagtgt atgcggcgac cgagttgctc    5700
ttgcccggcg tcaatacggg ataataccgc gccacatagc agaactttaa aagtgctcat    5760
cattggaaaa cgttcttcgg ggcgaaaact ctcaaggatc ttaccgctgt tgagatccag    5820
ttcgatgtaa cccactcgtg cacccaactg atcttcagca tcttttactt tcaccagcgt    5880
ttctgggtga gcaaaaacag gaaggcaaaa tgccgcaaaa aagggaataa gggcgacacg    5940
gaaatgttga atactcatac tcttcctttt tcaatattat tgaagcattt atcagggtta    6000
ttgtctcatg agcggataca tatttgaatg tatttagaaa aataaacaaa tagggcttcc    6060
gcgcacattt ccccgaaaag tgccacctga cgtc                                6094

<210> SEQ ID NO 14
<211> LENGTH: 481
<212> TYPE: DNA
<213> ORGANISM: Artificial Sequence
<220> FEATURE:
<223> OTHER INFORMATION: Synthetic Oligonucleotide

<400> SEQUENCE: 14
ggatctcacc atggagttgg gactgcgctg gggcttcctc gttgctcttt taagaggtgt     60
ccagtgtcag gtgcaattgg tggagtctgg gggaggcgtg gtccagcctg ggaggtccct    120
gagactctcc tgtgcagcgt ctggattcgc cttcagtaga tatggcatgc actgggtccg    180
ccaggctcca ggcaaggggc tggagtgggt ggcagttata tggtatgatg gaagtaataa    240
atactatgca gactccgtga agggccgatt caccatctcc agagacaatt ccaagaacac    300
gcagtatctg caaatgaaca gcctgagagc cgaggacacg gctgtgtatt actgtgcgag    360
aggcggtgac ttcctctact actactatta cggtatggac gtctggggcc aagggaccac    420
ggtcaccgtc tcctcagcct ccaccaaggg cccatcggtc ttccccctgg cccctctag    480 c                                                                   481

<210> SEQ ID NO 15
<211> LENGTH: 142
<212> TYPE: PRT
<213> ORGANISM: Homo sapiens

<400> SEQUENCE: 15

Met Glu Leu Gly Leu Arg Trp Gly Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Ala Phe
            35                  40                  45

Ser Arg Tyr Gly Met His Trp Val Arg Gln Ala Pro Gly Lys Gly Leu
        50                  55                  60
```

-continued

```
Glu Trp Val Ala Val Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Gln Tyr Leu Gln Met Asn Ser Leu Arg Ala Glu Asp Thr Ala Val
            100                 105                 110

Tyr Tyr Cys Ala Arg Gly Gly Asp Phe Leu Tyr Tyr Tyr Tyr Gly
        115                 120                 125

Met Asp Val Trp Gly Gln Gly Thr Thr Val Thr Val Ser Ser
    130                 135                 140
```

<210> SEQ ID NO 16
<211> LENGTH: 463
<212> TYPE: DNA
<213> ORGANISM: Artificial Sequence
<220> FEATURE:
<223> OTHER INFORMATION: Synthetic Oligonucleotide

<400> SEQUENCE: 16

```
ggatctcacc atgagggtcc ctgctcagct cctgggactc ctgctgctct ggctcccaga    60
taccagatgt gacatccaga tgacccagtc tccatcctcc ctgtctgcat ctgtaggaga   120
cagagtcacc atcacttgcc gggcgagtca gggcattagc aattatttag cctggtatca   180
gcagaaaaca gggaaagttc ctaagttcct gatctatgaa gcatccactt tgcaatcagg   240
ggtcccatct cggttcagtg gcggtggatc tgggacagat ttcactctca ccatcagcag   300
cctgcagcct gaagatgttg caacttatta ctgtcaaaat tataacagtg ccccattcac   360
tttcggccct gggaccaaag tggatatcaa acgaactgtg gctgcaccct ctgtcttcat   420
cttcccgcca tctgatgagc agttgaaatc tggaactgct agc                     463
```

<210> SEQ ID NO 17
<211> LENGTH: 127
<212> TYPE: PRT
<213> ORGANISM: Homo sapiens

<400> SEQUENCE: 17

```
Met Arg Val Pro Ala Gln Leu Leu Gly Leu Leu Leu Leu Trp Leu Pro
  1               5                  10                  15

Asp Thr Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Gly
         35                  40                  45

Ile Ser Asn Tyr Leu Ala Trp Tyr Gln Gln Lys Thr Gly Lys Val Pro
 50                  55                  60

Lys Phe Leu Ile Tyr Glu Ala Ser Thr Leu Gln Ser Gly Val Pro Ser
 65                  70                  75                  80

Arg Phe Ser Gly Gly Gly Ser Gly Thr Asp Phe Thr Leu Thr Ile Ser
                 85                  90                  95

Ser Leu Gln Pro Glu Asp Val Ala Thr Tyr Tyr Cys Gln Asn Tyr Asn
            100                 105                 110

Ser Ala Pro Phe Thr Phe Gly Pro Gly Thr Lys Val Asp Ile Lys
        115                 120                 125
```

<210> SEQ ID NO 18
<211> LENGTH: 508
<212> TYPE: DNA
<213> ORGANISM: Artificial Sequence
<220> FEATURE:
<223> OTHER INFORMATION: Synthetic Oligonucleotide

<400> SEQUENCE: 18

```
ggatctcacc atggggtcaa ccgccatcct caccatggag ttggggctgc gctgggttct      60
cctcgttgct cttttaagag gtgtccagtg tcaggtgcag ctggtggagt ctggggagg     120
cgtggtccag cctgggaggt ccctgagact ctcctgtgca gcgtctggat tcaccttcag    180
taactatgtc atgcactggg tccgccaggc tccaggcaag gggctggagt gggtggcaat    240
tatatggtat gatggaagta ataaatacta tgcagactcc gtgaagggcc gattcaccat    300
ctccagagac aattccaaga acacgctgta tctgcaaatg aacagcctga gagccgagga    360
cacggctgtg tattactgtg cgggtggata taactggaac tacgagtacc actactacgg    420
tatggacgtc tggggccaag ggaccacggt caccgtctcc tcagcctcca ccaagggccc    480
atcggtcttc cccctggcac cctctagc                                       508
```

<210> SEQ ID NO 19
<211> LENGTH: 143
<212> TYPE: PRT
<213> ORGANISM: Homo sapiens

<400> SEQUENCE: 19

```
Met Glu Leu Gly Leu Arg Trp Val Leu Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Gly Gly Tyr Asn Trp Asn Tyr Glu Tyr His Tyr Tyr
        115                 120                 125

Gly Met Asp Val Trp Gly Gln Gly Thr Thr Val Thr Val Ser Ser
    130                 135                 140
```

<210> SEQ ID NO 20
<211> LENGTH: 463
<212> TYPE: DNA
<213> ORGANISM: Artificial Sequence
<220> FEATURE:
<223> OTHER INFORMATION: Synthetic Oligonucleotide

<400> SEQUENCE: 20

```
ggatctcacc atgagggtcc ccgctcagct cctggggctc ctgctgctct gtttcccagg     60
tgccagatgt gacatccaga tgacccagtc tccatcctca ctgtctgcat ctgtaggaga    120
cagagtcacc atcacttgtc gggcgagtca ggcattacc aattatttag cctggtttca     180
gcagaaacca gggaaagccc taagtccct tatctatgct gcatccagtt tgcaaagtgg     240
ggtcccatca aagttcagcg gcagtggatc tgggacagat ttcagtctca ccatcagcag    300
cctgcagcct gaagattttg caacttatta ctgccaacag tataatagtt acccgatcac    360
cttcggccaa gggacacgac tggagattaa acgaactgtg gctgcaccat ctgtcttcat    420
```
cttcccgcca tctgatgagc agttgaaatc tggaactgct agc    463

<210> SEQ ID NO 21
<211> LENGTH: 127
<212> TYPE: PRT
<213> ORGANISM: Homo sapiens

<400> SEQUENCE: 21

Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Ile Thr Phe Gly Gln Gly Thr Arg Leu Glu Ile Lys
        115                 120                 125

<210> SEQ ID NO 22
<211> LENGTH: 490
<212> TYPE: DNA
<213> ORGANISM: Artificial Sequence
<220> FEATURE:
<223> OTHER INFORMATION: Synthetic Oligonucleotide

<400> SEQUENCE: 22
ggatctcacc atggagttgg gactagctg gttttcctc gttgctcttt taagaggtgt        60
ccagtgtcag gtccagctgg tggagtctgg gggaggcgtg gtccagcctg ggaggtccct     120
gagactctcc tgtgcagcgt ctggattcac cttcagtagc tatggcatgc actgggtccg     180
ccaggctcca ggcaagggc tggactgggt ggcaattatt tggcatgatg gaagtaataa     240
atactatgca gactccgtga agggccgatt caccatctcc agagacaatt ccaagaagac     300
gctgtacctg caaatgaaca gtttgagagc cgaggacacg gctgtgtatt actgtgcgag     360
agcttgggcc tatgactacg gtgactatga atactacttc ggtatggacg tctggggcca     420
agggaccacg gtcaccgtct cctcagcctc caccaagggc ccatcggtct tccccctggc     480
accctctagc                                                           490

<210> SEQ ID NO 23
<211> LENGTH: 145
<212> TYPE: PRT
<213> ORGANISM: Homo sapiens

<400> SEQUENCE: 23

Met Glu Leu Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu

```
                    50                  55                  60
Asp Trp Val Ala Ile Ile Trp His Asp Gly Ser Asn Lys Tyr Tyr Ala
 65                  70                  75                  80

Asp Ser Val Lys Gly Arg Phe Thr Ile Ser Arg Asp Asn Ser Lys Lys
                 85                  90                  95

Thr Leu Tyr Leu Gln Met Asn Ser Leu Arg Ala Glu Asp Thr Ala Val
            100                 105                 110

Tyr Tyr Cys Ala Arg Ala Trp Ala Tyr Asp Tyr Gly Asp Tyr Glu Tyr
            115                 120                 125

Tyr Phe Gly Met Asp Val Trp Gly Gln Gly Thr Thr Val Thr Val Ser
        130                 135                 140

Ser
145

<210> SEQ ID NO 24
<211> LENGTH: 463
<212> TYPE: DNA
<213> ORGANISM: Artificial Sequence
<220> FEATURE:
<223> OTHER INFORMATION: Synthetic Oligonucleotide

<400> SEQUENCE: 24
ggatctcacc atgagggtcc ctgctcagct cctggggctc ctgctgctct gtttcccagg     60
tgccagatgt gacatccaga tgacccagtc tccatcctca ctgtctgcat ctgtaggaga    120
cagagtcacc atcacttgtc gggcgagtca gggcattagc cattatttag cctggtttca    180
gcagaaacca gggaaagccc ctaagtccct gatctatgct gcatccagtt tgcaaagtgg    240
ggtcccatca agttcagcg gcagtggatc tgggacagat ttcactctca ccatcagcag    300
cctacagcct gaagattttg caacttatta ctgccaacag tataatagtt tcccgctcac    360
tttcggcgga gggaccaagg tggagatcaa acgaactgtg gctgcaccat ctgtcttcat    420
cttcccgcca tctgatgagc agttgaaatc tggaactgct agc                      463

<210> SEQ ID NO 25
<211> LENGTH: 127
<212> TYPE: PRT
<213> ORGANISM: Homo sapiens

<400> SEQUENCE: 25

Met Arg Val Pro Ala Gln Leu Leu Gly Leu Leu Leu Leu Cys Phe Pro
  1               5                  10                  15

Gly Ala Arg Cys Asp Ile Gln Met Thr Gln Ser Pro Ser Ser Leu Ser
                 20                  25                  30

Ala Ser Val Gly Asp Arg Val Thr Ile Thr Cys Arg Ala Ser Gln Gly
             35                  40                  45

Ile Ser His Tyr Leu Ala Trp Phe Gln Gln Lys Pro Gly Lys Ala Pro
         50                  55                  60

Lys Ser Leu Ile Tyr Ala Ala Ser Ser Leu Gln Ser Gly Val Pro Ser
 65                  70                  75                  80

Lys Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Tyr Asn
            100                 105                 110

Ser Phe Pro Leu Thr Phe Gly Gly Gly Thr Lys Val Glu Ile Lys
        115                 120                 125

<210> SEQ ID NO 26
```

<211> LENGTH: 469
<212> TYPE: DNA
<213> ORGANISM: Artificial Sequence
<220> FEATURE:
<223> OTHER INFORMATION: Synthetic Oligonucleotide

<400> SEQUENCE: 26

| | | |
|---|---|---:|
| ggatcccacc atggggtcaa ccgtcatcct cgccctcctc ctggctgttc tccaaggagt | | 60 |
| ctgtgccgag gtgcagctgg tgcagtctgg agcagaggtg aaaaagcccg gggagtctct | | 120 |
| gaagatctcc tgtaagggtt ctggatacag ctttaccagt tactggatcg gctgggtgcg | | 180 |
| ccagatgccc gggaaaggcc tggagtggat ggggatcatc tatcctggtg actctgatac | | 240 |
| cagatacagc ccgtccttcc aaggccaggt caccatctca gccgacaagt ccatcagcac | | 300 |
| cgcctacctg cagtggagca gcctgaaggc ctcggacacc gccatgtatt actgtgcgag | | 360 |
| acggatggca gcagctggcc cctttgacta ctggggccag ggaaccctgg tcaccgtctc | | 420 |
| ctcagcctcc accaagggcc catcggtctt ccccctggca ccctctagc | | 469 |

<210> SEQ ID NO 27
<211> LENGTH: 138
<212> TYPE: PRT
<213> ORGANISM: Homo sapiens

<400> SEQUENCE: 27

Met Gly Ser Thr Val Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Met Ala Ala Ala Gly Pro Phe Asp Tyr Trp
        115                 120                 125

Gly Gln Gly Thr Leu Val Thr Val Ser Ser
    130                 135

<210> SEQ ID NO 28
<211> LENGTH: 466
<212> TYPE: DNA
<213> ORGANISM: Artificial Sequence
<220> FEATURE:
<223> OTHER INFORMATION: Synthetic Oligonucleotide

<400> SEQUENCE: 28

| | | |
|---|---|---:|
| ggatctcacc atgagggtcc ccgctcagct tctcttcctt ctgctactct ggctcccaga | | 60 |
| taccactgga ggaatagtga tgacgcagtc tccagccacc ctgtctgtgt ctccagggga | | 120 |
| aagagccacc ctctcctgca ggaccagtca gagtattggc tggaacttag cctggtacca | | 180 |
| acagaaacct ggccaggctc ccaggctcct catctatggt gcatcttcca ggaccactgg | | 240 |
| tatcccagcc aggttcagtg gcagtgggtc tgggacagag ttcactctca ccatcagcag | | 300 |
| cctgcagtct gaagattctg cagttttatta ctgtcagcat tatgataact ggcccatgtg | | 360 |

```
cagttttggc caggggaccg agctggagat caaacgaact gtggctgcac catctgtctt    420
catcttcccg ccatctgatg agcagttgaa atctggaact gctagc                   466
```

<210> SEQ ID NO 29
<211> LENGTH: 128
<212> TYPE: PRT
<213> ORGANISM: Homo sapiens

<400> SEQUENCE: 29

```
Met Arg Val Pro Ala Gln Leu Leu Phe Leu Leu Leu Trp Leu Pro
1               5                   10                  15

Asp Thr Thr Gly Gly Ile Val Met Thr Gln Ser Pro Ala Thr Leu Ser
            20                  25                  30

Val Ser Pro Gly Glu Arg Ala Thr Leu Ser Cys Arg Thr Ser Gln Ser
        35                  40                  45

Ile Gly Trp Asn Leu Ala Trp Tyr Gln Gln Lys Pro Gly Gln Ala Pro
    50                  55                  60

Arg Leu Leu Ile Tyr Gly Ala Ser Ser Arg Thr Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Ser Ala Val Tyr Tyr Cys Gln His Tyr Asp
            100                 105                 110

Asn Trp Pro Met Cys Ser Phe Gly Gln Gly Thr Glu Leu Glu Ile Lys
        115                 120                 125
```

<210> SEQ ID NO 30
<211> LENGTH: 487
<212> TYPE: DNA
<213> ORGANISM: Artificial Sequence
<220> FEATURE:
<223> OTHER INFORMATION: Synthetic Oligonucleotide

<400> SEQUENCE: 30

```
ggatctcacc atggagtttg gctgtgctg gattttcctc gttgctcttt taagaggtgt    60
ccagtgtcag gtgcagctgg tggagtctgg gggaggcgtg gtccagcctg ggaggtccct   120
gagactctcc tgtgcagcct ctggattcac cttcattagc tatggcatgc actgggtccg   180
ccaggctcca ggcaagggc tggagtgggt ggcagttata tcatatgatg gaagtaataa    240
atactatgca gactccgtga agggccgatt caccatctcc agagacaatt ccaagaacac   300
gctgtatctg caaatgaaca gcctgagagc tgaggacacg gctgtgtatt actgtgcgag   360
agtattagtg ggagctttat attattataa ctactacggg atggacgtct ggggccaagg   420
gaccacggtc accgtctcct cagcctccac caagggccca tcggtcttcc ccctggcacc   480
ctctagc                                                             487
```

<210> SEQ ID NO 31
<211> LENGTH: 144
<212> TYPE: PRT
<213> ORGANISM: Homo sapiens

<400> SEQUENCE: 31

```
Met Glu Phe Gly Leu Cys Trp Ile Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
```

```
                35                  40                  45
Ile Ser Tyr Gly Met His Trp Val Arg Gln Ala Pro Gly Lys Gly Leu
 50                  55                  60

Glu Trp Val Ala Val Ile Ser Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Val Leu Val Gly Ala Leu Tyr Tyr Tyr Asn Tyr
                115                 120                 125

Tyr Gly Met Asp Val Trp Gly Gln Gly Thr Thr Val Thr Val Ser Ser
130                 135                 140

<210> SEQ ID NO 32
<211> LENGTH: 478
<212> TYPE: DNA
<213> ORGANISM: Artificial Sequence
<220> FEATURE:
<223> OTHER INFORMATION: Synthetic Oligonucleotide

<400> SEQUENCE: 32
ggatctcacc atgagggtcc ctgctcagct cctggggctg ctaatgctct ggatacctgg     60
atccagtgca gatattgtga tgacccagac tccactctct ctgtccgtca cccctggaca   120
gccggcctcc atctcctgca agtctagtca gagcctcctg catagtgatg gaaagacctt   180
tttgtattgg tatctgcaga agccaggcca gcctccacag ctcctgatct atgaggtttc   240
caaccggttc tctggagtgc cagataggtt cagtggcagc gggtcaggga cagatttcac   300
actgaaaatc agccgggtgg aggctgagga tgttgggctt tattactgca tgcaaagtat   360
acagcttccg ctcactttcg gcggagggac caaggtggag atcaaacgaa ctgtggctgc   420
accatctgtc ttcatcttcc cgccatctga tgagcagttg aaatctggaa ctgctagc     478

<210> SEQ ID NO 33
<211> LENGTH: 132
<212> TYPE: PRT
<213> ORGANISM: Homo sapiens

<400> SEQUENCE: 33

Met Arg Val Pro Ala Gln Leu Leu Gly Leu Leu Met Leu Trp Ile Pro
  1               5                  10                  15

Gly Ser Ser Ala Asp Ile Val Met Thr Gln Thr Pro Leu Ser Leu Ser
                 20                  25                  30

Val Thr Pro Gly Gln Pro Ala Ser Ile Ser Cys Lys Ser Ser Gln Ser
                 35                  40                  45

Leu Leu His Ser Asp Gly Lys Thr Phe Leu Tyr Trp Tyr Leu Gln Lys
 50                  55                  60

Pro Gly Gln Pro Pro Gln Leu Leu Ile Tyr Glu Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Leu Tyr Tyr
                100                 105                 110

Cys Met Gln Ser Ile Gln Leu Pro Leu Thr Phe Gly Gly Gly Thr Lys
                115                 120                 125

Val Glu Ile Lys
130
```

<210> SEQ ID NO 34
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 34
gaagatctca ccatg                                                    15

<210> SEQ ID NO 35
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 35
aactagctag cagttccaga tttcaactgc tcatcagat                           39

<210> SEQ ID NO 36
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 36
gaagatctca ccatg                                                    15

<210> SEQ ID NO 37
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 37
gctctagagg gtgccagggg gaagaccgat                                    30

<210> SEQ ID NO 38
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 38

Ser Ala Thr Gly Ser Lys Leu Gln Glu Asp Ser
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 39

Arg Ser Pro Ala Leu Pro Phe Val Ser
1               5